(12) United States Patent
Aboody et al.

(10) Patent No.: US 10,238,699 B2
(45) Date of Patent: Mar. 26, 2019

(54) TROPIC CELL BASED VIROTHERAPY FOR THE TREATMENT OF CANCER

(71) Applicants: CITY OF HOPE, Duarte, CA (US); UNIVERSITY OF CHICAGO, Chicago, IL (US); UNIVERSITY OF ALABAMA at BIRMINGHAM, Birmingham, AL (US)

(72) Inventors: Karen S. Aboody, Arcadia, CA (US); Alexander J. Annala, Arcadia, CA (US); David Curiel, St. Louis, MO (US); Maciej Lesniak, Chicago, IL (US)

(73) Assignees: CITY OF HOPE, Duarte, CA (US); UNIVERSITY OF CHICAGO, Chicago, IL (US); UNIVERSITY OF ALABAMA AT BIRMINGHAM, Birmingham, AL (US)

( * ) Notice: Subject to any disclaimer, the term of this patent is extended or adjusted under 35 U.S.C. 154(b) by 0 days.

(21) Appl. No.: 14/852,378

(22) Filed: Sep. 11, 2015

(65) Prior Publication Data

US 2016/0317591 A1 Nov. 3, 2016

Related U.S. Application Data

(63) Continuation of application No. PCT/US2014/026770, filed on Mar. 13, 2014.

(60) Provisional application No. 61/780,752, filed on Mar. 13, 2013.

(51) Int. Cl.
| | |
|---|---|
| A61K 35/761 | (2015.01) |
| C12N 7/00 | (2006.01) |
| A61K 35/30 | (2015.01) |
| A61K 45/06 | (2006.01) |
| A61K 35/545 | (2015.01) |

(52) U.S. Cl.
CPC ............ *A61K 35/761* (2013.01); *A61K 35/30* (2013.01); *A61K 45/06* (2013.01); *C12N 7/00* (2013.01); *A61K 35/545* (2013.01); *C12N 2710/10332* (2013.01)

(58) Field of Classification Search
CPC .................................................. A61K 35/761
See application file for complete search history.

(56) References Cited

FOREIGN PATENT DOCUMENTS

| WO | 2000067576 | 11/2000 |
|---|---|---|
| WO | 200168148 | 9/2001 |

OTHER PUBLICATIONS

Lee et al. Oncol Reports 2011;25:63-8.*
Aboody, et al., Neural stem cells display extensive tropism for pathology in adult brain: evidence from intracranial gliomas. Proc Natl Acad Sci U S A (23):12846-12851. (2000).
Aboody, et al., Development of a tumor-selective approach to treat metastatic cancer. PLoS One. 1:e23 (2006).
Aboody, et al., Stem and progenitor cell-mediated tumor selective gene therapy. Gene Ther 15(10): 739-52. (2008).
Ahmed, et al., The use of neural stem cells in cancer gene therapy: predicting the path to the clinic. Curr Opin Mol Ther 12(5): 546-52. (2010).
Ahmed, et al., Glioblastoma multiforme: can neural stem cells deliver the therapeutic payload and fulfill the clinical promise? Expert Rev Neurother. 11(6):775-777 (2011).
Ahmed, et al., Bone marrow mesenchymal stem cells loaded with an oncolytic adenovirus suppress the antiadenoviral immune response in the cotton rat model. Mol Ther 18(10): 1846-1856. (2010).
Ahmed, et al., Neural stem cell-based cell carriers enhance therapeutic efficacy of an oncolytic adenovirus in an orthotopic mouse model of human glioblastoma. Mol Ther 19(9): 1714-1726. (2011).
Ahmed, et al., A comparative study of neural and mesenchymal stem cell-based carriers for oncolytic adenovirus in a model of malignant glioma. Mol Pharm 8(5): 1559-1572 (2011).
Ahmed, et al., Maintaining and loading neural stem cells for delivery of oncolytic adenovirus to brain tumors. Methods Mol Biol. 797:97-109. (2012).
Alonso, et al., Targeting brain tumor stem cells with oncolytic adenoviruses. Methods Mol Biol. 797:111-125. (2012).
Anderson, et al., Noninvasive MR imaging of magnetically labeled stem cells to directly identify neovasculature in a glioma model. Blood 105(1):420-425. (2005).
Anthony, et al., Detection of brain pathology by magnetic resonance imaging of iron oxide micro-particles. Methods Mol Biol.686:213-227. (2011).
Arbab, et al., Efficient magnetic cell labeling with protamine sulfate complexed to ferumoxides for cellular MRI. Blood 104(4):1217-1223. (2004).

(Continued)

*Primary Examiner* — Scott Long
(74) *Attorney, Agent, or Firm* — Perkins Coie LLP; Lara J. Dueppen; Yang Tang

(57) ABSTRACT

In some embodiments, methods of killing tumor cells are provided. The methods may include contacting the tumor cell with a tropic cell that carries a modified oncolytic virus, wherein the virus comprises a tumor selective element and/or a capsid protein that binds a tumor-specific cell surface molecule. In another embodiment, methods of treating cancer are provided. The methods may include administering a therapeutically effective amount of a pharmaceutical composition to a subject, wherein the pharmaceutical composition includes a tropic cell that carries a modified oncolytic virus, wherein the virus comprises a tumor selective promoter element and/or a capsid protein that binds a tumor-specific cell surface molecule.

17 Claims, 65 Drawing Sheets

Specification includes a Sequence Listing.

(56) References Cited

OTHER PUBLICATIONS

Atencio, et al., Biological activities of a recombinant adenovirus p53 (SCH 58500) administered by hepatic arterial infusion in a Phase 1 colorectal cancer trial. Cancer Gene Ther (2006).
Bantubungi, et al., Stem cell factor and mesenchymal and neural stem cell transplantation in a rat model of Huntington's disease. Mol Cell Neurosci 37(3):454-470 (2008).
Bao, et al., Glioma stem cells promote radioresistance by preferential activation of the DNA damage response. Nature 444: 756-760 (2006).
Bao, et al., Stem cell-like glioma cells promote tumor angiogenesis through vascular endothelial growth factor. Cancer Res; 66(16): 7843-8 (2006).
Barbosa, et al., Glyceraldehyde-3-phosphate dehydrogenase of Paracoccidioides brasiliensis is a cell surface protein involved in fungal adhesion to extracellular matrix proteins and interaction with cells. Infect Immun; 74(1):382-389 (2006).
Barker, et al., Survival and functional status after resection of recurrent glioblastoma multiforme. Neurosurgery; 42(4):709-720 (1998).
Beier, et al., Temozolomide preferentially depletes cancer stem cells in glioblastoma. Cancer Res; 68: 5706-5715 (2008).
Beier, et al., Chemoresistance of glioblastoma cancer stem cells: Much more complex than expected. Mol Cancer 10:128 (2011).
Bello, et al., IS20I, a specific alphavbeta3 integrin inhibitor, reduces glioma growth in vivo. Neurosurgery; 52(1):177-185 (2003).
Benedetti, et al., Gene therapy of experimental brain tumors using neural progenitor cells. Nat Med. 6(4):447-450 (2000).
Bessis, et al., Immune responses to gene therapy vectors: influence on vector function and effector mechanisms. Gene Ther 11 Suppl 1: S10-7 (2004).
Bewig, et al., Accelerated titering of adenoviruses: BioTechniques 28, 870-873 (2000).
Bieler, et al., Impact of radiation therapy on the oncolytic adenovirus dl520: Implications on the treatment of glioblastoma. Radiother Oncol; 86:419-427 (2008).
Bloch, et al., Impact of extent of resection for recurrent glioblastoma on overall survival: Clinical article. J Neurosurg;117:1032-1038 (2012).
Brada, et al., Phase I dose-escalation and pharmacokinetic study of temozolomide (SCH 52365) for refractory or relapsing malignancies. Br J Cancer; 81:1022-1030 (1999).
Brustle, et al., In vitro-generated neural precursors participate in mammalian brain development, Proceedings of the National Academy of Sciences of the United States of America 94, 14809-14814 (1997).
Candolfi, et al., Intracranial glioblastoma models in preclinical neuro-oncology: neuropathological characterization and tumor progression. J Neurooncol; 85(2): 133-48 (2007).
Carney, et al., Migration and fate of therapeutic stem cells in different brain disease models. Neuroscience. 197:37-47 (2011).
Cattaneo, et al., Reprogrammed viruses as cancer therapeutics: targeted, armed and shielded. Nat Rev Microbiol; 6(7): 529-540 (2008).
Chahal, et al., MGMT modulates glioblastoma angiogenesis and response to the tyrosine kinase inhibitor sunitinib. Neuro Oncol. ;12(8):822-833 (2010).
Chakravarti, et al., Quantitatively determined survivin expression levels are of prognostic value in human gliomas. J Clin Oncol; 20(4)1063-1068 (2002).
Chakravarti, et al., Survivin enhances radiation resistance in primary human glioblastoma cells via caspase-independent mechanisms. Oncogene 23(45):7494-7506. (2004).
Chatrchyan, et al., Search for supersymmetry in pp collisions at $\sqrt{7}$ TeV in events with two photons and missing transverse energy. Phys Rev Lett; 106:211802 (2011).
Chiocca, et al., A phase I open-label, dose-escalation, multi-institutional trial of injection with an E1B-Attenuated adenovirus, ONYX-015, into the peritumoral region of recurrent malignant gliomas, in the adjuvant setting. Mol Ther;10(5):958-966 (2004).
Chiocca, et al., Phase IB Study of gene-mediated cytotoxic immunotherapy adjuvant to upfront surgery and intensive timing radiation for malignant glioma. J Clin Oncol; 29(27): 3611-3619 (2011).
Chivukula, et al., FNAB cytology of extra-cranial metastasis of glioblastoma multiforme may resemble a lung primary: A diagnostic pitfall. Cytojournal 2(1):9 (2005).
Conti, et al., Neural stem cell systems: physiological players or in vitro entities? Nat Rev Neurosci;11(3):176-187 (2010).
Cooney, et al., Adenoviral-mediated gene transfer of nitric oxide synthase isoforms and vascular cell proliferation. J Vasc Res; 43(5):462-472 (2006).
Corot, et al., Recent advances in iron oxide nanocrystal technology for medical imaging. Adv Drug Deliv Rev;58(14):1471-1504 (2006).
Coukos, et al., Use of carrier cells to deliver a replication-selective herpes simplex virus-1 mutant for the intraperitoneal therapy of epithelial ovarian cancer, Clin Cancer Res 5, 1523-1537 (1999).
Das, et al., Viral infection and neural stem/progenitor cell's fate: implications in brain development and neurological disorders. Neurochemistry international; 59(3):357-366 (2011).
Davison, et al., Integrin alpha5beta1-mediated adenovirus infection is enhanced by the integrin-activating antibody TS2/16. J. Virol;71(8):6204-6207 (1997).
Dembinski, et al., Reduction of nontarget infection and systemic toxicity by targeted delivery of conditionally replicating viruses transported in mesenchymal stem cells. Cancer Gene Ther; 17(4): 289-97 (2010).
Deorah, et al., Trends in brain cancer incidence and survival in the United States: Surveillance, Epidemiology, and End Results Program, 1973 to 2001. Neurosurg Focus; 20(4): E1 (2006).
Dey, et al., Cancer Stem Cells: The Final Frontier for Glioma Virotherapy. Stem Cell Rev; 7(1): 119-29 (2011).
Ehtesham, et al., Induction of glioblastoma apoptosis using neural stem cell-mediated delivery of tumor necrosis factor-related apoptosis-inducing ligand. Cancer Res; 62(24):7170-7174 (2002).
Einstein, et al., The changing face of neural stem cell therapy in neurologic diseases. Arch Neurol; 65(4): 452-456 (2008).
Fisher, et al., Striking out at disseminated metastases: the systemic delivery of oncolytic viruses, Current opinion in molecular therapeutics 8, 301-313 (2006).
Flax, et al., Engraftable human neural stem cells respond to developmental cues, replace neurons, and express foreign genes. Nat Biotechnol;16(11):1033-1039 (1998).
Fueyo, et al., A mutant oncolytic adenovirus targeting the Rb pathway produces anti-glioma effect in vivo. Oncogene;19(1):2-12 (2000).
Gage, et al., Mammalian neural stem cells. Science; 287(5457):1433-1438 (2008).
Gaspar, et al., Supratentorial malignant glioma: patterns of recurrence and implications for external beam local treatment. Int J Radiat Oncol Biol Phys; 24(1):55-57 (1992).
Geoerger, et al., Potentiation of radiation therapy by the oncolytic adenovirus dl1520 (ONYX-015) in human malignant glioma xenografts. Br J Cancer; 89:577-584 (2003).
Germano, et al., Adenovirus/herpes simplex-thymidine kinase/ ganciclovir complex: preliminary results of a phase I trial in patients with recurrent malignant gliomas. J Neurooncol; 65(3):279-289 (2003).
Giannini, et al., Patient tumor EGFR and PDGFRA gene amplifications retained in an invasive intracranial xenograft model of glioblastoma multiforme. Neuro Oncol;7:164-176 (2005).
Grossman, et al., Survival of patients with newly diagnosed glioblastoma treated with radiation and temozolomide in research studies in the United States. Clin Cancer Res;16:2443-2449 (2010).
Gul, et al., Valproic acid increases CXCR4 expression in hematopoietic stem/progenitor cells by chromatin remodeling. Stem Cells and Development 18(6):831-838 (2009).
Guo, et al., Oncolytic virotherapy: molecular targets in tumor-selective replication and carrier cell-mediated delivery of oncolytic viruses, Biochim biophysica acta 1785, 217-231 (2008).
Hanahan, et al., The hallmarks of cancer, Cell 100, 57-70 (2000).

(56) References Cited

OTHER PUBLICATIONS

Hart, et al., The adenovirus E4orf6 protein inhibits DNA double strand break repair and radiosensitizes human tumor cells in an E1B-55K-independent manner. J Biol Chem; 280: 1474-1481 (2005).
Haviv, et al., Adenoviral gene therapy for renal cancer requires retargeting to alternative cellular receptors. Cancer Res;62(15):4273-4281 (2002).
Heidenreich, et al., Inhibition of solid tumor growth by gene transfer of VEGF receptor-1 mutants. Int J Cancer;111:348-357 (2004).
Helleday, et al., DNA repair pathways as targets for cancer therapy. Nat Rev Cancer; 8:193-204 (2008).
Hingtgen, et al., Targeting multiple pathways in gliomas with stem cell and viral delivered S-TRAIL and Temozolomide. Mol Cancer Ther;7(11):3575-3585 (2008).
Hsu, et al., Local delivery of interleukin-2 and adriamycin is synergistic in the treatment of experimental malignant glioma. J Neurooncol 135-140 (2005).
Immonen, et al., AdvHSV-tk gene therapy with intravenous ganciclovir improves survival in human malignant glioma: a randomised, controlled study. Mol Ther;10(5):967-972 (2004).
Ito, et al., Therapeutic efficacy of PUMA for malignant glioma cells regardless of p53 status. Hum Gene Ther;16(6):685-698 (2005).
Izpisua, et al., Induced pluripotent stem cells and reprogramming: seeing the science through the hype. Nat Rev Genet;10(12):878-883 (2009).
Jiang, et al., A quantitative model of tumor-induced angiogenesis in the nude mouse. Neurosurgery; 57(2):320-324 (2005).
Jiang, et al., Comparative effect of oncolytic adenoviruses with E1A-55 kDa or E1B-55 kDa deletions in malignant gliomas. Neoplasia;7(1):48-56 (2005).
Jiang, et al., Examination of the therapeutic potential of Delta-24-RGD in brain tumor stem cells: role of autophagic cell death. J Natl Cancer Inst; 99(18): 1410-1414 (2007).
Jiang, et al., Oncolytic adenoviruses as antiglioma agents. Expert Rev Anticancer Ther; 6(5):697-708 (2006).
Kaetzel, et al., A dominant-negative mutant of the platelet-derived growth factor A-chain increases survival of hamsters implanted intracerebrally with the highly invasive CxT24-neo3 glioblastoma cell. J Neurooncol ;39(1):33-46 (1998).
Kajiwara, et al., Expression of survivin in astrocytic tumors: correlation with malignant grade and prognosis. Cancer; 97(4):1077-1083 (2003).
Kanai, et al., Oncolytic virus-mediated manipulation of DNA damage responses: synergy with chemotherapy in killing glioblastoma stem cells. J Natl Cancer Inst.;104(1):42-55 (2012).
Karapanagiotou, et al., Phase I/II trial of carboplatin and paclitaxel chemotherapy in combination with intravenous oncolytic reovirus in patients with advanced malignancies. Clin Cancer Res; 18:2080-2089 (2012).
Karen, et al., Temporal regulation of the Mre11-Rad50-Nbs1 complex during adenovirus infection. J Virol; 83:4565-4573 (2009).
Kawakami, et al., Substitution of the adenovirus serotype 5 knob with a serotype 3 knob enhances multiple steps in virus replication. Cancer Res; 63(6):1262-1269 (2003).
Kelly, et al., History of oncolytic viruses: genesis to genetic engineering. Mol Ther. 15(4): 651-9 (2007).
Kendall, et al., Neural stem cell targeting of glioma is dependent on phosphoinositide 3-kinase signaling. Stem Cells;26(6):1575-1586 (2008).
Kim, et al., Neural stem cell transplant survival in brains of mice: assessing the effect of immunity and ischemia by using real-time bioluminescent imaging. Radiology; 241(3):822-830 (2006).
Kim, et al., Combination of mutated herpes simplex virus type 1 (G207 virus) with radiation for the treatment of squamous cell carcinoma of the head and neck. Eur J Cancer;41:313-322 (2005).
Kim, et al., Human neural stem cells target experimental intracranial medulloblastoma and deliver a therapeutic gene leading to tumor regression. Clin Cancer Res;12(18):5550-5556 (2006).
Kim, et al., Stem cell-based cell therapy in neurological diseases: A review. J Neurosci Res; 87:2183-2200 (2009).
Kim, et al., Production and characterization of immortal human neural stem cell line with multipotent differentiation property. Methods Mol Biol.; 438:103-121 (2008).
Kim, et al., Production of immortalized human neural crest stem cells. Methods Mol Biol; 198:55-65. (2002).
Kitange, et al., Induction of MGMT expression is associated with temozolomide resistance in glioblastoma xenografts. Neuro Oncol;11(3):281-291 (2009).
Klopp, et al., Tumor irradiation increases the recruitment of circulating mesenchymal stem cells into the tumor microenvironment. Cancer Res; 67(24):11687-11695 (2007).
Komarova, et al., Targeting of mesenchymal stem cells to ovarian tumors via an artificial receptor. Journal of Ovarian Research 3:12 (2010).
Kuroda, et al., Telomerase-dependent oncolytic adenovirus sensitizes human cancer cells to ionizing radiation via inhibition of DNA repair machinery. Cancer Res;70:9339-9348 (2010).
Lakka, et al., Adenovirus-mediated expression of antisense MMP-9 in glioma cells inhibits tumor growth and invasion. Oncogene; 21(52):8011-8019 (2002).
Lamfers, et al., Homing properties of adipose-derived stem cells to intracerebral glioma and the effects of adenovirus infection. Cancer Lett ;274(1):78-87 (2009).
Lang, et al., Phase I trial of adenovirus-mediated p53 gene therapy for recurrent glioma: biological and clinical results. J Clin Oncol;21(13):2508-2518 (2003).
Lesniak, et al., Targeted therapy for brain tumours. Nat Rev Drug Discov 3(6):499-508 (2004).
Lesniak, et al., Dexamethasone mediated inhibition of local IL-2 immunotherapy is dose dependent in experimental brain tumors. J Neurooncol; 70(1):23-28 (2004).
Lesniak, et al., Comparative analysis of paracrine immunotherapy in experimental brain tumors. Neurosurgical Focus;9(6) (2000).
Lesniak, et al., Gene therapy for experimental brain tumors using a xenogenic cell line engineered to secrete hIL-2. J Neurooncol; 64(1-2):155-160 (2003).
Lesniak, et al., Brain tumors: controversies and challenges in management, Expert review of neurotherapeutics 5, 1-2 (2005).
Lesniak, et al., Gene therapy for malignant glioma, Expert review of neurotherapeutics 6, 479-488 (2006).
Lesniak, et al., Advances in neurooncology: novel therapies and clinical trials, Expert review of anticancer therapy 7, S1 (2007).
Li, et al., Integrin alpha(v)beta1 is an adenovirus coreceptor. J Virol;75(11):5405-5409 (2001).
Li, et al., Long-term tracing of adenoviral expression in rat and rabbit using luciferase imaging. J Gene Med;7(6):792-802 (2005).
Lin, et al., Novel method for visualizing and modeling the spatial distribution of neural stem cells within intracranial glioma. Neuroimage; 37 Suppl 1:S18-26 (2007).
Liu, et al., Developmental origins of brain tumors. Curr Opin Neurobiol; 22:844-849 (2012).
Lowenstein, et al., Uncertainty in the translation of preclinical experiments to clinical trials: Why do most phase III clinical trials fail? Curr Gene Ther; 9:368-374 (2009).
Lowenstein, et al., Immunology of viral-vector-mediated gene transfer into the brain: an evolutionary and developmental perspective. Trends Immunol; 23(1): 23-30 (2002).
Markert, et al., Conditionally replicating herpes simplex virus mutant, G207 for the treatment of malignant glioma: results of a phase I trial. Gene Ther; 7(10):867-874 (2000).
Marshall, et al., arshall GP, 2nd, Scott EW, Zheng T, Laywell ED, Steindler DA. Ionizing radiation enhances the engraftment of transplanted in vitro-derived multipotent astrocytic stem cells. Stem Cells; 23(9):1276-1285 (2005).
Meier, et al., Adenovirus triggers macropinocytosis and endosomal leakage together with its clathrin-mediated uptake. J Cell Biol;158(6):1119-1131 (2002).
Miletic, et al., Bystander killing of malignant glioma by bone marrow-derived tumor-infiltrating progenitor cells expressing a suicide gene. Mol Ther;15(7):1373-1381 (2007).
Modo, et al., Tracking transplanted stem cell migration using bifunctional, contrast agentenhanced, magnetic resonance imaging. Neuroimage;17(2):803-811 (2002).

(56) References Cited

OTHER PUBLICATIONS

Modo, et al., Mapping transplanted stem cell migration after a stroke: a serial, in vivo magnetic resonance imaging study. Neuroimage; 21(1):311-317 (2004).
Modo, et al., Understanding stem cell-mediated brain repair through neuroimaging. Curr Stem Cell Res Ther; 1(1):55-63 (2006).
Mohan, et al., Outcome in elderly patients undergoing definitive surgery and radiation therapy for supratentorial glioblastoma multiforme at a tertiary care institution. Int J Radiat Oncol Biol Phys; 42(5):981-987 (1998).
Mourad, et al., Why are systemic glioblastoma metastases rare? Systemic and cerebral growth of mouse glioblastoma. Surg Neurol; 63(6):511-519 (2005).
Muja, et al., Magnetic resonance imaging of cells in experimental disease models. Prog Nucl Magn Reson Spectrosc; 55(1):61-77 (2009).
Nandi, et al., Low-dose radiation enhances survivin-mediated virotherapy against malignant glioma stem cells. Cancer Res; 68(14):5778-5784 (2008).
Nicholas, et al., Molecular heterogeneity in glioblastoma: therapeutic opportunities and challenges. Semin Oncol; 38(2):243-253 (2011).
Niewiesk, et al., Diversifying animal models: the use of hispid cotton rats (*Sigmodon hispidus*) in infectious diseases. Lab Anim; 36(4): 357-72 (2002).
Niewiesk, et al., Cotton rats (*Sigmodon hispidus*): an animal model to study the pathogenesis of measles virus infection. Immunol Lett; 65(1-2): 47-50 (1999).
Ogungbo, et al., Metastasis to the Parotid Gland. J Neurooncol 74:227-338 (2005).
Ostermann, et al., Plasma and cerebrospinal fluid population pharmacokinetics of temozolomide in malignant glioma patients. Clin Cancer Res;10:3728-3736 (2004).
Ottolino-Perry, et al., Intelligent design: Combination therapy with oncolytic viruses. Mol Ther: 18:251-263 (2010).
Parker, et al., Oncolytic viral therapy of malignant glioma, Neurotherapeutics 6, 558-569 (2009).
Petrini, et al., The mammalian Mre11-Rad50-nbs1 protein complex: Integration of functions in the cellular DNA-damage response. Am J Hum Genet; 64:1264-1269 (1999).
Pluchino, et al., Injection of adult neurospheres induces recovery in a chronic model of multiple sclerosis. Nature; 422:688-694 (2003).
Pluderi, et al., Long-term inhibition of glioma growth by systemic administration of human PEX. J Neurosurg Sci; 47(2):69-78 (2003).
Power, et al., Taming the Trojan horse: optimizing dynamic carrier cell/oncolytic virus systems for cancer biotherapy. Gene Ther;15(10): 772-779 (2008).
Pulkkanen, et al., Gene therapy for malignant glioma: current clinical status. Mol Ther; 12(4): 585-98 (2005).
Rahman, et al., Antiangiogenic therapy and mechanisms of tumor resistance in malignant glioma. J Oncol; 2010:251231 (2010).
Rajagopalan, et al., Bone marrow metastases from glioblastoma multiforme—A case report and review of the literature. J Neurooncol;72(2):157-161 (2005).
Ring, et al., Direct reprogramming of mouse and human fibroblasts into multipotent neural stem cells with a single factor. Cell Stem Cell;11(1):100-109 (2012).
Rosso, et al., A new model for prediction of drug distribution in tumor and normal tissues: Pharmacokinetics of temozolomide in glioma patients. Cancer Res; 69:120-127 (2009).
Sampson, et al., Immunologic escape after prolonged progression-free survival with epidermal growth factor receptor variant III peptide vaccination in patients with newly diagnosed glioblastoma. J Clin Oncol 2010; 28(31): 4722-4729.
Sarkaria, et al., Use of an orthotopic xenograft model for assessing the effect of epidermal growth factor receptor amplification on glioblastoma radiation response. Clin Cancer Res; 12(7 Pt 1):2264-2271 (2006).
Schmidt, et al., Brain tumor tropism of transplanted human neural stem cells is induced by vascular endothelial growth factor. Neoplasia;7:623-629 (2005).
Schoenfeld, et al., Sample-size formula for the proportional-hazards regression model. Biometrics;39(2):499-503 (1983).
Sebestyen, et al., An oncolytic adenovirus redirected with a tumor-specific T-cell receptor. Cancer Res;67(23):11309-11316 (2007).
Selznick, et al., Molecular strategies for the treatment of malignant glioma—genes, viruses, and vaccines. Neurosurg Rev; 31(2): 141-55 (2008).
Shah, et al., Glioma therapy and realtime imaging of neural precursor cell migration and tumor regression. Ann Neurol; 57(1):34-41 (2005).
Sheehan, et al., Improving the radiosensitivity of radioresistant and hypoxic glioblastoma. Future Oncol; 6(10): 1591-601 (2010).
Singh, et al., Identification of human brain tumour initiating cells. Nature;4 32(7015):396-401 (2004).
Smitt, et al., Treatment of relapsed malignant glioma with an adenoviral vector containing the herpes simplex thymidine kinase gene followed by ganciclovir. Mol Ther;7(6):851-858 (2003).
Sonabend, et al., Oncolytic adenoviral therapy for glioblastoma multiforme. Neurosurg Focus 20(4):E19 (2006).
Sonabend, et al., Biodistribution of an oncolytic adenovirus after intracranial injection in permissive animals: a comparative study of Syrian hamsters and cotton rats. Cancer Gene Ther;16(4):362-372 (2009).
Sonabend, et al., Mesenchymal stem cells effectively deliver an oncolytic adenovirus to intracranial glioma. Stem Cells; 26(3): 831-841 (2008).
Stoica, et al., Identification of cancer stem cells in dog glioblastoma. Vet Pathol; 46(3): 391-406 (2009).
Stracker, et al., Adenovirus oncoproteins inactivate the Mre11-Rad50-NBS1 DNA repair complex. Nature; 418:348-352 (2002).
Studebaker, et al., Oncolytic measles virus prolongs survival in a murine model of cerebral spinal fluid-disseminated medulloblastoma. Neuro Oncol; doi: 10.1093/neuonc/nor231 (2012).
Stupp, et al., Effects of radiotherapy with concomitant and adjuvant temozolomide versus radiotherapy alone on survival in glioblastoma in a randomised phase III study: 5-year analysis of the EORTC-NCIC trial. Lancet Oncol; 10(5): 459-66 (2009).
Stupp, et al., Radiotherapy plus concomitant and adjuvant temozolomide for glioblastoma. N Engl J Med; 352(10):987-996 (2005).
Stupp, et al., The role of radio- and chemotherapy in glioblastoma. Onkologie;28(6-7):315-317 (2005).
Thaci, et al., Pharmacokinetic study of neural stem cell-based cell carrier for oncolytic virotherapy: targeted delivery of the therapeutic payload in an orthotopic brain tumor model. Cancer Gene Ther;19(6):431-442 (2012).
Thomas, et al., Syrian hamster as a permissive immunocompetent animal model for the study of oncolytic adenovirus vectors. Cancer Res;66(3):1270-1276 (2006).
Thomas, et al., Use of the Syrian hamster as an animal model for oncolytic adenovirus vectors. Methods Mol Med; 130: 169-83 (2007).
Thu, et al., Iron labeling and pre-clinical MRI visualization of therapeutic human neural stem cells in a murine glioma model. PLoS One; 4(9): e7218 (2009).
Thumma, et al., Long-term survival after gamma knife radiosurgery in a case of recurrent glioblastoma multiforme: A case report and review of the literature. Case Report Med;2012:545492 (2012).
Tobias, et al., The art of gene therapy for glioma: A review of the challenging road to the bedside. J Neurol Neurosurg Psychiatry; 84:213-222 (2013).
Toth, et al., Cotton rat tumor model for the evaluation of oncolytic adenoviruses. Hum Gene Ther; 16(1): 139-46 (2005).
Toth, et al., Immunocompetent, semi-permissive cotton rat tumor model for the evaluation of oncolytic adenoviruses. Methods Mol Med; 130: 157-168 (2007).
Tran, et al., Survival comparison between glioblastoma multiforme and other incurable cancers. J Clin Neurosci; 17:417-421 (2010).
Tsai, et al., Impact of human neutralizing antibodies on antitumor efficacy of an oncolytic adenovirus in a murine model. Clin Cancer Res;10(21):7199-7206 (2004).
Tuominen, et al., Mediastinal metastasis of glioblastoma multiforme evolving from anaplastic astrocytoma. J Neurooncol 75:225-226 (2005).

(56) References Cited

OTHER PUBLICATIONS

Tyler, et al., Enhanced transduction of malignant glioma with a double targeted Ad5/3-RGD fibermodified adenovirus. Mol Cancer Ther; 5(9):2408-2416 (2006).
Tyler, et al., Neural stem cells target intracranial glioma to deliver an oncolytic adenovirus in vivo. Gene Ther; 16(2): 262-78 (2009).
Ubiali, et al., Allorecognition of human neural stem cells by peripheral blood lymphocytes despite low expression of MHC molecules: role of TGF-beta in modulating proliferation. Int Immunol; 19(9): 1063-74 (2007).
Ulasov, et al., An oncolytic adenoviral vector carrying the tyrosinase promoter for glioma gene therapy. Int J Oncol;31(5):1177-1185 (2007).
Ulasov, et al., Comparative evaluation of survivin, midkine and CXCR4 promoters for transcriptional targeting of glioma gene therapy. Cancer Biol Ther; 6(5): 679-685 (2007).
Ulasov, et al., Targeting adenovirus to CD80 and CD86 receptors increases gene transfer efficiency to malignant glioma cells. J Neurosurg;107(3):617-627 (2007).
Ulasov, et al., Combination of adenoviral virotherapy and temozolomide chemotherapy eradicates malignant glioma through autophagic and apoptotic cell death in vivo. Br J Cancer; 100(7):1154-1164 (2009).
Ulasov, et al., Novel recombinant adenoviral vector that targets the interleukin-13 receptor alpha2 chain permits effective gene transfer to malignant glioma. Hum Gene Ther;18(2):118-129 (2007).
Ulasov, et al., Survivin-driven and fiber-modified oncolytic adenovirus exhibits potent antitumor activity in established intracranial glioma. Hum Gene Ther; 18(7): 589-602 (2007).
Utsuki, et al., Glioblastoma multiforme metastasis to the axis. Case report. J Neurosurg;102(3):540-542 (2005).
Van Beusechem, et al., Conditionally replicative adenovirus expressing degradation-resistant p53 for enhanced oncolysis of human cancer cells overexpressing murine double minute 2. Mol Cancer Ther;4(6):1013-1018 (2005).
Van Houdt, et al., The human surviving promoter: a novel transcriptional targeting strategy for treatment of glioma. J Neurosurg;104(4):583-592 (2006).
Vichai, et al., Sulforhodamine B colorimetric assay for cytotoxicity screening. Nat Protoc; 1(3):1112-1116 (2006).
Wen, et al., Malignant gliomas in adults. N Engl J Med; 359(5):492-507 (2008).
Wickham, et al., Integrins alpha v beta 3 and alpha v beta 5 promote adenovirus internalization but not virus attachment. Cell;73(2):309-319 (1993).
Wildner, et al., Subcutaneous administration of a replication-competent adenovirus expressing HSV-tk to cotton rats: dissemination, persistence, shedding, and pathogenicity. Hum Gene Ther;13(1):101-112 (2002).
Wohlfahrt, et al., A capsid-modified, conditionally replicating oncolytic adenovirus vector expressing trail leads to enhanced cancer cell killing in human glioblastoma models. Cancer Res;67(18):8783-8790 (2007).
Wu, et al., Double modification of adenovirus fiber with RGD and polylysine motifs improves coxsackievirus-adenovirus receptor-independent gene transfer efficiency. Hum Gene Ther;13(13):1647-1653 (2002).
Xu, et al., Neuronatin in a subset of glioblastoma multiforme tumor progenitor cells is associated with increased cell proliferation and shorter patient survival. PLoS One;12;7:e37811 (2012).
Yamada, et al., Transcriptional expression of survivin and its splice variants in brain tumors in humans. J Neurosurg;99(4):738-745 (2003).
Yamamoto, et al., Current issues and future directions of oncolytic adenoviruses. Mol Ther;18(2):243-250 (2010).
Yamanaka, et al.,Induced pluripotent stem cells: past, present, and future. Cell Stem Cell;10(6):678-684 (2012).
Zhang, et al., VEGF is a chemoattractant for FGF-2-stimulated neural progenitors. J Cell Biol 163: 1375-1384 (2003).
Zhang, et al., In vivo magnetic resonance imaging tracks adult neural progenitor cell targeting of brain tumor. Neuroimage; 23(1):281-287 (2004).
Zhao, et al., Neural stem cell tropism to glioma: Critical role of tumor hypoxia. Mol Cancer Res; 6:1819-1829 (2008).
Zheng, et al., Fiber-knob modifications enhance adenoviral tropism and gene transfer in malignant glioma. J Gene Med;9(3):151-160 (2007).
Zhu, et al., Early inactivation of p53 tumor suppressor gene cooperating with NF1 loss induces malignant astrocytoma. Cancer Cell;8(2):119-130 (2005).
Zhu, et al., Incorporating the survivin promoter in an infectivity enhanced CRAdanalysis of oncolysis and antitumor effects in vitro and in vivo. Int J Oncol; 27(1): 237-46 (2005).

\* cited by examiner

FIG. 19A
FIG. 19B
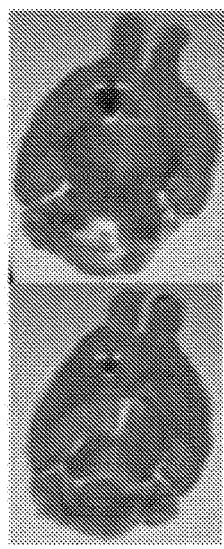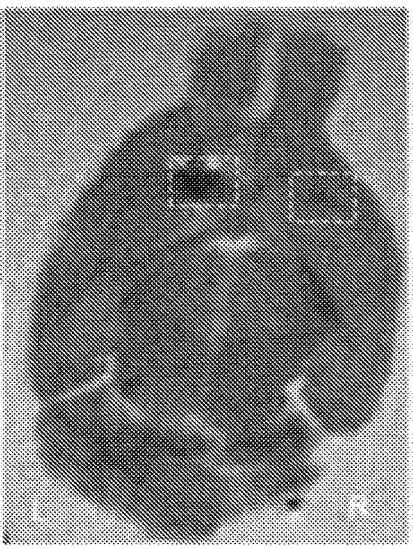
FIG. 19C
FIG. 19D
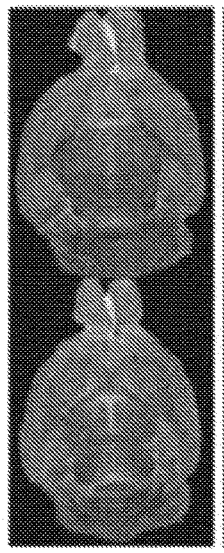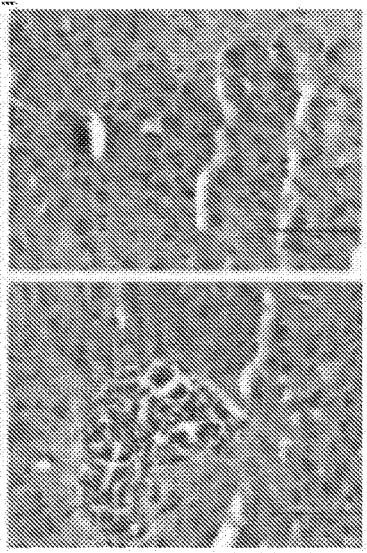

FIG. 20A
FIG. 20B
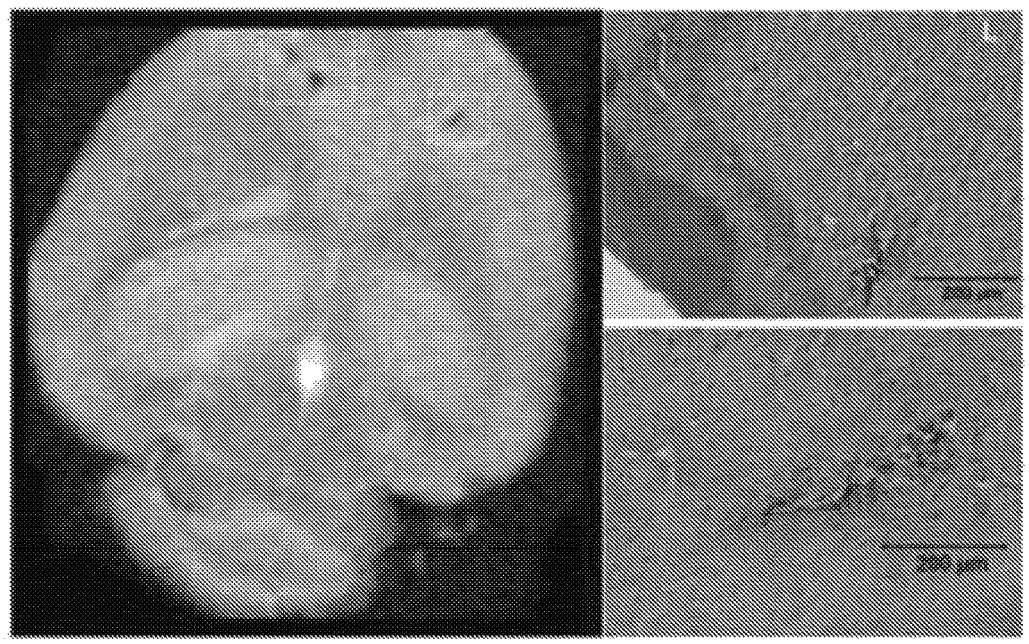
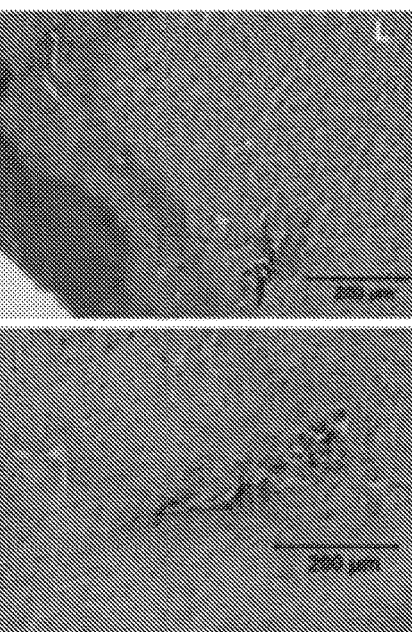
FIG. 20C
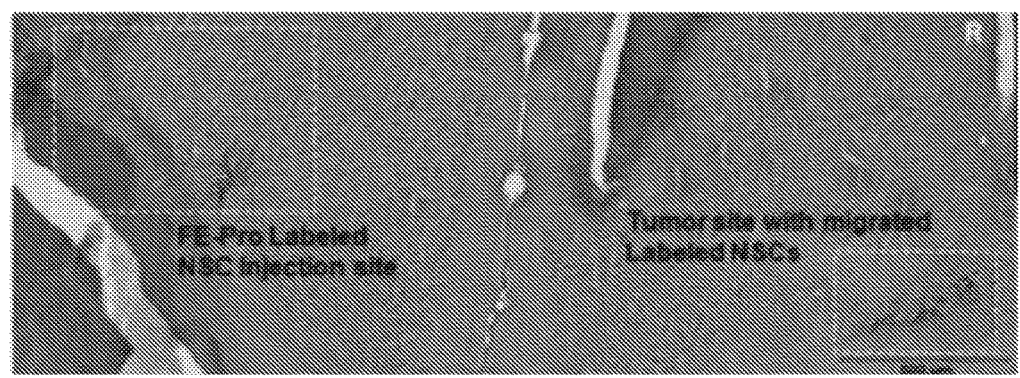

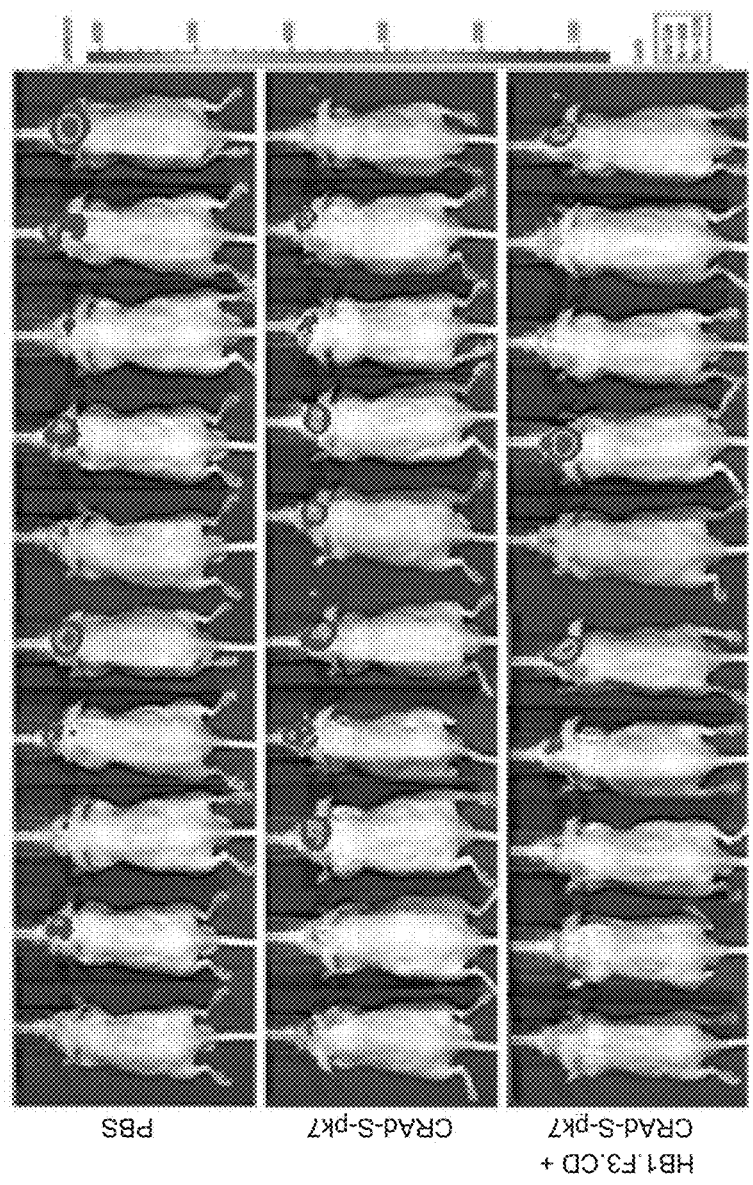
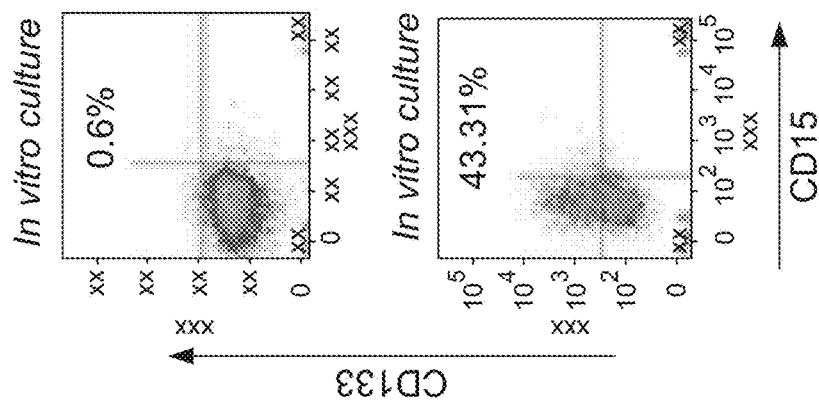
FIG. 34A
FIG. 34B

TROPIC CELL BASED VIROTHERAPY FOR THE TREATMENT OF CANCER

PRIORITY CLAIM

This application is a continuation of International Patent Application No. PCT/US14/26770, filed Mar. 13, 2014, which claims priority to U.S. Provisional Application No. 61/780,752, filed Mar. 13, 2013, which is hereby incorporated by reference as if fully set forth herein, including the drawings.

STATEMENT OF GOVERNMENT INTEREST

The present invention was made with government support under Grant Nos. R01CA122930, K99-CA160775, and R01CA138587, awarded by the National Cancer Institute (NCI); Grant Nos. U01NS069997 and R01NS077388, awarded by the National Institute of Neurological Disorders and Stroke, and Grant No. RSG-07-276-01-MGO awarded by the American Cancer Society. The Government has certain rights in the invention.

BACKGROUND

Treatment of cancer typically involves surgical resection, standard chemotherapy and/or radiation therapy to remove or kill tumor cells. However, the effectiveness of these treatments are often limited because of the invasiveness of the tumor and/or collateral damage to healthy tissues. Brain cancer is one of many types of cancer that can exhibit a limited response to traditional cancer treatment.

Glioblastoma (GBM) is the most common primary brain tumor and portends the worst prognosis among all central nervous system (CNS) malignancies (Deorah et al. 2006). Unlike other solid organ malignancies, GBMs are generally confined to the CNS and rare case reports of metastatic disease is rare (Ogungbo et al. 2005; Tuominene et al. 2005; Chivukula et al. 2005; Mourad et al. 2005; Rajagopalan et al. 2005; Utsuki et al. 2005).

The mean overall survival (OS) has only slightly improved over the last 30 years (Stupp et al. 2009). The current standard of care relies on surgical resection, fractioned radiotherapy and chemotherapy (Wen & Kesari 2008). The therapeutic efficacy of most of these treatment modalities is limited due to the invasive nature of the tumors. By the time gliomas are diagnosed they have often already infiltrated diffusely and are therefore extremely difficult to remove by complete surgical resection. The low oxygen level in the glioma environment negatively affects radiotherapy (Sheehan et al. 2010); while cellular heterogeneity and glioma stem cells account for the emergence of resistance to therapeutic regimens (Sampson et al. 2010; Bao et al. 2006). Therefore, there is an urgency to develop novel therapies capable of overcoming the common resistance mechanisms of gliomas (Dey et al. 2011).

The median survival after surgical intervention alone is approximately six months and the addition of radio-/chemotherapy can extend this time up to twelve months (Stupp et al. 2005a; Lesniak et al. 2004). Failed therapy is most often associated with local recurrence in the proximity of the original tumor (Gaspar et al. 1992). Consequently, efforts aimed at developing new therapies have focused on treatment strategies that target the tumor environment but spare normal and healthy surrounding brain cells. It would be desirable to generate new methods of treating GBM and other forms of cancer using such a strategy.

SUMMARY

In one embodiment, a method of killing a tumor cell is provided. The method may include contacting the tumor cell with a tropic cell that carries a modified oncolytic virus, wherein the virus comprises a tumor selective element and/or a capsid protein that binds a tumor-specific cell surface molecule.

In another embodiment, a method of treating cancer is provided. The method may include administering a therapeutically effective amount of a pharmaceutical composition to a subject, wherein the pharmaceutical composition includes a tropic cell that carries a modified oncolytic virus, wherein the virus comprises a tumor selective promoter element and/or a capsid protein that binds a tumor-specific cell surface molecule. In some embodiments, the method may also include administering one or more additional therapeutic agents (e.g., a chemotherapeutic or radiation therapy) in combination with the pharmaceutical composition.

In some embodiments, the tropic cell used in the methods described herein is an embryonic stem cell (ESC), embryonic germ cell (ESG), induced pluripotent stem cell (iPSC), embryonic carcinoma cell (ECC), bone marrow stem cell, adult stem cell, hematopoietic stem cell, neural stem cell or mesenchymal stem cell. In one embodiment, the stem cell is from a neural stem cell line HB1.F3-CD.

In some embodiments, the oncolytic virus is a modified conditionally replicating adenovirus (CRAd) wherein in some aspects, the tumor selective promoter element is a survivin promoter, a cyclooxygenase-2 (COX-2) promoter, prostate specific antigen (PSA) promoter, a CXCR4 promoter, or a STAT3 promoter; and the tumor specific cell surface molecule is selected from an integrin, an EGF receptor family member, a proteoglycan, a disialoganglioside, B7-H3, cancer antigen 125 (CA-125), epithelial cell adhesion molecule (EpCAM), vascular endothelial growth factor receptor 1, vascular endothelial growth factor receptor 2, carcinoembryonic antigen (CEA), a tumor associated glycoprotein, cluster of differentiation 19 (CD19), CD20, CD22, CD30, CD33, CD40, CD44, CD52, CD74, CD152, mucin 1 (MUC1), a tumor necrosis factor receptor, an insulin-like growth factor receptor, folate receptor α, transmembrane glycoprotein NMB, a C—C chemokine receptor, prostate specific membrane antigen (PSMA), recepteur d'origine nantais (RON) receptor, and cytotoxic T-lymphocyte antigen 4.

BRIEF DESCRIPTION OF THE DRAWINGS

(FIG. 9A) Cytotoxicity was assayed by LDH release and is presented as percent toxicity and normalized to untreated controls (Mean+SD is presented, * $p<0.05$). (FIG. 9B) Viral replication was determined by E1A copy number using qPCR and presented as copies per ng total DNA. Experiments were performed twice in triplicates.

(FIG. 10A) U373MG CD133+ cells were injected s.c. in the right hind leg for tumor formation. After 12 days, when the tumor reached 100 mm$^3$, mice were randomly divided in three groups: mock, AdWT or CRAd-S-pk7 treatment and were injected with respective virus at 100 vp/cell or PBS for mock. Twenty four hours later, each group was further divided in two: one group received single dose of radiation of 2Gy, the other group was the non-irradiated control. Tumor volumes were measured daily for 6 days with the volumes on the day of irradiation taken at 100%. (FIG. 10B) Viral replication as measured by E1A qPCR from day 2 post-radiation mice from each group. *$p<0.05$ (FIG. 11A) Five consecutive injections of TMZ at 70 mg/kg/day (▼) achieve 100% survival for 80 days post U87MG implantation, whereas 5 TMZ injections at 10 mg/kg/day (○) had significant increase in survival compared to mock treatment ( ) ($p<0.05$). (FIG. 11B) Single intracranial injection of CRAd-Spk7 at 5×109 vp/mouse (Δ) achieves significant increase in survival compared to mice that received two (○) or one (▼) injection of CRAd-S-pk7 at dose of 3×109 vp/mouse or mock control ( ) ($p<0.05$) (FIG. 11C) Five consecutive injections of TMZ at 10 mg/kg/day followed by two CRAd-S-pk7 treatments each at 3×109 vp/mouse (Δ) demonstrated significant additive effect on mice survival compared to mock (■) ($p<0.02$), double injections of CRAd-S-pk7 each at 3×109 vp/mouse (Δ) ($p<0.02$) or 5 consecutive injections of TMZ at 10 mg/kg/day (▼) ($p<0.02$).

(FIG. 15a) bright phase image of mouse brain; (FIG. 15b) grayscale rendering; (FIG. 15c) live NSC-mCherry cells visualized using the Cy3 channel (red band-pass filter); (FIG. 15d) U87MG-GFP cells are visualized using a GFP channel (green band-pass filter); (FIG. 15e) overlay of Cy3 and GFP channels; (FIG. 15f) overlay of grayscale, GFP and Cy3 captured images.

(FIG. 16A) The ability of NSC to deliver the two oncolytic adenoviruses, CRAd-CXCR4-5/3 and CRAd-S-pk7, to U87MG cells was assessed using the same migration plate and assay methods used in FIG. 5A. NSCs were incubated with each vector for 1 hour at a viral titer of 100 vp/cell. After loading of NSCs, cells were lifted and plated in multi-well migration inserts ($10^5$ NSC/well) above U87MG cells, which had been plated two days prior to NSC plating. Twenty-four hours after plating of loaded or non-loaded NSCs, the number of migrating cells was quantified. Bar graph represents the average number of migrating cells counted per random 10× field view.

FIGS. 19A, 19B, 19C and 19D illustrate MRI Visualization of FE-Pro-labeled NSCs targeting human glioma in an orthotopic mouse model according to one embodiment. (FIG. 19A) Consecutive T2-weighted MR images of mouse brain in 30% sucrose and 4% PFA. FE-Pro-labeled NSCs are shown as hypo intense (dark) signals (dotted boxes) in the left hemisphere and in the contralateral right hemisphere, where human U251 glioma cells were implanted. (FIG. 19B) Higher magnification, Prussian blue stained sections from the areas outlined by the boxes in (A) (top, left hemisphere; bottom, right hemisphere). (FIG. 19C) Consecutive T2-weighted MRI images of mouse brain in Fomblin that received PBS sham injection on left hemisphere and human glioma U251 on the right hemisphere. No low-intensity signals (dotted boxes) were detected in this control. (FIG. 19D) Higher magnification, Prussian blue stained sections from the areas outlined by the boxes in (C) (top, left hemisphere; bottom, right hemisphere). MRI conditions: 7.0 Tesla, Rapid Acquisition Relaxation Enhancement sequence, 78 μm/pixel, 300 μm/slice, TR/TE=1500/23.1 ms. Scale bars=100 μm (B and D)

FIGS. 20A, 20B and 20C show the sensitivity of MRI monitoring of FE-Pro-labeled NSCs targeting human glioma according to one embodiment. (FIG. 20A) T2-weighted MR image of mouse brain in Fomblin, showing two distinct signal voids generated by FE-Pro-labeled NSCs that were injected ~200 μm apart from each other on the left hemisphere and a hypointense signal generated by FE-Pro-labeled NSCs that migrated to the contralateral tumor site (dotted boxes). Approximately 600 FE-Pro-labeled NSCs constituted a detectable signal void. (FIG. 20B and FIG. 20C) Prussian blue stained section from the region shown in (FIG. 20A). Higher magnification images (FIG. 20B) of the regions outlined in (FIG. 20C), showing PB positive labeled NSCs corresponding to the hypointense signal sites in (FIG. 20A). MRI conditions: 7.0 Tesla, Rapid Acquisition Relaxation Enhancement sequence, 78 μm/pixel, 300 μm/slice, TR/TE=1500/23.1 ms. Scale bars=200 μm (B), 500 μm (C).

(FIG. 21a) HB1.F3-CD cells were stained for surface antigens, known to participate in adenovirus anchorage. Numbers in the top right corner of each dot plot represent percentages of positive cells. Gates were drawn based on an isotype control stained sample. y-Axis, SSC-A; x-axis, AlexaFluor647-A. (FIG. 21b) Cytopathic effects of CRAd-S-pk7 on HB1.F3-CD cells. Cells were infected with different concentrations of CRAd-S-pk7 (1, 10, 50 and 100 i.u.) and viability was evaluated by MTT viability assay at day 5 post-infection. (FIGS. 21c-21d) The replicative capacity of CRAd-S-pk7 was measured by quantitative RT-PCR and presented as number of viral E1A copies per ng of DNA from the infected cells. The extent of viral replication was determined at day 3 post-infection (FIG. 21c) with different concentrations of CRAd-S-pk7 and at the indicated time points after infection (FIG. 21d) with 50 i.u. of CRAd-S-pk7. To determine the best loading conditions for NSCs the carrier cells in adherent vs. suspension conditions were infected at different time intervals. Transduction efficiency was determined via flow cytometry (FIG. 21e) for adenovirus hexon protein. Instead, the adenovirus replication was quantified via quantitative RT-PCR (FIG. 21f). All conditions were conducted in triplicates and repeated in three separate experiments (error bars represent standard error of measurement (SEM); *, P-value<0.001; , P value<0.01; *, P-value<0.05; NS, not significant).

(FIG. 22a) The supernatant and cells, infected with 50 i.u./cell of CRAd-S-pk7, were collected and analyzed separately. The viral progeny inside the cells (cell associated) and the progeny released by the infected cells (released virus) over time were measured by the titer assay. The supernatant of HB1.F3-CD cells infected with different concentrations of CRAd-S-pk7 (0, 1, 10, 50 and 100 i.u./cell) was collected 5 days post-infection and used to infect different glioma cell lines (U87, U251, U118 and N10) and a lung adenocarcinoma cell line (A549). Viability was assessed 3 days later via crystal violet staining (FIG. 22b) and MTT viability assay (FIG. 22c). Error bars represent SEM; *, P-value<0.05.

(FIG. 23a) 9-10 week old nude mice were injected in the right hemisphere, 3 mm deep, with $5 \times 10^5$ HB1.F3-CD-GFP cells loaded or not with 50 i.u. of CRAd-S-pk7. Intracranial distribution of GFP positive cells was evaluated at the indicated time points for both loaded and non-loaded cells (n=3 per time point per group). (FIG. 23b) Positive GFP cells were quantified based on number of cells per high power field (HPF) (630×). Values on the y axis represent the mean number of GFP positive cells per HPF for each animal. Bars: 400 μm (H&E); 100 μm (IHC). NS, not significant; ND, none detected.

(FIG. 24a) 7 week old nude mice were injected in the right hemisphere, 3 mm deep, with $2 \times 10^5$ U87 malignant glioma cells. Three weeks later, $5 \times 10^5$ HB1.F3-CD-GFP cells loaded or not with 50 i.u CRAd-S-pk7 were injected in the right hemisphere using the same burr hole. Intracranial distribution of GFP positive cells was evaluated at the indicated time points for both loaded and non-loaded cells (n=3 per time point per group). (FIG. 24b) A representative distribution of the carrier cells at day 5 post-injection. GFP positive cells are found at the glioma-brain interface (depicted in the left column); while no GFP cells were detected elsewhere in the brain (the middle and right column). (FIG. 24c) Positive GFP cells in the glioma-brain interface were quantified based on number of cells per high power field (HPF) (630×). Values in y axis represent the mean number of GFP positive cells per HPF for each animal. Bars: 400 μm (H&E); 100 μm (IHC). NS, not significant; ND, none detected.

(FIG. 25a) Nude mice harboring orthotopic U87 malignant glioma in the right hemisphere were injected with HB1.F3-CDGF cells loaded or not with CRAd-S-pk7, using the same burr-hole. In vivo CRAd-Spk7 hand-out from infected GFP-labeled HB1.F3-CD to U87 glioma cells was detected via immunohistochemistry. A representative area within the tumor where hand out of CRAd-S-pk7 is evident (*) was magnified and shown in the right panel. Cells that are positive for both GFP and hexon (arrowheads) represent infected HB1.F3-CD that are releasing adenovirus; while hexon-positive, GFP-negative, DAPI positive (arrow) represent glioma cells infected with adenovirus. To show that loaded NSCs can travel longer distances and still successfully deliver adenovirus, CRAd-S-pk7 loaded HB1.F3-CD.Fluc was injected in the contralateral hemisphere (FIG. 25b). Migration of NSCs was visualized via photon flux imaging at 72 hour (FIG. 25c). (FIG. 25d) To show that migrating NSCs were still replicating and releasing adenovirus animals were sacrificed at 72 hours post NSC injection; tumor containing sections were stained with antibodies for adenovirus hexon (i) and human CD44 (ii) to show human glioma cells. Tu, tumor Bars: 100 μm.

(FIG. 27a) Animals were injected intracranially (right hemisphere) with HB1.F3-CD cells loaded with CRAd-S-pk7 and sacrificed at the indicated time points (n=6 per time point). Brains and other organs were harvested and adenovirus biodistribution was evaluated using qRT-PCR for E1A. HB1.F3-CD intracranial distribution in hamster (FIG. 27b) and cotton rat (FIG. 27c) was evaluated by using a highly sensitive two-step nested PCR for v-myc. Presence of NSCs in each hemisphere was analyzed separately: right (R) vs. left (L). For DNA loading control, in the nested PCR, a housekeeping gene (GAPDH) was used. (FIG. 27d) Intracranial distribution of the HB1.F3-CD carrier cells loaded or not with CRAd-S-pk7 after injection in hamster brains. Animals were injected intracranially (right hemisphere) with HB1.F3-CD cells loaded or not with CRAd-S-pk7 and sacrificed at the indicated time points (n=3 per time point). Bars: 400 μm (H&E); 100 μm (IHC). ND, none detected (FIG. 28A) Relative gene expression of a panel of stem cell and differentiation marker mRNA was tested with qRT-PCR in neural stem cell-base cell carrier. (FIG. 28B) To compare the differentiation status of both NSC lines, ReNcells and HB1.F3.CD cells were plated for 3 days and stained with antibodies against the stem cell markers Nestin, Sox-2, and Oct4 as well as the astrocytic lineage marker, GFAP. Mean fluorescence intensity of the representative FACS plots. Bars represent means from three independent experiments, error bars refer to 95% confidence intervals. (FIG. 28C) Representative FACS plots shown the expression profile of differentiated markers.

(FIG. 29A) The receptors for adenoviral entry into NSCs were evaluated by FACS. Representative FACS plots of the adenoviral entry receptors expressed on ReNcells and HB1.F3.CD cells as quantified. $10^5$ HB1.F3.CD and ReNcells were plated and after 48 hours cells were stained with antibodies against human adenoviral entry receptors expressed on the surface of HB1.F3.CD and ReNcells. (FIG. 29B) FACS analysis from three independent experiments was added and represented in the bar graph. ReNcells expressed higher levels of CAR, $\alpha_v\beta_3$, and syndecan-1 compared with HB1.F3.CD cells using student's t test (P<0.001). The entry receptor $\alpha_v\beta_5$ and perlecan was expressed at comparable levels. Bars represent means from three independent experiments, error bars refer to 95% confidence intervals. (FIG. 29C) qRT-PCR was used to validate the expression of adenoviral entry receptor and HSPG protein expression on ReNcells and HB1.F3.CD cells. Analysis revealed that both NSC cell lines expressed CD44 and Glypican-1 at comparable levels, while ReNcells expressed Syndecan-2 and HB1.F3.CD cells expressed Syndecan-1.

(FIG. 30A) Relative gene expression of survivin mRNA of ReNcells and HB1.F3.CD cells as well as various glioma cell lines was tested with qRT-PCR after 3 days of incubation. Bars represent means from three independent experiments, error bars refer to 95% confidence intervals. (FIG. 30B) CRAd-S-pk7 replication kinetics in NSCs was assessed by measuring relative mRNA expression with quantitative real-time PCR (qRT-PCR). Cells were infected with 50 infectious units (I.U.)/cell. At 4 d.p.i adenovirus E1A, E1B, pTp, and fiber transcripts were expressed at higher levels in HB1.F3.CD cells compared with ReN cells, with the statistical significance observed for E1B using student's t test with welch's correction (P=0.16). Dots represent means from three independent experiments, error bars refer to 95% confidence intervals. (FIG. 30C) Viral permissiveness of HB1.F3.CD and ReNcells at different infectious units (0.1-100 I.U./cell). Total viral progeny was measured at 3 d.p.i. by using Adeno-X Rapid Titer Kit (Clontech, Mountain View, Calif.) according to the manufacturer's protocol. HB1.F3.CD cells expressed significantly higher viral progeny than ReNcells, compared using student's t test. Bars represent means from six independent experiments, error bars refer to 95% confidence intervals. (FIG. 30D) To assess viral permissiveness over time (2-5 d.p.i). HB1.F3.CD and ReN cells were plated and infected with CRAd-S-pk7 at an infectious dose of 50 I.U./cell. D-I. Cell associated viral titer (intracellular virus titer) was analyzed with a titer assay. HB1.F3.CD cells showed significantly higher titer levels at 2, 4, and 5 d.p.i., compared to ReN cells using student's t test. Bars represent means from five independent experiments, error bars refer to 95% confidence intervals. D-II. Cell free virus titer was significantly higher at 2, 3, 4 and 5 d.p.i. compared to ReNcells using student's t. Bars represent means from five independent experiments, error bars refer to 95% confidence intervals. (FIG. 30E) NSC migration in response to different glioma cell lines was evaluated by a transwell migration chamber assay, and quantified. U87 and U373 cells significantly stimulated HB1.F3.CD migration over ReNcells, while U118 cells stimulated more ReNcells migration. Comparison between groups was performed using student's t test. Bars represent means from three independent experiments, error bars refer to 95% confidence intervals. * P<0.05, P<0.01, *P<0.001. Data shown are Mean±SEM.

(FIG. 32A) HB1.F3.CD cells were transfected with a liposome-based method with 0, 2, 4, or 6 ug of MPIOs. FACS analysis was performed in order to test the effectiveness of MPIO-Flash Red transfection. Minimal loss of fluorescents was detected up to 5 days. (FIG. 32B) Trypan blue exclusion was used to detect the toxicity of MPIO transfection to the HB1.F3.CD carrier cell. At 17 MPIOs/cell NSCs there was significant viability differences compared with non-transfected HB1.F3.CD cells, compared by student's t test. Bars represent means from four independent experiments, error bars refer to 95% confidence intervals. (FIG. 32C) The differentiation status of HB1.F3.CD cells was tested 4 days post transfection with varying concentration of MPIOs. mRNA levels were measured by qRT-PCR and their relative mRNA expression is expressed compared with non-transfected HB1.F3.CD cells.

(FIG. 33A) A transwell chamber assay was used to measure the viral progeny released from NSCs, and subsequently capable of infecting glioma cells. HB1.F3.CD and ReNcell (ReN) cells were infected with 50 I.U./cell of CRAd-S-pk7 in the upper chambers of the transwell assay in the following ratio to glioma cells (1:2, 1:10, 1:50, 1:100). Glioma cells were placed on the bottom chambers of the transwell assay and cells were harvested and infectivity was measured by quantitative RT-PCR for the viral E1A gene. Bars represent means from three independent experiments, error bars refer to 95% confidence intervals. Student's t test was used. (FIG. 33B) Cytotoxicity by trypan blue exclusion 96 hours post co-culture. Bars represent means from five independent experiments, error bars refer to 95% confidence intervals. Student's t test was used. *P<0.05, **P<0.01. (FIG. 33C) CRAd-S-pk7 virus loaded NSCs inhibit xenograft growth and prolong survival of mice with orthotopic glioblastoma. $2.5 \times 10^5$ U87MG cells were injected stereotactically into the right hemisphere of the brains of athymic nude mice (n=8/group). Three days post glioma establishment, both NSC lines were infected with 50 I.U./cell of CRAd-S-pk7. Separate groups of mice received an injection of either $5 \times 10^5$ HB1.F3.CD or ReN cells loaded with CRAd-S-pk7 in a volume of 2.5 µL/mouse, 2-3 mm away from the original tumor site. Two additional groups of mice received either $2.5 \times 10^7$ I.U. of CRAd-S-pk7 alone or PBS in an identical volume and location in the brain. Survival curves were obtained by the Kaplan-Meier method and overall survival time was compared between groups using log-rank test.

FIGS. 34A, 34B, 34C and 34D show the efficacy of HB1.F3.CD NSCs as a cell carrier for CRAd-S-pk7 virus in human-derived glioma xenografts according to one embodiment. (FIG. 34A) To demonstrate a major difference between glioma cells maintained in culture versus in vivo, in vitro cultured or in vivo cultured GBM43 cells were harvested at 2 weeks and stained for CD133 and CD15 (markers of glioma stem cells) and analyzed by FACS. (FIG. 34B) To test the HB1.F3.CD cell line as a cell carrier for adenovirus against the GBM43FL glioma xenograft, $5 \times 10^4$ cells were implanted in the right hemisphere of nude mice. Three days after implantation, animals received intratumoral therapy of either $5 \times 10^5$ HB1.F3.CD cells infected with 50 I.U./cell of CRAd-S-pk7, CRAd-S-pk7 alone (2.5×10$^7$ I.U.), HB1.F3.CD cells alone, or PBS. Animals were monitored for tumor volume by bioluminescence imaging at 14 days post-therapy. (FIG. 34C) Overall survival of mice bearing GBM43 human glioma xenografts (n=7/group). Survival curves were obtained by the Kaplan-Meier method and overall survival time was compared between groups using log-rank test. (FIG. 34D) The same injection strategy was used for mice bearing GBM12 human glioma xenografts (n=10/group). NSCs significantly increased the efficacy of CRAd-S-pk7 in both GBM43 and GBM12 models, as shown by the survival increase between the CRAd-S-pk7 group and the CRAd-S-pk7 loaded HB1.F3.CD group (P=0.02 for both GBM43 and GBM12 models).

(FIG. 35A) GBM43FL glioma cells were cultured and exposed to a total of 10 Gy radiation (XRT) treatment (5 days×2 Gy), temozolomide (50 µM), or cocultured with HB1.F3.CD-GFP$^+$ cells loaded with the oncolytic virus (OV) CRAd-S-pk7 (50 I.U./cell). Following 72 hours of incubation, cells were collected and stained for glioma stem cell markers CD133 and CD15 and subjected to FACS analysis. Representative FACS plots show the percentage of CD15$^+$, CD133$^+$, or CD15$^+$CD133$^+$GBM43FL cells. (FIG. 35B) The % positive populations of GSCs in the three treatment groups. The OV loaded NSC treatment group significantly reduced all three populations of GSCs compared to the XRT or TMZ treatment groups (P<0.001), compared using student's t test. Bars represent means from three independent experiments, error bars refer to 95% confidence intervals. (FIG. 35C) The OV-loaded HB1.F3.CD therapy was tested in vivo. GBM43FL cells were FACS sorted and 5×10$^3$ CD133$^+$ cells were intracranially implanted in the brains of nude mice (n=7/group). Three days post tumor implantation animals were treated either with PBS, 5×10$^5$ HB1.F3.CD cells, 5×10$^5$ HB1.F3.CD cells loaded with 50 I.U./cell of CRAd-S-pk7, or 2.5×10$^7$ I.U. of CRAd-S-pk7 intratumorally. Survival curves were obtained by the Kaplan-Meier method and overall survival time was compared between groups using the log-rank test.

(FIG. 36A) Serial axial T1 weighted images of a mouse brain 3 days post implantation without tumor (top panel) and with tumor (bottom panel). Arrowheads point to the area of hypointense signal extending from the site of NSC injection towards the tumor graft. (FIG. 36B) Serial coronal T1 weighted images show an alternative view of OV-loaded NSCs without tumor (top panel) or with tumor (bottom panel). (FIG. 36C) Prussian blue staining of the corresponding animal brains confirmed the presence of iron MPIOs at the (C1) NSC implantation site, (C2) at the tumor border, and (C3) inside the tumor mass.

(FIG. 37A) Hematoxylin and eosin (H & E) staining of the migratory path of NSCs from the (A1) injection site represented by the (*) to the tumor site. Magnified views of the migration path: (A2) Injection site, (A3) center of migration path, (A4) end of migration site or tumor. (FIG. 37B) H&E staining was confirmed by (B1) dapi and (B2) GFP staining. (B3) HB1.F3.CD-GFP$^+$ cells were also positive for human nestin along the migratory path. (B3-2) Corresponds to the slightly elongated shape seen in (A4) along the migratory path where nestin staining is spread out (arrowhead) as opposed to (B3-1) a bunched (arrowhead) shaped which corresponds to (A2) or NSC implantation site. (FIG. 37C) Mice were also sacrificed at 72 hours post NSC implantation. (C2) Shows the borders of the tumor (represented by dotted line) and HB1.F3.CD-GFP$^+$ positive cells inside (C1) human CD44$^+$ tumor foci. (C3) HB1.F3.CD-GFP$^+$ cells that co-localizing with CD44$^+$ cells also stained positive for nestin. (C4) Merge.

(FIG. 38B, 38F, 38J) Early stages of viral replication represented by the positive staining for E1A (white arrow head) inside the tumor border (dotted line). (38C, 38G, 38K) Intermediate stages of viral replication denoted by the co-staining of E1A and hexon. (38D, 38H, 38L) Hexon positive staining represents the late phases of viral infection.

(FIG. 39A) Overall survival of U87MG bearing mice. (FIG. 39B) Overall survival of GBM43FL bearing mice. CRAd-S-pk7 loaded HB1.F3.CD extended the efficacy of OV alone in both U87MG and GBM43FL models (P<0.001, P=0.03 respectively). Survival curves were obtained by the Kaplan-Meier method and overall survival time was compared between groups using the log-rank test.

(FIG. 40A): Surface marker expression of irradiated and chemotherapy-treated NSCs at 24 hours as analyzed by fluorescence-activated cell sorting (FACS). Shown are representative FACS plots (left) and the percentage of positive and mean fluorescent intensity of the surface markers of untreated compared with treated neural stem cells (right). (FIG. 40B): Transcription level of surface receptors associated with NSC migration at 12 and 24 hours after XRT-TMZ treatment. Relative mRNA transcripts were analyzed by quantitative real-time polymerase chain reaction and were compared with untreated NSCs. (FIG. 40C): Functional migration of XRT-TMZ-treated NSCs at 48 hours after treatment. The percentage of distance change was greater for XRT-TMZ-treated NSCs than untreated control NSCs. *, p<0.05; ***, p<0.001. Abbreviations: APC, allophycocyanin; FITC, fluorescein isothiocyanate; MFI, mean fluorescence intensity; NSC, neural stem cell; PE, phosphatidylethanolamine; Rx, radiation therapy-temozolomide therapy; SSC, side scatter; TMZ, temozolomide; uPAR, urokinase plasminogen activator receptor; VEGFR, vascular endothelial growth factor receptor; XRT, radiation therapy.

(FIG. 41A, 41B): Viral replication was evaluated daily up to 96 hours after treatment with 0, 10, 50, or 100 M TMZ (FIG. 41A) and 0, 2, or 4 Gy of XRT (FIG. 41B). (FIG. 41C): CRAd-S-pk7 viral titer levels 96 hours after XRT-TMZ treatment of infected NSCs. Treatment with both XRT and TMZ slightly reduced viral titer levels at high doses of TMZ, but no change was observed when treated with TMZ concentrations closer to physiologically relevant levels. *, p<0.05. Abbreviations: DMSO, dimethyl sulfoxide; IU, infectious units; TMZ, temozolomide; XRT, radiation therapy.

(FIG. 42A): Cytotoxicity of patient-derived GBM43 tumor cells 96 hours after coculture with CRAd-S-pk7-loaded NSCs at the NSC to GBM43 cell ratios of 1:0, 1:2, 1:5, 1:10, or 1:50. Top: Representative light microscope pictures of GBM43 viability. Bottom: Mean luciferase intensity values represented as the percentages of viable glioma cells compared with control. (FIG. 42B): U251 and U87 glioma cell viability measured by 3-(4,5-dimethylthiazol-2-yl)-2,5-diphenyltetrazolium bromide at 96 hours after treatment. The addition of CRAd-S-pk7 (50 infectious units) to conventional XRT-TMZ therapy reduced the percentage of glioma cell viability in both tested cell lines. The IC50 values of TMZ for U251 and U87 cells when treated with XRT-TMZ decreased by 31 and 15 M, respectively, when OV was added. , p<0.01; *, p<0.001. Abbreviations: NSC, neural stem cell; OV, oncolytic virus; TMZ, temozolomide; XRT, radiation therapy.

(FIG. 43A): Survival of animals treated with escalating doses of intraperitoneally administered TMZ (0, 5, 10, or 30 mg/kg). (FIG. 43B): Survival of animals treated with XRT (2 Gy) or a combination of XRT (2 Gy) and TMZ (2.5, 5, 10, or 30 mg/kg). (FIG. 43C): Survival of animals treated with the optimized dose of 2 Gy XRT and 5 mg/kg TMZ in addition to 5×10$^5$ or 3×10$^6$ NSCs loaded with 50 infectious units of CRAd-S-pk7. The addition of 5×10$^5$ or 3×10$^6$ loaded NSCs to XRT-TMZ treatment increased the median survival of glioma-bearing mice by 7 and 11 days, respectively. *, p<0.05; , p<0.01; *, p<0.001. Abbreviations: ND, not determined; ns, no significance; NSC, neural stem cell; TMZ, temozolomide; XRT, radiation therapy.

(FIG. 44A): Cytotoxicity of U251 and U87 glioma cell lines and GBM39 patient-derived cell line treated with Rx-OV or OV-Rx. Left: The percentage of viability of glioma cells measured by 3-(4,5-dimethylthiazol-2-yl)-2,5-diphenyltetrazolium bromide 96 hours after treatment. Right: Representative light microscope pictures of U87 glioma cell viability (magnification, ×10). (FIG. 44B): Percentage of apoptotic GBM43 cells at 48 hours after treatment with Rx-OV or OV-Rx treatment protocols as measured by the expression of active caspase-3-positive tumor cells by FACS (bottom). Top: Representative FACS plots. *, p<0.05; , p<0.01; *, p<0.001. Abbreviations: DMSO, dimethyl sulfoxide; OV-Rx, ionizing radiation-temozolomide therapy 24 hours after oncolytic virus; PE, phycoerythrin; Rx-OV, oncolytic virus 24 hours after ionizing radiation-temozolomide therapy.

(FIG. 45A): Survival of animals treated with both therapeutic scheduling protocols. Intracranial GBM43 (3.5×10$^5$ cells per animal) was established, and the animals received an intratumoral (IT) injection of loaded NSCs (5×10$^5$) on day 5 followed by 5 consecutive days of XRT-TMZ (2 Gy and 5 mg/kg) therapy beginning on day 6 or alternatively XRT-TMZ therapy starting on day 6 for 5 consecutive days followed by an IT injection of loaded NSCs on day 12. A 9-day preferential median survival was observed in mice that received upfront NSC-based oncolytic therapy. (FIG. 45B): Fluorescent microscopy of mouse brain tissue bearing GBM43 xenografts (left). Top: Anti-cleaved caspase-3 (green). Bottom: Overlay; anti-cleaved caspase-3 (green) and anti-4',6-diamidino-2-phenylindole (blue). Magnification, ×20. Scale bar=50 m. For each treatment group, five images were taken using the ↓20 objective, and the number of positive cells was quantified per field of view (right). *, p<0.05; , p<0.01; *, p<0.001. Abbreviations: FOV, field of view; NSC, neural stem cell; OV-Rx, XRT-TMZ therapy 24 hours after oncolytic virus-loaded NSCs; Rx-OV, oncolytic virus-loaded NSCs 24 hours after XRT-TMZ therapy; TMZ, temozolomide; XRT, radiation therapy.

(FIG. 46A): Protein expression of the Mre11-Rad50-NBS1 complex proteins Rad50 (153 kDa) and Mre11 (81 kDa) at 12, 24, 36, and 48 hours after infection with 50 infectious units of CRAd-S-pk7 or ONYX-015. Western blots show that Rad50 and Mre11 protein expression are reduced at both 36 and 48 hours after infection with CRAd-S-pk7 but not ONYX-015. (FIG. 46B): Immunofluorescent staining of radiation induced γH2AX foci under a confocal laser microscope. Top: Anti-γH2AX (green); bottom: Dapi (blue). Magnification, ×63. Scale bar=20 μm. (FIG. 46C): Quantification of γH2AX foci resolution over 72 hours after XRT treatment. The number of γH2AX foci per cell was counted and grouped according to the following range of foci per cell: 0-50 (red arrows), 51-100 (yellow arrows), 101-200 (blue arrows), and 200 (orange arrows). Left: Time effect was determined by ordinal logistic regression analysis. The number of γH2AX foci was significantly resolved over time in XRT-OV-treated cells (p=0.020), whereas there was no significant change in the number of foci over time in OV-XRT-treated cells (p=0.386). Right: Representative overlay images of each range of foci per cell (anti-γH2AX, green, and anti-DAPI, blue). Magnification, ×63. Scale bar=20 μm. Abbreviations: Dapi, 4',6-diamidino-2-phenylindole; OV-XRT, radiation therapy 24 hours after oncolytic virus; XRT-OV, oncolytic virus 24 hours after radiation therapy.

DETAILED DESCRIPTION

Figure 1:
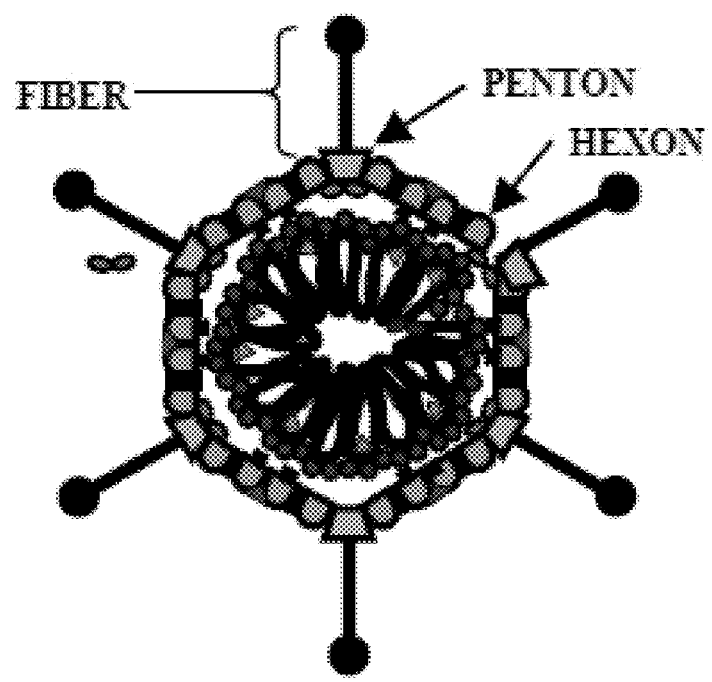
FIG. 1 illustrates generalized Ad vector particles according to one embodiment. Capsid structures shown are the hexon protein which comprises the bulk of the virion, the penton base that contains integrin binding RGD motifs, and the protruding fiber molecule, that binds the primary Ad receptor, CAR.

Methods for killing tumor cells and treating cancer using tropic cells (e.g., stem cells) that carry a modified oncolytic virus are provided herein. Such methods may be used to treat any cancer or tumor cell type including, but not limited to those related to bone cancer, bladder cancer, brain cancer, breast cancer, cancer of the urinary tract, carcinoma, cervical cancer, colon cancer, esophageal cancer, gastric cancer, head and neck cancer, hepatocellular cancer, liver cancer, lung cancer, lymphoma and leukemia, melanoma, ovarian cancer, pancreatic cancer, pituitary cancer, prostate cancer, rectal cancer, renal cancer, sarcoma, testicular cancer, thyroid cancer, and uterine cancer. In addition, the methods may be used to treat tumors that are malignant (e.g., primary or metastatic cancers) or benign (e.g., hyperplasia, cyst, pseudocyst, hematoma, and benign neoplasm).

In some embodiments, the methods described herein may be used to target brain tumor cells, thereby eradicating brain tumors and treating brain cancer. Brain tumors represent a heterogeneous group of central nervous system (CNS) neoplasms. The World Health Organization (WHO) recognizes approximately 100 different types of brain tumors based on pathologic diagnosis. In general, these tumors can be classified into either primary or secondary, depending on whether they originate in the brain or simply spread to the central nervous system. Approximately half of all primary brain tumors are glial cell neoplasms and more than three quarters of all glial tumors are astrocytomas. Astrocytomas differ in their pathologic and clinical behavior; some astrocytomas are classified as low-grade tumors, meaning they are slow growing, while others such as glioblastoma multiforme (GBM), represent the most aggressive type of tumor know to occur within the CNS. The natural history of patients with GBM has intensified research in the area of drug discovery and drug delivery to the CNS. Conventional therapy for glioblastomas consists primarily of surgical debulking followed by radiation therapy. The median survival after surgical intervention alone is six months and the addition of radiation therapy extends the median survival to 9 months (Mohan et al. 1998; Barker et al. 1998). Most recently, temozolomide, an oral chemotherapeutic agent, has been approved the FDA for the treatment of malignant brain tumors. When used in conjunction with adjuvant radiotherapy, temozolomide significantly prolongs survival and up to 26% of patients are alive at two years (Stupp et al. 2005b).

Oncoviral Therapy

The methods described herein may include a step of contacting a tumor cell with a tropic cell that carries a modified oncolytic virus.

Oncolytic adenoviral therapy is a novel modality of anti-cancer treatment. This therapy includes the use of conditionally replicative adenoviruses (CRAds) to kill neoplastic cells (Jiang et al. 2006; Sonabend et al. 2006). The specificity of adenoviral replication is achieved by different strategies such as capsid modifications to bind proteins found on tumor cell membranes (Ulasov et al. 2007c; Tyler et al. 2006; Sebestyen et al. 2007; Wolhfahrt et al. 2007), incorporation of tumor promoter sequences to control the expression of viral genes (Ulasov et al. 2007d; Van Houdt et al. 2006; Ulasov et al. 2007b), and the deletion of viral genomic sequences to limit the replication to cells with particular pathway alterations that are characteristic of cancer cells (Fueyo et al. 2000).

Cancer is a multistage genetic disease that involves alterations in multiple molecular pathways related to growth control and cell death (Hanahan & Weinberg 2000). There are many genes that have been identified in recent years, which could be potential targets for novel cancer therapy. Knowledge of the molecular mechanisms underlying oncogenesis and the development of the viral vector as a vehicle for gene delivery have permitted the formulation of the concept of cancer gene therapy. Strategies for cancer gene therapy adopt ideas and technologies ranging from generating the immune response against tumor antigens to directly attacking tumor cells. However, the therapeutic efficacy of most of the cancer gene therapy approaches is significantly compromised by the inability of the current viral vectors to deliver genes in vivo and target systemic metastasis. To overcome this problem, researchers have used the viruses' ability to spread from their site of infection to the neighboring cells. Infected cells are killed, as they become the factories for producing the new infectious viral particles (VPs). The process of infection is particularly attractive to cancer gene therapy because it not only amplifies therapeutic genes in a tumor-selective manner, but also has the potential to lyse and kill the infected tumor cells.

The use of replicating viruses against cancer is also referred to as virotherapy. The success of this approach depends on the ability to identify and engineer viruses that replicate specifically in tumor cells, but not in the normal cells. These viruses, termed oncolytic viruses, are essentially tumor-specific, self-replicating, lysis-inducing cancer killers. Many oncolytic viruses that belong to several viral families have been identified or engineered. They include herpes simplex viruses, adenovirus, retroviruses paramyxoviruses, and poxviruses (Guo et al. 2008). These viruses can be categorized into four major groups on the basis of their oncolytic restriction: (1) mutation/deletion derived viruses, (2) transcriptionally targeted oncolytic viruses, (3) transductionally targeted oncolytic viruses, and (4) "naturally smart" viruses. Oncolytic viruses for cancer exploit the difference of the molecular makeup between the tumor cells and their normal counterparts; they also utilize recombinant DNA technology to engineer viral vectors to selectively replicate in the tumor cells and destroy them. According to the embodiments described herein, any suitable oncovirus that selectively infects and lyses tumor or cancer cells may be used in accordance with the methods described herein. Oncolytic viruses that may be used in accordance with the methods described herein may include, but are not limited to HSV1, adenovirus, reovirus, vaccinia virus, vesiculostomatitis virus, and poliovirus. In certain embodiments, the oncovirus is an adenovirus.

In some embodiments, the modified oncolytic virus carried by a tropic cell for use in the methods described herein is an adenovirus. The human adenovirus is a non-enveloped icosahedral particle that encapsulates up to a 36-kilobase double-stranded DNA genome (FIG. 1). The Ad capsid is comprised of several minor and three major capsid proteins: hexon is the most abundant structural component and constitutes the bulk of the protein shell; five subunits of penton form the penton base platform at each of the twelve capsid vertices to which the twelve fiber homo-trimers attach. At the distal tip of each linear fiber is a globular knob domain which serves as the major viral attachment site for cellular receptors. Entry of adenovirus into cells involves two distinct steps: attachment to a primary receptor molecule at the cell surface, followed by interaction with molecules responsible for virion internalization.

Initial high-affinity binding of the virion occurs via direct binding of the fiber knob domain to its cognate primary cellular receptor, which is the 46 kD coxsackie and adenovirus receptor (CAR) for most serotypes including Ad2 and Ad5, which are widely used in gene therapy approaches. Following receptor binding, receptor-mediated endocytosis of the virion is affected by interaction of penton base Arg-Gly-Asp (RGD) motifs with cellular integrins including $\alpha v \beta 3$ and $\alpha v \beta 5$ (Wickham et al. 1993), $\alpha v \beta 1$ (Li et al. 2001), $\alpha_3 \beta 1$ and $\alpha_5 \beta 1$ (Davison et al. 1997). Virus enters the cell in clathrin-coated vesicles (Meier et al. 2002) and is transported to endosomes. Subsequent acidification of the endosome results in virion disassembly and release of the virus remains into the cytosol, then to the nucleus where viral replication takes place.

In some embodiments, the oncolytic viruses, such as the adenovirus, may be modified to increase specificity to a target tumor cell. Such modifications to oncolytic viruses include, but are not limited to, (1) transductional targeting, which involves modifying one or more viral coat or capsid proteins to increase viral entry into a target cell and (2) non-transductional targeting, which involves modifying the viral genome so that it only replicates in cancer cells. Examples of non-transductional targeting include transcriptional targeting by replacing all or part of the wild-type viral promoter with a tumor-selective promoter element; and attenuation, which involves introducing deletions into the viral genome that eliminate functions that are important for replication in normal cells but not tumor cells.

In some embodiments, modified adenoviruses that are used in the methods described herein may include a tumor selective promoter element. The tumor selective promoter element may include a survivin promoter, a cyclooxygenase-2 (COX-2) promoter, prostate specific antigen (PSA) promoter, a CXCR4 promoter, a STAT3 promoter, or any other suitable promoter that lends to tumor specificity.

In other embodiments, modified adenoviruses that are used in the methods described herein may alternatively or additionally include a tumor specific cell surface molecule for transductionally targeting a tumor cell. In such an embodiment, a viral coat or capsid protein (e.g., fiber, hexon or penton) is modified so that it targets and infects a tumor cell by binding a tumor-specific cell surface molecule.

Tumor-specific molecules that may be targeted by the modified capsid or envelope protein may include any membrane protein or biomarker that is expressed or overexpressed in tumor cells including, but not limited to, integrins (e.g., integrin $\alpha v \beta 3$, $\alpha 5 \beta 1$), EGF Receptor Family (e.g., EGFR2, Erbb2/HER2/neu, Erbb3, Erbb4), proteoglycans (e.g., heparan sulfate proteoglycans), disialogangliosides (e.g., GD2, GD3), B7-H3 (aka CD276), cancer antigen 125 (CA-125), epithelial cell adhesion molecule (EpCAM), vascular endothelial growth factor receptors 1 and 2 (VEGFR-1, VEGFR-2), CD52, carcinoembryonic antigen (CEA), tumor associated glycoproteins (e.g., TAG-72), cluster of differentiation 19 (CD19), CD20, CD22, CD30, CD33, CD40, CD44, CD74, CD152, mucin 1 (MUC1), tumor necrosis factor receptors (e.g., TRAIL-R2), insulin-like growth factor receptors, folate receptor $\alpha$, transmembrane glycoprotein NMB (GPNMB), C—C chemokine receptors (e.g., CCR4), prostate specific membrane antigen (PSMA), recepteur d'origine nantais (RON) receptor, cytotoxic T-lymphocyte antigen 4 (CTLA4), and other tumor specific receptors or antigens.

Conditionally Replicative Adenoviruses (CRAds)

Figure 2:
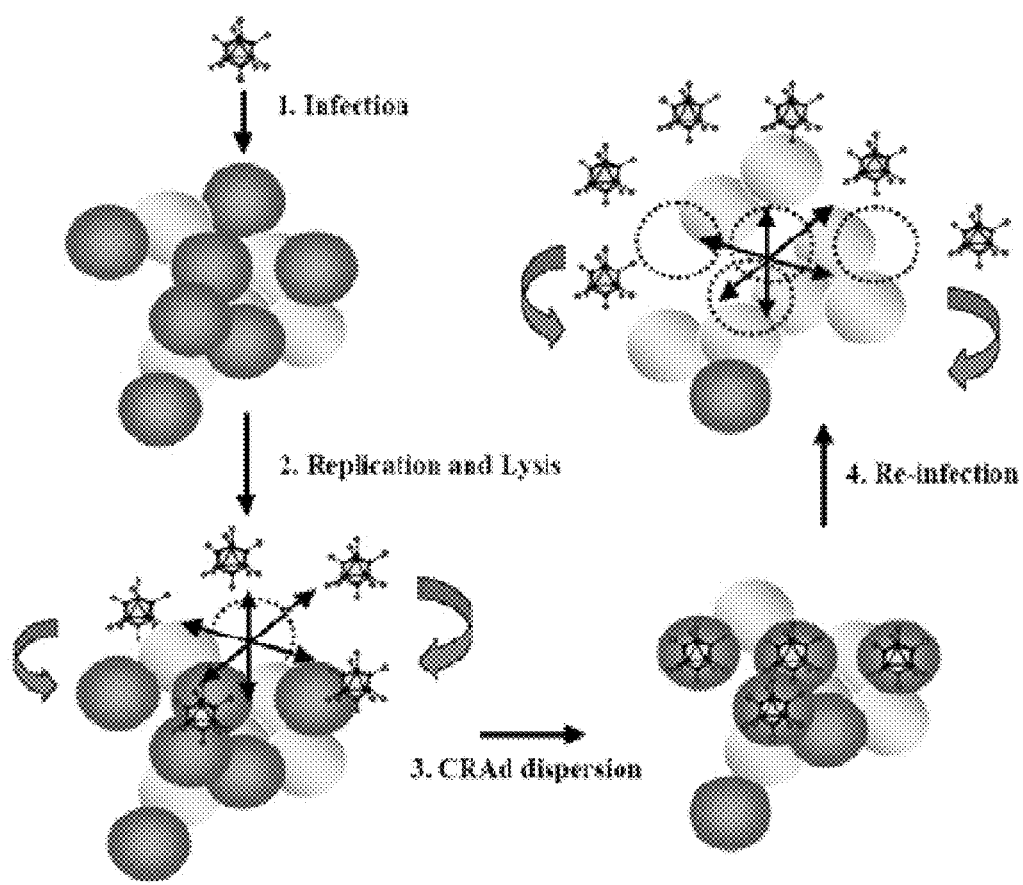
FIG. 2 illustrates conditionally replicative virus-based therapy according to one embodiment. In conventional non-replicative vector based-gene therapy, the vector enters the target cell and expresses the effector gene to kill the tumor cells. In replicative virus-based therapy, the CRAd infects the target cell type (1, dark cell). The CRAd then replicates in the infected target cell and kills the cell by cytolysis as a consequence of lytic infection (2). Then, the released virus disperses and infects surrounding target cells (3). Target cells are then infected and the cycle begins again (4).

In certain embodiments, the modified oncolytic virus that may be used in accordance with the methods described herein are modified adenoviruses. For example a modified adenovirus may be a conditionally replicative adenovirus (CRAd). CRAd vectors are engineered to selectively replicate within and kill tumor cells through the use of tumor-selective promoter elements that transcriptionally restrict expression of genes responsible for CRAd replication. On this basis, initial tumor cell transduction is not the terminal event, and post-transductional amplification occurs through lateral infection in a multiplicative fashion. According to some embodiments, CRAds are rendered replication incompetent via deletion of the essential DA gene, thus requiring near-quantitative tumor transduction for antitumor efficacy, making these vectors powerful anti-tumor agents (FIG. 2).

In cancer gene therapy, CRAd replicative specificity is based on tumor-specific transcriptional control of the essential early genes required for replication. For CRAds, the adenovirus genome is genetically modified to include a heterologous promoter region with the required tumor-specific expression profile. The ideal tumor specific promoter element would exhibit the widest differential between "tumor on/normal brain off" expression profiles, which is important to ablation of unwanted replication and possible toxicity from ectopically localized CRAds. However, few glioma relevant promoter elements have been identified and well characterized for their use in CRAds.

As an adenovirus-based cancer gene therapy approach, CRAd efficacy is dependent on vector-mediated tumor transduction. Of note, human trials carried out to date have demonstrated relatively inefficient gene transfer to tumor achieved by Ad vectors employed in in vivo delivery schemas. This is likely due to a relative paucity of the primary adenovirus receptor (CAR) on tumor cells. Indeed, a relative paucity of CAR has been shown to limit Ad vector efficacy in a number of tumor contexts, possibly representing a barrier to realizing the full benefit of CRAds for cancer gene therapy applications. Therefore, in some embodiments, cellular transduction via CAR-independent pathways by modifying an adenovirus capsid protein to target a tumor-specific cell surface molecule.

In certain embodiments, CRAds that may be used in accordance with the methods described herein include i) a fiber modification containing a polylysine binding motif that binds with high affinity to heparan sulfate proteoglycans and ii) E1A transcription under the control of survivin promoter (referenced herein as "CRAd-Survivin-pk7" or "CRAd-S-pk7").

CRAd-Survivin-pk7 was generated for the treatment of malignant gliomas. For transcriptional targeting towards gliomas, the survivin promoter was incorporated upstream from viral gene E1A. The rationale for the use of this promoter is that it is highly active in gliomas whereas it remains relatively silent in the surrounding brain parenchyma (Van Houdt et al. 2006; Ulasov et al. 2007b; Chakravarti et al. 2002; Chakravarti et al. 2004; Kajiwara et al. 203; Yamada et al. 2003). To enhance viral transduction into glioma cells, the capsid of this vector was then modified to bind heparan sulfate proteoglycans expressed in these tumors (Ulasov et al. 2007a; Zheng et al. 2007). As evidenced by the studies described below, CRAd-S-pk7 exhibits potent anti-tumoral activity in mice bearing intracranial human glioma xenografts (Ulasov et al. 2007a), including the highly aggressive CD133+ glioma stem cell model (Nandi et al. 2008a). In addition, this CRAd virus elicits a synergistic therapeutic effect when combined with low dose radiation and with the chemotherapeutic agent temozolomide, two therapies that are often used as part of the standard of care for patients with malignant glioma. When used to treat brain cancer, the modifications described above provide CRAd-S-pk7 the necessary tumor specificity allowing for selective replication in glioma cells and minimal toxicity to normal brain tissue (Ulasov et al. 2007a). Furthermore, CRAds have the capacity to kill different subsets of glioma cells similarly without being confined by the resistance that conventional therapies face (Jiang et al. 2007).

Tropic Cells for Delivery of Oncovirus

Several clinical trials using oncolytic viruses have been performed to treat malignant brain tumors (Selznick et al. 2008; Chiocca et al. 2011). Despite some degree of therapeutic efficacy shown in these clinical trials overall, they have fallen short of expectations, as local injection of adenoviral vectors fails to reach scattered infiltrative tumor cells within the brain parenchyma (Chiocca et al. 2004; Ehtesham et al. 2002). The reason behind these shortcoming is largely a result of the distribution limitations involved with local delivery of virolytic agents, for example, i) the limited distribution of viral vectors after intratumoral injection, ii) the immune clearance induced shortly after injection, and iii) the inability of the currently available vectors to target disseminated tumor burdens. Because the therapeutic effect of intracerebral injections of CRAds is only seen in the vicinity of the injection site, a broader vector distribution is necessary to impact all tumor cells.

To overcome these hurdles, tropic cell carriers may be used to improve targeting and distribution while reducing the immune response towards viral vectors. In one embodiment, tropic cells, which possess an intrinsic, programmed, induced, or enhanced tropism for pathologies, may be used as carriers of the oncoviral vectors described above. Each carrier tropic cell/oncolytic virus combination represents a unique biotherapeutic system with different kinetics of therapeutic virus replication and in vivo tumor homing ability. As such, each combination is unique and should be examined extensively.

Tropic cells that may be used to carry a modified oncovirus according to the methods described herein may be any suitable type of cell that exhibits tropism to a tumor or tumor cell. The tropism that the cells exhibit toward the tumor or tumor cell may be intrinsic to the tropic cell, or, in some embodiments, the tropism may be programmed using genetic engineering, induced or enhanced by exposing the cells to exogenous chemical factors, or otherwise manipulating the cells to improve or enhance tropism to the target tumor or tumor cell (Kamarova et al. 2010; Gul et al. 2009). Tropic cell or cells used in accordance with the embodiments described herein may include, but are not limited to, stem cells, progenitor cells, stromal cells, fibroblasts, endothelial cells, pericytes, and immune cells (e.g., T-cells and other lymphocytes; monocytes, macrophages, and other inflammatory cells; and other immune cells). The tropic cells may be in any endogenous physiological state (i.e., wild type, naïve, activated), or may be genetically modified to express one or more factor to enhance tropism. In one embodiment, the tropic cells that may be used to carry a modified oncovirus are stem cells. Stem cells that may be used in accordance with the embodiments described herein, may include any totipotent, pluripotent, or multipotent stem cell including, but are not limited to, embryonic stem cells (ESC), embryonic germ cells (ESG), induced pluripotent stem cells (iPSC), embryonic carcinoma cells (ECC), bone marrow stem cells, adult stem cells, and tissue specific stem cells (e.g., hematopoietic stem cells, neural stem cells or mesenchymal stem cells).

In one embodiment, the stem cells that are used in accordance with the methods described herein are neural stem cells (NSCs). Neural stem cells (NSCs) of the CNS have recently received a great deal of attention because of their therapeutic potential for neurological disorders. NSCs are defined as CNS progenitor cells that have the capacity for self-renewal and multipotent potential to differentiate into three major cells in CNS: neuron, astrocytes, and oligodendrocytes (Conti & Cattaneo 2010). NSCs display intrinsic tumor tropism that can be exploited for targeted anti-cancer drug delivery to invasive and metastatic cancer (Aboody et al. 2000; Benedetti et al. 2000). In theory, the tumor homing property of NSCs offers a significant advantage over other targeted therapies, such as antibody directed drug delivery, due to their ability to detect various cues generated by satellite tumor foci and respond to such cues by extravasating through complex tissue microenvironments and migrating to distant diseased areas (Ahmed & Lesniak 2011). Glioblastoma multiforme (GBM) is the most common and aggressive primary CNS tumor in adults, and is characterized by its propensity to infiltrate throughout the brain and cause relapses in patients due to the existence of an aberrant chemo- and radio-resistant glioma stem cell population (Nicholas et al. 2011). Thus, a true cure for this formidable disease cannot arise from the application of traditional antineoplastic principles; it requires a dynamic agent capable of targeting scattered diseases burden as well as eliminating the tumor initiating cancer stem cells effectively with minimal disruption of the existing delicate neural architecture. (Alonso et al. 2012).

NSCs have been used to deliver cancer toxic agents and transgenes to tumors in the brain. For example, NSCs have been shown to selectively deliver therapeutic genes to intracranial tumor sites including prodrug activating enzymes (cytosine deaminase, carboxylesterase, thymidine kinase), interleukins (IL-2, IL-4, IL-12, IL-23), interferon-β, apoptosis-promoting genes (tumor necrosis factor-related apoptosis-inducing ligand) and metalloproteinases (PEX) (Aboody et al. 2008).

Figure 3:
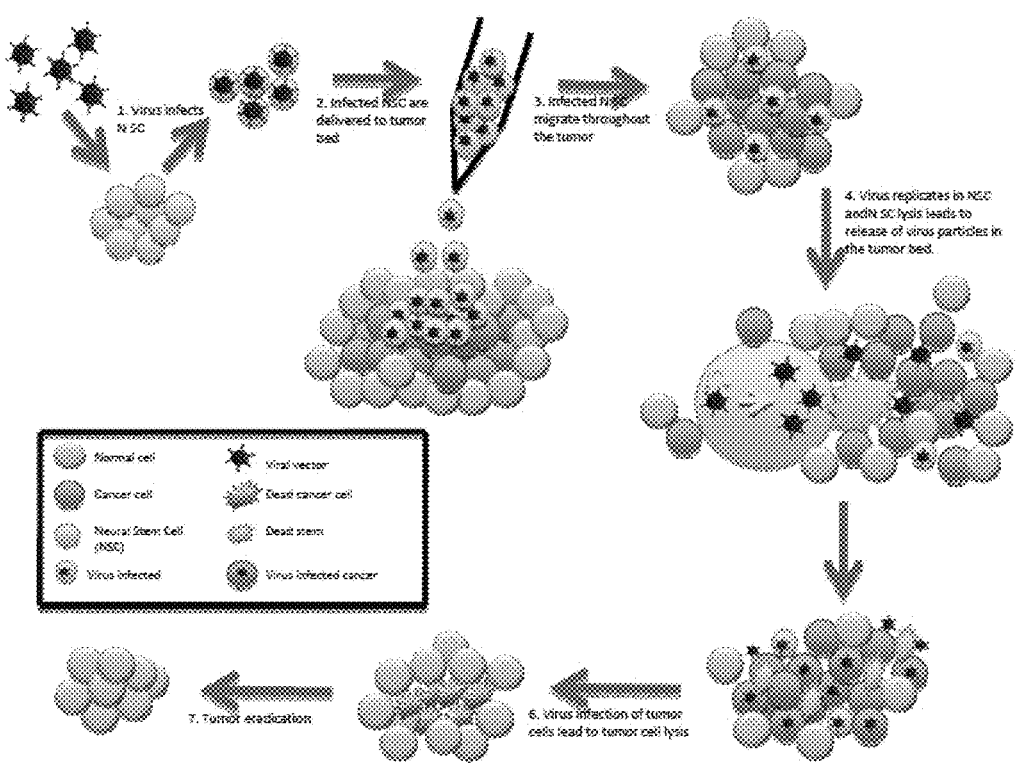
FIG. 3 shows a schematic representation showing CRAd-loaded NSC mechanism of action according to one embodiment. Following infection of NSC with CRAd, the NSCs function as carriers of the oncolytic virus to deliver it throughout the tumor bed, enhancing viral delivery and spread and potentiating the anti-tumor effect.

Given their ability to localize to tumor sites, tropic cell mediated CRAd delivery offers a more specific and thorough therapeutic effect than local delivery of CRAds alone (FIG. 3). One benefit to using a cell-based delivery approach of an adenovirus is that a tropic cell is capable of responding to diverse pathological signals released by tumor tissue (Aboody et al. 2008; Zhang et al. 2004; Shah et al. 2005). Tropic cell specificity and tropism is likely mediated by several cell surface receptors as well as secreted cytokines and growth factors.

Additionally, extracellular matrix proteins have been associated with the tumor-tropism of stem cells (Aboody et al. 2008). While the exact mechanism of their tumor affinity has yet to be fully elucidated, neural stem cells (NSC) are currently being examined as viable vehicles for targeting and delivering CRAds to disseminated tumor cells. The endogeneity of NSC to the CNS renders them a vastly explored vehicle for vector delivery in the brain. NSCs also have the ability to invade tumor foci and track single insidious tumor cells infiltrating into normal tissue away from the primary tumor mass (Aboody et al. 2008). Experiments evaluating the delivery potential of NSC revealed that these cells possess an inherent tropism and unique capacity to target invading glioma stem cells in vitro as well as in vivo (Zhang et al. 2004; Shah et al. 2005; Tyler et al. 2009). In terms of delivering an oncolytic adenovirus, loading NSC cells with CRAds does not significantly compromise their homing abilities (Tyler et al. 2009). NSC permissivity for Ad-vectors is due to the fact that NSC express some Ad-target surface receptors including: $a_v\beta_3$ and $a_v\beta_5$ integrins, adhesion proteins targeted by vectors possessing RGD motifs, CAR, CD46, and syndecan and perlecan, two heparan sulfate proteoglycans that bind to vectors containing a poly-L-lysine (pk7) modification. A luciferase assay analyzing the transduction of NSC with various recombinant Ad vectors revealed that the pk-7 modified vector, AdWT-pk7, showed the greatest transduction capacity followed by the AdWT.

In addition to providing a carrier function, it is also important that NSC allow for adequate CRAd genome amplification to achieve optimal infectivity and sustained tumor toxicity upon reaching distant glioma cells. Tumor specific promoters (TSPs) are important to this process. Qualitative RT-PCR revealed that two tumor specific promoters, survivin and CXCR4, allow for robust transcriptional activity in most glioma cells, while exhibiting modest activity in normal cell lines. As such, CRAd-S-pk7 and CRAd-CXCR4-5/3 were compared to two oncolytic vectors possessing these promoters by evaluating their activity in NSC mediated delivery to gliomas. The results indicate relatively attenuated replicative cytotoxicity in NSC, but sufficient replicative cytotoxicity in U87MG tumor cells. In particular, CRAd-S-pk7 displayed limited toxicity to NSC carrier, superb levels of NSC transduction, potent cytotoxicity to glioma cells, and was delivered to U87MG cells in vitro (Tyler et al. 2009).

When comparing the effectiveness of delivering NSC loaded with CRAd-S-pk7 versus CRAd-S-pk7 alone, results show that vector distribution to distant tumor cells is drastically enhanced when mediated by a stem cell carrier. In addition, an in vivo efficacy study investigating the ability of NSC-loaded-CRAd-S-pk7 to reduce U87MG tumor growth in athymic mice revealed an overall reduction in tumor volume when compared to mice receiving intratumoral injections of CRAd-S-pk7 alone. At the same time, NSC modulate the immune response and effectively decrease the endogenous anti-Ad immunity. As described in the Examples below, adenoviral vector targeted to GBM, when rendered selectively replicative via transcriptional/transductional modification and delivered via NSCs, will demonstrate the superior specificity required for human clinical trials and allow full realization of the potential benefits of a CRAd approach for malignant glioma.

Since one of the major limitations of virotherapy is poor spread following injection, the Examples below illustrate that tropic cells such as neural stem cells (NSC) can more effectively migrate and deliver an oncolytic adenovirus to intracranial glioma than local injection of the virus alone. This form of carrier mediated delivery leads to enhanced viral replication in the tumor and a much more potent anti-tumor response than local injection of the virus alone. Moreover, these studies further suggest that NSC exhibit enhanced migration in response to focal brain irradiation, an important finding given the role of radiotherapy in the management of brain tumor patients. Taken together, these are significant findings, which directly bypass one of the major barriers to effective virotherapy, as NSC pose considerable advantages as vehicles for oncolytic virotherapy for brain tumors.

In some embodiments, the methods of treating cancer described herein may include a step of administering a therapeutically effective amount of a pharmaceutical composition which includes a tropic cell that carries a modified oncolytic virus, such as those described above. In one embodiment, the pharmaceutical composition may include a stem cell that carries a modified oncolytic virus. The tropic cells carrying an oncolytic virus that may be used in accordance with the methods described herein may be administered, by any suitable route of administration, alone or as part of a pharmaceutical composition. A route of administration may refer to any administration pathway known in the art, including but not limited to aerosol, enteral, nasal, ophthalmic, oral, intracranial, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

The term "effective amount" as used herein refers to an amount of a compound that produces a desired effect. For example, a population of cells may be contacted with an effective amount of a compound to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see Remington: The Science and Practice of Pharmacy, 21$^{st}$ Edition, Univ. of Sciences in Philadelphia (USIP), Lippincott Williams & Wilkins, Philadelphia, Pa., 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

In some embodiments, the tropic cells carrying an oncolytic virus described above may be administered in combination with ionizing radiation therapy or radiotherapy ("XRT") used in accordance with the standard of care for glioma, GBM, or any other cancer. In such embodiments, the XRT may be administered by any suitable method and at any suitable dose in accordance with standard practice in oncology. In some embodiments, the tropic cells carrying an oncolytic virus described above may be administered in combination with one or more additional therapeutic or diagnostic agents. "In combination" or "in combination with," as used herein, means in the course of treating the same disease in the same patient using two or more agents, drugs, treatment regimens, treatment modalities or a combination thereof, in any order. This includes simultaneous administration, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration. In one embodiment, the tropic cells carrying an oncolytic virus are delivered prior to the XRT, the one or more additional therapeutic or diagnostic agents, or a combination thereof. For example, as described in Example 9 below, applying oncolytic virus (OV)-loaded NSCs together with XRT and temozolomide (TMZ) can increase the median survival of glioma bearing mice by approximately 46%. The timing and order of therapeutic implementation may impact therapeutic outcome. When OV-loaded NSCs are delivered prior to rather than after XRT and TMZ treatment, the median survival of mice bearing patient-derived GBM43 glioma xenografts is extended by 30%.

Examples of therapeutic agents that may be administered in combination with the oncoviral-loaded tropic cells described above include, but are not limited to therapeutic or diagnostic agents such as chemotherapeutic agents, therapeutic antibodies and fragments thereof, toxins, radioisotopes, enzymes (e.g., enzymes to cleave prodrugs to a cytotoxic agent at the site of the tumor), nucleases, hormones, immunomodulators, antisense oligonucleotides, nucleic acid molecules (e.g., mRNA molecules, cDNA molecules or RNAi molecules such as siRNA or shRNA), chelators, boron compounds, photoactive agents and dyes. The therapeutic agent may also include a metal, metal alloy, intermetallic or core-shell nanoparticle bound to a chelator that acts as a radiosensitizer to render the targeted cells more sensitive to radiation therapy (XRT) as compared to healthy cells.

Chemotherapeutic agents that may be used in accordance with the embodiments described herein are often cytotoxic or cytostatic in nature and may include, but are not limited to, alkylating agents, antimetabolites, anti-tumor antibiotics, topoisomerase inhibitors, mitotic inhibitors hormone therapy, targeted therapeutics and immunotherapeutics. In some embodiments the chemotherapeutic agents that may be used as therapeutic agents in accordance with the embodiments of the disclosure include, but are not limited to, 13-cis-Retinoic Acid, 2-Chlorodeoxyadenosine, 5-Azacitidine, 5-Fluorouracil, 6-Mercaptopurine, 6-Thioguanine, actinomycin-D, adriamycin, aldesleukin, alemtuzumab, alitretinoin, all-transretinoic acid, alpha interferon, altretamine, amethopterin, amifostine, anagrelide, anastrozole, arabinosylcytosine, arsenic trioxide, amsacrine, aminocamptothecin, am inoglutethimide, asparaginase, azacytidine, bacillus calmette-guerin (BCG), bendamustine, bevacizumab, bexarotene, bicalutamide, bortezomib, bleomycin, busulfan, calcium leucovorin, citrovorum factor, capecitabine, canertinib, carboplatin, carmustine, cetuximab, chlorambucil, cisplatin, cladribine, cortisone, cyclophosphamide, cytarabine, darbepoetin alfa, dasatinib, daunomycin, decitabine, denileukin diftitox, dexamethasone, dexasone, dexrazoxane, dactinomycin, daunorubicin, decarbazine, docetaxel, doxorubicin, doxifluridine, eniluracil, epirubicin, epoetin alfa, erlotinib, everolimus, exemestane, estramustine, etoposide, filgrastim, fluoxymesterone, fulvestrant, flavopiridol, floxuridine, fludarabine, fluorouracil, flutamide, gefitinib, gemcitabine, gemtuzumab ozogamicin, goserelin, granulocyte—colony stimulating factor, granulocyte macrophage-colony stimulating factor, hexamethylmelamine, hydrocortisone hydroxyurea, ibritumomab, interferon alpha, interleukin-2, interleukin-11, isotretinoin, ixabepilone, idarubicin, imatinib mesylate, ifosfamide, irinotecan, lapatinib, lenalidomide, letrozole, leucovorin, leuprolide, liposomal Ara-C, lomustine, mechlorethamine, megestrol, melphalan, mercaptopurine, mesna, methotrexate, methylprednisolone, mitomycin C, mitotane, mitoxantrone, nelarabine, nilutamide, octreotide, oprelvekin, oxaliplatin, paclitaxel, pamidronate, pemetrexed, panitumumab, PEG Interferon, pegaspargase, pegfilgrastim, PEG-L-asparaginase, pentostatin, plicamycin, prednisolone, prednisone, procarbazine, raloxifene, rituximab, romiplostim, ralitrexed, sapacitabine, sargramostim, satraplatin, sorafenib, sunitinib, semustine, streptozocin, tamoxifen, tegafur, tegafur-uracil, temsirolimus, temozolomide (TMZ), teniposide, thalidomide, thioguanine, thiotepa, topotecan, toremifene, tositumomab, trastuzumab, tretinoin, trimitrexate, alrubicin, vincristine, vinblastine, vindestine, vinorelbine, vorinostat, or zoledronic acid.

Therapeutic antibodies and functional fragments thereof, that may be used as therapeutic agents in accordance with the embodiments of the disclosure include, but are not limited to, alemtuzumab, bevacizumab, cetuximab, edrecolomab, gemtuzumab, ibritumomab tiuxetan, panitumumab, rituximab, tositumomab, and trastuzumab and other antibodies associated with specific diseases listed herein.

Toxins that may be used as therapeutic agents in accordance with the embodiments of the disclosure include, but are not limited to, ricin, abrin, ribonuclease (RNase), DNase I, Staphylococcal enterotoxin-A, pokeweed antiviral protein, gelonin, diphtheria toxin, *Pseudomonas* exotoxin, and *Pseudomonas* endotoxin.

Radioisotopes that may be used as therapeutic agents in accordance with the embodiments of the disclosure include, but are not limited to, $^{32}$P, $^{89}$Sr, $^{90}$Y, $^{99m}$Tc, $^{99}$Mo, $^{131}$I, $^{153}$Sm, $^{177}$Lu, $^{186}$Re $^{213}$Bi, $^{223}$Ra and $^{225}$Ac.

In some embodiments, the tropic cells carrying an oncolytic virus described above may include a diagnostic agent to enable tracking of the tropic cells. Diagnostic agents that may be used in accordance with such embodiments include, but are not limited to isotopes used in imaging modalities such as magnetic resonance imaging (MRI) (e.g., $^{13}$C, $^{15}$N, $^{19}$F, $^{26}$Fe), positron emission tomography (PET) or PET-CT (e.g., $^{11}$C, $^{13}$N, $^{15}$O, $^{18}$F, $^{82}$Rb, $^{89}$Zr, $^{124}$I), or single-photon emission computed tomography (SPECT) (e.g., $^{64}$Cu, $^{99m}$Tc, $^{123}$I, $^{131}$I, $^{111}$In).

In accordance with some embodiments, the tropic cells carrying an oncolytic virus described above (e.g., NSCs loaded with an oncolytic virus such as CRAd-Survivin-pk7) may be administered in combination with TMZ. In some aspects, the TMZ is administered after administration of the tropic cells carrying the oncolytic virus. In further embodiments, NSCs loaded with an oncolytic virus may be administered in combination with TMZ and XRT in accordance with the standard of care for glioma or GBM. In some aspects, the TMZ and XRT are administered after administration of the tropic cells carrying the oncolytic virus.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

CRAd-Survivin-pk7 Exhibits Selective and Potent Oncolytic Effect in Human Glioma As described in this and other Examples below, transcriptional and transductional control of viral replication enhances the oncolytic effect of a virus against malignant glioma. In previous studies, it has been shown that among the available promoters that are over-expressed in malignant brain tumors, survivin is a suitable candidate for transcriptional control of viral replication (Ulasov et al. 2007b). This finding is further supported by other independent studies which show that survivin expression in gliomas is associated with poor prognosis, increased rates of recurrence, and resistance to chemo- and radiotherapy (Chakravarti et al. 2002; Chakravarti et al. 2004; Kajiwara et al. 203; Yamada et al. 2003). Moreover, comparative studies involving enhancement of viral infectivity via modification of the fiber-knob region of the adenovirus also suggest that a pk7 modified virus, which binds heparan sulfate proteoglycans (HSPG) expressed on the surface of malignant glioma cells, offers superior levels of infectivity as compared to several other modifications, including RGD insertion, knob switching (Ad3) technology, or the use of xenotype fibers (Zheng et al. 2007).

Figure 4:
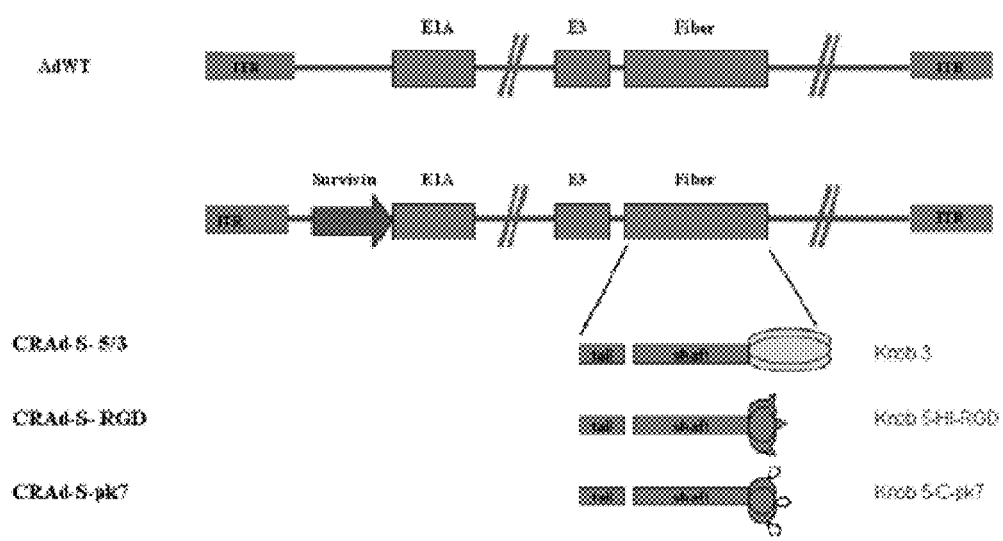
FIG. 4 shows the structure of the conditionally replicative adenoviral vectors according to some embodiments.

To test this in the setting of a novel oncolytic adenovirus, three conditionally replicative adenoviral vectors were constructed (CRAd-Survivin-5/3, CRAd-Survivin-RGD, and CRAd-Survivin-pk7) that bind to CD46, $\alpha_v\beta3/\alpha_v\beta5$, or HSPG, respectively (FIG. 4). The targeting and oncolytic efficiency of the CRAds were examined in vitro and in vivo.

Figure 5:
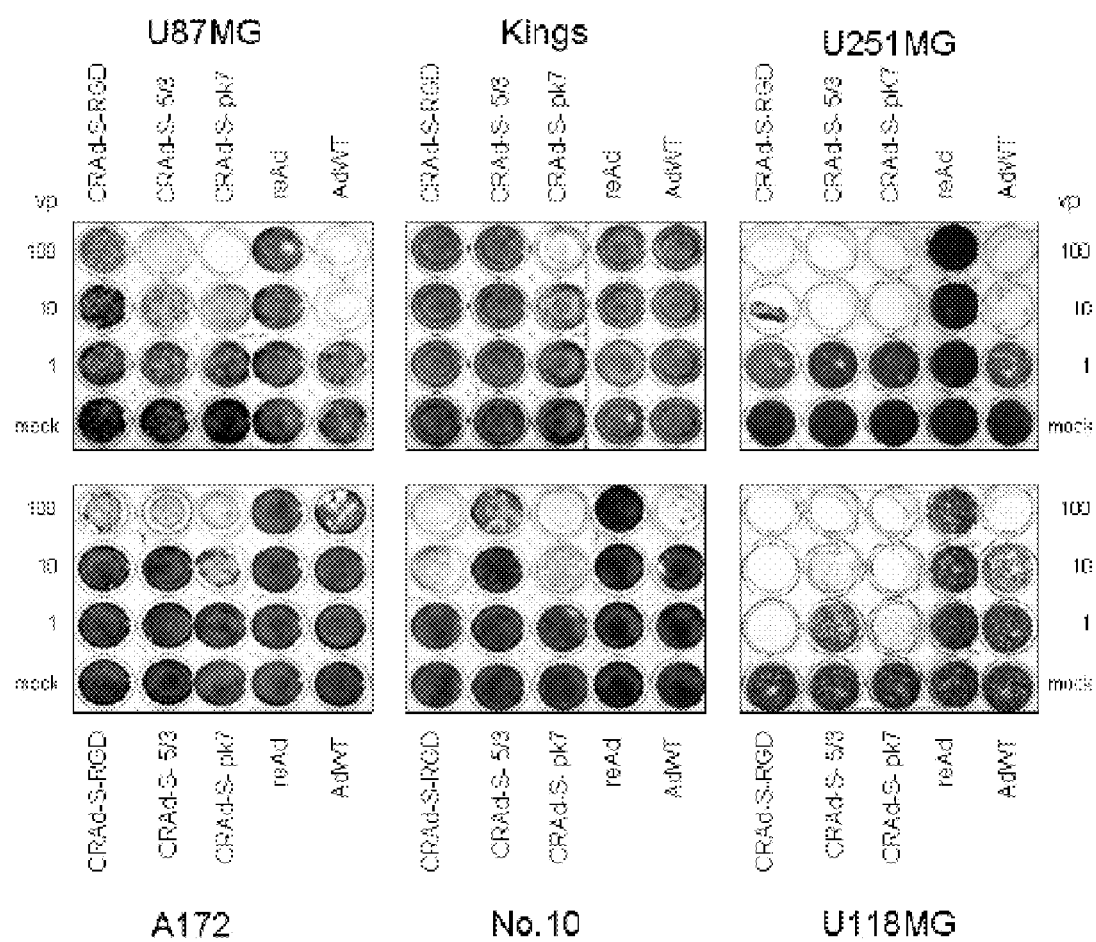
FIG. 5 shows that CRAd-Survivin-pk7 exhibits selective oncolytic potential in human glioma cells according to one embodiment. CRAds at indicated doses were incubated with human glioma cells: U118MG, Kings, No. 10, U87MG, U251MG and A172. Lateral virus spread and oncolytic effect was visualized after staining of adherent cells with crystal violet. Experiments were repeated twice, independently.

First, to assess the oncolytic effect of the CRAds, U87MG, Kings, U251 MG, A172, No. 10, and U118MG glioma cell lines were exposed to CRAd-S-pk7, CRAd-S-5/3, CRAd-S-RGD, AdWT or replication-deficient read virus at 1, 10 and 100 vp/cell. Cytotoxic effect was then assessed via crystal violet staining. Of the tested vectors, CRAd-S-pk7 demonstrated dose-dependent cytolytic effect in all human glioma cell lines (FIG. 5). The virus induced cell killing in doses as low as 1 vp/cell in U118MG and at 10 vp/cell in U87MG and U251MG. Kings, No. 10 and A172 cells displayed lower cytotoxicity levels (~10 fold less) than U118MG. Of note, the oncolytic effect of CRAd-Survivin-pk7 (CRAd-S-pk7) was superior to AdWT in five out of the six tested cell lines. No cytotoxic effect was observed for the control, replication defective-reAd-vector.

Figure 6:
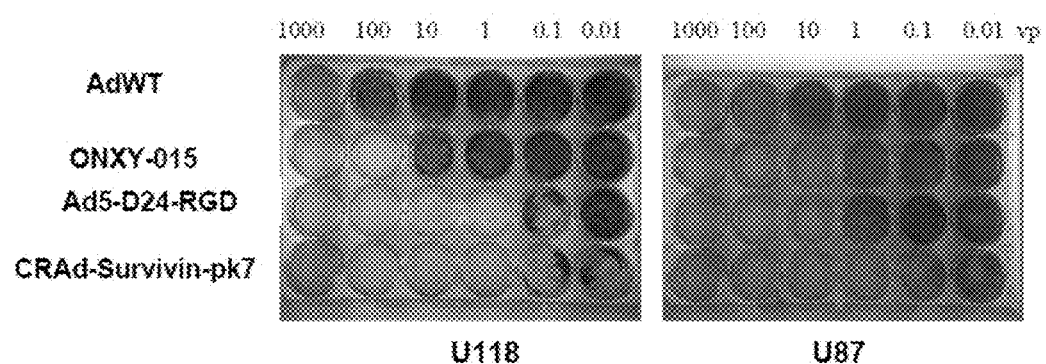
FIG. 6 illustrates the oncolytic effect of CRAds according to one embodiment. Of the tested vectors, CRAd-Survivin-pk7 was successful in killing glioma in both of the representative cell lines tested. These results are representative of two other cells lines and four patient samples.

The oncolytic efficacy of CRAd-Survivin-pk7 and ONYX-015 and Ad5-D24-RGD was compared (FIG. 6). ONYX-015 was previously tested in a phase I study of human glioma and found to be safe but lacking in significant efficacy. Most recently, the FDA has approved Ad5-D24-RGD for phase I/II glioma study to begin in the next few months in select academic centers in the USA.

Figure 7A:
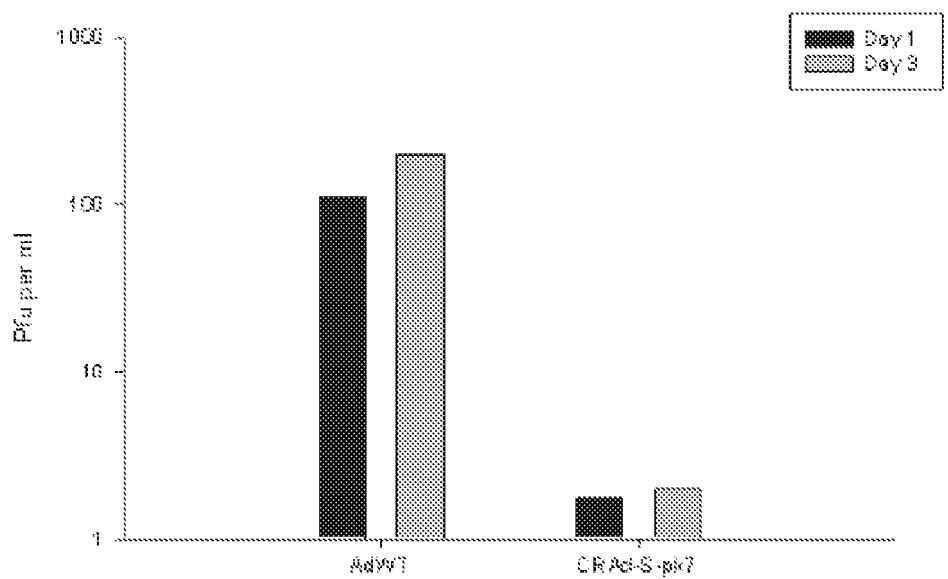
FIGS. 7A and 7B show evaluation of CRAd-mediated toxicity in normal human brain slices according to one embodiment. Human brain tissue slices were infected with 500 vp/cell of Ad vectors. Twenty four or 72 hours post-infection, progeny (FIG. 7A) were isolated from media and tissue slices and titrated in HEK293 cells. Alternatively, LDH (FIG. 7B) release was measured from slice media. Results are presented as pfu per ml (A) and % Toxicity
Figure 7B:
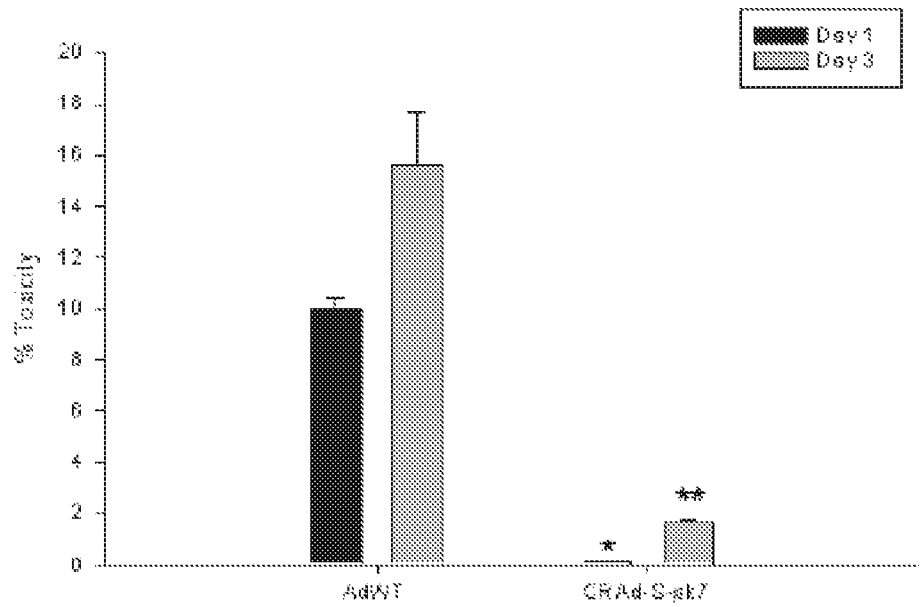

To determine the potential cytotoxicity mediated by CRAd-S-pk7 infection, the activity of the virus in normal human brain was tested. Human brain slices were infected with AdWT, CRAd-S-pk7, or were mock-infected. Replication was measured by titration of progeny released from slices and media at day 1 and 3. As shown in FIG. 7A, CRAd-S-pk7 demonstrated significantly lower replication activity in normal brain tissue on both day 1 (1.77 vs 112.02 for AdWT, $p<0.05$) and day 3 (1.99 vs 199.52 for AdWT, $p<0.01$). To assess virally induced toxicity, the expression of cellular proteins in the media was measured. Consistent with the replication data, CRAd-Spk7 showed significantly less LDH release vs AdWT (1.64+0.11 vs. 15.63+2.082, $p<0.05$) (FIG. 7B).

Figure 8A:
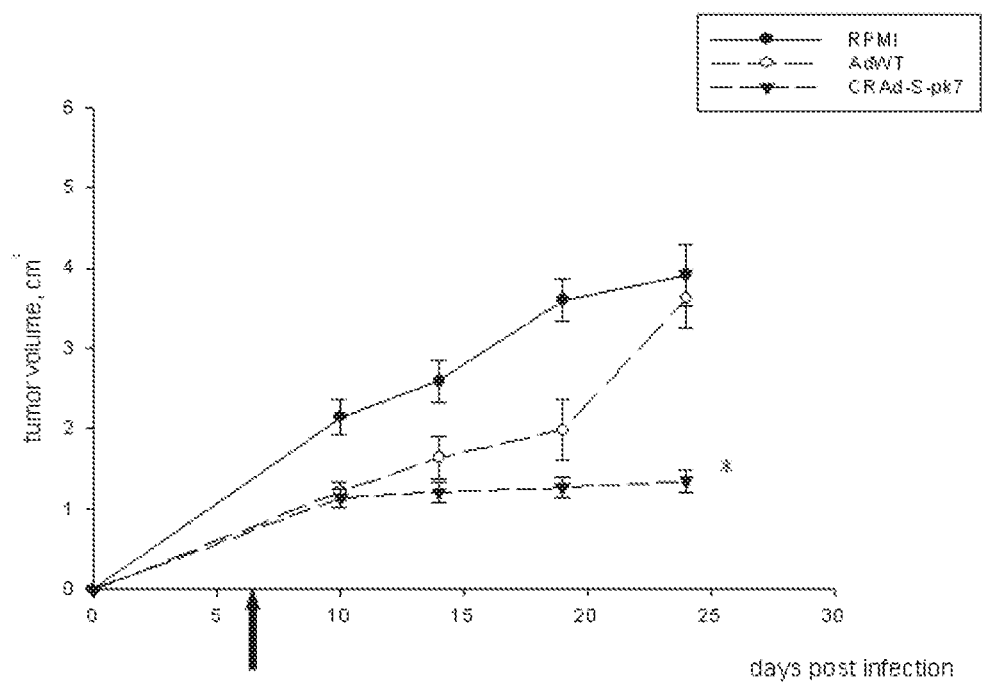
FIGS. 8A and 8B illustrate the efficacy of CRAd-S-pk7 in vivo according to one embodiment. Animals with (FIG. 8A) flank as well as (FIG. 8B) intracranial tumors were treated with CRAd-S-pk7 and tumor growth and survival were assessed.
Figure 8B:
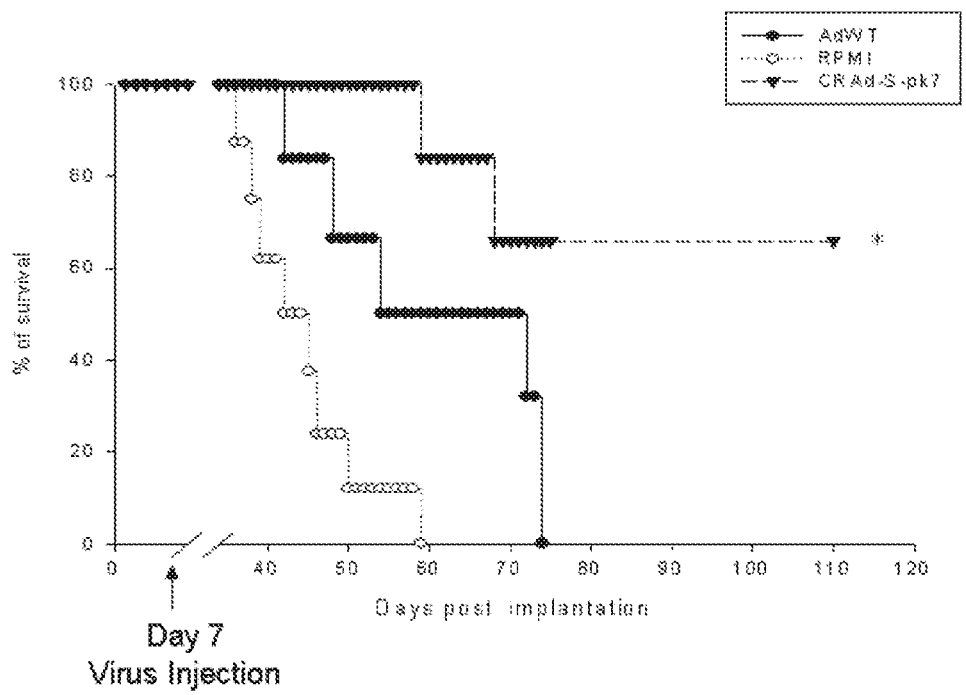

Next, the efficacy of CRAd-S-pk7 was examined against xenograft models of glioma (FIG. 8). (A) U87MG glioma cells were injected into the flank of nude mice (n=6/group) and allowed to grow to 0.7 cm$^3$ in size. CRAd-S-pk7 or AdWT vectors were injected intratumorally at a dose of $1\times10^{11}$ vp/mouse. The results are presented at tumor volume in cm$^3$ over time. CRAd-S-pk7 virus reduced tumor growth by at least 300% as compared with vehicle-injected tumor or AdWT ($p<0.001$). The data points represent the mean+ standard deviation. (B) Kaplan-Mayer survival curves following intracranial injections of AdWT, CRAd-S-pk7 or RPMI in athymic mice (n=6/group) bearing U87MG-glioma. The median survival of mice treated with RPMI was 44 days. In contrast, the median survival of AdWT treated group was 71 days ($p<0.05$). Sixty-seven percent of mice treated with CRAd-S-pk7 were long term survivors >110 days ($p<0.005$). Both the flank and intracranial experiments were repeated twice with similar results.

Example 2

Figure 9A:
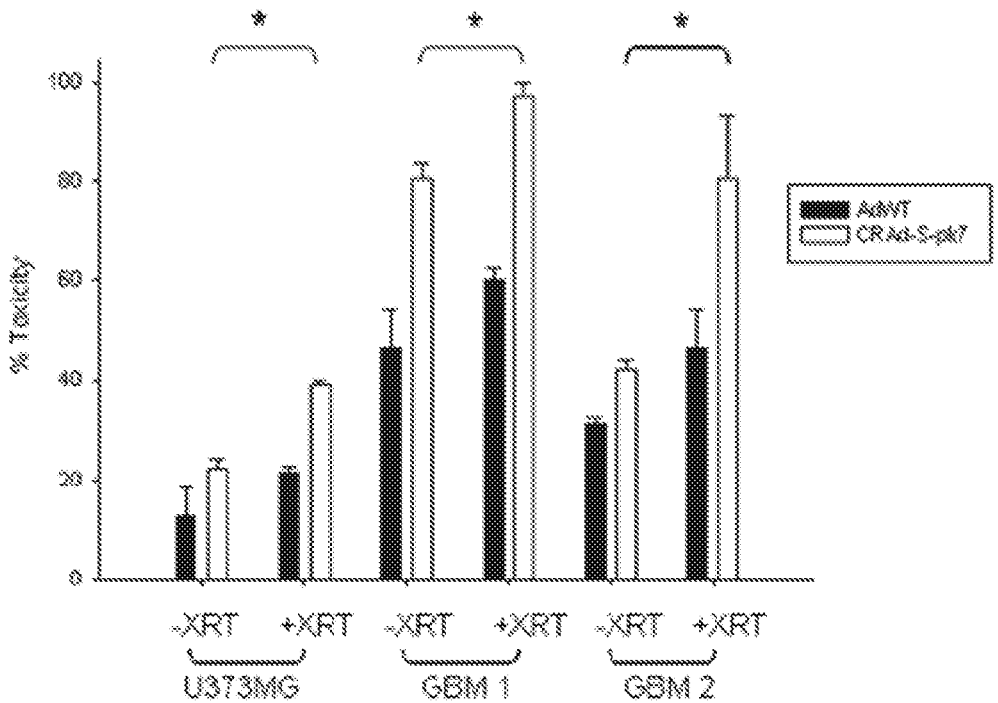
FIGS. 9A and 9B illustrate survivin induced killing of CD133+ cells in vitro in response to radiation according to one embodiment. Cells were infected with CRAd-S-pk7 or AdWT and 24 h later exposed to 2Gy of radiation. They were then grown for a 24 hr more in complete media.
Figure 9B:
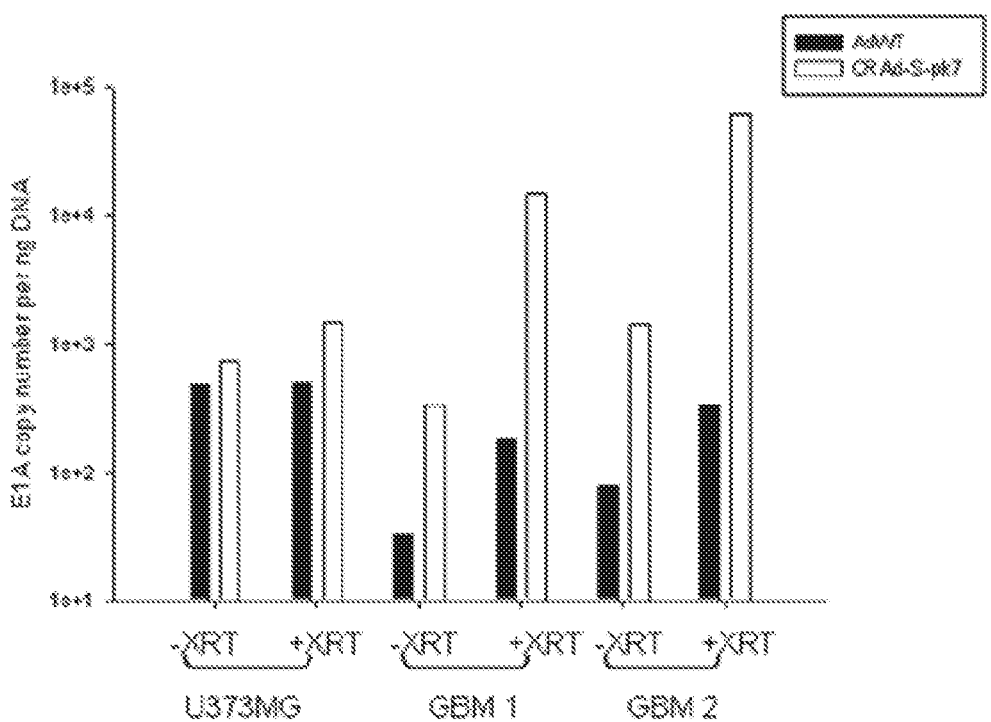

Combined Efficacy of Survivin-mediated Virotherapy and Radiotherapy Against Malignant Glioma CD133+ Stem Cells Next, the response of brain tumor samples enriched for CD133+ cells in response to CRAd-S-pk7 and radiation therapy (XRT) was examined. To determine whether the CRAd could preferentially target CD133+ cells in conjunction with radiation, CD133+ cells from U373MG, GBM1 and GBM2 were infected with wild-type and CRAd-S-pk7 adenovirus. The cells were then assayed for cytotoxicity and replication efficiency. The toxicity in cells or tumor tissues infected by CRAd-S-pk7 was significantly higher as compared to those that were AdWT infected (U373MG 22.09+2.05 vs. 12.9+5.49; GBM1 80.41+2.82 vs. 46.6+7.58; and GBM2 41.9+1.85 vs. 30.98+1.97) ($p<0.05$) as shown in FIG. 9A. The virolytic effect of CRAd-S-pk7 was further enhanced when the cells were exposed to 2Gy radiation. The level of toxicity, as measured by LDH release, increased to 38.99+0.76, 96.82+3.11, and 80.41+12.82 ($p<0.05$) for U373MG, GBM1 and GBM2, respectively (FIG. 9A). The absolute increase in toxicity was significantly greater for CD133+ than CD133− stem cells. This data correlated with the increased viral replication in radiated cells particularly those infected with CRAd-S-pk7 (FIG. 9B). In fact, radiation exposure induced 1.97, 43.62, and 42.63 fold increase of viral replication for U373MG, GBM1 and GBM2 respectively.

Figure 10A:
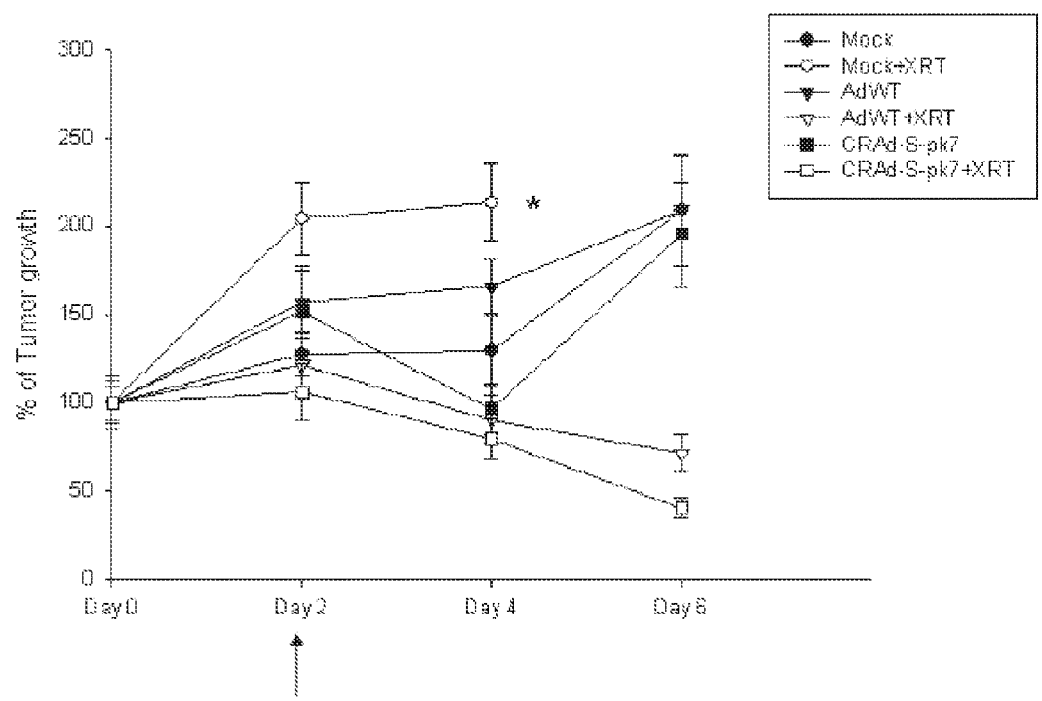
FIGS. 10A and 10B show in vivo tumor growth rate in nude mice according to one embodiment.
Figure 10B:
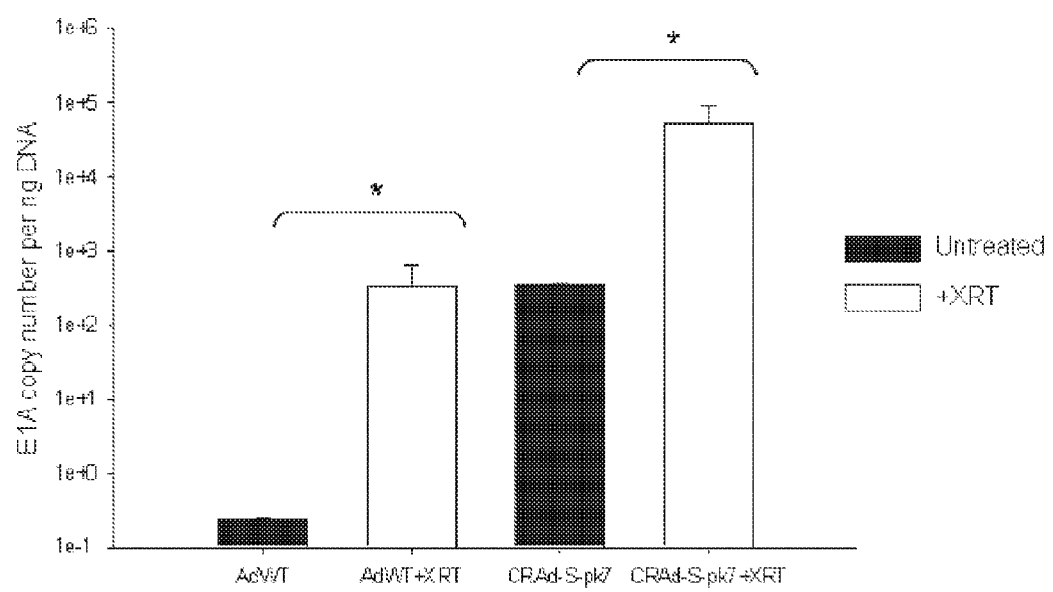

To examine whether survivin regulated viral toxicity was increased in vivo in response to low-dose radiation, nude mice were injected with $3 \times 10^5$ CD133+U373MG glioma cells. The cells were injected under the skin to facilitate local radiation and allow for precise tumor measurement. After the tumors reached a volume of 100 mm$^3$, the mice were randomly divided into six groups. As shown in FIG. 10A, the tumors sizes on the day of radiation were taken as 100% and the changes in size were measured over a 6-day period. In response to radiation, the CRAd-S-pk7 virus significantly reduced the tumor volume by 60% when compared with other treatment regimens (p<0.05). To ascertain the viral replication in response to radiation, three mice from each group were sacrificed at day 2 after irradiation and the tumors were resected. Viral copy number was ascertained from DNA isolated from these tumors (FIG. 10B). The CRAd-S-pk7+XRT group showed about a 100 fold increase in viral replication compared to CRAd-S-pk7 alone.

Example 3

Figure 11A:
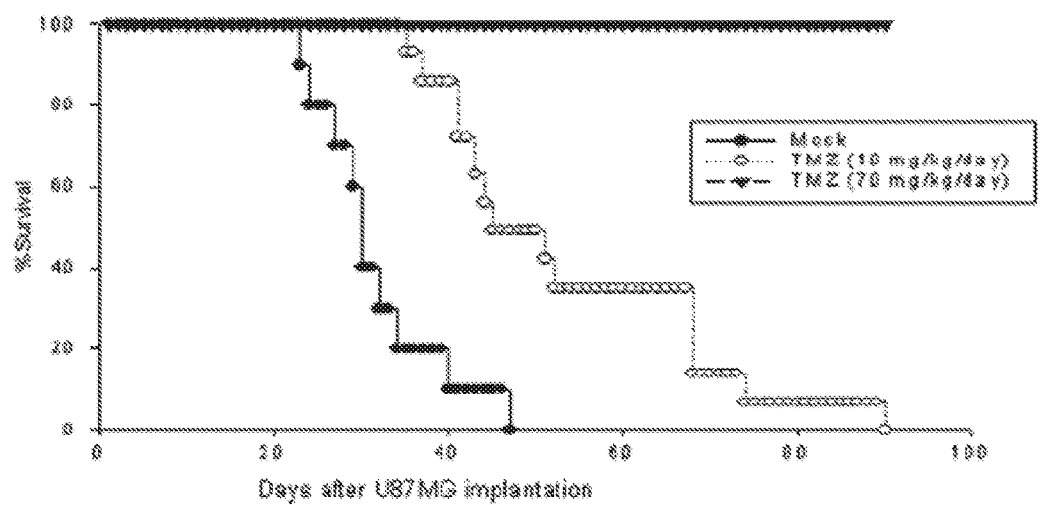
FIGS. 11A, 11B and 11C show in vivo anti-tumor activity of CRAd-S-pk7 in combination with TMZ according to one embodiment.
Figure 11B:
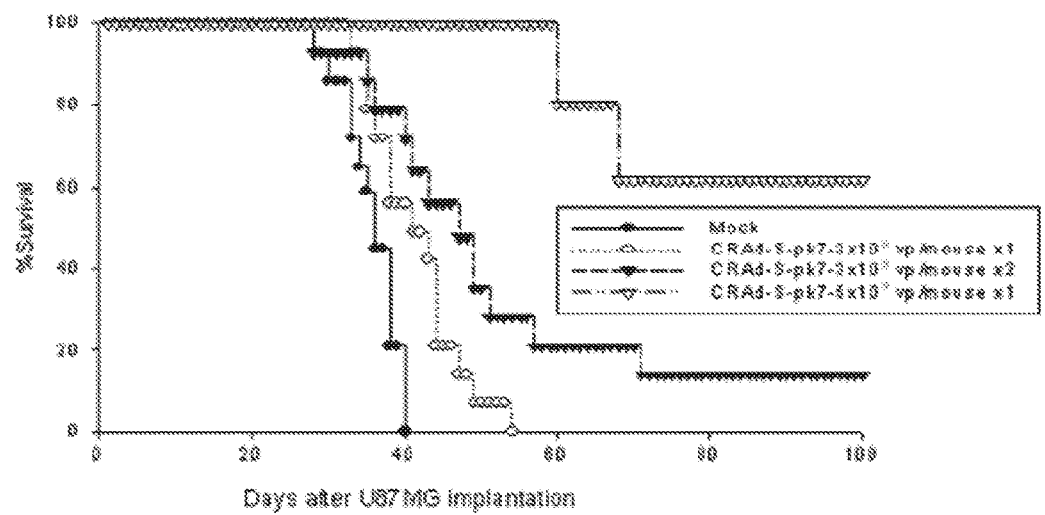

Combined Efficacy of Survivin-mediated Virotherapy and Temozolomide-based Chemotherapy Against Malignant Glioma Because temozolomide (TMZ) is the standard of care for patients with GBM, the efficacy of TMZ and CRAd-S-pk7 combination was evaluated in vivo in mice with U87MG intracranial (i.c.) glioma xenografts. To employ a dose that resembles the partial therapeutic effect of TMZ seen in the clinical scenario, different doses of TMZ were tested. Based on those studies, a dose of 10 mg/kg/day×5 days of intraperitoneal (i.p.) TMZ was chosen to study the efficacy of a TMZ and CRAd-S-pk7 combination treatment, since this dose led to an increase in survival but remained non-curative (FIG. 11A) (log-rank test, p<0.05). Additionally, different doses of i.c. CRAd-S-pk7 injections were tested to investigate which dose provides an increase in survival that could be further enhanced by the addition of co-adjuvant TMZ. A dose of $3 \times 10^9$ vp/mouse×2 injections of CRAd-S-pk7 was chosen for testing the therapeutic effects of TMZ+CRAd-S-pk7 combination, since it led to a partial efficacy that could be further enhanced (FIG. 11B) (log-rank test p<0.05).

Figure 11C:
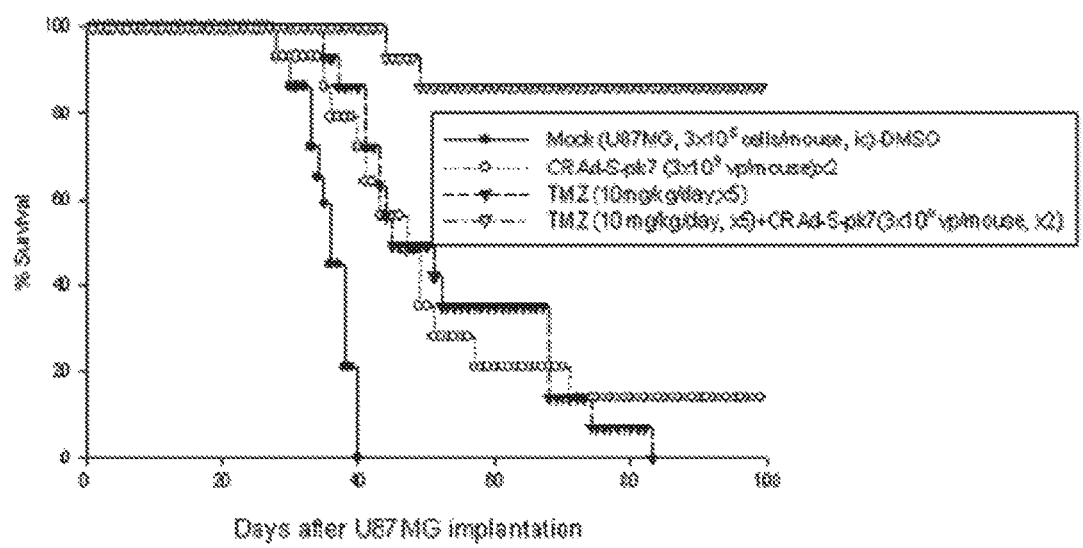

Based on the above findings, the combination of TMZ and CRAd-S-pk7 was tested for efficacy in terms of survival (FIG. 11C). The combination of TMZ (10 mg/kg/day×5) plus two i.c. injections of CRAd-S-pk7 $3 \times 10^9$ vp/mouse led to a 90% of long term survivors (>90 days) (LTS). In contrast, treatment with TMZ 10 mg/kg/day×5 alone led to a median survival of 51 days (Standard Error 2.45) with 7% LTS, treatment with CRAd-S-pk7 $3 \times 10^9$ vp/mouse×2 alone led to a median survival of 49 days (SE 2.0) with 14% LTS, and mock treated animals had a median survival of 37 days (SE 0.5) with no LTS (FIG. 11C) (log-rank test, p<0.01). Consistent with the finding of an additive cytotoxic effect of TMZ and CRAd-S-pk7 in vitro experiments, this treatment combination led to an improved survival in mice bearing intracranial human glioma xenografts.

Example 4

Figure 12:
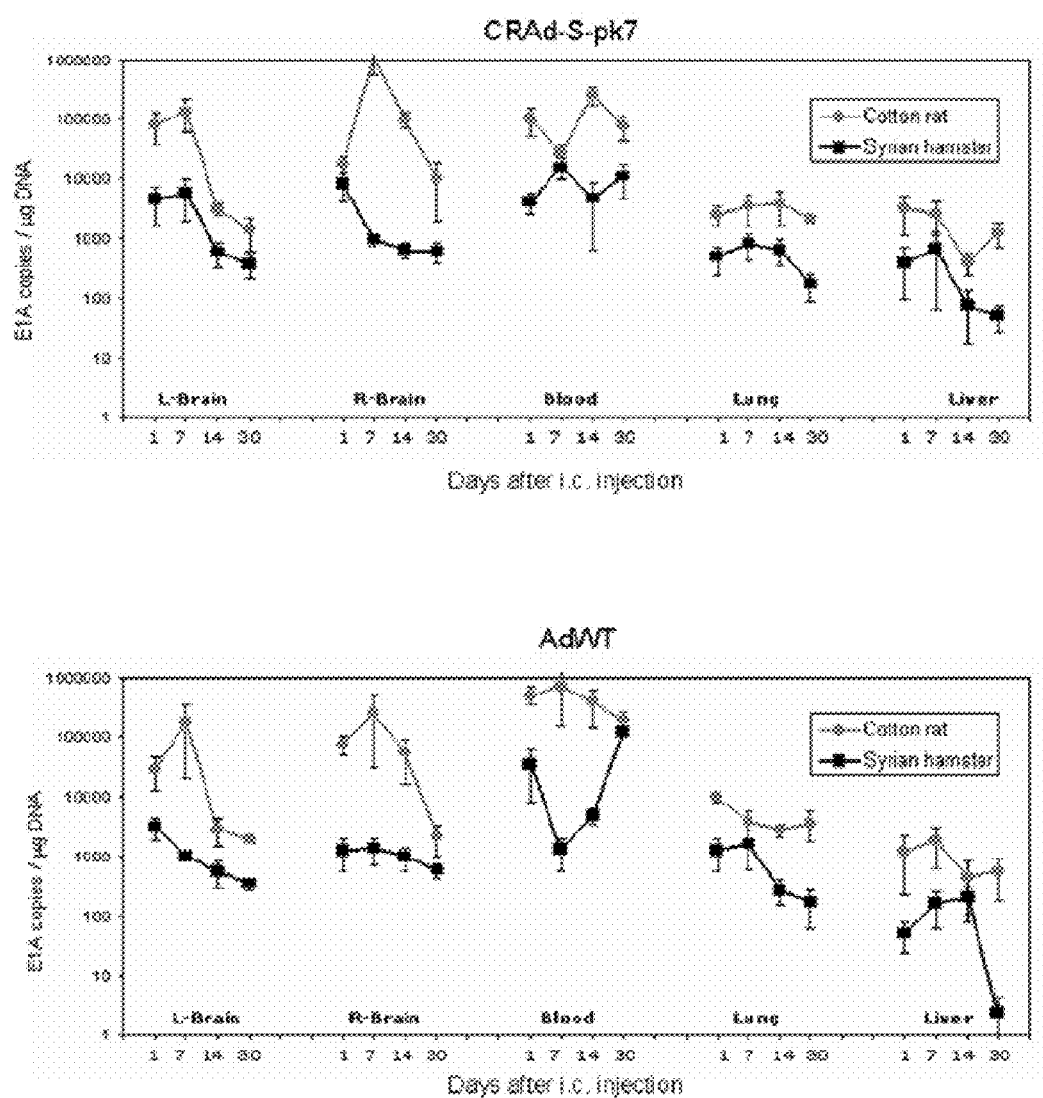
FIG. 12: Viral genomic copies were determined by amplification of E1A viral gene by qPCR according to one embodiment after intracranial injection of 4.5×10$^9$ vp of CRAd-S-pk7 (top) or AdWT (bottom) into the right parietal lobe of Syrian hamsters (black lines) and Cotton rats (gray lines). Animals were sacrificed 1, 7, 14 and 30 days after intracranial injection. Cotton rats exhibited a multiple log higher number of viral genomic copies than Syrian hamsters in all organs and time points studied ($p<0.001$). In Syrian hamsters as well as Cotton rats, the number of viral copies among different organs varied significantly, with higher number of viral copies in the brain and blood than that seen on liver and lung for both CRAd-S-pk7 and AdWT ($p=0.03$).

CRAd-Survivin-pk7 Exhibits a Favorable Safety Profile Following Intracranial Injection Because the Cotton rat (CR) is a semipermissive animal and the Syrian hamster (SH) is a fully permissive model for adenoviral replication, the most appropriate model for biodistribution and toxicology studies could not be determined without first comparing the two animal species head to head. To characterize the replication of the Ad vectors in these two immunocompetent and permissive organisms, viral genomic copies were quantified in the brain, blood, lung and liver at days 1, 7, 14 and 30 after intracranial injection of CRAd-S-pk7 or AdWT (FIG. 12). To do so, the viral gene E1A was amplified by real-time PCR (≤50 copies of vector/1 μg genomic DNA). Following injection of the same amount of viral particles for both models, Cotton rats exhibited at least one log unit higher number of viral genomic copies than that found on Syrian hamsters. The difference between the two animal models remained significant (p<0.001) after controlling virus type, organ, and time point. Moreover, in Cotton rats but not in Syrian hamsters, there was a significant interaction between organ and day, meaning that the relation between viral copies over time was different among organs (p=0.01). These data suggest that the Cotton rat is a more sensitive model for studying the biodistribution and toxicity of an oncolytic virus following intracranial administration.

Figure 13:
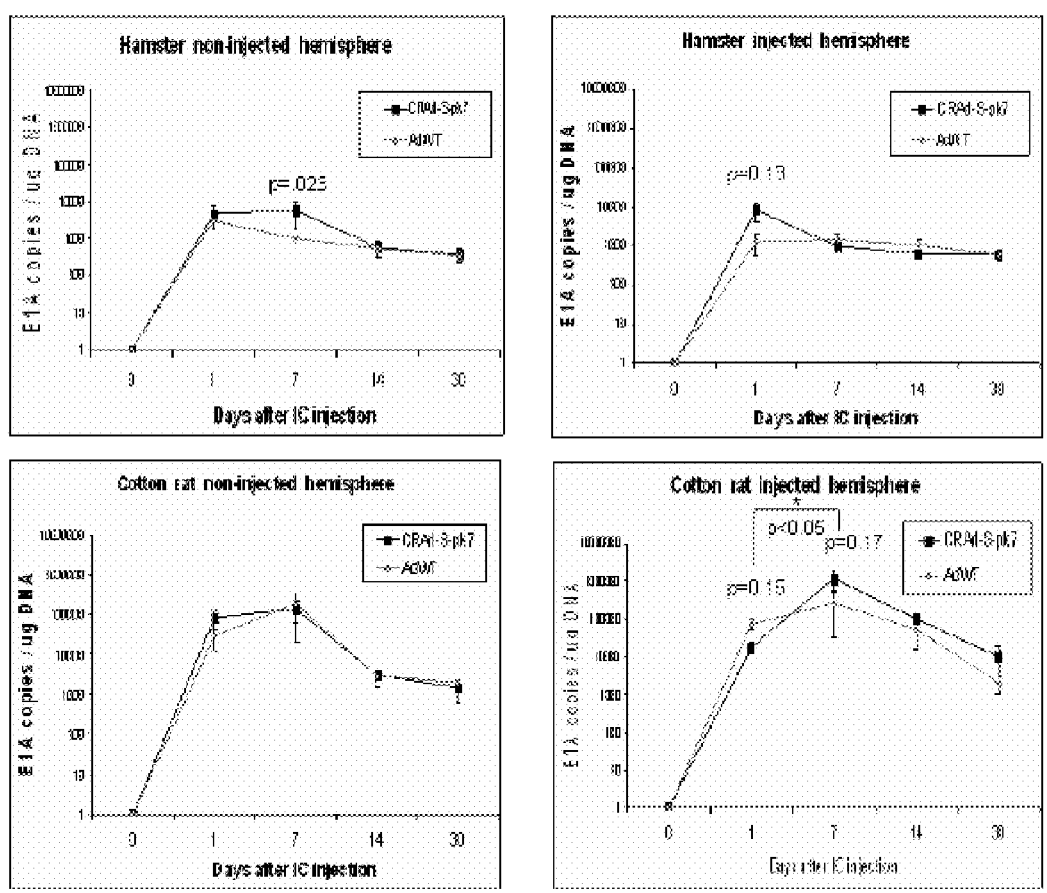
FIG. 13 shows viral genomic copies in the brain of Syrian hamsters and Cotton rats were quantified by qPCR for viral gene E1A following intracranial injection of CRAd-S-pk7 or AdWT according to one embodiment. (A) A comparison of viral genomic copies of CRAd-Spk7 (black lines) and AdWT (gray lines) in the injected (right) and non-injected (left) hemispheres. In the case of Syrian hamsters (top) as well as Cotton rats (bottom), there is no statistically significant difference in the number of viral genomic copies of CRAd-S-pk7 and AdWT ($p>0.05$). An increase in the number of viral genomic copies over time was noted in the injected hemisphere of Cotton rats at day 7 following intracranial (i.c.) injection of CRAd-S-pk7 in comparison to day 1 ($p<0.05$).

To obtain a quantitative assessment of the presence of CRAd-S-pk7 and AdWT in the brain of Syrian hamsters and Cotton rats, the genomic copies of these two vectors were compared in the injected and noninjected hemispheres. Interestingly, there was no statistically significant difference in the number of viral genomic copies for CRAd-S-pk7 vs. AdWT in the case of the injected hemisphere or non-injected hemisphere in any of the time points studied (FIG. 13). To understand the distribution of the vectors throughout the brain, the genomic copies of CRAd-S-pk7 and AdWT in the ipsilateral (right brain) and contralateral (left brain) hemispheres were compared to the site of injection. In the brain of Syrian hamsters, the number of genomic copies was similar in both hemispheres for CRAd-S-pk7 and AdWT, suggesting an even distribution of the virus throughout the brain with a similar amount of viral particles independent of the distance from the injection site. In contrast, in the case of Cotton rat brain, a difference in the number of genomic copies of both vectors was noted between the injected and the non-injected hemispheres. There was a lower number of CRAd-S-pk7 genomic copies in the hemisphere contralateral to the site of injection in comparison to the injected hemisphere (right brain). Irrespective of the amount of viral particles encountered in the brain of Syrian hamsters or Cotton rats, all animals were reactive and appeared to have maintained a normal behavior and movements until the time of their sacrifice, dismissing the possibility of neurotoxicity. In addition, no histological signs of neurotoxicity were noted on brain slices.

Figure 14:
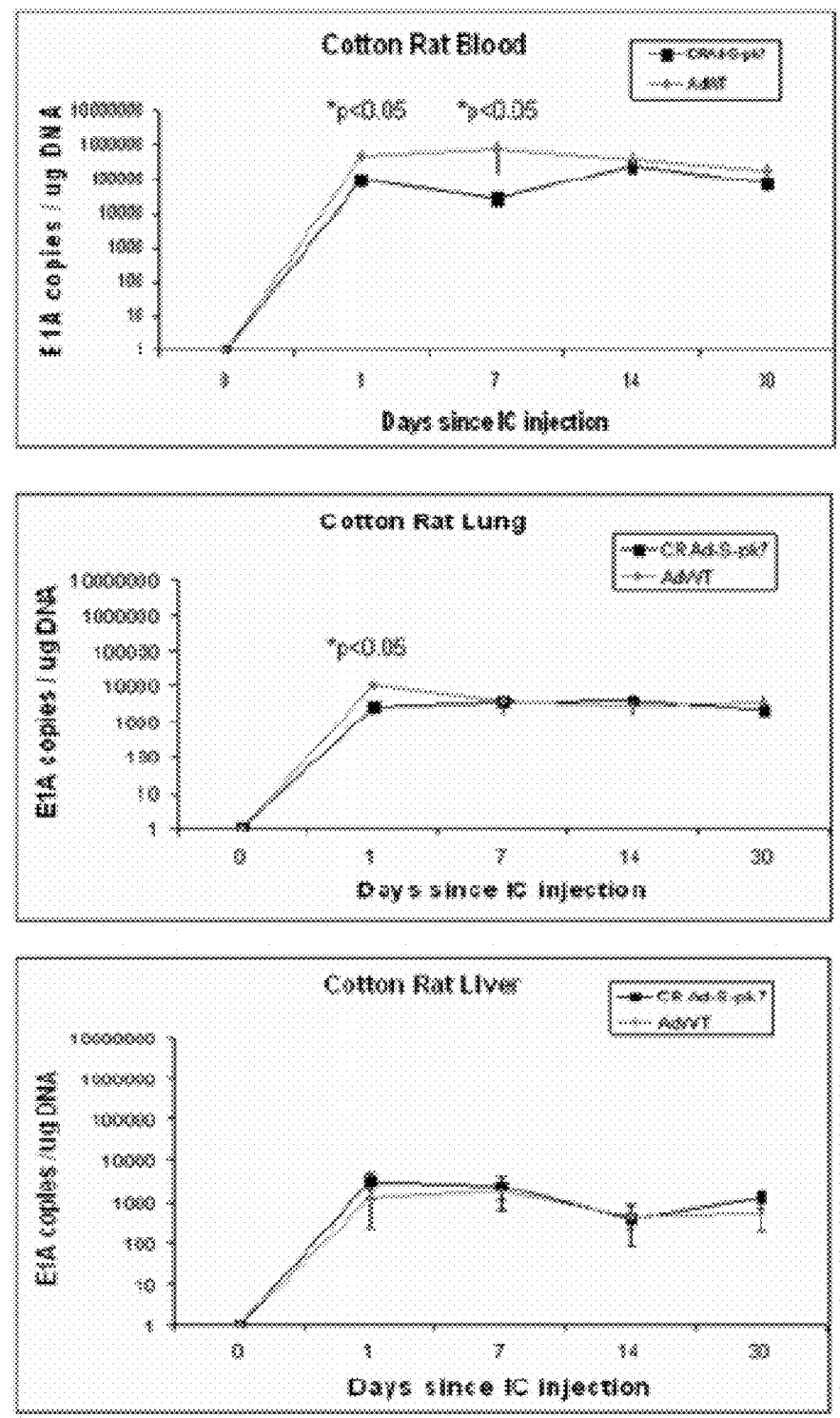
FIG. 14 illustrates viral biodistribution following i.c. injection of CRAd-S-pk7 and AdWT was investigated in the blood, lung and liver by determination of viral genomic copies using qPCR for viral gene E1A according to one embodiment. Comparison of the number of viral genomic copies of AdWT (gray line) and CRAd-S-pk7 (black line) in the blood (left), lung (middle) and liver (right) of Cotton rats showed a significantly lower number of genomic copies of CRAd-S-pk7 in comparison to AdWT in blood (day 1 and 7 following i.c. injection) and in the lung (day 1 following i.c. injection) ($p<0.05$). For graphic representation on a logarithmic scale, 0 was substituted for 1.
Figure 15A:
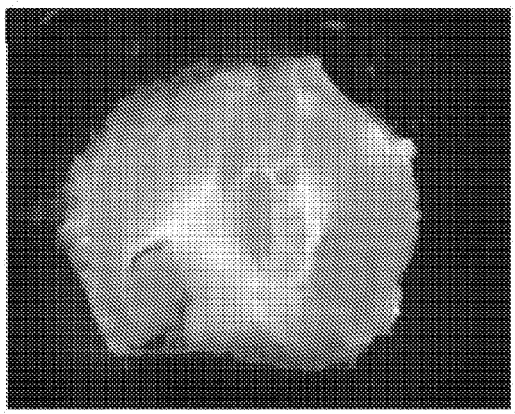
FIGS. 15A, 15B, 15C, 15D, 15E and 15F illustrate that NSCs migrate in response to glioma. In vivo assessment of NSC migratory potential toward malignant glioma according to one embodiment. 5×10$^5$ U87MG-GFP cells were injected into the right hemisphere of male nude mice. Two weeks later, 5×10$^4$ NSC-mCherry cells were injected directly contralateral to the site of U87MGGFP injection. To observe NSC-mCherry migration, mice were sacrificed, brains were extracted and underwent serial 500 μm axial sectioning on a vibratome until a total cut depth of 3 mm was reached. The data presented shows a mouse brain that was extracted 12 days after NSC-mCherry implantation. Images were captured using a fluorescent stereomicroscope.
Figure 15B:
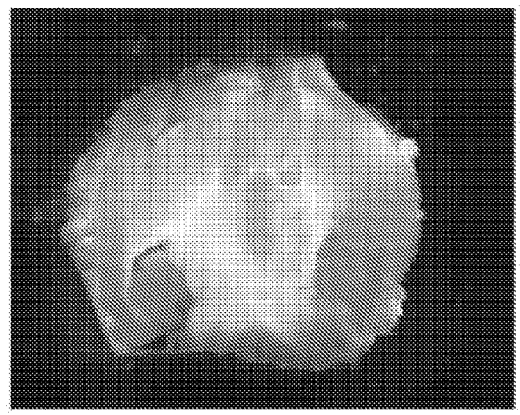
Figure 15C:
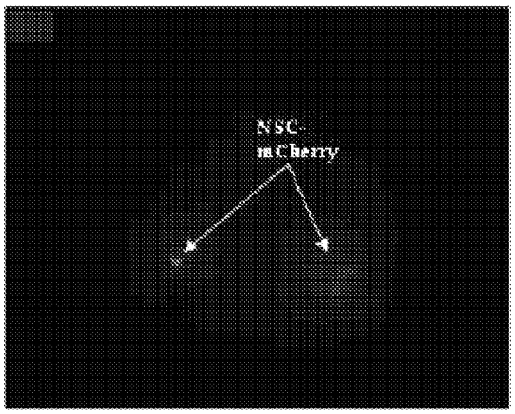
Figure 15D:
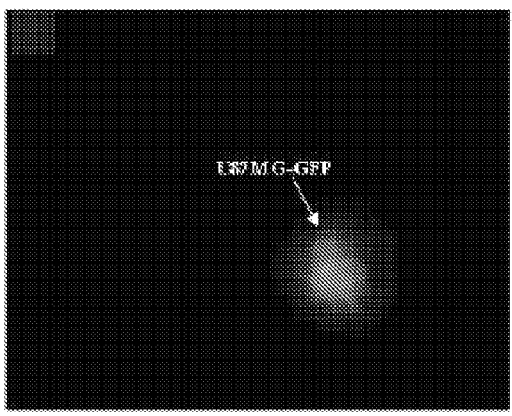
Figure 15E:
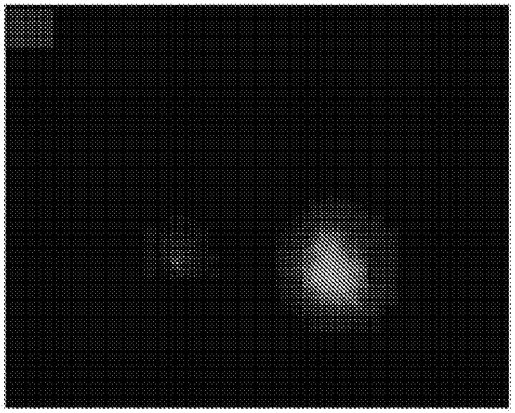
Figure 15F:
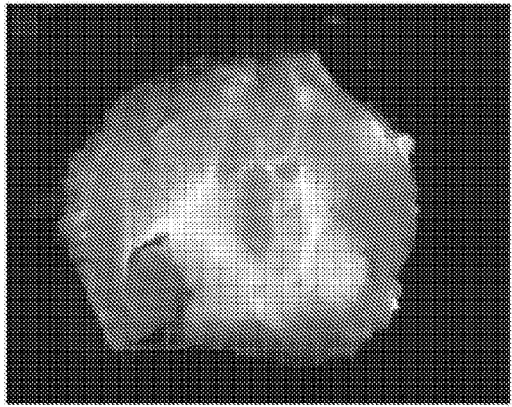

The modifications that have been made to target CRAd-Spk7 towards gliomas might have an effect on its pharmacokinetics in comparison to AdWT in the setting of permissive and immunocompetent organisms. In order to explore this possibility, the distribution of CRAd-S-pk7 and AdWT was compared in the blood, lung, and liver of Syrian hamsters and Cotton rats after intracranial injection. In the case of Syrian hamsters, there was no statistically significant difference between CRAd-S-pk7 and AdWT in the blood, lung, or liver in any of the time points studied. In the case of Cotton rats, there was a significantly higher number of viral genomic copies in the blood for AdWT compared to CRAd-S-pk7 on day one and seven after intracranial injection (p<0.05), and in lung on day one after intracranial injection (p<0.05) (FIG. 14).

Example 5

Maintaining and Loading Neural Stem Cells for Delivery of Oncolytic Adenovirus to Brain Tumors Early in vivo experiments with oncolytic viruses revealed that infected virus-producing cells could also mediate antitumor activity when administered in the place of naked virus (Coukos et al. 1999). This led to the hypothesis that producer cells can be used to hide the therapeutic virus from the host immune system and delivered systemically in order to travel precisely to the disseminated tumor burden. As described in the Examples herein, NSC can be used as a carrier for stealth delivery of an oncolytic adenovirus in vivo for antiglioma therapy (Tyler et al. 2009). At least in theory, oncolytic viruses can be ideal anticancer agents to be loaded into NSC for the following reasons: first, oncolytic viruses can replicate selectively in the tumor cells and thus should be able to amplify the therapeutic gene efficacy at the tumor sites; secondly, once the oncolytic virus is released from the loaded NSC at the delivery sites, it can also distinguish tumors from normal tissues and induce tumor cell-specific cytolysis.

In order to achieve the maximum delivery and therapeutic efficacy in vivo, NSCs need to be loaded/infected with the maximum dose of oncolytic virus without affecting the carrier cell survival and their tumor homing property. The kinetics with which the virus interacts with the carrier cell must be compatible with the in vivo trafficking of the carrier cell to the tumor. The timing of the oncolytic virus life cycle is a critical determinant factor for this phase. To act as Trojan horse vehicles and successfully hide the oncolytic virus from the host immune system, the cell carriers should ideally reach the tumor site before the viral antigen is displayed on their surface. Moreover, the ex vivo virus loading capacity must be synchronized with the in vivo delivery route and the migration rate of the carrier cell in order to maximize the delivery of the therapeutic oncolytic virus at the tumor sites. Each virus has very different kinetics of entry, replication, and progeny release. Basically, careful ex vivo examination of the interaction between the cell carrier (CC) and the individual virus needs to be done in order to maximize therapeutic virus delivery in vivo at the tumor site.

Below is a detailed overview of oncolytic adenovirus delivery techniques using NSCs as cell carriers according to one embodiment. The protocol outlined in this example describes techniques necessary to load an oncolytic adenoviral vector into NSC for a stealth in vivo therapeutic virus delivery approach for antiglioma therapy.

Materials

Cell Culture. The following materials are used for culturing NSCs: Normal tissue culture equipment, i.e., incubators with CO2 laminar, biohazard flow hood; heat inactivated fetal bovine serum (Life Technologies); Dulbecco's modified Eagle's media (DMEM; Life Technologies) containing 50 U/ml of penicillin-streptomycin (Life Technologies) for A549 cell culture; 0.25% Trypsin (Invitrogen); 15-ml conical tubes; 0.22- and 0.45-μm filters; sterile phosphate buffer saline (PBS), pH 7.4 (Invitrogen); hemocytometer; and trypan blue (Sigma).

Maintenance of Neural Stem Cells. The following materials are used to maintain NSCs in culture: (1) ReNcell NSC Maintenance Medium (CHEMICON) contains DMEM/F12 w/o HEPES, w/L-glutamine human serum albumin, human transferring, putrescine dihydrochloride, human recombinant insulin, L-thyroxine, triiodothyronine, progesterone, sodium selenite, heparin, and corticosterone. Maintenance medium should be stored at −20° C. until ready to use. Upon thawing, the maintenance medium should be stored at 2-8° C. and given a 1-month expiration date; (2) ReNcell NSC Freezing Medium (CHEMICON); (3) basic fibroblast growth factor (bFGF; FGF-2; specific activity >2×10$^6$ U/mg CHEMICON); (4) epidermal growth factor (EGF; specific activity >1×10$^7$ U/mg; CHEMICON); (5) Laminin (Sigma); (6) DMEM/F12 w/o HEPES, w/L-Glutamine (CHEMICON); and (7) accutase (CHEMICON).

Large-Scale Production of Oncolytic Adenovirus Vectors. The following materials are used for large-scale production: (1) A549 cell; (2) 175-mm flask; (3) DMEM medium; and (4) Virus dialysis buffer: 100 mM Tris-HCl (pH 7.4), 10 mM MgCl2, and 10% (v/v) glycerol.

Purification of Adenovirus by CsCl Banding. The following materials are used to purify adenovirus: (1) 10 and 100 mM Tris-HCl (pH 8.0), autoclave sterilized; (2) 5% sodium deoxycholate, filter sterilized; (3) Glycerol, autoclave sterilized; (4) Beckman SW 28 rotor and ultra-clear tubes; (5) Slide-A-Lyser dialysis cassettes (Pierce, Rockford, Ill., USA); (6) Dialysis buffer: 10 mM Tris-HCl (pH 8.0).

Viral Particle Number Determination. The following materials are used to determine the number of viral particles: (1) virus lysis buffer: 0.1% sodium dodecyl sulfate (SDS), 0.02 M Tris-HCl (pH 7.4), 1 mM EDTA; (2) spectrophotometer capable of reading optical density at 260 nm; (3) measuring cuvette; (4) 1.5-ml Eppendorf tubes; and (5) heating blocks.

Methods

Large-Scale Adenovirus Production. Because the purity and functional integrity of recombinant viral vectors' preparation are extremely critical for ex vivo loading into carrier cells as well as in vivo therapeutic efficacy, this part of the methods section briefly summarizes methods used for the propagation and analysis of oncolytic adenoviral stocks to be loaded into stem cells for in vivo delivery.

First, the propagation of oncolytic adenoviral vectors is performed in the A549 cell line. Because most of the viruses remain associated with the infected cells until the cells are lysed at a very late phase of infection, high-titer stocks can be prepared by concentrating infected A549 cells. Infect A549 cell monolayer with the "low-passage" adenovirus stock in the 75-mm dish 102 A.U. Ahmed et al. and gradually scaling up to a 150-mm dish. For each large-scale preparation, use at least twenty to thirty 150-mm dishes.

Next, when a complete cytopathic effect (CPE) is reached (~48 h post infection, no more than 96 h), collect the cells in the media (20-25 ml for each 150-mm dish). Spin down the cells at 129×g (800 rpm) for 10 min in the Eppendorf 5810R benchtop centrifuge. Discard the supernatant and resuspend the cell pellets in 1.5-3.0 ml of 0.1 M Tris-HCl buffer (pH 8.0) per 150 mm pellet. All 150-mm dishes do not have to be prepared concurrently. It is often convenient to prepare ten dishes at time Next, the virus is released by snap freezing the cell plate in liquid nitrogen and thawing in the 37° C. water bath. Repeat this process three times. Transfer the freeze/thaw cell lysate to Beckman (25×89 mm) polyallomer centrifuge tubes and spin out the cell debris at 4,000×g (7,697×g) for 10 min in the Beckman CS-15R benchtop centrifuge using prechilled (4° C.) F0630 rotor. Alternatively, centrifuge the samples in 50-ml Falcon tubes in a Sorvall RCSC-Plus using the SLA-600TC rotor at 4,890×g for 10 min. Remove the supernatants and transfer them to clean 50-ml Falcon tubes.

Vector Purification by CsCl Ultracentrifugation. Purification of an oncolytic Ad vector is a three-step process. First, a discontinuous CsCl gradient is established that removes the majority of the cellular debris and unpackaged viral particles. The discontinuous CsCl gradient is established as follows. The following CsCl solutions are prepared and filter sterilized:

TD=8 g NaCl+0.38 g KCl+0.1 g Na2HPO4, 3 g Tris base per liter H2O, pH to 7.5 with HCl
1.25 g/ml=36.16 g CsCl+100 ml TD
1.35 g/ml=51.2 g CsCl+100 ml TD
1.40 g/ml=62 g CsCl+100 ml TD Prechill a swing bucket rotor (Beckman SW28 or equivalent) to 4° C., then prepare CsCl gradients by carefully layering 7.6 ml of 1.4 g/ml of CsCl beneath 11.4 ml of 1.25 g/ml CsCl solution in Beckman (25×89 mm) ultra-clear centrifuge tubes. Very carefully overlay the gradients with the cell-free media containing viral particles from above (~19 ml per gradient). If the viral stock is less than 19 ml, use 0.1 mM Tris-HCl (pH 7.9) to complete the volume.

Once the tubes are well-balanced, they are centrifuged at 100,000×g in SW 28 rotor for 2 h at 15° C. Sorvall Discovery 100S ultracentrifuge with Superspin rotors or any other suitable centrifuge may be used alternatively. Then, in a laminar flow hood, very carefully remove the tubes from the rotor, and then secure one tube with a three-pronged clamp attached to a stand. Generally, two milky layers are observed; the upper band of which consist of low-density, empty, assembled adenoviral particles while the lower band represents mature encapsidated viral particles. Collect the lower band by puncturing either side of the tube using a 5-ml syringe and 19-gauge needle. The area between the defective (upper band) and infectious viral particles (lower band) may appear turbid. Avoid removing this turbid area. All of the cirus bands are then collected together.

For the second step, a continuous CsCl gradient is established to completely separate infectious and defective viral particles. To accomplish this step, the collected virus from the previous step is loaded into Beckman 13×15-mm ultra-clear centrifuge tubes. Fill the tubes to within 2-3 mm to the top with 1.35 g/ml CsCl solution. The tubes are then centrifuged at 150,000×g at 15° C. for 16-20 h using the Beckman SW 55 swing out rotor. Sorvall Discovery 100S ultracentrifuge with TH-660 rotor or any other suitable centrifuge may be used alternatively. After the centrifuge, the continuous gradient looks like the step gradients one, except there is only one band. Collect the virus bands, which should be located centrally to the tube. Keep the CsCl-purified viral fraction on ice at all times.

For the third step, CsCl is removed from concentrated viral stock by desalting. Briefly, Transfer the viral vector into Pierce slide-A-Lyzer dialysis cassette. Dialysis in 500-ml dialysis buffer for 30 min, twice. Repeat the dialysis in 1,000-ml dialysis buffer for 1 h for three times. Remove the vector suspension from the dialysis cassette and aliquot in sterile Eppendorf tubes in such volume that repeated freeze-thaw can be avoided in order to prevent loss of activity. Keep vector aliquots in a −80° C. freezer. All of the steps in this protocol use of 30-ml centrifuge tubes for Beckman SW28 rotors or equivalent. Other tube size can be used as long the solution volumes are adapted. The contaminants, such as unpackaged virus, may have a similar density to that of the mature virion. This can cause the distance between the two bands to be very small after the CsCl gradient separation. In the large-diameter tube, such as 30-ml tube, bands of similar density of virus appear thinner and further separated. Thus, the recovery of viral bands is easier in the 30-ml tube compared to small-volume tube.

Viral Particle Determination. This method determines the titer of a viral stock suspension using viral particles as units by establishing the correlation between the number of VPs and the DNA contained. This can easily be measured by absorbance at 260 nm (OD260) using a spectrophotometer. Each OD260 unit represents approximately $1.1 \times 10^{12}$ adenovirus particles. The OD260 reading between 0.1 and 1.0 should only be used to do the final calculation because only at this range can the OD260 reading accurately reflect the amount of DNA for most spectrophotometers. The method is performed as follows:

First, a virus lysis buffer is prepared, followed by the following dilution of purified viral stock with the virus lysis buffer: (a) 1:3 dilution=33.3 µl viruses+66.7 µl of VLB; (b) 1:5 dilution=20 µl viruses+80 µl of VLB; and (c) 1:10 dilution=10 µl viruses+90 µl of VLB. After mixing briefly by vortex, the samples are incubated at 56° C. for at least 10 min. The samples are then centrifuged and allowed to cool down. Next, the spectrophotometer is turned on, the 260/280 program is selected, and the UV lamp is allowed to warm up for at least 10 min before reading samples. For each sample, OD260 is measured in a spectrophotometer. 100 µl of VLB is used as a blank. To calculate the number of viral particles per ml in the stock, use the following formula (disregarding the OD260 reading out of 0.1-1.0 range): OD260×dilution factor×$1.1 \times 10^{12}$=VP/ml Viral Titration by Rapid Titer Assay. This assay takes advantage of the fact that every cell infected with adenovirus expresses viral proteins. The percentage of cells that are infected in a specific stock of virus may be measured by monitoring the number of cells expressing viral protein (Bewig & Schmidt 2000). The viral titers that can be obtained by using this assay are much quicker (within 48 h) than any other conventional assay. The complete kit for such an assay can be purchased from Clontech (Adeno-X™ Rapid Titer Kit). This kit measures the production of viral hexon proteins in infected cells by immunohistochemical analysis. A brief overview of the method follows:

Seed $1 \times 10^4$ healthy HEK 293 cells in each well of a 96-well plate for 24 h at 37° C.

Using media as a diluent, prepare tenfold serial dilution of viral stock from 10-2 to 10-8 ml.

Add viral dilution drop wise to well. Each dilution of virus should be assayed in triplicates to ensure accuracy.

Incubate cells at 37° C. in 5% CO2 for 48 h.

After 48 h, aspirate the media and allow cells to dry in hood for 10 min.

Fix the cells by very gently adding ice-cold 100% methanol to each well.

Incubate the plate at −20° C. for 10 min.

Aspirate methanol. Gently wash wells three times with PBS. At this point, cells can be stored at 4° C. for 48 h in PBS before moving on to the next steps.

Dilute the mouse anti-hexon antibody 1:1,500 in PBS containing 1% BSA.

Aspirate the PBS from final wash. Then, add anti-hexon antibody dilution to each well. Incubate for 1 h at 37° C.

Remove the anti-hexon antibody. Then, gently rinse the wells three times with PBS.

Dilute the HRP-conjugated rat anti-mouse antibody 1:850 to each well. Incubate for 1 h at 37° C.

Before removing the rat anti-mouse HRP-conjugated antibody, prepare the DAB working solution by diluting 10×DAB substrate 1:10 with a 1× stable peroxidase buffer. Allow the DAB working solution to come to room temperature, but do not allow the 10×DAB substrate to warm to room temperature.

Aspirate the HRP-conjugated antibody. Gently rinse each well three times with PBS+1% BSA.

Add the DAB working solution to each well. Incubate at room temperature for 10 min.

Observe under the microscope. All the adenovirus-infected cells should become brown. If one is having difficulties identifying the positive cells from brown staining, the cells can be incubated longer in the DAB working solution.

Count a minimum of three fields of brown and black positive cells using a microscope with a 20× objective, and calculate the mean number of positive cells in each well.

Calculate infectious units (IUs)/ml for each well as follows:

$$\frac{\left(\frac{\text{Infected cells}}{\text{Field}}\right) \times \left(\frac{\text{Fields}}{\text{Well}}\right)}{\text{Volume virus (ml)} \times \text{(Dilution factor)}}$$

For 96-well plate (area=0.32 cm2) and 20× objective (field area=0.64 mm2), fields/well=50. For the 10× objective (field area=2.54 mm2), fields/well=12.6.

Culture and Maintenance of NSC. Human NSCs (ReNCell) were obtained from Millipore and maintained according to the manufacturer's protocol. Briefly, these NSCs were isolated from the cortical region of 14-week-old fetal tissue and immortalized by retroviral transduction and insertion of the c-myc gene. Cells were characterized according to their expression of nestin, SOX-2, CD133, and CD44 stem cell markers. Subcultures of human NSCs for experimentation were conducted as follows.

For thawing neural stem cell lines, coat the tissue culture plastic with laminin (Sigma) at a concentration of 20 µg/ml in serum-free DMEM in 37° C. and 5% CO2 atmospheric conditions 4 h before NSC plating. Thaw a frozen vial as quickly as possible by placing the vial in 37° C. water bath for 1-2 min. Immediately remove the vial from the water bath and decontaminate by wiping the vial with 70% ethanol. Transfer the contents of the vile into 15-ml Falcon tube with 4 ml of ReNCell NSC Maintenance Medium, supplemented with 20 ng/ml bFGF and 20 ng/ml EGF (complete ReNCell medium). Centrifuge at 246×g for 5 min. Aspirate the medium from the tube and resuspend the cell pellet with 8 ml of complete ReNCell medium. Pipet the medium containing NSCs into one laminin-coated 10-cm dish. Gently swirl dish to evenly distribute cells. Place dishes into 37° C. and 5% CO2 incubator For maintaining the neural stem cell lines, precoat the tissue culture plastic dishes as described above with laminin (Sigma) 4 h before NSC plating. Discard the culture medium by aspiration. Rinse the cell monolayer once with 1×PBS. Detach the NSCs by adding 3 ml/10-cm dish of Accutase solution and incubate at 37° C. for 2-3 min. Observe the cells under an inverted microscope until all the cells are detached from the plate. NSCs should not be kept in the Accutase solution for more than 5 min. The dish can be gently tapped to help the cells detach. Add 3 ml of complete medium and transfer the cells by gently pipetting into 15-ml Falcon tube. Centrifuge the cell solution at 246× g, resuspend the pellet in the 3-ml complete ReNCell medium, and transfer 1 ml into laminin-precoated 10-cm dish. Initially, the NSCs grow rapidly, doubling 8-10 h in the presence of FGF and EGF. Cells should not be allowed to reach confluence as it causes the cells to differentiate. If the cells split 1:2 or 1:3 ratio from 70 to 80% confluent dish, cells need to split 2-3 times a week. After 25-30 passages, the NSCs start to slow down. The most common problem for passaging NSC is the fact that cells appear healthy when plated, but die overnight or fail to grow due to the residual Accutase solution. Care needs to be taken to avoid this.

Ex vivo Optimization of the Therapeutic Virus Loading Into Carrier Cells The goal of the ex vivo loading phase is not only to infect as many carrier cells as possible, but also to keep them alive post in vivo delivery. This is so the cells can home in on the tumor and produce a high amount of therapeutic virus. This section briefly describes the optimization experiments of these important parameters in the in vitro setting.

For cell viability analysis of the cell carrier, determine the maximum ex vivo virus loading dose that has minimal impact on the survival of the carrier cell using the following method: First, plate $1 \times 10^4$ cells/well NSCs in a 96-well plate. On the following day, infect the cell monolayer with 0.01-1,000 IU/cells (tenfold dilution) of the oncolytic virus. Infect each IU in triplicate wells. After 2 h of incubation, remove the virus-containing media, wash the cell two times with PBS, and add fresh complete ReNCell medium. 72 h and 96 h post infection, count the viable cells in each infected condition by using Trypan blue exclusion method To test carrier cell viability by trypan blue exclusion method, transfer medium from the infected well to 1.5-ml Eppendorf tubes. Detach the cell monolayer by adding 50 µl Accutase solution. Transfer the detached cells from each well to the corresponding 1.5-ml Eppendorf tube. Mix 10 µl of cell suspension with 10 µl of trypan blue solution. Transfer immediately to the counting chamber of the hemocytometer. Viable cells exclude trypan blue while dead cells stain blue due to trypan blue uptake. Count the viable cells in three squares in the counting areas of the hemocytometer. Average the three counts. Calculate the total number of viable cells using the following formula: Viable cells (cells/ml)=Average count×dilution factor $(2) \times 10^4$ To determine a dose-response analysis of viral replication and progeny release, plate carrier cells at a density of 2.5×104 cells/well in 24-well laminin-precoat tissue culture plate. On the following day, infect the cell monolayer with oncolytic adenovirus as described above. 72 h post infection, collect the supernatant from the infected monolayer. Detach the infected cells by Accutase treatment, neutralize with the complete medium, and transfer the cell suspension in a 1.5-ml Eppendorf tube. Centrifuge the cell solution at 1,000×g and resuspend the pellet in the 50 µl PBS. Release the virus by snap freezing the cell plate in liquid nitrogen and thaw in the 37° C. water bath. Repeat this process three times. Transfer the freeze/thaw cells into tabletop centrifuge tubes and spin out the cell debris at 6,172×g for 10 min. Measure the virus titer in the supernatants (progeny released by the carrier cell) and in the cell plate (viral replication in the carrier cell) by using the protocol for rapid titer assay described above.

For preparing neural stem cells for ex vivo loading. Remove the culture medium by aspiration. Rinse the cell monolayer once with 1×PBS. Detach the NSCs by adding 3 ml Accutase solution/10-cm to the dish of Accutase solution and incubate at 37° C. for 2-3 min. Add an equal volume of ReNCell complete medium and transfer the cell suspension into 15-ml Falcon tube. Measure the cell concentration in the cell suspension by hemocytometer. Centrifuge the cell solution at 1,000×g. Remove the medium from the tube by aspiration and wash the pellet with PBS two times. After the second wash, resuspend the NSCs in PBS at the appropriate cell concentration. To achieve optimum ex vivo loading, the carrier cells should be incubated with the oncolytic virus in a minimum volume ($5\times10^6$ carrier cells in 100-µl volume). Add the proper dose of oncolytic virus in the NSC suspension and gently triturate the cells. Incubate at room temperature for 2 h. Centrifuge the cell solution at 1,000×g and wash the pellet three times with 1×PBS. After the last spin, remove the supernatant by aspiration and resuspend the pellet in PBS at the appropriate cell concentration. Place virus-loaded NSCs on ice until ready to use. Prior to in vivo injection, cells can be maintained on ice for 1-2 h.

Example 6

Neural Stem Cells Loaded with CRAd-Surivin-pk7 Effectively Migrate and Deliver a Therapeutic Payload in Malignant Glioma One important aspect of NSC-mediated delivery of an oncolytic vector is that both the vector and the carrier are 'bio-responsive' to molecular and physiologic cues of glioma. To examine if NSCs migrate specifically in response to glioma in vivo, in vivo migration was assayed using a two-color fluorescent confocal microscopy approach. Using U87MG cells constitutively expressing green fluorescent protein (U87MG-GFP) and NSCs constitutively expressing the mCherry red fluorescent protein (NSC-mCherry), a clear and detailed anatomic representation of specific NSC migration was provided in response to glioma pathophysiology. It was observed that specific and appreciable engraftment of NSCs-mCherry cells into malignant glioma after NSCs-mCherry were injected in the hemisphere directly contralateral to the U87MG-GFP injection site (FIG. 15). These in vivo results confirm in vitro studies which demonstrate that these NSCs are capable of migrating to U87MG cells in a specific manner. Of note, it was observed that these cells were present for up to 21 days after injection, indicating that these cells engraft and remain viable in the tumor region for a sustained period of time.

Figure 16A:
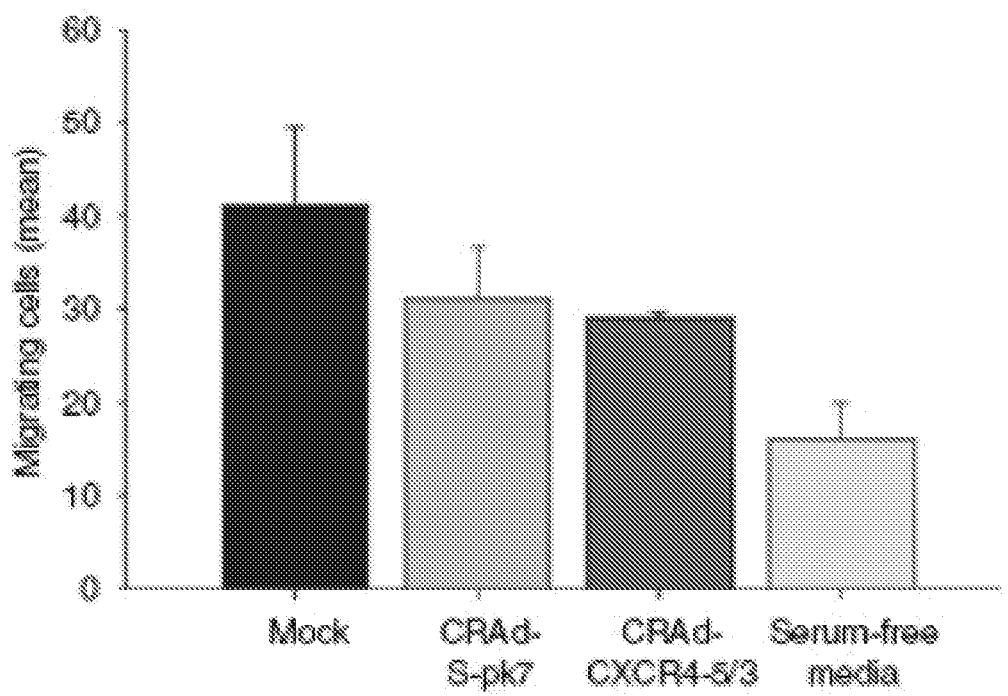
FIGS. 16A and B show that NSC deliver an oncolytic virus to U87MG cells in vitro according to one embodiment.
Figure 16B:
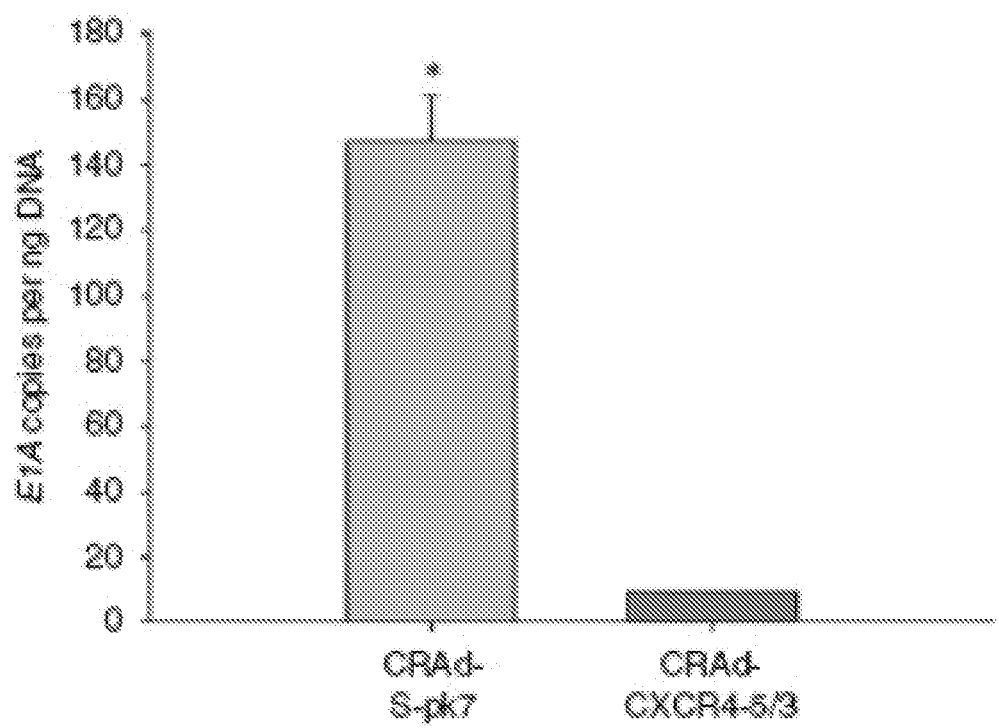
(FIG. 16B) The ability of NSC to deliver a replicating adenovirus was assessed by removing the cells at the bottom of the chamber and quantifying the number of viral E1A copy numbers forty-eight hours after initial plating of NSC at the top of the migration chamber. The graph represents the number of viral E1A copies that were quantified from cells in the bottom of the migration chamber. * indicates a p-value<0.05.

Having demonstrated the ability of NSCs to internalize and remain permissive for Ad genome amplification, these findings were tested by performing delivery studies using the two viral vectors which were shown to effectively infect NSCs, CRAd-S-pk7 and CRAd-CXCR4-5/3. This study was performed to determine which type of vector is better suited for NSC-mediated delivery; one with a low NSC replicative cytotoxicity/high U87MG cytotoxicity (CRAd-CXCR4-5/3), or one with a moderate NSC replicative cytotoxicty/high U87MG cytotoxicity (CRAd-S-pk7). Using a matrigel migration plate, these studies indicated that incubation of NSCs with an oncolytic vector does not significantly affect NSC migration (see Tyler et al, 2009. Appendix). As shown in FIG. 16, CRAd-S-pk7 demonstrated better NSC-mediated delivery, indicated by an increased E1A copy number measured in the U87MG cells plated at the bottom of the migration chamber. Taken together, FIGS. 16A and 16B indicate that NSC can internalize CRAd-S-pk7, migrate to U87MG, and remain permissive for viral replication, suggesting the feasibility of this carrier/vector combination for future in vivo studies.

Figure 17:
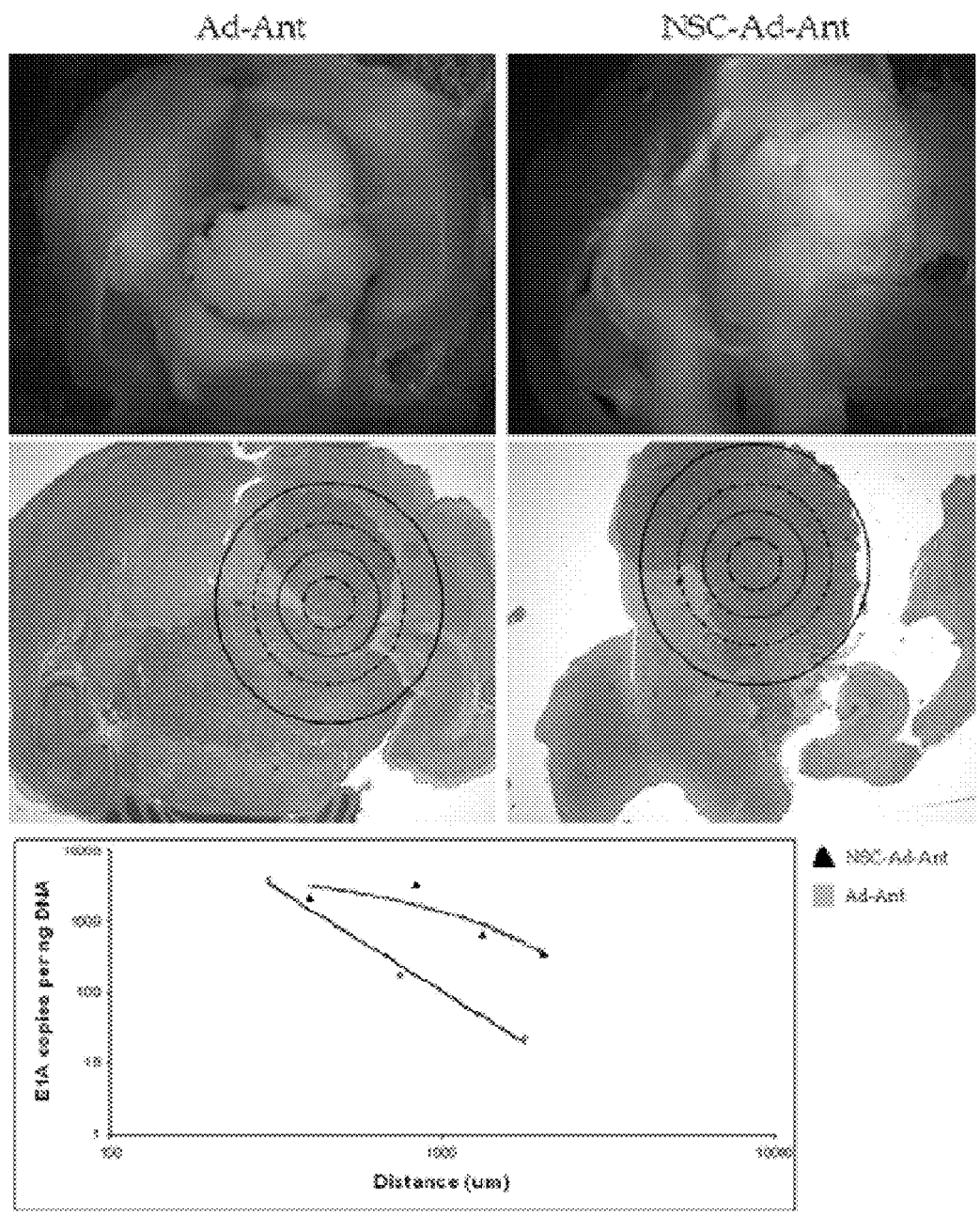
FIG. 17 shows that NSC Deliver CRAd-S-pk7 oncolytic adenovirus and enhance vector distribution in an intracranial glioma model according to one embodiment. To investigate the role of NSC in CRAd distribution throughout U87MG-GFP tumors, mice were sacrificed at day 12 after loaded NSC-mCherry implantation anterior to the tumor injection site (26 days after U87MG-GFP implantation). After fluorescent microscope observations were recorded, the same mice brains were fixed and embedded in paraffin tissue blocks. The processed tissue then underwent serial 6 μm sections onto glass slides or slides specifically made for laser capture microdissection analysis. After the injection site had been identified by H&E, sections of tissue were laser-captured at varying distances from the injection site in separate tubes. DNA was extracted from the collected tissue and the number of viral E1A copy numbers was quantified by polymerase chain reaction techniques. As shown (middle row, H&E), tissue was collected separately at increasing distances from the identified injection site by drawing concentric circles of increasing diameter around the injection site. Viral E1A copy numbers were quantified (y-axis) as a function of the distance from the injection site (x-axis). Best fit trend lines and equations were obtained using Microsoft Excel. Data shown is representative of n=4 mice from each group sacrificed at day 12 after viral injection anterior to the tumor injection site (loaded or Ad by itself). Ad: CRAd-S-pk7; Ant: Anterior injection; NSC: NSC-mCherry.

A primary goal of NSC-mediated delivery of an oncolytic adenovirus is to achieve adequate distribution of an oncolytic vector. Because these NSCs demonstrated a characteristic ability to engraft and distribute throughout the tumor bed, it was tested whether this would allow for better distribution of an oncolytic vector when compared to delivery of genes using only Ad by itself. To study NSC-mediated viral gene delivery, qPCR of laser-captured brain tissue sections from mice receiving injections of CRAd-S-pk7 was conducted with or without loading into NSC-mCherry cells anterior to the tumor injection site (FIG. 17). First, it was found that CRAd-S-pk7-loaded NSCs that were injected anterior to the U87MG-GFP injection site (NSC-Ad-Ant) demonstrated an enhanced E1A gene distribution away from the injection site and throughout the tumor. When delivered by NSC, CRAd-S-pk7 E1A gene distribution could be best-described using an exponential function ($y=5262.4e^{-0.0013x}$; $R2=0.8098$). On the other hand, CRAd-S-pk7, when injected alone (Ad-Ant), demonstrated E1A gene distribution which dropped drastically when tissue was sampled at increasing distances away from the injection site and throughout the tumor. CRAd-S-pk7, delivered alone, could be best-described using a power function ($y=5E+^{10x-2.8938}$; $R2=0.9888$). What's more, at a site corresponding to a distance of roughly 5 mm away from the site of injection, NSC-Ad-Ant delivery demonstrated approximately a 15-fold increase in E1A copy numbers (NSC-Ad-Ant: 352 copies; Ad-Ant: 23 copies). These findings indicate that NSC-mediated delivery of an adenovirus results in enhanced distribution of a given oncolytic virus.

Figure 18:
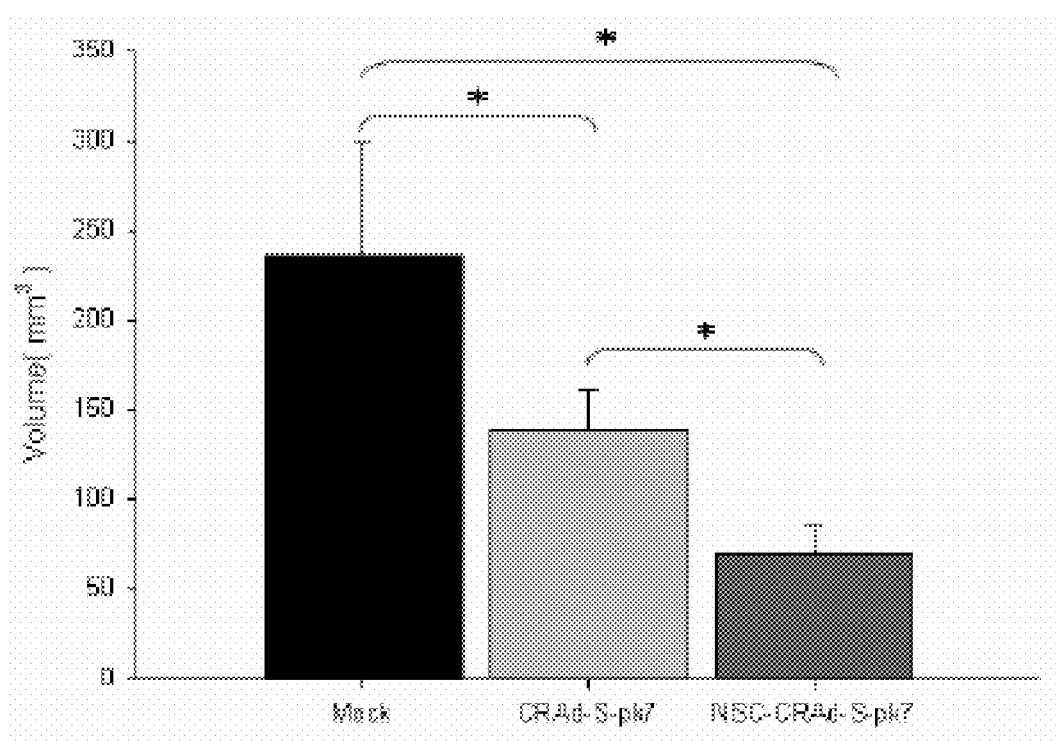
FIG. 18 illustrates that NSC-mediated delivery of a CRAd shows an enhanced antitumor effect according to one embodiment. Male, athymic (nude) mice received injections of $1 \times 10^6$ U87 tumor cells into the right hind leg (flank). One week after tumor implantation, the tumor was visible and the mice received intratumoral injections as follows: 100 μl of PBS solution (MOCK; n=5); (b) 1×107 vp of CRAd-S-pk7 (n=5); or (c) $1 \times 10^6$ NSC loaded with 1000 vp/cell (1×107 vp; n=5) of CRAd-S-pk7. Ten days after experimental treatment, tumor volumes were recorded for each treatment group. Data is presented as mean tumor volume for each experimental group, with error bars representing standard deviation in a treatment group. * indicates a p-value<0.05.

Ultimately, the benefit of any proposed therapy would be a reduction or delay in tumor growth. To investigate the therapeutic efficacy of NSC-mediated CRAd delivery, an in vivo study using thymic mice that had received injections of U87 tumor cells was performed. As shown in FIG. 18, mice receiving intratumoral injections of CRAd-loaded NSC showed an overall reduction in tumor volume (mean volume ($mm^3$): 69.4+16.5), when compared to mice receiving intratumoral injection of CRAd-S-pk7 (138.1+22.7) or saline solution (MOCK: 235.9+63.3). These results indicate a clear benefit to NSC-mediated CRAd delivery to tumors in vivo.

Example 7

Pre-clinical MRI Visualization of Therapeutic Human Neural Stem Cells in a Murine Glioma Model As with any cell-based therapy, the efficacy of NSC treatment largely depends on the ability of the stem cells to adequately target and distribute throughout tumor sites. To maximize therapeutic benefit, optimal timing of treatment regimens must be determined according to the spatio-temporal migration rate of stem cells to tumor sites. NSC-glioma distribution has been previously analyzed quantitatively using 3-D modeling and mathematical algorithms. Assuming a 50 micron radius of action around the NSCs, this model predicts a minimum of 70-90% coverage of the primary tumor mass and invasive tumor foci (Lin et al. 2007). However, dynamic determination of NSC migration and tumor distribution in real time is essential for optimizing treatments in preclinical models and designing clinical protocols. Bioluminescence and optical fluorescent imaging have been employed as non-invasive methods to track NSC migration and monitor therapeutic efficacy in animal models (Shah et al. 2005). However, the clinical utility of these imaging modalities is limited by poor tissue penetration and low spatial resolution, making them impractical for use in patient trials. Although positron emission tomography (PET) is commonly used in pre-clinical and clinical studies for visualization of various tumors and drug interactions and for understanding tumor metabolism with high specificity, its low spatial resolution and radiation dose, make it less ideal for clinical tracking of cells to tumors (Modo 2006), which require extended periods of observation.

Clinical Magnetic Resonance Imaging (MRI), however, has high spatial resolution (approximately 1 $mm^3$) with excellent soft tissue contrast for non-invasive, dynamic in vivo assessment of cellular trafficking at multiple time points. MRI cellular tracking is a rapidly expanding field, and many studies have been published during the last decade. Relevant cellular tracking studies include murine-derived stem or progenitor cells transplanted into the brain, spinal cord or vasculature using strongly T1-weighted paramagnetic contrast labels such as gadolinium (Modo et al. 2002; Modo et al. 2004), and using T2 and T2*-weighted super-paramagnetic iron oxide nanoparticles (SPIOs) (Corot et al. 2006).

To establish the feasibility of using MRI to visualize homing of NSCs to the tumor site, it was first confirmed that labeling NSCs with Fe-Pro does not affect cell viability, proliferation, survival, or migratory capacity. Next, brains were removed from mice four days after intracranial administration of FE-Pro-labeled NSCs (total of 14 days after contralateral U251 glioma implantation), and were analyzed using ex vivo MRI. Low intensity T2-weighted signal was observed at the NSC injection site, as well as at the tumor site, that was distinguishable from native low signal in the surrounding tissue (FIGS. 19A and 20A). Injection of FE-Prolabeled HB1.F3 cells ($1.0 \times 10^4$ to $2.5 \times 10^5$ cells) resulted in equally detectable hypointense MRI signals at the contralateral tumor site. Post-MRI histological analysis with Prussian blue confirmed the presence of iron labeled NSCs at the tumor site (FIGS. 19B, 20B and 27C), correlating with the hypointense MRI signals (FIGS. 19A and 20A). These data suggest that relatively low numbers of FE-Pro-labeled NSCs can be tracked by MRI for migration and distribution.

The ability of MRI to perform high resolution imaging of NSC sites was demonstrated by injecting 2 doses of 5000 FE-Pro-labeled NSCs, 500 μm apart. Two distinct signal voids were observed (FIG. 20A). These hypointense signals corresponded to the spatial distribution of the PB-positive iron-labeled cells (FIGS. 20A and 20B). A fraction of the FE-Pro-labeled NSCs migrated to and infiltrated the tumor site in all contralateral samples (FIGS. 19A, 20A and 20B). The intensity of the T2-w signal at the NSC injection site and tumor site appeared to correlate to the density of PB-positive labeled NSCs at these sites (FIGS. 20A and 20B). The estimated number of FE-Pro-labeled NSCs extracted from representative brain sections that gave rise to detectable T2-w signal loss in 300-μm thick MRI slices was as few as 600 NSCs (data not shown). Sham injection (PBS), contralateral to the tumor implants (FIG. 19C) resulted in no hypointense signal in MRI images and correlated with a lack of PB staining in these histological samples (FIG. 19D). Because the tumors were very small (~200-500 mm), which mimicked residual glioma foci, the tumors themselves did not yield detectable MRI signal.

In summary, a genetically engineered oncolytic adenovirus described herein shows significant efficacy in brain glioma models, including a CD133+ glioma stem cell model, under conditions of a large tumor burden (Ulasov et al. 2007a; Nandi et al. 2008b). The virus, CRAd-Survivin-pk7 (CRAd-S-pk7), incorporates transcriptional control of E1A expression by means of a tumor selective promoter—survivin—that is highly overexpressed and restricted to malignant brain tumors (Van Houdt et al. 2006; Ulasov et al. 2007e). Survivin expression in gliomas is associated with poor prognosis and increased rates of recurrence (Chakravarti et al. 2002; Chakravarti et al. 2004; Kajiwara et al. 203; Yamada et al. 2003). In addition to transcriptional control, transductional control was also incorporated using a polylysine binding motif within the adenoviral fiber in order to enhance the infectivity of the CRAd to heparan sulfate proteoglycans which are highly over-expressed on the surface of tumor cells. This modification has resulted in a 10,000-fold increase in viral infectivity of glioma cells in vivo vs. the wild-type vector (Zheng et al. 2007). Of high translational significance, CRAd-S-pk7 exhibits anti-tumor synergy when combined with radiotherapy (Nandi et al. 2008b) or temozolomide (Ulasov et al. 2009)-based chemotherapy, two of the standard treatment regimens utilized in patients with malignant glioma.

Transcriptional control of viral replication and transductional control of viral infectivity in overcoming one of the major limitations associated with oncolytic virotherapy, viral attenuation. To date, several vectors—including HSV and adenoviral vectors—have been tested in clinical trials and while safe, all have shown poor levels of intratumoral replication (Chiocca et al. 2004; Markert et al. 2000; Lang et al. 2003). In each case, the virus was so attenuated secondary to safety concerns that it effectively failed to exert the desired oncolytic effect in patients. In contrast, CRAd-S-pk7 contains an intact E1A region which is responsible for viral replication replicates as well as the wild-type vector. At the same time, its preclinical safety profile indicates that viral replication is restricted to tumor cells, with limited, if any, infectivity of adjacent brain.

As described herein, the use of cell carriers for delivery of CRAds helps to overcome two additional challenges associated with virotherapy, viral delivery and immune response. Neural stem cells (NSC) were used as delivery vehicles for CRAd-S-pk7 and it has been shown that NSCs-loaded with CRAd-S-pk7 not only migrate throughout the tumor mass to deliver the virus to distant tumor sites but also exert a more potent antitumor effect than local injection of the virus alone. Moreover, stem cells attenuate the immune response to CRAds, thereby further enhancing the oncolytic potential of the virotherapy described herein.

Example 8

CRAd-Survivin-pk7 Loaded HB1.F3-CD NSCs In Vitro and in Animal Models of Glioma

The Example above utilized a commercially available NSC line that is not FDA approved for clinical use in patients. Because each stem cell line has unique biotherapeutic properties with different kinetics of therapeutic virus replication and in vivo tumor homing ability, the use of the FDA-approved HB1.F3 NSC line (which is approved for use in human clinical trials) was investigated for its ability to deliver of CRAd-S-pk7 to tumors in different glioma models.

As described below, a potent oncolytic adenovirus may be delivered via an FDA-approved NSC cell line to infiltrating malignant glioma. Recently, neural stem cell (NSC) carriers were shown to be superior to mesenchymal stem cells (MSCs) in delivering CRAd-S-pk7 to orthotopic glioma models and therefore NSCs enhance the therapeutic potential of oncolytic virotherapy (Ahmed et al. 2011b). To progress to clinical trial, it is important to characterize and quantify the pharmacokinetic properties of NSCs as cell carriers. Here, it is reported that the immortalized neural stem cell line (HB1.F3-CD) is an effective cell carrier for CRAd-S-pk7. First, evidence shows that HB1.F3-CD is able to replicate and release infectious progeny that can kill glioma cell lines. Then, it was shown that inherent tumor tropic properties of HB1.F3-CD were not altered post infection in nude mice bearing orthotopic human glioma and produce infectious virus progeny for more than a week after reaching the tumor site. In addition, it was observed that the HB1.F3-CD carrier significantly reduced the non-specific therapeutic virus distribution in the animal brain. Furthermore, to better characterize the systemic biodistribution of adenovirus after intracranial injection of NSCs loaded with CRAd-S-pk7, cotton rats and hamsters were used. Carrier cells did not disseminate to distant organs and high titers of infectious progeny are present only at the injected hemisphere.

Materials and Methods

Cell Lines and Vectors. HB1.F3-CD, are a v-myc immortalized human neural stem cell (hNSC) line, derived from the human fetal brain that constitutively expresses cytosine deaminase (CD) (Kim et al. 2006a). The HB1.F3 cell line is chromosomally and functionally stable. The normal karyotype of this cell line is stable for at least 32 passages in vitro. Tumor tropism and transgene expression have also been confirmed for up to 30 passages. In vitro and in vivo studies have shown that HB1.F3 NSCs retain their inherent tumor-tropic properties, localizing to the primary tumor site and distant tumor foci without any long-term evidence of de novo tumor formation. Evaluation of directed migration in response to conditioned media from human glioma lines demonstrated that insertion of a foreign gene (i.e. cytosine deaminase, CD) into NSCs had no significant effect on their tumor tropic properties. Of note, transduction with retrovirus, lentivirus, or adenovirus did not affect their tumor tropism (Aboody et al. 2008; Lin et al. 2007; Kendall et al. 2008). The cells retain tumor-tropism in the context of dexamethasone or prior focal irradiation and remain non-tumorigenic.

NSCs were maintained as adherent cultures in DMEM supplemented with 10% fetal bovine serum (FBS) (Atlanta Biologicals, Lawerenceville, Ga., USA), 2 mmol/l L-glutamine, 100 units/ml penicillin, 100 ug/ml streptomycin and 0.25 ug/ml amphotericin B (Invitrogen, Carlsbad, Calif., USA). U87MG, U251MG, U118MG and A549 carcinoma cell lines were purchased from American Type Culture Collection (ATCC, Manassas, Va., USA); while N10 glioma was purchased from the Japanese Tumor Tissue Bank (Tokyo, Japan). All cells were grown in minimal essential medium (MEM) with 10% FBS, 100 µg/ml penicillin and 100 µg/ml streptomycin.

The replication competent adenoviral vector CRAd-S-pk7 harbors two genetic mutations (Ulasov et al. 2007a; Ulasov et al. 2007b): a) fiber modification was achieved by insertion of 7 poly-Lysine repeats (pk7) in the C-terminal of knob domain; while b) human survivin promoter drives expression of the E1A region.

Human primary brain tumor specimen and normal brain tissue may be obtained from patients undergoing surgery in accordance with a protocol approved by the IRB at the University of Chicago. Tumor specimens may be confirmed as WHO grade IV malignant glioma by an attending neuropathologist. For magnetic separation of CD133 glioma stem cells, the samples may be dissociated and resuspended in PBS containing 0.5% bovine serum albumin. CD133+ cells may be isolated using the Miltenyi Biotec CD133 isolation kit. Positive magnetic cell separation (MACS) may be done using several MACS columns in series. The purity of isolated cells may be determined by staining with CD133/2-APC (Miltenyi Biotec) or isotype control antibody following analysis on a BD FACSCalibur (BD Biosciences). Sterile aliquots of CD133+ and CD133− cells may be resuspended in complete medium and maintained for experiments. All human tissue specimens may be treated with 1% hyaluronidase (Sigma) and 2% collagenase (Sigma) enzymes and subsequently minced through 70 µm strainers. After several washings in PBS solution, cells may then be cultured in flasks containing 10% FBS-DMEM supplemented with 100 µg/mL ampicillin/streptomycin and 20 ng/ml of EGF (Chemicon) and FGF-b (Chemicon) growth factors. Cells may be maintained in a humidified atmosphere containing 5% $CO_2$ at 37° C.

Generation of green fluorescent protein (GFP)- or firefly luciferase (Fluc)-expressing HB1.F3-CD. To detect the distribution of NSCs in vivo, GFP- and Fluc-expressing HB1.F3-CD cell lines were generated. GFP expressing cells were infected with a replication-incompetent retroviral construct; whereas for Fluc, cells were infected with a replication incompetent lentiviral vector, as previously described (Ahmed et al. 2011a). A 4 ug/ml puromycin in Dulbecco's modified Eagle's medium media was used to isolate stable expressing clones.

Antibodies and other reagents. For flow cytometer, cells were stained with mouse anti-human CAR (Abcam, Cambridge, Mass.), CD138, avb3, avb5 (Ebioscience, San Diego, Calif.) and rat anti-human perlecan; followed by AlexaFluor647 (Invitrogen)-conjugated secondary antibodies. Adenovirus-transduced cells were detected using a goat anti-hexon fluorescein isothiocyanate (FITC)-conjugated antibody (Millipore, Billerica, Mass.). For immunofluorescence, FITC-conjugated anti-GFP antibody, biotin-conjugated anti-hexon and FITC-conjugated immunoglobulin controls were purchased from Abcam; human CD44 rabbit monoclonal antibody purchased from Epitomics (Burlingame, Calif.); AlexaFluor555-streptavidin and Alexafluor350 donkey anti-rabbit were purchased from Invitrogen.

Flow Cytometry. For detection of surface receptors, cells were detached using trypsin/EDTA and stained with primary antibodies for 1 hour at 4° C., followed by secondary antibodies for 30 minutes at 4° C. For quantification of adenovirus transduction of HB1.F3-CD, 48 hours after infection, cells were detached, washed with PBS and then permeabilized with a methanol/acetone solution (as per Millipore protocol) before staining with FITC conjugated goat anti-Hexon. Cells were analyzed using a BD FACS Canto cytometer (Becton Dickinson, Franklin Lakes, N.J.) and graphs were rendered using FloJo software (TreeStar, Ashland, Oreg.).

Cell viability assays. NSC and glioma viability was determined using the MTT cell proliferation kit (Roche Diagnostics, Mannheim, Germany). Briefly, 3000 cells/well were plated in a 96-well plate the day before infection. NSCs were infected with different concentrations of CRAd-Spk7; instead glioma cells were incubated with the supernatant of previously infected NSCs. Viability was determined three days later, as described by the manufacturer's protocol.

Viability of glioma cells after incubation with the supernatant of previously infected NSCs was also assessed via crystal violet. NSCs were infected earlier with CRAd-S-pk7 at different concentrations 1, 10, 50 and 100 infectious units per ml (IU/ml). Five days later, the supernatant was collected and used to infect glioma cell lines and A549 carcinoma plated in 24-well plates. Three days later viability was determined. Shortly after aspirating the media the cell layer was covered with the crystal violet solution (1%) and incubated for 20 minutes at room temperature. Then wells were washed carefully and let dry at room temperature. Images were taken with an inverted microscope.

Determination of adenoviral E1A copies via quantitative PCR. Total DNA from cultured cells or animal tissues was extracted using DNeasy Tissue Kit (Qiagen, Valencia, Calif., USA). Adenoviral E1A gene expression was quantified via quantitative real-time PCR using iQ™ SYBR green super-mix (Bio-Rad, Hercules, Calif., USA), using primers described elsewhere (Sonabend et al. 2009). For each animal model separate standard curves of E1A copies containing 100 ng DNA were generated. The sensitivity of this assay was set to detect as low as 5 E1A copies per 100 ng DNA. All samples were run in triplicates using an Opticon2 system (Bio-Rad). Results are expressed as E1A copy number per 100 ng DNA.

Immunohistochemistry. For immunohistochemistry (IHC), brains were sectioned in 10 µm thick sections. After thawing, sections underwent fixation/permeabilization with a solution of 50/50 acetone/methanol, at −20° C. for 5 minutes. Then, the slides were washed with ice-cold phosphate buffered saline (PBS) and blocked with 10% BSA for 30 minutes. The slides were incubated overnight at 4° C. with primary antibodies and 1 hour at room temperature with the secondary antibody. After washing the excess antibody, slides were mounted with Prolong® Gold antifade reagent with 46-diamidino-2-phenyl indole (DAPI) (Invitrogen). Fluorescent images were documented with an inverted Axiovert200 Zeiss microscope (Carl Zeiss Microscopy, Thornwood, N.Y.).

In vivo tracking of NSCs with bioluminescence imaging. For in vivo tracking of NSC migration to the tumor, photon flux imaging (Ahmed et al. 2011a) was used. Mice were imaged for Fluc activity following intraperitoneal injection of D-luciferin (4.5 mg/animal in 150 µl saline), and photon counts were recorded 10 minutes after D-luciferin administration by using a cryogenically cooled high-efficiency charged-coupled device camera system (Xenogen IVIS200 Optical Imaging System, Caliper Life Sciences, Mountain View, Calif.).

Determination of adenoviral progeny titers. For quantification of the infectious progeny released or inside the NSCs, the supernatant and cell mass were collected separately. Cells were resuspended in 200 µl of PBS and freeze-thawed three times to release the viral progeny. Then, the supernatant and the cell suspension were centrifuged for 5 minutes at 4000 rpm to spin down the cell debris and 20 µl from each sample were used to infect a confluent layer of 293-HEK (Human Embryonic Kidney) cells, as per Adeno Rapid-X Titer Kit protocol (Clontech, Mountain View, Calif., USA). 48 hours later the cell layer was fixed/permeabilized with methanol and stained for hexon plaques. Infectious units (i.u./ml) values quantified through this protocol are similar to plaque forming units (Pfu).

For determination of adenoviral titers in animal organs, the tissue was collected at the time points indicated, resuspended in PBS to provide a concentration of 1 µg/µl and then homogenized. For each sample, the same amount of tissue, in 50 µl, was freeze-thawed three times, the debris was spun down and 20 µl were used to infect 293-HEK cells, as above. Instead, for determination of circulating infectious viral progeny titers in animals, their serum was analyzed by using the same protocol.

Detection of v-myc positive NSCs via nested PCR. A 2 step nested PCR was used to detect presence of v-myc in animal tissues. In the first step, a 588 base pair (bp) region from the v-myc gene was amplified using forward primer 5'-CCTTTGATTTCGCCAAT-3' (SEQ ID NO:1), reverse 5'-GCGAGCTTCTCCGACACCACC-3' (SEQ ID NO:2). By using 1 µl from the first PCR and a second pair of primers: forward 5'-TCACAGCCAGATATCCAGCA-GCTT-3' (SEQ ID NO:3), reverse 5'-ACTTCTCCTCCTC-CTCCTCG 3' (SEQ ID NO:4) a 166 bp sequence from the v-myc gene was amplified. As a DNA loading control a housekeeping gene, GAPDH was used: forward primer 5'-CATTGACAACTACAT-3' (SEQ ID NO:5) and reverse 5'-TCTCCATGGTGGTGAAGAC-3' (SEQ ID NO:6), to amplify a 220 bp sequence. The sensitivity and specificity was determined by spiking animal DNA with different dilutions of human neural stem cell DNA. PCR products were resolved on a 2% agarose gel, stained with ethidium bromide, and bands were quantified using the Chemidoc Gel documentation system (Bio-Rad).

Ex vivo loading. The total number of cells to be injected in vivo was based on previous studies, where infection with 50 i.u./cell of CRAd-S-pk7 virus resulted in maximum progeny released over time with minimum toxicity to carrier cell and proved superior survival benefit to glioma bearing mice (Ahmed et al. 2011a; Ahmed et al. 2011 b). To optimize the ex vivo loading protocol, infection efficiency of CRAd-S-pk7 virus was examined. For this, cell suspension and monolayer of HB1.F3.CD cells were incubated with DMEM (10% FBS) containing 50 i.u./cell CRAd-S-pk7 virus for 1, 2 and 4 hours. Infected cells were than washed and cultured for 24 hours. Cells were than harvested and subject to FACS analysis with goat anti-Hexon FITC conjugated antibody (Millipore) and measurement of viral DNA replication by PCR method as described previously.

Animal experiments. Murine models have been widely used for preclinical gene therapy studies with adenovirus and other viruses. Particularly in the field of oncology, nude mouse xenografts models, as well as transgenic glioma models have provided valuable models for in vivo analyses of therapeutic modalities. Thus, murine model has unique advantages as a method for preclinical evaluation of new therapeutic agents including CRAd agents.

Since human Ads replicate only in human cells, toxicology studies with Ad vectors are hampered by the lack of a permissive nonhuman host. Recent evidence, however, suggest that the Syrian Hamster is a rodent species that is fully permissive for human Ads (Thomas et al. 2006). Therefore the efficacy of the vector was examined using this model.

Animals were cared for according to a study-specific animal protocol approved by The University of Chicago Institutional Animal Care and Use Committee. Intra-cranial (IC) engraftment, distribution and survival of HB1.F3.CD-GFP loaded or not with CRAd-Spk7 were studied in normal mouse and hamster brains and in the presence of orthotopic U87 human glioma xenografts in nude mice. In brief, seven to eight-week-old male nude mice (Harlan Laboratories, Madison, Wis., USA) were anesthetized with an IP injection of ketamine hydrochloride (25 mg/ml)/xylazine (2.5 mg/ml) cocktail. For IC injection, a midline incision was made, and a 1-mm burr hole centered 2 mm posterior to the coronal suture and 2 mm lateral to the sagittal suture was made. Animals were placed in a stereotactic frame and injected with a 26 Gauge Hamilton needle $2 \times 10^5$ U87 cells or PBS, in 2.5 µl volume, 3 mm deep into the brain. Twenty-one days after tumor implantation, mice were injected IC, using the same burr hole as above, with $5 \times 10^5$ HB1.F3.CD-GFP loaded or not with 50 i.u./cell of CRAd-S-pk7.

For determination of HB1.F3.CD-GFP cell viability after IC injection, mice were sacrificed at the described time points. Their brains were snap-frozen in a mixture of 2-Nm-ethyl-bromide and methyl-butane; then cut coronally at the injection site in 2 pieces and embedded in OCT in a dry ice-methylbutane bath. Sections of 10 μm, spanning approximately 2 mm of tissue, were stained with the described antibodies. The selection criteria for high power field (HPF) were based on quantifying those areas with the highest number of HB1.F3.CD-GFP cells. That meant counting GFP positive cells at the injection site in normal mouse brains; while in glioma bearing mice cells were counted on the tumor-normal brain interface. The mean number of GFP (+) positive per HPF (630×) was plotted to compare between different groups.

Four to five week-old male hamsters (Harlan Laboratories) were anesthetized with an intramuscular (IM) injection of ketamine hydrochloride (25 mg/ml) and injected IC as above with $5 \times 10^5$ HB1.F3-CD-GFP loaded or not with 50 i.u./cell of CRAd-S-pk7, 5 mm deep into the brain. Hamsters were sacrificed on day 1, 7 and 30; then brains were processed as above. Intracranial CRAd-S-pk7 replication delivered by direct injection or loaded onto carrier cells, HB1.F3-CD, was quantified via qRT-PCR and titer assay. Three weeks after injecting $2 \times 10^5$ U87 cells IC, the same location was injected with either $2.5 \times 10^7$ i.u. CRAd-S-pk7 per animal or $5 \times 10^5$ HB1.F3-CD loaded with 50 i.u./cell of CRAd-S-pk7. Animals were sacrificed 4, 7 and 14 days later; their brain hemispheres separated, then homogenized. Viral replication was quantified via qPCR for adenoviral E1A and by using AdenoX titer kit for progeny.

Systemic distribution and replication of CRAd-S-pk7 delivered IC by HB1.F3-CD carrier cells, was studied in hamsters and cotton rats. Cotton rats were anesthetized with an intraperitoneal (IP) injection of ketamine hydrochloride (25 mg/ml)/xylazine (2.5 mg/ml) cocktail, while hamsters underwent the same procedure as above. $5 \times 10^5$ HB1.F3-CD cells loaded or not with 50 i.u./cell of CRAd-S-pk7 were injected per animal. Animals were sacrificed at the indicated time points and their brain hemispheres separated (the injected right hemisphere vs. left hemisphere). To quantify systemic adenovirus distribution, serum, lungs, kidneys, liver and spleen were harvested from each animal. All tissues were weighed; the same amount of PBS (μl) per μg tissue was added and then homogenized. Total DNA was isolated form animal tissues using DNeasy Tissue Kit (Qiagen). Adenoviral E1A gene expression was quantified by quantitative real-time PCR using iQ™ SYBR green supermix from Bio-Rad (Hercules, Calif.). All samples were run in triplicates using an Opticon2 system (Bio-Rad). Results are expressed as E1A copy number per 100 ng DNA. Adenoviral titers in animal's tissues and serum (Table 1, below) were determined.

TABLE 1

Detection of infectious adenoviral progeny in animal tissues

| Tissue | Day Sacrificed | Nude Mouse | Hamster | Cotton Rat |
|---|---|---|---|---|
| Serum | Day 1 | NA | 0/6 | 0/6 |
|  | Day 4 | NA | 0/6 | 0/6 |
|  | Day 7 | NA | 0/6 | 0/6 |
|  | Day 14 | NA | 0/6 | 0/6 |
|  | Day 30 | NA | 0/6 | 0/6 |
| Right Hemisphere (injected) | Day 1 | NA | 4/6 | 5/6 |
|  | Day 4 | 5/5 | NA | NA |
|  | Day 7 | 5/5 | 0/6 | 0/6 |
|  | Day 14 | 5/5 | 0/6 | 0/6 |
|  | Day 30 | NA | 0/6 | 0/6 |
| Right Hemisphere (non-injected) | Day 1 | NA | 0/6 | 0/6 |
|  | Day 4 | 4/5 | NA | NA |
|  | Day 7 | 2/5 | 0/6 | 0/6 |
|  | Day 14 | 1/5 | 0/6 | 0/6 |
|  | Day 30 | NA | 0/6 | 0/6 |

Infectious adenoviral progeny was determined in the tissues of injected animals at the indicated time points. NA, means that such tissue was not available (NA) for the indicated animal at that specific time point.

Statistical analysis. The statistical analysis presented was performed using GraphPad Prism Software, v4.0 (GraphPad Software, La Jolla, Calif.). Where applicable, a standard independent two sample t-test was applied. A P value<0.05 was considered statistically significant (*P value<0.001; P value<0.01; *P value<0.05).

Results

Figure 21A:
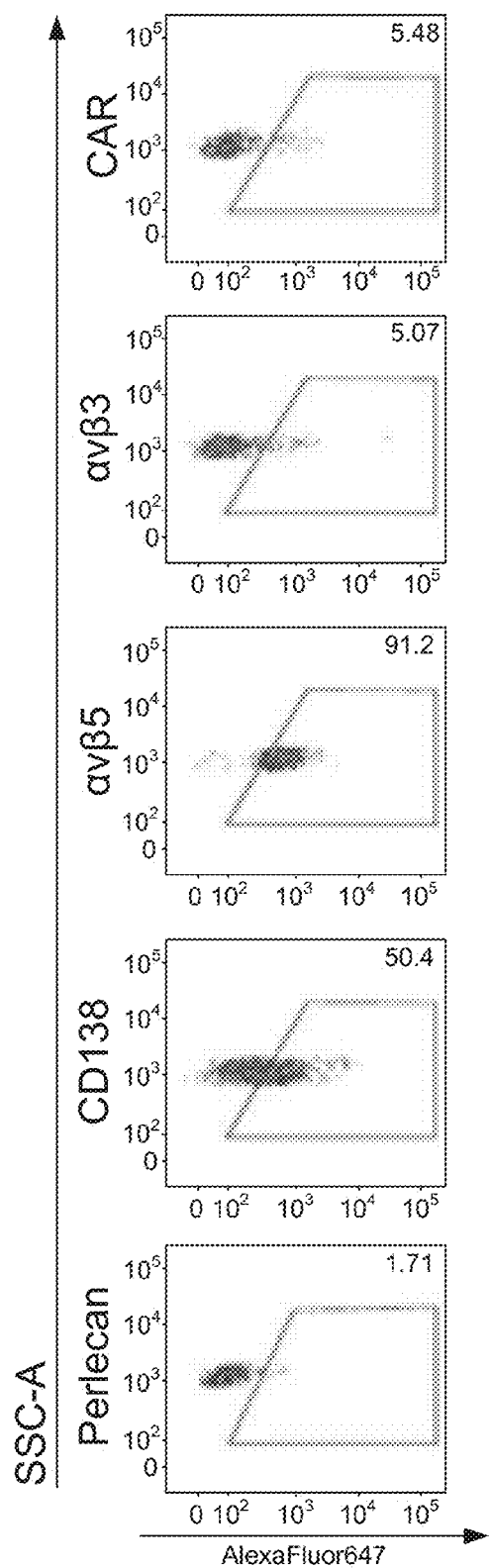
FIGS. 21A, 21B, 21C, 21D, 21E and 21F illustrate that the HB1.F3-CD neural stem cell line is permissive to CRAd-S-pk7 replication according to one embodiment.

Permissiveness of HB1.F3-CD neural stem cell carrier for CRAd-S-pk7 infection. The goal of ex-vivo loading is to effectively infect as many carrier cells as possible. Thus, to evaluate the permissiveness of NSC to CRAd infection, the expression of adenovirus cell attachment and internalization receptors in NSCs was examined (FIG. 21A). Although NSCs expressed minimal levels of the adenovirus primary attachment receptor CAR, about 50% of NSCs expressed CD138, one of many heparin sulfate proteoglycans that can function as a primary binding receptor. Also, 91% of NSCs expressed the $\alpha_v\beta_5$ internalization receptor.

Figure 21B:
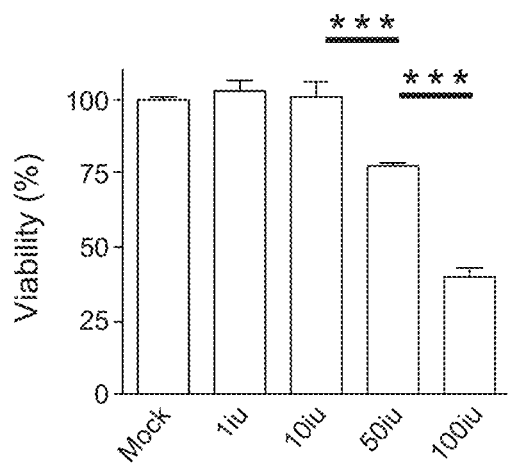
Figure 21C:
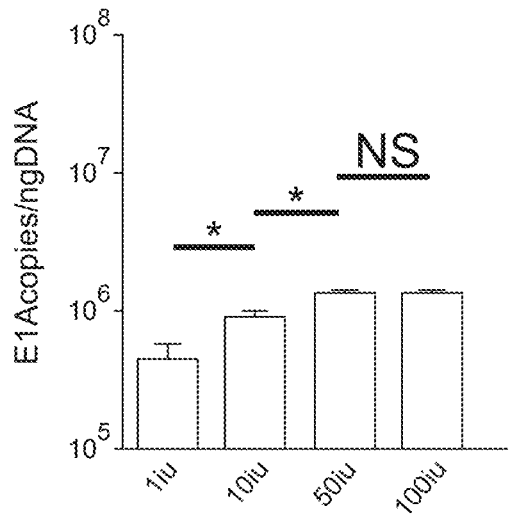
Figure 21D:
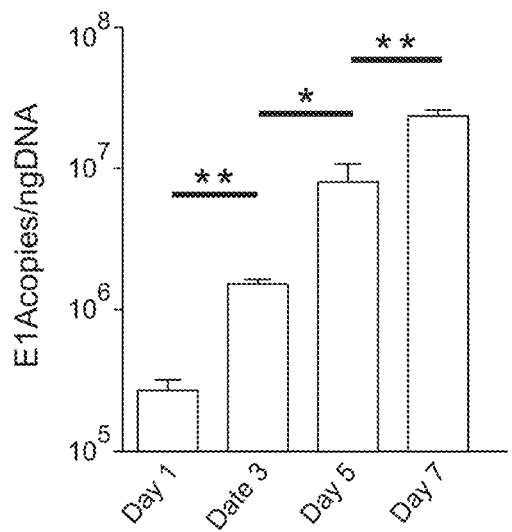

In order to establish an optimal loading dose for in vivo delivery, an MTT assay was performed to evaluate the toxicity induced by CRAd-S-pk7 virus during this process (FIG. 21B). At the low dose (1-10 i.u./cell) CRAd-S-pk7 did not induce toxicity to NSCs. However, the viability was reduced about 25% at the dose of 50 i.u./cell and about 50% when NSCs were infected with 100 i.u./cell. Next, to establish the replication kinetics of CRAd-S-pk7 in NSCs, the NSCs were infected/loaded with varying concentrations of CRAd. As shown in FIG. 21C, the viral DNA replication at day 3 was highest when loaded with 50 i.u./cell, amounting to $1.6 \times 10^6$ E1A copies/ng DNA. At this loading dose, the viral burst size was about 5 and 2-fold larger than the loading dose of 1 and 10 i.u./cell respectively (**p=0.002 and *p=0.024). When NSCs were loaded with 100 i.u./cell, the CRAd-S-pk7 DNA replication did not improve significantly as compared to 50 i.u./cell (p=0.56), and NSC viability was significantly reduced at this level. Combining toxicity data along with DNA replication data, a loading dose of 50 i.u./cell was selected to further evaluate NSCs as a carrier system for oncolytic virotherapy. At this loading dose, viral DNA replication continued to increase up to 7 days post infection (FIG. 21D).

To establish an optimal exposure time in order to achieve maximum infectivity/loading, while minimizing oncolytic virus mediated toxicity, adenovirus transduction rates were measured by analyzing Ad-hexon expression and viral DNA replication after varying CRAd-S-pk7 incubation times with both HB1.F3-CD adherent monolayer and suspension cells (1-4 hours). After incubating NSCs in suspension at the loading dose of 50 i.u./cell for 2 hours, a maximum loading/infection of the CRAd-S-pk7 was achieved (**p=0.002)

Figure 21E:
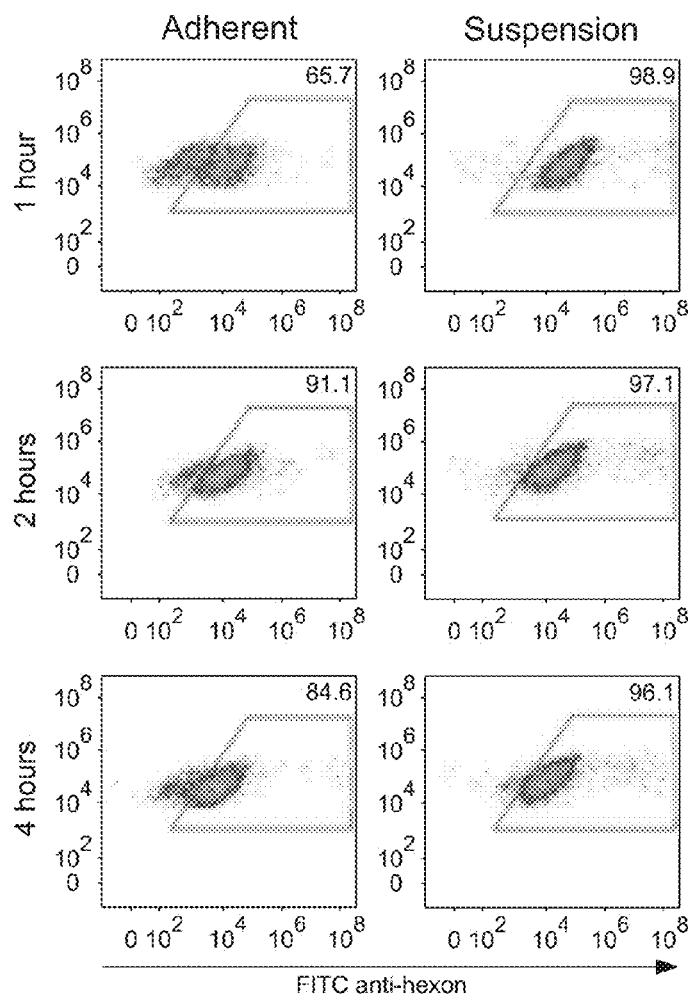
Figure 21F:
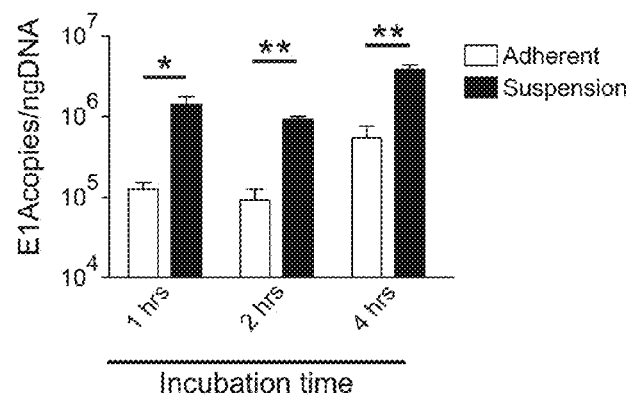

(FIGS. 21E, 21F). Based on these data, it was decided to load/infect NSCs in suspension at the loading dose of 50 i.u./cell for 2 hours.

Figure 22A:
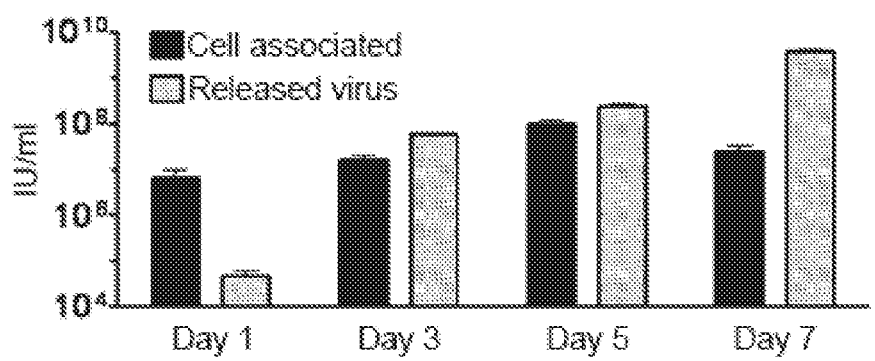
FIGS. 22A, 22B and 22C show Adenoviral progeny released from infected HB1.F3-CD effectively lyses glioma cell lines according to one embodiment.
Figure 22B:
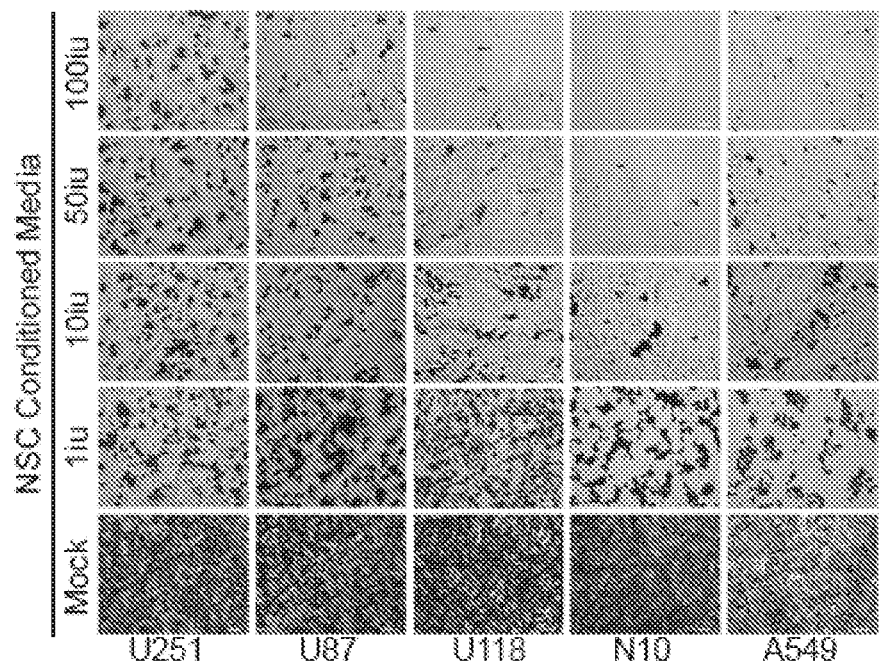
Figure 22C:
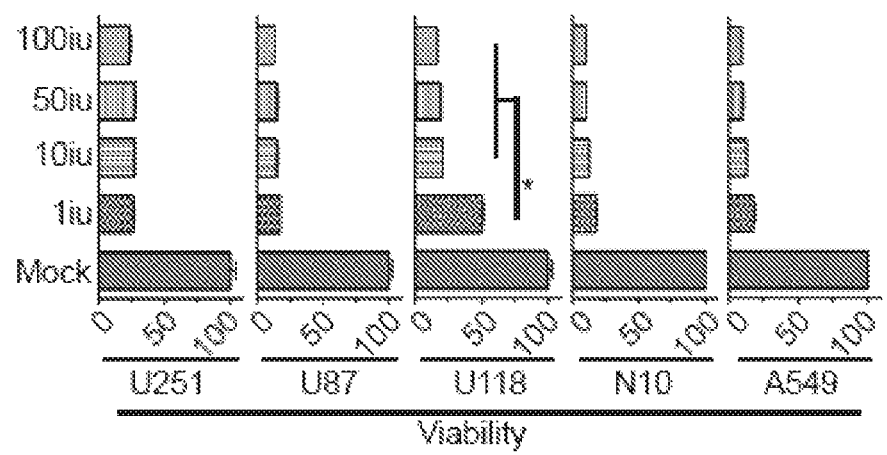

HB1.F3-CD loaded with CRAd-S-pk7 produces infectious progeny and induces glioma cell oncolysis. To assess the ability of this carrier system to produce infectious adenoviral progeny, tumor cells were incubated with the supernatant of previously infected HB1.F3-CD cells. At day 5 post infection the intracellular virus titer reached its maximum. At day 7 post infection, the intracellular viral titer decreased as the titer of the cell-free viral progeny reached its maximum level, indicating that it takes about 5-6 days for the CRAd-S-pk7 to complete its life cycle in the HB1.F3.CD carrier system (FIG. 22A). Next, to evaluate the oncolytic capacity of the viral progeny released from CRAd-S-pk7 infected NSCs, a panel of four human glioma cell lines was exposed to the supernatant of NSCs loaded/infected with various doses of CRAd-S-pk7 for 120 hours. FIG. 22B is a pictorial representation of tumor cell toxicity produced by the therapeutic viral progeny from infected HB1.F3-CD cells. Regardless of the loading dose, the released CRAd-S-pk7 viral progeny was able to induce tumor cell killing in all tested glioma cell lines at day 3 post incubation (FIG. 22C). As compared to the tested glioma cell lines, NSC carrier cells were much more resistant to CRAd-S-pk7 mediated oncolysis (FIG. 21B, 22C) (Ahmed et al. 2011 b).

Figure 23A:
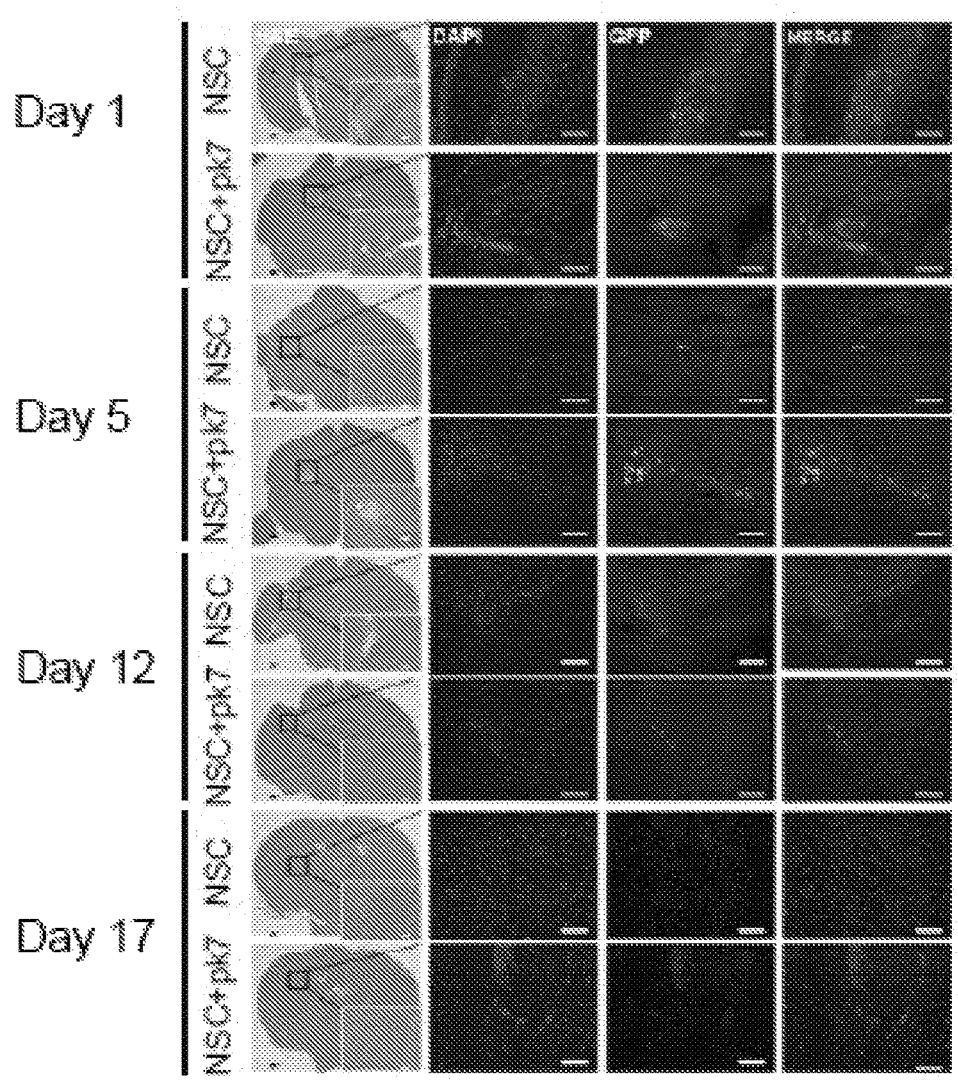
FIGS. 23A and 23B show intracranial distribution of the HB1.F3-CD carrier cells loaded or not with CRAd-S-pk7 after injection in nude mouse brains according to one embodiment.
Figure 23B:
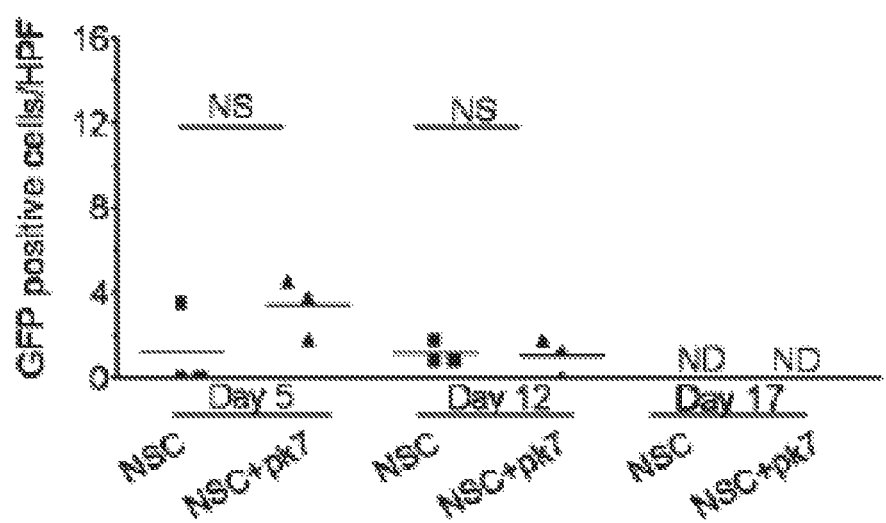

Distribution of the CRAd-S-pk7 loaded HB1.F3-CD carrier cells in nude mouse brains. The intrinsic tumor homing properties of NSCs are the key attribute to their utility as a cell carrier for oncolytic virotherapy. Therefore, it is important to examine how adenovirus loading affects the engraftment, distribution and survival of the implanted NSC in the animal brain. In order to monitor the implanted stem cell distribution effectively, the HB1.F3-CD cells were further modified to express GFP by using a replication incompetent retroviral vector, as described in Material and Methods. $5 \times 10^5$ NSCs loaded with or without the CRAd-S-pk7 virus (50 i.u./cell) were stereotactically implanted in the brains of nude mice. Viability and distribution of NSCs were assessed at the indicated time points (1, 5, 12 and 17 days post NSC implantation) via immunohistochemistry. On day 1 (FIG. 23A), a majority of the implanted cells were localized and clumped together at the injection site. On day 5, the clumping was significantly reduced and most of the cells were located at the implanted site. Most importantly, CRAd-S-pk7 loading appeared to have had minimal or no effect on the viability of the carrier cell as measured by the number of GFP positive HB1.F3-CD cells present in the section of animal brains at day 5 and day 12 post implantation (FIG. 23B). Also to be noted: NSCs were not detectable in the contralateral hemisphere (NSCs were implanted on the right side). At day 17 of post implantation, the NSCs were undetectable in animal brains via immunohistochemical analysis.

Figure 24A:
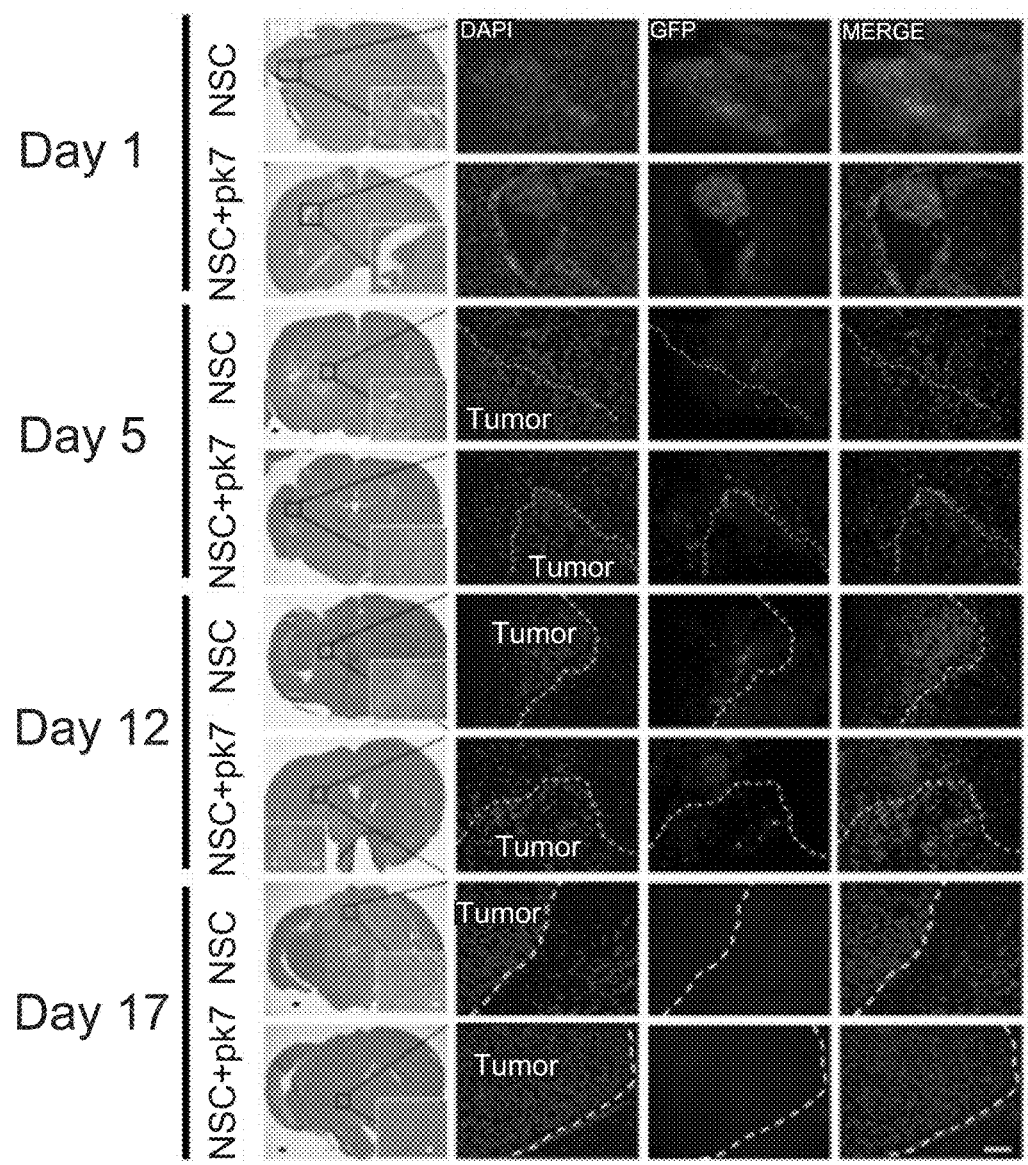
FIGS. 24A, 24B and 24C show intracranial distribution of the HB1.F3-CD carrier cells loaded or not with CRAd-S-pk7 after injection in nude mouse brains bearing human orthotopic U87 glioma xenografts according to one embodiment.
Figure 24B:
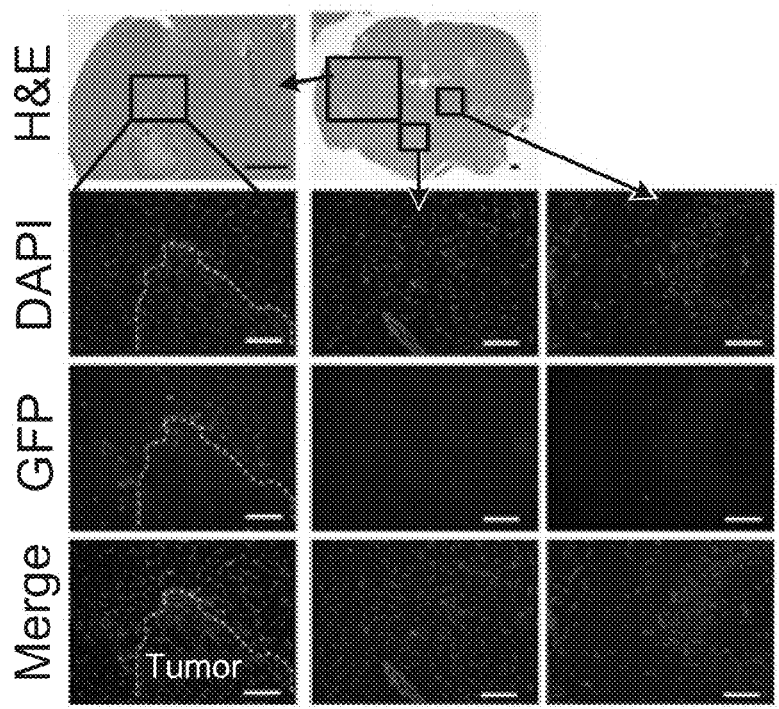
Figure 24C:
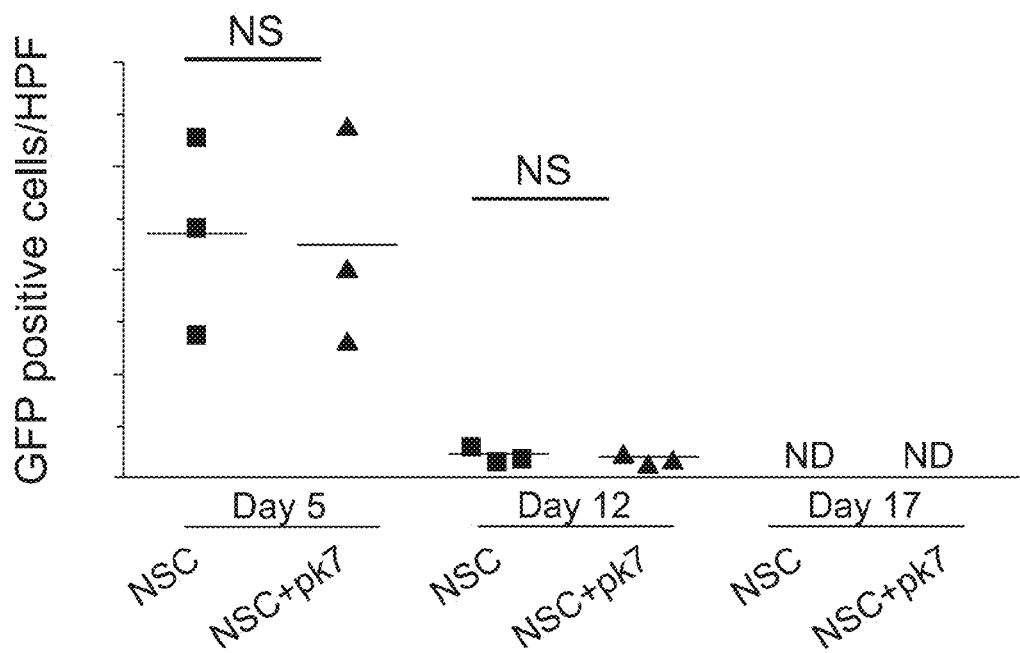

Distribution of CRAd-S-pk7 loaded HB1.F3-CD in nude mouse brain bearing orthotropic U87 human glioma xenograft. Next, the adenovirus loading effects on the NSCs' engraftment, distribution and survival, were examined in the animal brain bearing a human glioma xenograft. On day 1, the distribution was very similar to the animal brain without any tumor as cells clumped at the injection site (FIG. 24A). On day 5, implanted cells were distributed around the tumor (FIGS. 24A and 24B). Again, NSCs were not observed migrating to the hemisphere contralateral to the implanted hemisphere. The total number of NSC-GFP positive cells that surrounded the U87 xenograft did not differ between infected vs. non-infected NSC, showing no difference in cell survival (FIG. 24C). After 12 days post implantation, the viability of NSCs drops to 1 NSC/hpf (high power field) for both infected and noninfected and became undetectable at 17 days post implantation. Taken together, this data indicates that loading oncolytic virus into NSCs had a minimal effect on their viability and engraftment capacity in vivo.

Figure 25A:
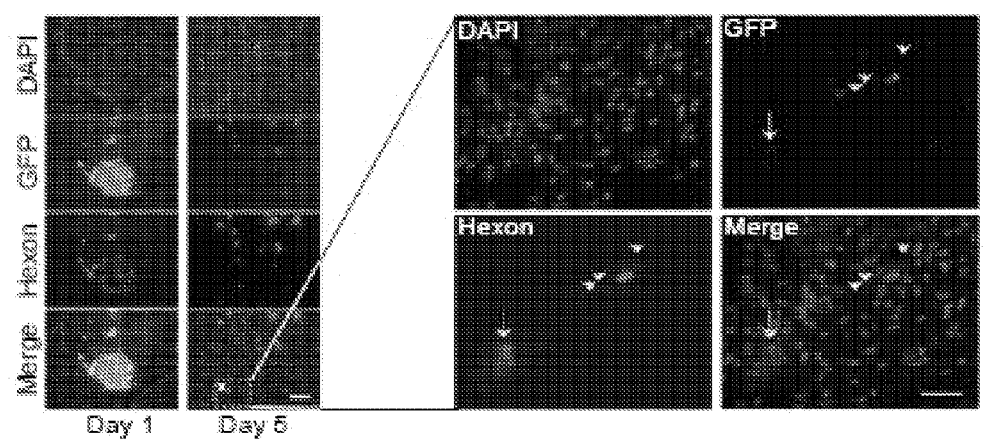
FIGS. 25A, 25B, 25C and 25D show in vivo hand-off of CRAd-S-pk7 from NSCs to glioma cells according to one embodiment.

In vivo delivery of the therapeutic CRAd-S-pk7 virus by the HB1.F3-CD carrier cell. To assess the clinical relevancy of carrier-based oncolytic virotherapy, virus hand off ability and the intracranial distribution of the therapeutic virus was investigated in vivo. The HB1.F3-CD cells infected with CRAd-S-pk7 virus were implanted in the brain of nude mice bearing U87 human xenograft tumor as described previously. Mice were sacrificed at days 1 and 5 post implantation and animal brains were subject to immunohistochemical analysis for GFP (carrier cell specific) and adenoviral hexon protein. As shown in FIG. 25A, implanted carrier cells were clumped together at the injected site at 24 hours post implantation. At 5 days post implantation, the carrier cells surrounded the tumor and, most importantly, the GFP negative tumor cells were positive for hexon staining (FIG. 25A, right panel, arrows). Taken together, these data indicate that carrier cells loaded with CRAd-S-pk7 are able to hand off the therapeutic virus to their surrounding tumor cells.

Figure 25B:
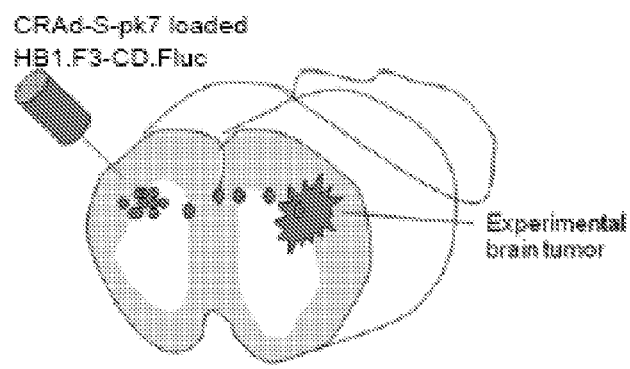
Figure 25C:
Figure 25D:
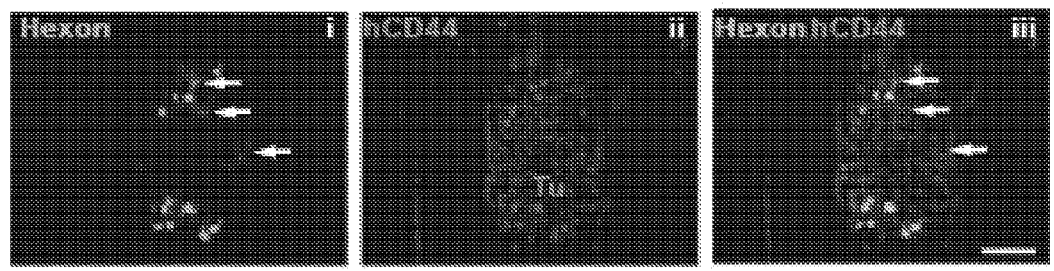

Glioma foci/microsatellites can be located further away from the initial implanted site of the therapeutic NSC and loaded NSCs will have to migrate longer distances before delivering the payload. To examine whether CRAd loaded HB1.F3.CD can migrate to disseminated tumor foci and deliver the therapeutic payload effectively, it was first established HB1.F3.CD cells stably expressing F-luciferase (Luc) gene by lentivirus mediated transduction. The HB1.F3.CD-Luc cells were then loaded with 50 i.u./cells of CRAd-S-pk7 and implanted in the contralateral hemisphere of the U87 xenograft containing animals (FIG. 25B). As shown in FIG. 25C with bioluminescence imaging, at 72 hours post implantation adenovirus loaded HB1.F3-CD.Fluc cells were able cross the midline and migrate to the contralateral hemisphere. Animals were sacrificed and brain tissue was subject to immunohistochemical analysis for adenovirus hexon positive HB1.F3.CD cells in the U87 tumor foci stained with human specific anti-CD44 antibody (FIG. 25D-ii). Ad hexon positive cells were observed in the xenograft tumor foci located in the contralateral hemisphere indicating that implanted CRAd loaded HB1.F3.CD cells were able to migrate to the distance tumor foci and deliver the therapeutic payload (FIG. 25D-i-iii).

Figure 26A:
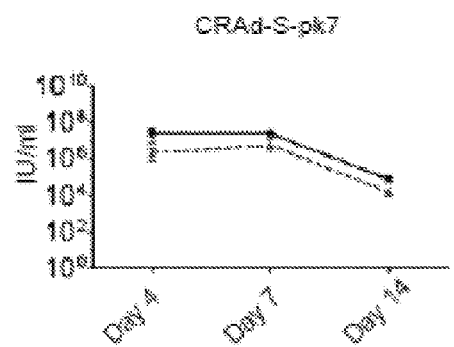
FIGS. 26A, 26B, 26C and 26D show carrier cell adenovirus delivery achieves lower off-site viral titers according to one embodiment. Nude mice harboring orthotopic U87 malignant glioma in the right hemisphere were injected, using the same burr-hole, with HB1.F3-CD-GFP cells loaded with CRAd-S-pk7 or the equivalent amount of oncolytic adenovirus ($2.5 \times 10^7$ i.u./mouse). In vivo CRAd-S-pk7 replication (n=5 per group per time point) was quantified for each hemisphere separately (right hemisphere/injected vs. left hemisphere/non-injected) via qRT-PCR (FIG. 26a, 26b) for adenoviral E1A and by adenoviral progeny titer assay (FIG. 26c, 26d). Error bars represent SEM; *, P value<0.001; , P-value<0.01; *, P-value<0.05; Non significant differences are not depicted.

Carrier cell delivery reduces off-site levels of adenoviral titers. Intracranial distribution of CRAd-S-pk7 post implantation was then evaluated for the naked virus or virus loaded HB1.F3-CD cell carrier, in nude mouse brains bearing human glioma xenografts. Five animals from each group were sacrificed at 4, 7 and 14 days post implantation and were subject to viral distribution analysis by examining the presence of the viral DNA as well as infectious progeny. As shown in FIG. 26A, the amount of infectious viral particles recovered from both the injected and the contralateral hemisphere of the animal brains that received naked CRAd-S-pk7 virus was very similar. On the other hand, when the therapeutic virus was delivered loaded into carrier cells, the viral distribution was more robust (about 2-log greater) and localized at the injected hemisphere (FIG. 26B) as compared to the contralateral hemisphere (**p<0.01). As shown in Table 1, the infectious viral progeny was recovered in two out of five animal brains from the contralateral non-injected hemisphere (FIG. 26D) as compared to all five animals in the virus alone group (*p<0.05).

Figure 27A:
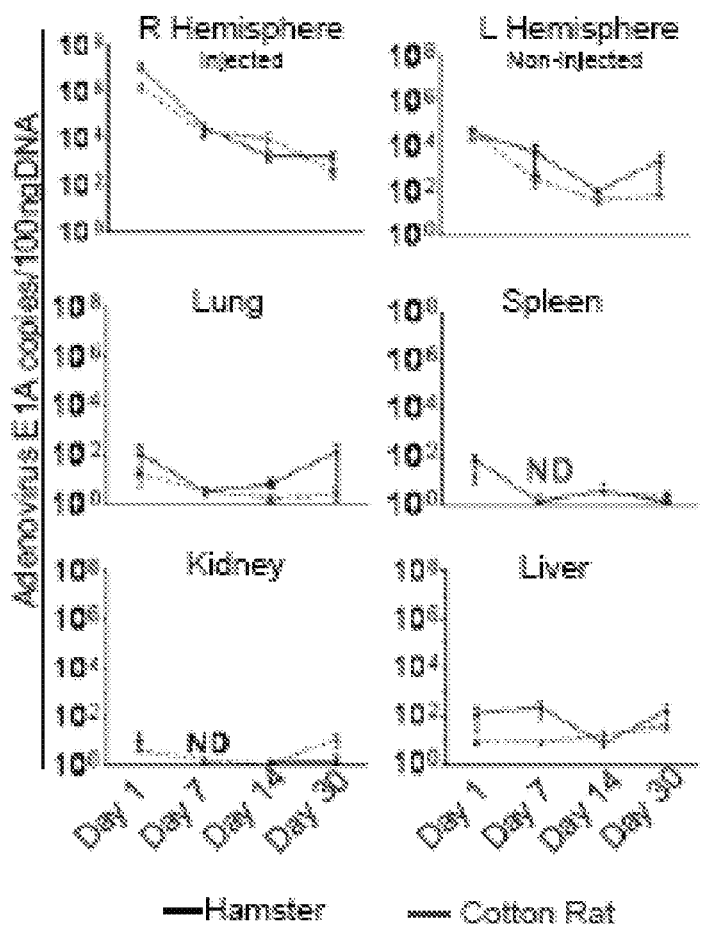
FIGS. 27A, 27B, 27C and 27D show biodistribution of CRAd-S-pk7 and HB1.F3-CD in hamsters and cotton rats according to one embodiment.
Figure 27B:
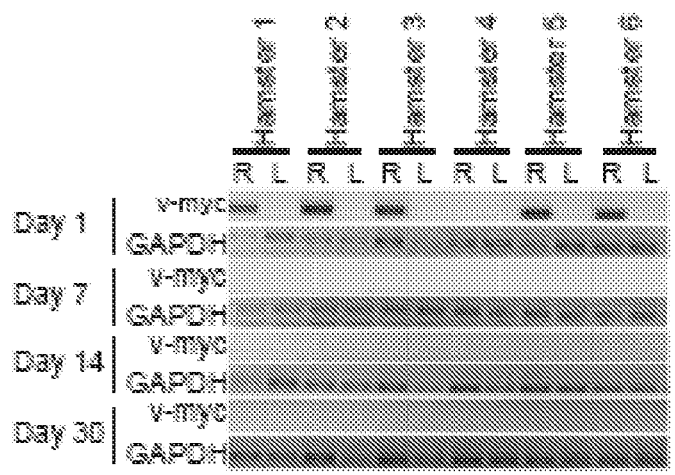
Figure 27C:
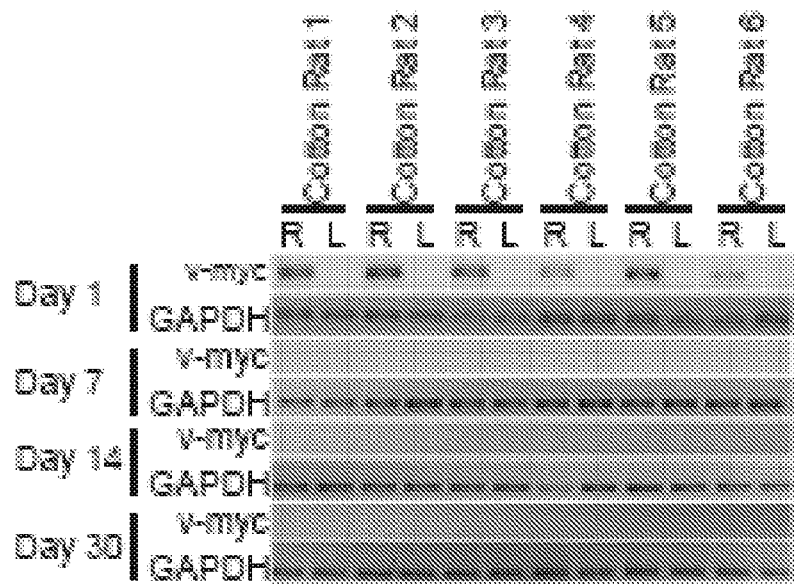
Figure 27D:
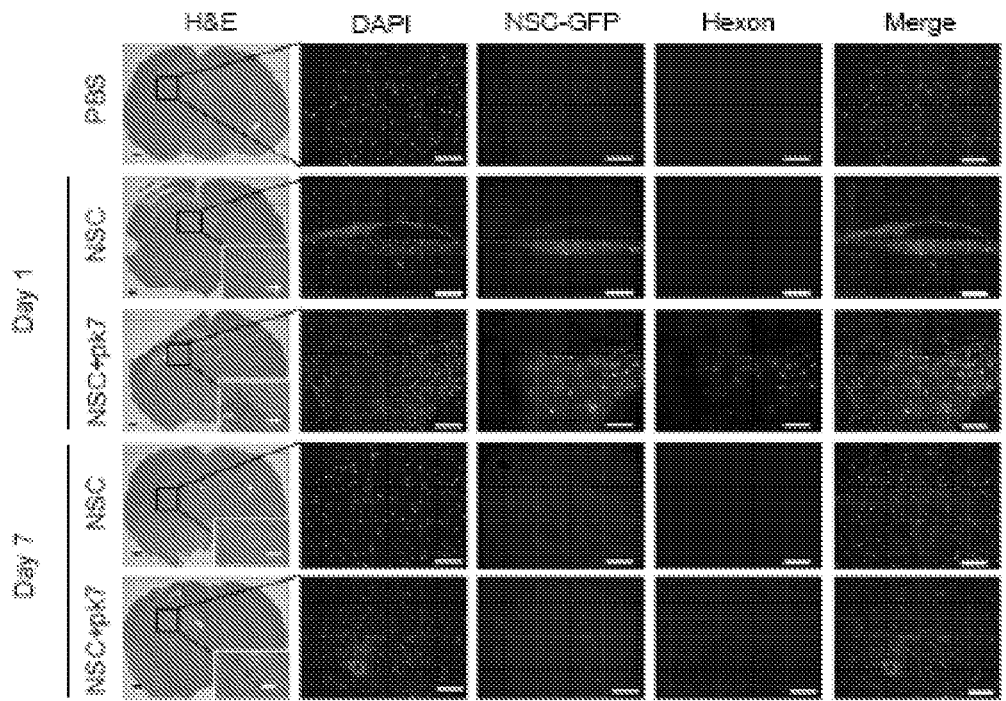

Evaluation of intracranial viral distribution in the semi-permissive cotton rat and hamster model. To examine the adenovirus replication in immunocompetent semi-permissive hosts, cotton rat and hamster animal models, a previously established quantitative real-time PCR (qRT-PCR) protocol was utilized to monitor viral DNA copies over time (Sonabend et al. 2009). In both hamster and cotton rat models, adenoviral replication was predominately localized at the injection site (right hemisphere) and over time the viral replication gradually decreased to less than 100 copies of E1A (FIG. 27A). The recovered adenoviral E1A copies on the non-injected left hemisphere were about 2-log lower as compared to the injected site. Moreover, infectious progeny were only detected in the injected right hemisphere (Table 1). The liver was the only organ outside of the brain where viral replication was detectable up to 7 days post implantation. In other organs, viral DNA was only detectable at 24 hours post implantation. Additionally infectious progeny were not detected in hamster or cotton rat sera (Table 1). To investigate whether loaded NSCs were migrating away from the original injection site, a highly sensitive, nested PCR based method was used detect DNA from a single HB1.F3-CD cell in 100 ng of host DNA. By using this method a HB1.F3-CD specific v-myc PCR signal was detected in the implanted right hemisphere of the brain in both of the animal models (FIGS. 27B and 27C). The HB1.F3-CD signals were only detectable at 24 hours post implantation. HB1.F3-CD distribution in the tissue of implanted brains was very similar to that observed in the nude mice experiments. Both CRAd loaded and unloaded HB1.F3-CD cells were predominately found clumping together at the injected sites after 1 day of implantation (FIG. 27D). However, viable HB1.F3-CD cells were not observed at 7 days post implantation. Taken together, carrier cells were only detectable in the implanted hemisphere of the animal brains at 24 hours post implantation.

Discussion

Virus-infected cells can serve as delivery vehicles to improve adenovirus distribution in tumors, hide the virus from the host immune system and act as in situ virus producing factories that generate oncolytic virus progeny at the tumor beds. Specifically, cells with inherent tumor tropic properties are a very attractive candidate for the anti-glioma oncolytic virotherapy carrier system. Neural stem cells constitute one such carrier system that has demonstrated unique tropism towards brain neoplasia in animal models. In the last decade many studies have shown that NSCs expressing/carrying the therapeutic payload have anti-glioma activity and based on these promising results, the FDA has recently approved the HB1.F3-CD immortalized stem cell line for a clinical trial (Thu et al. 2009).

The carrier properties of both MSCs and NSCs have been studied (Tyler et al. 2009; Sonabend et al. 2008). As shown by the studies described herein, these carrier systems may be loaded with adenovirus to increase its distribution to the tumor site by acting as micro-factories for virus replication. Also, stem cell carrier systems not only hide the payload from the immune system but have the capability to suppress antiviral innate immune responses (Ahmed et al. 2011b; Ahmed et al. 2010a). This allows for enhanced dissemination, increased persistence of adenovirus and can result in enhanced therapeutic benefits. Moreover, delivery of oncolytic adenovirus in the orthotropic human glioma xenograft model via NSCs can improve the median animal survival by ~50% (Ahmed et al. 2011a). Nevertheless, such carrier systems need to be optimized before undergoing clinical testing.

Any new therapeutic intervention must go through rigorous pharmacological evaluation before it can translate into a clinical setting. Accordingly, the studies described above characterize the pharmacokinetic properties of glioma-tropic oncolytic adenovirus loaded HB1.F3-CD carrier system in three different animal models: nude mouse, hamster and cotton rat. It was shown that NSCs can be loaded with CRAd-S-pk7 and release new infectious progeny that can effectively lyse glioma cells. Further, it was observed that when injected in mice brains bearing human glioma xenograft, NSCs loaded with CRAd-S-pk7 home to glioma and hand off therapeutic adenoviral payload to tumor cells. In models permissive to adenovirus replication (hamster and cotton rat), high adenoviral E1A replication was detected only at the injection site. Furthermore, adenoviral replication declines and becomes barely detectable over 30 days. On the other hand, implanted NSCs were detected only at the injected hemisphere for less than a week. Thus, data presented in this report argue in favor of the possible future utilization of a neural stem cell-based carrier to enhance the therapeutic potential of the anti-glioma oncolytic virotherapy.

The clinical outcome of any cell carrier system for oncolytic virotherapy relies on proper synchronization of three important steps in both space and time (Power & Bell 2008). The ideal carrier cell should i) be easily infected with the therapeutic virus; ii) produce high levels of progeny that can infect target tumor cells; iii) be relatively resistant to oncolytic virus mediated toxicity. Even though the HB1.F3-CD cell carrier system express a very minimal amount of the primary adenovirus attachment receptors (CAR) (FIG. 21A), they express high levels (50%) of CD138 (Syndecan), a heparan sulfate proteoglycan receptor that binds to the polylysine residues (pk7) of modified CRAd-S-pk7 fibers. The adenoviral internalization into target cells is mediated by the integrin family receptors $\alpha v \beta 3$ and $\alpha v \beta 5$ and almost 91.2% of HB1.F3-CD cells express $\alpha v \beta 5$ on their surface.

Once internalized, the virus starts replicating its genome within 24 hours and gradually increases over time (FIGS. 21D, 22A). The cell associated infectious progeny reached its maximum at day 5-post infection, while the cell free virus titer reached its peak at $1 \times 10^9$ i.u./ml after 7 days of infection (FIG. 22A). The fundamental objective of the ex vivo loading phase is to productively load/infect as many cell carriers as possible with minimal exposure to the therapeutic virus. With the loading dose of 50 i.u./cell, the maximum amount of viral DNA replication was observed and only about a 25% decrease in the carrier cell viability at 120 hours post loading (FIGS. 21B, 21C). Based on this data a loading dose of 50 i.u./cell was selected for use moving forward. The infection of HB1.F3-CD cells in suspension with the CRAd-S-pk7 at a loading dose of 50 i.u./cell lead to the infection of almost 100% of carrier cells after a period of 2 hours (FIGS. 21E, 21F). It would be desirable to optimize the ex vivo loading capacity of each carrier cell/oncolytic virus pair system as it's governed by the oncolytic virus life cycle within the particular cell type used for delivery; for example the standard infection protocol for VSV infection specify a shorter (1 hour) loading time for Vaccinia virus (Power & Bell 2008).

Figure 26B:
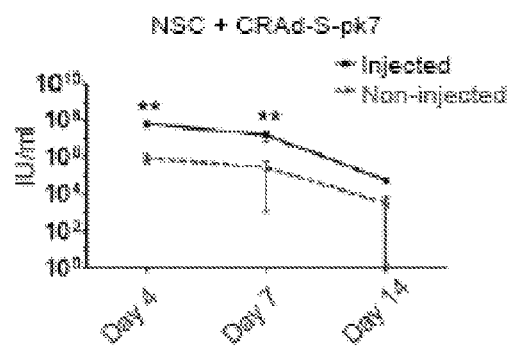
Figure 26C:
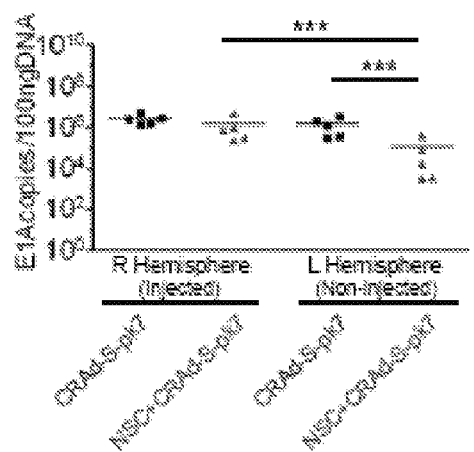
Figure 26D:
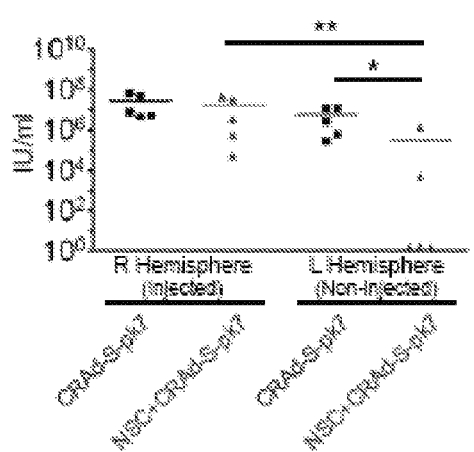

An effective cell carrier system must be able to produce high quantities of infectious progeny upon arrival at the tumor site. HB1.F3-CD cells loaded/infected with 1 i.u./cell of CRAd-S-pk7 virus produced sufficient amounts of infectious progeny to induce oncolysis on human glioma cell lines (FIGS. 22B, 22C). Moreover, loaded cells produced high intratumoral levels of progeny at the tumor site that were similar to naked CRAd injection (FIGS. 26C, 26D). Most importantly intracranial delivery of the oncolytic adenovirus loaded into HB1.F3-CD significantly decreased the unwanted distribution of therapeutic virus out of the animal brain (***p<0.001), thus reducing the vector related toxicity (FIG. 27A). Cell carriers can deliver CRAd-Spk7 to the tumor site when injected at a distance from the tumor and NSCs tumor tropic properties are not diminished by the loading/infection of oncolytic adenovirus (Ahmed et al. 2011a).

The timing of the oncolytic viral life cycle is an important determinant of maintaining the tumor homing ability of the carrier cells. To achieve true 'targeted-delivery' of the therapeutic virus, the carrier cell accumulates in tumor beds before the viral progeny are released. According to in vitro observations, the viral progeny released from the HB1.F3-CD carrier cell peaked at day 7 post loading (FIG. 22A), therefore carrier cells should ideally reach the tumor site before this time. Further, a majority of the tumor specific migration of NSCs occurred within 24-48 hours post implantation (Ahmed et al. 2011a). Therefore, the replication cycle of CRAd-S-pk7 oncolytic virus in the HB1.F3-CD should accommodate the tumor homing ability of this carrier system.

The preclinical characterization of most oncolytic adenovirus vectors have thus far been restricted to human xenograft models in immunodeficient mice. While these immunodeficient mice can serve as valuable models to evaluate the therapeutic efficacy of adenovirus based oncolytic vectors, the virus does not replicate in mouse tissue, and therefore prevents us from being able to vigorously evaluate safety and vector related toxicity. On the other hand, semipermissive animal models to adenovirus replication, such as cotton rat and hamster, have proven to be very useful for studying oncolytic adenovirus safety profiles (Toth et al. 2005; Toth et al. 2007; Thomas et al. 2007). Accordingly, the biodistribution and safety profile of CRAd-S-pk7 after intracranial delivery of loaded NSCs in these immunocompetent animal models was characterized. To assess the distribution of both the adenovirus and carrier cell, sensitive PCR methods were used.

Both models show similar distribution of NSCs and CRAd-S-pk7. NSCs are found only at the injection site without any non-specific migration. However, a decreased amount of the non-specific spread of CRAd was observed when delivered with the carrier cell system, as evidenced by the 2 log lower adenoviral titers in the contralateral hemisphere (FIGS. 26B, 26C, and 27A). It has been previously reported that after intracranial delivery the oncolytic virus can spread throughout the brain due to the presence of media such as cerebro-spinal fluid (CSF) (Studebaker et al. 2012). However, this may be less of a concern as compared to other target tissue, such as the liver, as the effect of neutralizing antibody appears to be far weaker in the brain due to the distinct nature of the immune system in the CNS (Lowenstein 2002; Bessis et al. 2004).

Moreover, reports from early clinical trials with adenovirus vector-based anti-glioma gene therapy have uniformly reported sufficient tolerability and absence of serious adverse events (Pulkkanen & Yla-Herttuala 2005). In this study, after the delivery via carrier cells, adenovirus replication in the brain decreased to barely detectable levels over 30 days. Also, very low levels of adenovirus E1A copies were detected in the other harvested organs (FIG. 27A) and none of the animals implanted with NSC loaded CRAd-S-pk7 showed any sign of systemic toxicity. Taken together, intracranial injection of adenovirus loaded NSCs appears safe in all three tested animal models with no adverse side effects observed. Even though cotton rats were able to support oncolytic adenovirus replication more effectively than hamsters (Sonabend et al. 2009), they are more aggressive and difficult to handle during any surgical procedure (Niewiesk & Prince 2002; Niewiesk 1999).

Most of the pre-clinical studies on the efficacy of NSC-based anti-glioma therapeutics have been evaluated to target disseminated tumor sites beyond the primary tumor in small animal models. To study the efficacy of virus loaded cell carriers in animals with larger brains and therefore larger sized tumors than nude mice, a spontaneous GBM model in the brachycephalic canine breeds may be used (Candolfi et al. 2007). Canine GBM is highly invasive and mimics human GBM characteristics such as necrosis with pseudopalisading, neovascularization, and endothelial proliferation (Stoica et al. 2009). The most important aspect of the canine model is its comparable brain size to humans. This characteristic is essential for a good preclinical model in order to precisely assess such pharmacokinetic properties as toxicity, dosage, side effects, as well as more accurately measure delivery strategies. Furthermore, the therapeutic efficacy of most anti-glioma gene therapeutic approaches are commonly evaluated in immunocompromised animal models using xenogenic cell lines post transplantation with only a short interval of time between engraftment and treatment. The circumstances in human GBM completely differ as tumor initiation is usually sporadic and clinical symptoms can be observed months to years after initial establishment of tumor, resulting in increased heterogeneity. Moreover, when a carrier cell system is injected into animal models such as the one used herein, it becomes vulnerable to the immune response generated towards any foreign antigen. The effects of such an immune response were observed when a rapid decline of implanted stem cell numbers in the immunocompetent cotton rat and hamster models were observed over time (FIGS. 27B, 27C, and 27D). As a result, the NSC viability is even more affected in immunocompetent animal models as compared to immunocompromised nude mice (FIGS. 23 and 24). In the clinical setting, some degree of immune response towards the stem cell-based carrier may be observed, as the immortalized HB1.F3.CD cell line may be mismatched to human leukocyte antigens and thus may be allogeneic to glioma patients. Despite low expression of MHC class II and co-stimulatory molecules, in vitro allorecognition of NSCs by peripheral blood lymphocytes has been reported (Ubiali et al. 2007; Ahmed et al. 2010b).

These observations favor of the use of readily available autologous NSC sources. However, there are some limitations to currently available technologies for isolating and expanding autologous NSCs in culture to produce a sufficient number of viable cells for a successful transplantation. Thus, in some embodiments, immunosuppressive drugs may be used to prolong the half-life of the therapeutic NSCs. Taking this into consideration, the studies described herein suggest that such an immune response would be less robust as compared to direct adenovirus injection (Ahmed et al. 2011 b). Most currently available cancer gene therapies have failed to sustain anti-tumor effects in the tumor microenvironment long enough to achieve clinically relevant therapeutic efficacy (Cattaneo et al. 2008). This is partly due to the mounting of a host immune response against the administered therapeutic agents. A wealth of preclinical data suggests that in vivo transplanted NSCs can act as immunosuppressants (Einstein & Ben-Hur 2008). Results from several studies in both rodent and non-human primate models of experimental autoimmune encephalomyelitis (EAE) indicate that NSCs transplanted by either intrathecal or intravenous injection promote bystander immunodulation within the CNS via the release of various soluble molecules (Einstein & Ben-Hur 2008; Pluchino et al. 2003). It was reported that CRAd loaded NSC transiently secret immunosupressive cytokines IL-10 and significantly reduced CRAd mediated CNS injury (Ahmed et al. 2011a). This immunosuppressive quality of NSCs is a very attractive attribute for a cell carrier given that it will allow therapeutic payloads such as oncolytic viruses to be shielded from host immunosurveillance. Therefore, the NSC-based oncoviral delivery system would likely be safer than the direct virus injection into the tumor.

In summary, it has been demonstrated that a neural stem cell-based cell carrier can significantly improve the safety and biodistribution profile of the anti-glioma oncolytic virotherapy in an animal model. Such a carrier system has shown the ability to support the delivery of a similar dose of therapeutic virus at the implanted site, as compared to a naked virus, and also reduce the leaky distribution of the virus throughout the animal brain. Moreover, nude mouse, cotton rat and hamster animal models were compared to evaluate the pharmacological and safety profiles of the cell-based oncolytic virotherapy.

Example 9

The Timing of Neural Stem Cell-based Virotherapy is Critical for Optimal Therapeutic Efficacy when Applied with Radiation and Chemotherapy for the Treatment of Glioblastoma In order to advance the NSC-based virotherapy described herein toward a clinical trial, the studies described below were performed to characterize the safety profile and efficacy of the novel therapy in an adjuvant setting with the current standard of care for GBM, radio- and chemotherapy (XRT-TMZ). In preclinical models, the oncolytic virus (OV) G47Δ acts synergistically with TMZ in effectively killing glioma stem cells, an important population of glioma cells believed to be significant for disease initiation, advancement, recurrence, and resistance to conventional therapy (Kanai et al. 2012). In the clinical setting, oncolytic reovirus given to patients in combination with chemotherapy was well tolerated in a phase I/II clinical trial for treatment of head and neck cancers (Karapanagiotou et al. 2012). Furthermore, in a phase II/III clinical trial that enrolled 36 patients with glioma, patients who received the experimental arm consisting of adenovirus encoding HSV-Tk and intravenous ganciclovir injections followed by postoperative radiotherapy survived 24.7 weeks longer than patients who received standard postoperative radiotherapy alone (Immonen et al. 2004).

Therefore, because of the promising interactions between viruses and conventional therapy, to the studies described below were conducted to investigate the three-way cooperation between cell carrier, oncolytic adenovirus, and conventional XRT-TMZ for the treatment of glioma. To date, no one has previously investigated the interactions of these three therapies together. Therefore, for the first time, the therapeutic efficacy and safety monitoring of CRAd-S-pk7-loaded NSCs is determined when in the presence of XRT-TMZ for the treatment of human GBM. The goals of this study were to mimic the clinical situation in an experimental model and develop a clinically relevant protocol for combining stem cell-based oncolytic therapy with conventional treatment for GBM patients. Here it was demonstrated that combining stem cell-based oncolytic therapy with XRT-TMZ does not negatively impact the properties of stem cells as a virus carrier or manufacturer in situ. Furthermore, in an orthotropic xenograft model of human glioma established with a patient-derived GBM line, CRAd-S-pk7-loaded NSCs administered intracerebrally in concurrence with XRT-TMZ treatment extended the median survival of mice when compared to treatment with XRT-TMZ alone. Moreover, NSCs should be administered prior to XRT-TMZ treatment because of the possible radiosensitizing effect of oncolytic adenovirus to glioma cells. Thus, data presented in this study will allow us to evaluate an NSC-based cell carrier for the targeted delivery of anti-glioma oncolytic virotherapy and develop a rational clinical protocol for the filing of a future investigational new drug (IND) application for a human clinical trial involving recurrent and newly diagnosed patients with malignant glioma. These data support both the efficacy and safety of this cell carrier-based anti-glioma oncolytic virotherapy.

Materials and Methods

Cell culture. HB1.F3-CD, a v-myc immortalized human NSC line, originated from the human fetal brain and was modified to constitutively express cytosine deaminase (CD) (Kim et al. 2008; Kim et al. 2006). Glioma cell lines U87MG and U251 MG were purchased from the American Type Culture Collection (Manassas, Va., http://www.atcc.org), whereas GBM43-Fluc and GBM39, both primary human glioma specimens isolated from patients, were kindly provided by Dr. C. David James of the University of California, San Francisco. All adherent cultures were maintained in Dulbecco's modified Eagle's medium (Cellgro, Manassas, Va., http://www.cellgro.org) supplemented with 10% fetal bovine serum (Atlanta Biologicals, Lawrenceville, Ga., http://www.atlantabio.com), 2 mmol liter$^{-1}$ L-glutamine, 100 units ml$^{-1}$ penicillin, 100 μg ml$^{-1}$ streptomycin, and 0.25 μg ml$^{-1}$ amphotericin B (Invitrogen, Carlsbad, Calif., http://www.invitrogen.com).

For subculture and in vivo passaging of the cells, HB1.F3-CD, U87MG, and U251MG cell lines were cultured at 37° C. in a humidified cell incubator, with 5% CO2 and were subcultured for experimentation using 0.25% trypsin/2.21 mmol/1 EDTA solution (Cellgro, Manassas, Va.). GBM43 and GBM39 were passaged in the flank of mice in order to maintain their original tumor phenotype and molecular signature. For carrying out experiments flank tumors were processed through 70 μm cell strainers (BD Biosciences, Franklin Lakes, N.J.), treated with ACK lysing buffer (Lonza, Allendale, N.J.), and cultured in DMEM 10% FBS. The remaining cells were stored in liquid nitrogen in a 90% FBS/10% Dimethyl Sulfoxide (DMSO) (Sigma-Aldrich, St. Louis, Mo.) freezing medium and resurrected as needed.

Viral vectors. The replication-competent adenoviral vector CRAd-S-pk7 is made up of two genetic mutations to confer tumor selectivity and replication: (a) a fiber modification by the insertion of seven polylysine (pk7) into the C terminus of the wild-type fiber protein and (b) a survivin promoter inclusion upstream of the viral E1A gene (Ulasov et al. 2007). CRAd-S-pk7 was used for viral loading of NSCs at 50 infectious units (IU) per cell for 1.5 hours at ~23° C. in a suspension of 1×10$^6$ cells per 100 μl of phosphate-buffered saline (PBS) or as adherent cells for all experiments (Thaci et al. 2012; Ahmed et al. 2011; Chatrchyan et al.). ONYX-015 adenovirus was used only in immunoblotting experiments at the infectious dose of 50 IU per cell.

Chemotherapy and Radiotherapy. For all studies, the cells and mice received XRT in accordance with the University of Chicago's radiation safety guidelines and protocols. All cells received a single dose of 2 Gy XRT. For animal studies, 10 Gy fractioned dose radiotherapy (2 Gy for 5 consecutive days) was used. The animals were irradiated with a lead cover shielding their entire body, with only their heads exposed. For in vitro studies, cells were administered TMZ based on their IC50 values when also treated with XRT simultaneously, which were as follows: HB1.F3-CD=15 µM; U251=44 µM; U87=25 µM; GBM43=37 µM; and GBM39=50 µM. For in vivo studies, the mice received 2.5, 5, 10, or 30 mg/kg TMZ via intraperitoneal injection.

TMZ preparation and dilution. For in vitro studies, 100 mg of TMZ (temozolomide) was dissolved in DMSO to yield a stock concentration of 50 mM. TMZ was further diluted in culturing medium to yield desired working concentrations. For in vivo studies, 100 mg of TMZ was diluted in DMSO to obtain a stock concentration of 10 mg/kg. TMZ was further diluted in sterile PBS to obtain the final working concentrations.

Flow Cytometry. For detection of surface antigens, the cells were stained with primary antibodies for 1 hour at 4° C. in fluorescence-activated cell sorting (FACS) buffer (0.5% bovine serum albumin—0.05% sodium azide) in PBS. After the cells were washed, secondary antibodies were added in FACS buffer for 0.5 hour at 4° C. After fluorescent labeling, the samples were washed and acquired on a BD FACSCanto cytometer (BD Biosciences, Franklin Lakes, N.J., http://www.bdbiosciences.com) and analyzed using FlowJo (Tree Star, Ashland, Oreg., http://www.treestar.com). The following primary antibodies were used: fluorescein isothiocyanate (FITC)-conjugated anti-Oct4 (Millipore, Billerica, Mass., http://www.millipore.com), phosphatidylethanolamine (PE)-conjugated anti-Nestin (BD Biosciences), biotinylated Sox2 (R&D Systems, Minneapolis, Minn., http://www.rndsystems.com), and PE-conjugated active caspase-3 (BD Biosciences). For a secondary antibody, streptavidin conjugated to Alexa 647 (Invitrogen) was used. All antibody dilutions were used according to the manufacturer's recommendation.

Evaluation of Relative Gene Expression by Quantitative Real-Time Polymerase Chain Reaction. Relative expression of mRNA transcripts was evaluated for the human receptors vascular endothelial growth factor receptor 2 (VEGFR2), CXCR4, CD44, and urokinase plasminogen activator receptor (uPAR) after exposure to 2Gy of XRT and 15 µM TMZ for 12 and 24 hours. Transcript levels were measured and analyzed using quantitative real-time polymerase chain reaction (qRTPCR). Briefly, total cellular RNA was sequestered using the RNeasy Tissue Kit (Qiagen, Valencia, Calif.) according to the manufacturer's protocol. For each sample, 500 ng of purified messenger RNA (mRNA) was reverse transcribed to complementary DNA (cDNA) using the iScript cDNA Synthesis Kit (Bio-Rad Laboratories, Hercules, Calif.). qRT-PCR was carried out with iQ SYBR green supermix (Bio-Rad Laboratories, Hercules, Calif.). Each transcript of interest was amplified in triplicates at its optimized annealing temperature and products were analyzed using the Opticon 2 software (Bio-Rad Laboratories, Hercules, Calif.). Relative expression was evaluated using the $\Delta$CT method ($\Delta$CT=CT gene of interest–CT human Actin). Expression data are presented as fold change of the linearized $\Delta$CT ($2-\Delta$CT) over control expression level.

Assessment of NSC Migration. To analyze the migratory capacity of loaded HB1.F3-CD cells to tumor cells in the presence of XRT-TMZ treatment, a wound healing assay was carried out using cell culture inserts (catalog no. 80209; Ibidi, München, Germany, http://www.ibidi.de). Migration analysis was conducted by measuring the average distance traveled as compared with that of mock cells. Briefly, cells were plated in cell culture-inserts maintained in a 24-well plastic dish and neural stem cells (NSCs) were plated after viral infection on the left half at a density of 2×104 in 100 µl of TMZ conditioned culturing medium. Afterwards the plate was irradiated. A line was drawn in precisely the same location over the inner right half of the insert to serve as a stationary point to measure how far cells have migrated. After 24 h of treatment, culture-inserts were removed and 200 µl of GBM43 conditioned culturing medium was added to the wells and images were taken over 24 h using a Nikon Eclipse TS100 microscope with the NIS-Elements F3.2 imaging software (Nikon Instruments, Melville, N.Y.).

Analysis of Viral Replication. To detect the level of viral replication, NSCs were infected with 50 IU of CRAd-S-pk7 and treated with XRT-TMZ. Cells were collected, and the total DNA was isolated from cultured cells using a DNeasy tissue kit (Qiagen, Valencia, Calif., http://www.qiagen.com). Adenoviral E1A gene expression was quantified via qRT-PCR using iQ SYBR Green supermix (Bio-Rad, Hercules, Calif., http://www.bio-rad.com), using primers and protocol previously described (Sonabend et al. 2009). The quantification of infectious viral progeny of NSCs was conducted using the Adeno-X rapid titer kit protocol (Clontech, Mountain View, Calif., http://www.clontech.com) as described elsewhere (Thaci et al. 2012). The titration unit (IU/ml) values quantified through this protocol are similar to plaque-forming units. Briefly, a standard curve of E1A copies containing 100 ng of DNA was generated for HB1.F3-CD cells. The sensitivity was set to detect as low as 5 E1A copies per 100 ng of DNA. DNA amplification was carried out using the Opticon 2 system (Bio-Rad Laboratories, Hercules, Calif.), and the detection was performed by measuring the binding of the fluorescent dye, SYBR green. Each sample was run in triplicates. Results are presented as E1A copy number per 100 ng of DNA.

In vitro Glioma Cell Toxicity Studies. A green fluorescent protein (GFP) expressing HB1.F3-CD cell line was generated as described elsewhere (Ahmed et al. 2011a). GBM43-Fluc cells were plated in 12-well plates and cocultured with HB1.F3-CDGFP cells loaded with CRAd-S-pk7 in the following NSC to glioma cell ratios: 1:0, 1:2, 1:5, 1:10, and 1:50. After 96 hours, the cells were collected, lysed with reporter lysis buffer (Promega, Madison, Wis., http://www.promega.com), and added to luciferase assay reagent (Promega) according to the manufacturer's protocol. Following lysate preparation, the mean fluorescence intensity (MFI) was estimated for each group of cocultured cells using the GloMax 20/20 Luminometer (Promega). The mean luciferase intensity values were represented as the percentage of cells viable compared with mock cells. U251, U87, and GBM39 cell viability was determined using 3-(4, 5-dimethylthiazol-2-yl)-2,5-diphenyltetrazolium bromide (MTT) cell proliferation kit (Roche Diagnostics, Mannheim, Germany, http://www.roche-applied-science.com). The viability was subsequently determined by MTT as described by the manufacturer's protocol. Cell viability was expressed as the percentage of cells alive compared with the dimethyl sulfoxide-treated control.

Animal Experiments. All of the animals were cared for according to a study-specific animal protocol certified by the University of Chicago Institutional Animal Care and Use Committee. The animals underwent intracranial stereotactic surgery, and $3.5 \times 10^5$ GBM43 cells were implanted in a 2.5-µl volume of PBS. Animal surgery and treatment protocols were as follows. 6-8 week old athymic/nude male mice (Harlan Laboratories, Madison, Wis.; Jackson Laboratories, Bar Harbor, Me.) were anesthetized with an intraperitoneal injection of ketamine hydrochloride (25 mg ml-1)/xylazine (2.5 mg ml-1) mixture. For intracranial (IC) injection, a midline incision was made, and a 1 mm burr hole centered 2 mm posterior to the coronal suture and 2 mm lateral to the sagittal suture was precisely made. Animals were injected with a 26-Gauge Hamilton needle 3 mm deep into the brain.

To determine an optimal TMZ and radiation (XRT) dosing protocol, mice were treated with TMZ alone (0 mg/kg, 5 mg/kg, 10 mg/kg, or 30 mg/kg), XRT alone (2 Gy), or a combination of 2 Gy XRT and TMZ (2.5 mg/kg, 5 mg/kg, 10 mg/kg, or 30 mg/kg). TMZ and XRT therapy was repeated daily beginning on day 6 for 5 consecutive days. To evaluate the therapeutic efficacy of HB1.F3-CD cells loaded with CRAd-S-pk7 administered in combination with TMZ and XRT therapy mice were IC injected using the same burr hole as above with either 5×105 or 3×106 virus loaded NSCs 5 days post tumor injection, followed by TMZ (5 mg/kg) and XRT (2 Gy) treatment on day 6 for 5 consecutive days. To determine whether the timing of administration of virus loaded NSCs influences therapeutic outcome two treatment protocols were followed: 1) mice received an IT injection of virus loaded NSCs (5×105) on day 5 post IC GBM43 injection followed by 5 subsequent daily TMZ (5 mg/kg) and XRT (2 Gy) treatments starting on day 6; 2) mice received 5 consecutive days of TMZ (5 mg/kg) and XRT (2 Gy) treatment starting on day 6 post IC GBM43 injection, followed by IT injection of 5×105 virus loaded NSCs on day 12 post IC GBM43 injection.

For safety monitoring mice received IC injection of 5×105 virus loaded NSCs on day 0, followed by 5 consecutive daily treatments of DMSO, TMZ (30 mg/kg), or TMZ (30 mg/kg) in conjunction with XRT (2 Gy) starting on day 1. Mice were monitored weekly for weight loss and symptoms of malignant cellular transformation.

For measurement of tumor volume on day 5, the mice were imaged for Fluc activity following intraperitoneal injection of D-luciferin (Gold Biotechnology, St. Louis, Mo., http://www.goldbio.com) (4.5 mg per animal in 150 µl of saline), and photon counts were recorded 10 minutes after D-luciferin administration by using a cryogenically cooled high-efficiency charged-coupled device camera system (Xenogen IVIS200 optical imaging system; Caliper Life Sciences, Mountain View, Calif., http://www.caliper.com) (Ahmed et al. 2011a). Representative hematoxylin- and eosin-stained mouse brain tissue pictures were captured with an AxioCam Color MR digital camera attached to an Olympus BX41 microscope and rendered in AxioVision version 3.0 software.

Western Blot. For protein analysis, U87 or U251 cells were cultured in 100-mm plates. The cells were harvested, washed, and lysed by the addition of 200 µl of mammalian protein extraction reagent (Pierce, Rockford, Ill., http://www.piercenet.com) supplemented with protease and phosphatase inhibitor cocktail. 40 µg of protein per lane was run on 10% Tris-HCl gel and was transferred by semidry electrophoretic transfer onto a polyvinylidene difluoride membrane. The membrane was blocked with 2% nonfat dry milk and stained with anti-Mre11 (Cell Signaling Technology, Danvers, Mass., http://www.cellsignal.com), anti-Rad50 (Cell Signaling Technology), and anti-β-actin (Santa Cruz Biotechnology, Dallas, Tex., http://www.scbt.com) antibodies, followed by the secondary anti-rabbit antibody conjugated with HRP (Cell Signaling Technology). All antibodies were diluted according to the manufacturer's recommendation. ImmunStar WesternC was used to develop the reaction. Images were captured using Bio-Rad's ChemiDoc imaging system.

Immunofluorescence. GBM43 cells were grown directly in four-well chamber slide (Lab-Tek, Hatfield, Pa., http://www.labtek.net) cell culture dishes. The cells were fixed and stained according to the manufacturer's protocol. The anti-phosphohistone H2A.X (Cell Signaling Technology) primary antibody was used at a 1:600 dilution overnight at 4° C. For immunofluorescence of animal tissue, the brains were embedded in optimal cutting temperature compound (Tissue-Tek) and frozen in a dry ice-2-methylbutane bath. Sections of 8 µm, spanning ~2 mm of tissue, were stained according to the manufacturer's protocol. The anti-cleaved caspase-3 (Cell Signaling Technology) primary antibody was used at a 1:600 dilution overnight at 4° C. The cells and tissues were washed, and goat anti-rabbit antibody conjugated with FITC (Santa Cruz Biotechnology) secondary antibody was added for 2 hours at ~23° C. in the dark. Secondary antibody was diluted according to the manufacturer's recommendation. After incubation with secondary antibody, the cells and tissues were washed and mounted with ProLong Gold antifade reagent with 4',6-diamidino-2-phenylindole (Molecular Probes). All images were captured on a Zeiss Axiovert 200M inverted fluorescent microscope.

Statistical Analysis. All of the statistical analyses were performed using GraphPad Prism 4 (GraphPad Software Inc., San Diego, Calif., http://www.graphpad.com). The data represent the results for assays performed in triplicate or more, and all values were calculated as means±SE. For continuous variables, comparisons between groups were made using Student's t test or analysis of variance with Bonferroni or Dunnett's post hoc test. Survival curves were generated by the Kaplan-Meier method, and the log-rank test was used to compare the distribution of survival times. All reported p values were two-sided and were considered statistically significant at a p value of <0.05 (*, $p<0.001$; , $p<0.01$; *, $p<0.05$).

Results

Figure 40A:
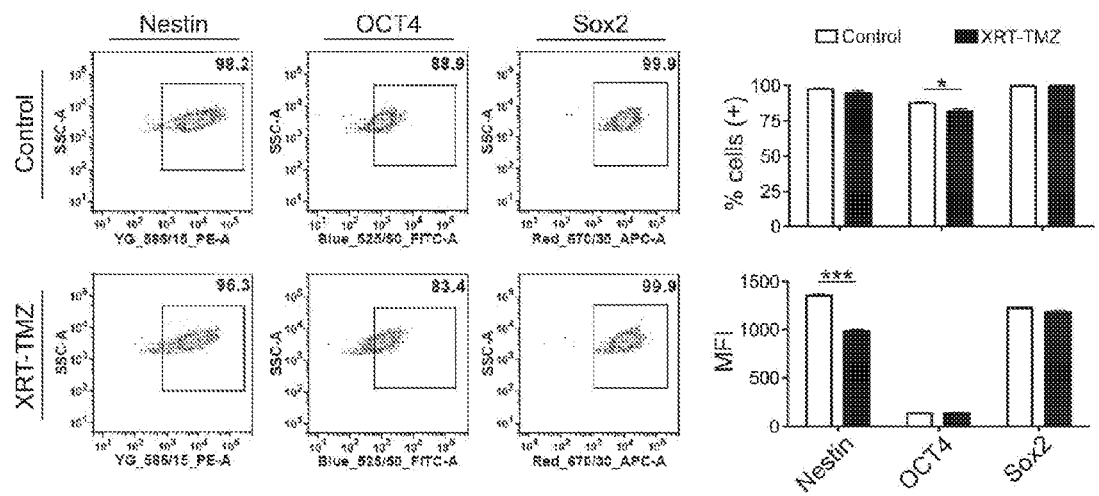
FIGS. 40A, 40B and 40C show the characterization of surface markers and migration of loaded NSCs treated with XRT-TMZ according to one embodiment.
Figure 47A:
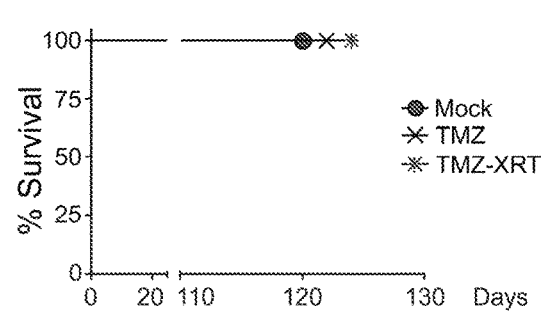
FIGS. 47A and 47B illustrate survival (FIG. 47A) and weight loss (FIG. 47B) in mice, four months after treatment with loaded NSCs in combination with TMZ, XRT, or both.
Figure 47B:
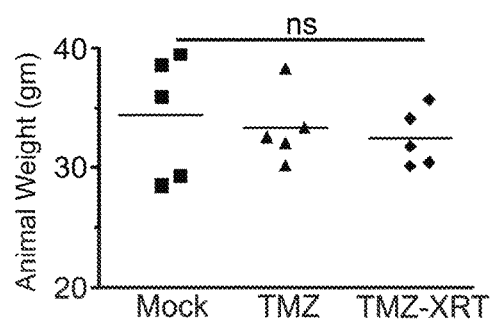

Neural Stem Cells Retain Their Migratory Properties in the Presence of Irradiation and Temozolomide. NSCs have an inherent pathotropism toward glioma, which is critical for their utility as cell carriers. Therefore, it is critical that such intrinsic molecular properties and phenotypes of NSCs are maintained during radio-chemotherapy (XRT-TMZ). Thus, it was first evaluated whether general stem cell characteristics would be altered during therapy. pharmacokinetic studies have revealed that the peak concentration of TMZ measured in a patient's blood is 50 µmol/l (Beier et al. 2008; Rosso et al. 2009; Brada et al. 1999; Ostermann et al. 2004) and 5 µmol/l in the cerebral spinal fluid (Ostermann et al. 2004), and the intratumoral concentration of TMZ is likely to be in the range of 5-50 µM. Therefore, NSC properties after exposure to 15 µM TMZ, the IC50 for HB1.F3-CD cells in vitro were evaluated, in combination with 2 Gy of ionizing radiation (Stupp et al. 2005). As shown in FIG. 40A, at 24 hours after exposure to conventional therapy, the NSC markers Nestin and Sox2 were found present in almost all the adenovirus-loaded control cells (97.4±0.8% and 99.8±0.2%, respectively). Oct4, a marker of self-renewal for undifferentiated cells, was expressed in 87.6±1.1% of the loaded NSCs. It was observed that Sox2 expression levels were not significantly altered from XRT-TMZ therapy; however, Nestin and Oct4 decreased slightly. The percentage of Oct4 positive cells decreased to 81±2% (*, $p<0.05$), whereas the MFI was not reduced. For Nestin, the reverse was observed: the percentage of positive cells remained unchanged, whereas the MFI was reduced by 27% (***, $p<0.001$) (FIG. 40A). Because of the high priority of safety when working with the undifferentiated v-myc immortalized HB1.F3-CD stem cell line (Kim et al. 2008), an in vivo safety monitoring experiment was performed to test the effect of XRT-TMZ on loaded HB1.F3-CD cellular transformation. CRAd-S-pk7-loaded NSCs were implanted in the brains of nude mice with no tumor burden. Subsequently, 1 day after implantation mice received 30 mg/kg of TMZ and 2 Gy of radiation for 5 consecutive days. The mice were monitored for weight loss and survival, and at the end of 4 months, the mice that were injected with loaded NSCs and treated with XRT-TMZ showed no significant weight loss or other symptoms of malignant transformation (FIG. 47).

Figure 40B:
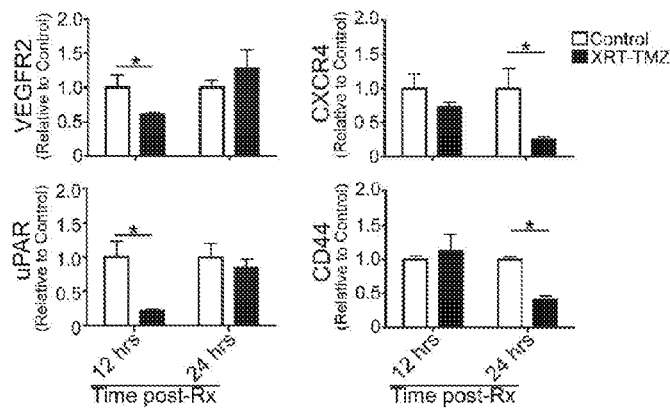
Figure 40C:
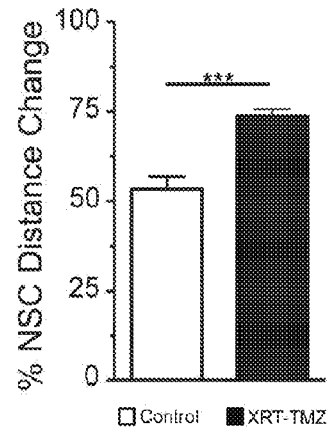

Furthermore, the capacity of NSCs to home to glioma cells has been linked to the expression of chemoattractant receptors expressed on their surface (Ahmed et al. 2011 b). Therefore, the transcription level of various chemokine receptors that have been attributed to the migration of NSCs was evaluated both in the absence and presence of XRT-TMZ at 12 and 24 hours after treatment. VEGFR2 and uPAR transcription was inhibited transiently at 12 hours (*, $p<0.05$) and recovered at 24 hours in the presence of XRT-TMZ. Moreover, CD44 and CXCR4 expression was found reduced only after 24 hours of treatment, *, $p<0.05$ (FIG. 40B). To evaluate whether these fluctuations in transcription of chemokine receptors had any effect on the functional pathotropism of loaded carrier cells, a wound healing assay was performed. It was found that XRT-TMZ did not reduce but rather increased the migration of loaded NSCs in vitro (***, $p<0.001$) (FIG. 40C). Taken together, it was concluded that the exposure to conventional anti-glioma therapies exerts a minimal effect on the phenotypic and chemoattractant markers of NSCs but does not alter their tumor-tropic migration.

Figure 41A:
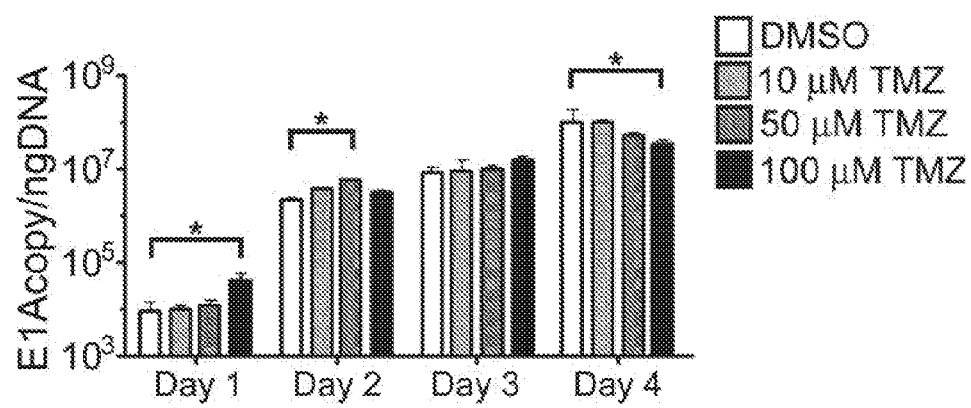
FIGS. 41A, 41B and 41C show evaluation of CRAd-Survivin-pk7 (CRAd-S-pk7) replication in neural stem cells (NSCs) treated with XRT-TMZ according to one embodiment. Viral replication of CRAd-S-pk7 was measured by quantitative real-time polymerase chain reaction and presented as a number of viral E1A copies per nanogram of DNA from infected NSCs.

Radio-Chemotherapy Minimally Reduces Oncolytic Virus Replication Within Carrier Cells. In order for a stem cell to be an effective carrier of OV, it must support viral replication. To determine the impact of XRT-TMZ treatment on the ability of NSCs to replicate CRAd-S-pk7, viral replication was quantified by viral E1A DNA copy number or infectious progeny present in NSCs. As shown in FIG. 41A, TMZ had a bimodal effect on the adenoviral E1A copies (E1A per nanogram of DNA). On days 1 and 2, it was noticed that TMZ at 100 and 50 µM, respectively, increased the E1A copies per nanogram of DNA between 2.5- and 4.5-fold (*, $p<0.05$). No difference was noted on day 3, whereas there was a 3-fold decrease in E1A copies per nanogram of DNA on day 4 at the highest TMZ concentration of 100 M (*, $p<0.05$).

Figure 41B:
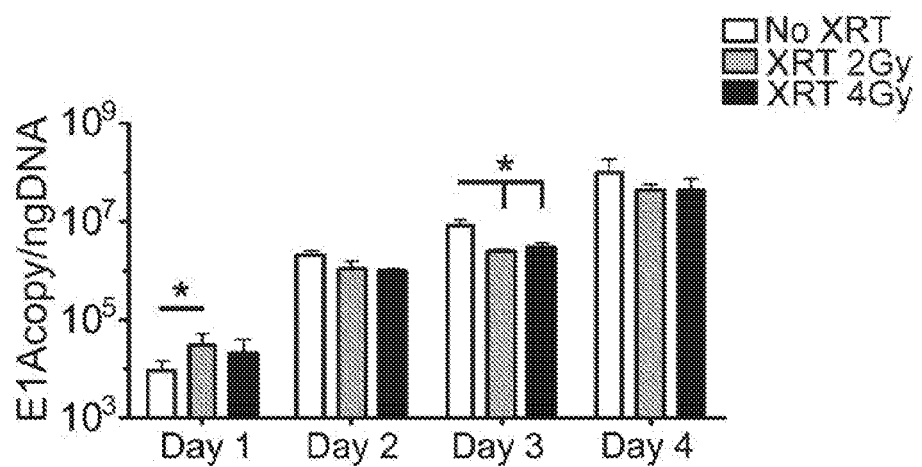
Figure 41C:
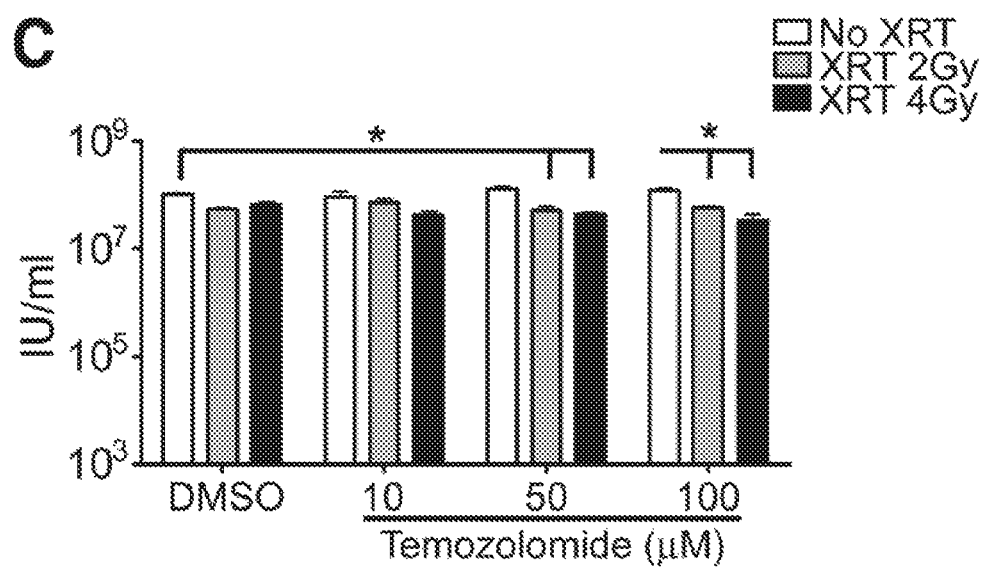

Similar to TMZ, 2 Gy irradiation showed a trend toward increased E1A copy number on day 1, followed by a significant reduction of E1A copy on day 3 (*, $p<0.05$) (FIG. 41B). In order to quantify the effect of concurrent XRT-TMZ on viral replication, viral progeny titers were assessed 96 hours after infection and noted that high-dose TMZ (50-100 µM) and radiation reduced production of infectious progeny in NSCs from $1.03\times10^8 \pm 2.2\times10^6$ IU/ml in untreated NSCs to $5.1\times10^7 \pm 9.4\times10^6$ IU/ml in NSCs treated with 2 Gy XRT and 50 MTMZ (*, $p<0.05$) (FIG. 41C). At the same time, NSCs treated with TMZ concentrations more closely related to those found to accumulate in the cerebral spinal fluid of patients (~5 µM) (Rosso et al. 2009; Ostermann et al. 2004), and 2 Gy radiation had no significant effect on adenoviral progeny titers (FIG. 41C). Based on these data, it was concluded that conventional therapy caused minimal interference with the ability of HB1.F3-CD cells to support therapeutic virus replication but did not increase CRAd-S-pk7 titers.

Figure 42A:
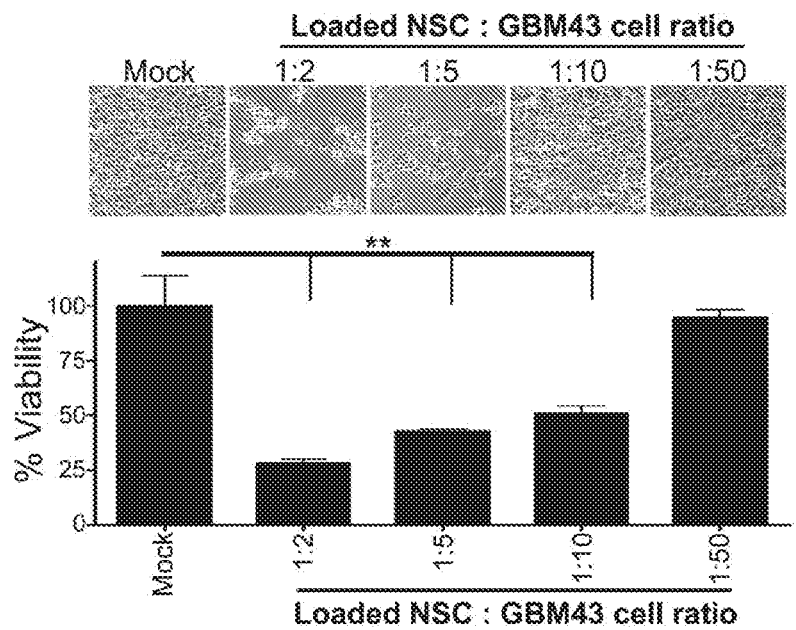
FIGS. 42A and 42B illustrate antitumor effects of CRAd-Survivin-pk7 (CRAd-S-pk7)-loaded NSCs and their combination with XRT-TMZ against glioma cell lines in vitro according to one embodiment.

Loaded NSCs in Addition to Conventional Therapy Increase Glioma Cell Cytotoxicity In vitro. It was previously shown that loaded NSCs can deliver the viral payload to glioma cells that are grown continuously under in vitro conditions (Thaci et al. 2012). Because long-term passage in vitro can alter glioma cell phenotype and molecular profile, the sensitivity of the patient-derived glioma line GBM43 was tested toward the adenovirus-loaded NSCs generated as discussed herein. GBM43 cells are passaged in mouse flanks and used for experiments without any in vitro passaging to retain their original glioma characteristics (Sarkaria et al. 2006; Giannini et al. 2005). First, it was tested whether loaded NSCs can induce toxicity to GBM43 when cocultured at different glioma to NSC ratios and found that adenovirus-loaded NSCs can induce significant toxicity up to a ratio of 1 NSC per 10 glioma cells at 96 hours after treatment (**, $p<0.01$) (FIG. 42A).

Figure 42B:
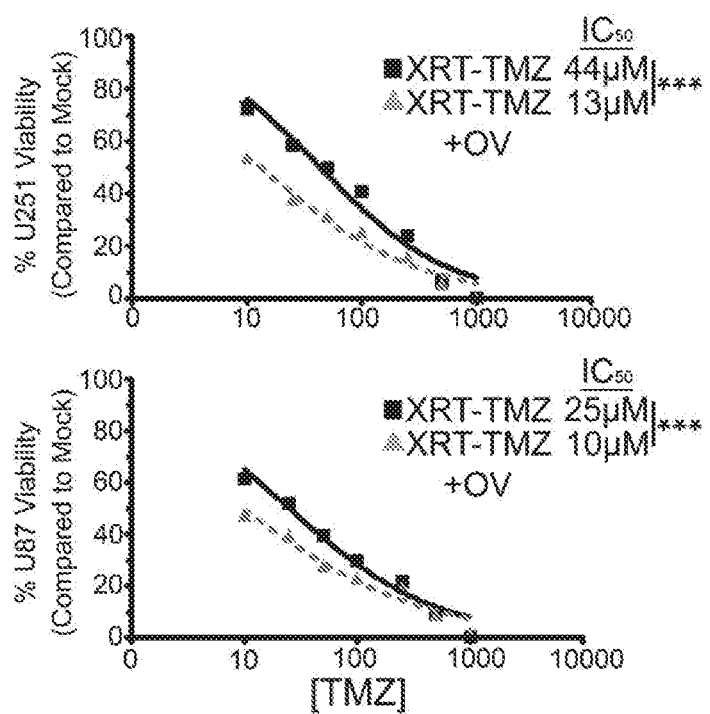

Next, it was tested whether CRAd-S-pk7 could enhance the therapeutic efficacy of conventional XRT-TMZ. U251 or U87 glioma cells were treated with conventional therapy consisting of 2 Gy XRT and varying concentrations of TMZ $(0-1\times10^3$ M) or conventional treatment plus 50 IU of CRAd-S-pk7, and cell viability was measured by MTT at 96 hours. In both cell lines, combination therapy was more cytotoxic to glioma cells compared with conventional XRT-TMZ alone. The IC50 values for TMZ decreased from 44 and 25 M without oncolytic adenovirus infection to 13 and M when oncolytic virotherapy was added to the treatment of U251 and U87 glioma cells, respectively (***, $p<0.001$) (FIG. 42B).

Figure 43A:
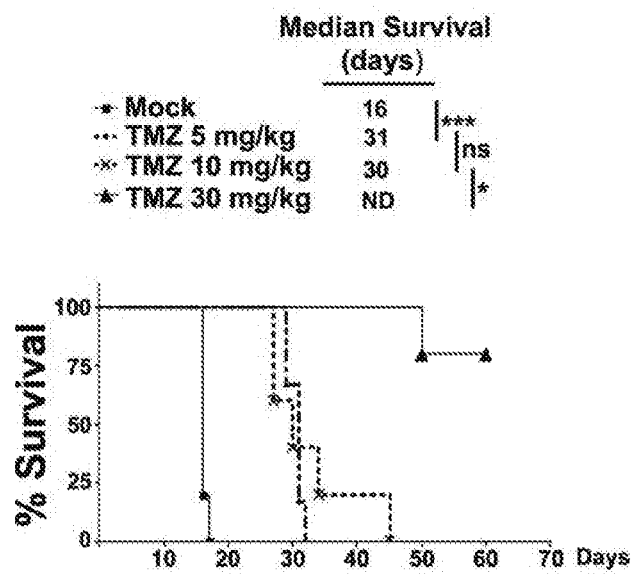
FIGS. 43A, 43B and 43C illustrate the in vivo efficacy of CRAd-Survivin-pk7 (CRAd-S-pk7)-loaded NSCs and XRT-TMZ treatment against human-derived glioma xenografts according to one embodiment. Intracranial GBM43 (3.5×10$^5$ cells per animal) was established, and the animals were treated for 5 consecutive days beginning on day 6 after tumor cell implantation.
Figure 48A:
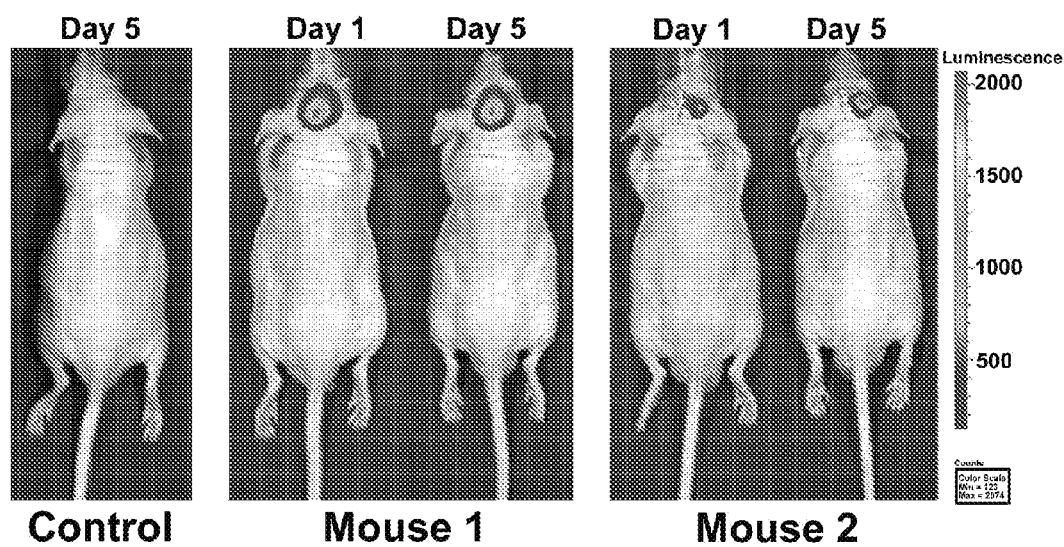
FIGS. 48A and 48B are bioluminescence images (FIG. 48A) and histological sections (FIG. 48B) of mouse brains illustrating that tumor burden is established by day 1 of treatment with GBM43 cells, and disease burden is established on day 5 after treatment.
Figure 48B:
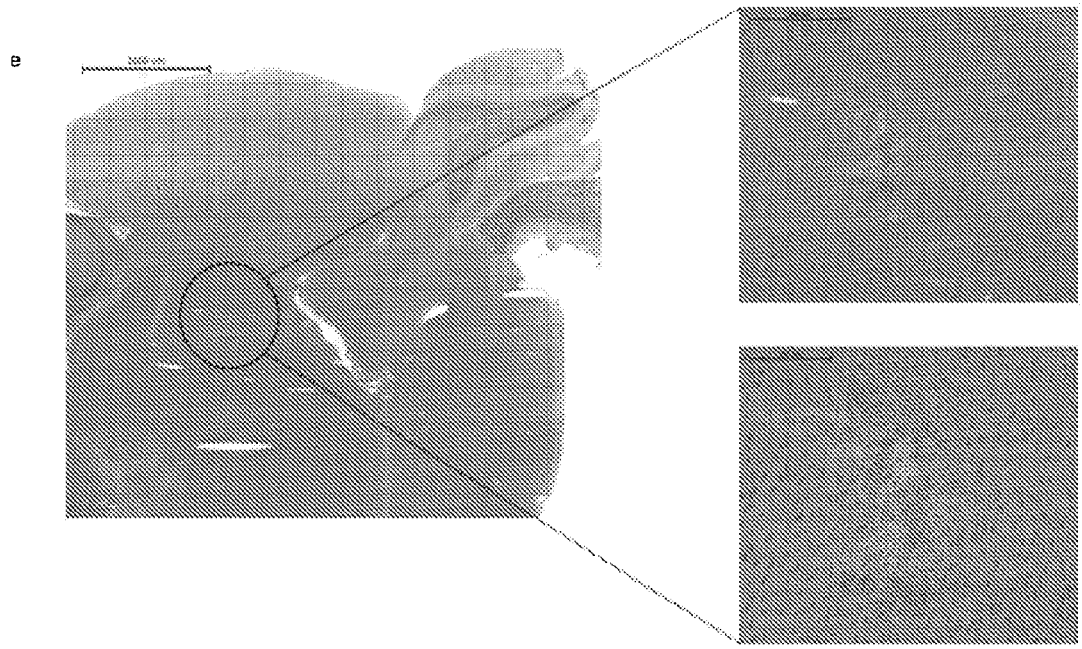

Oncolytic Adenovirus-Loaded NSCs Extend Survival of Glioma-Bearing Animals Treated With Conventional Chemo-Radiotherapy. In order to evaluate the therapeutic efficacy of OV-loaded NSCs (NSC-OV) in combination with XRT-TMZ therapy as compared with XRT-TMZ therapy alone, a suboptimal treatment protocol was established for XRT-TMZ in vivo. This would allow for an assessment as to whether the loaded NSCs could work jointly with conventional XRT-TMZ to increase the survival of animals bearing orthotropic human glioma xenografts. To test the combination therapy, a tumor model was established as described in Materials and Methods above. The intracranial implantation of $3.5\times10^5$ GBM43 cells results in an established tumor burden by day 1 of treatment (5 days after injection) as demonstrated by bioluminescence imaging and histological sections of mouse brains (FIG. 48). It was found that when mice bearing GBM43 were administered TMZ intraperitoneally at a dose of 30 mg/kg, the majority of animals (four out of five) survived long term (75 days), whereas, at the doses of 5 and 10 mg/kg, animals succumbed to the disease despite a significant increase in their survival when compared with mock-treated animals (***, $p<0.001$ (FIG. 43A). Next, survival of mice receiving both XRT and TMZ simultaneously was examined.

Figure 43B:
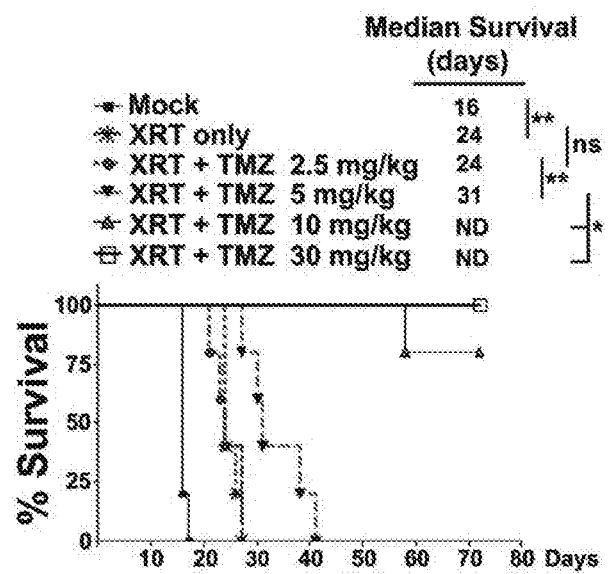

As shown in FIG. 43B, 10 Gy fractionated radiotherapy (2 Gy per day for 5 days) alone prolonged median animal survival by 50% (16-24 days) when compared with mock-treated animals (, $p<0.01$). The addition of 2.5 mg/kg of TMZ proved no better than radiation alone, whereas 5 mg/kg of TMZ in combination with XRT increased animal survival by 7 days (from 24 to 31 days) when compared with XRT-treated animals (, $p<0.01$). When higher doses of TMZ (10 and 30 mg/kg) were administered in combination with XRT, most mice lived long term. Based on these results, the suboptimal treatment regimen of 5 mg/kg of TMZ and 10 Gy of fractionated radiotherapy (2 Gy per day for 5 days) was selected to test whether the CRAd-S-pk7-loaded NSCs added an additional survival benefit in an animal model of glioma.

Figure 43C:
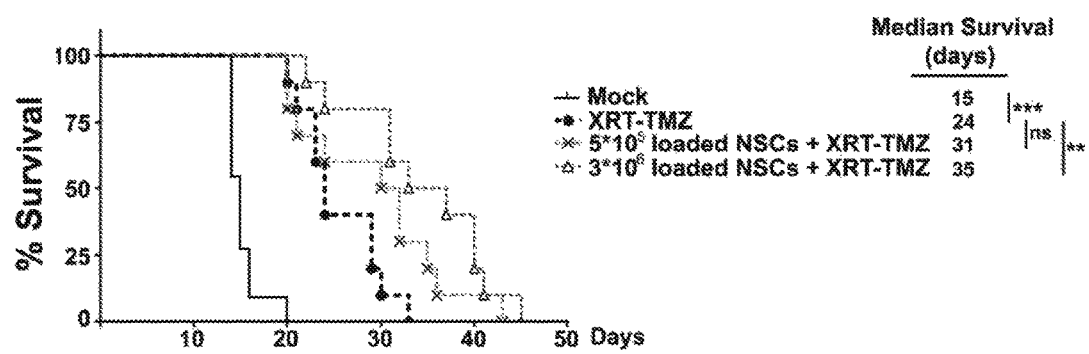

Finally, to test the in vivo efficacy of the multimodality anti-glioma therapy, intracranial GBM43 xenografts were established in nude mice. Five days after establishing intracranial glioma xenografts, the animals were injected with CRAd-S-pk7-loaded NSCs at two different doses: $5 \times 10^5$ or $3 \times 10^6$ (the maximum number of NSCs that could fit in a 2.5-μl injection volume) adenovirus-loaded NSCs. The next day, the animals began the previously established 5-day regimen of XRT-TMZ. As shown in FIG. 43C, the intratumoral injection of $5 \times 10^5$ loaded NSCs in combination with XRT-TMZ increased median survival by 29% over mice treated with XRT-TMZ alone. Furthermore, a dose-dependent increase in the median survival time was observed. When the number of OV-loaded NSCs was increased from $5 \times 10^5$ to $3 \times 10^6$, the median survival was increased by an additional 13% ($5 \times 10^5$ NSC-OV-XRT-TMZ-treated group=31 days median survival; $3 \times 10^6$ NSC-OV-XRT-TMZ-treated group=35 days median survival). Compared with XRT-TMZ treatment alone, the addition of $3 \times 10^6$ NSC-OV significantly increased the median survival by approximately 46% (XRT-TMZ-treated group=24 days median survival; $3 \times 10^6$ NSC-OV-XRT-TMZ-treated group=35-day median survival) (**, $p<0.01$) (FIG. 43C).

Administration of Loaded NSCs Prior to Chemo-Radiotherapy Demonstrates the Greatest Survival Benefit. In the clinical setting there are two possible schedules when loaded NSCs could be realistically administered to patients: (a) before XRT-TMZ therapy and into the resection cavity during the time of surgery or (b) after XRT-TMZ therapy via an alternative clinical delivery approach if protocol specified. Depending on the mechanism of interaction, the relative timing and order of the treatment regimen could have a differential outcome on treatment efficacy, and therefore it is an important clinical consideration (Ottolino-Perry et al. 2010). To determine which would provide the greatest benefit, these scenarios were mimicked both in vitro and in the animal model.

Figure 44A:
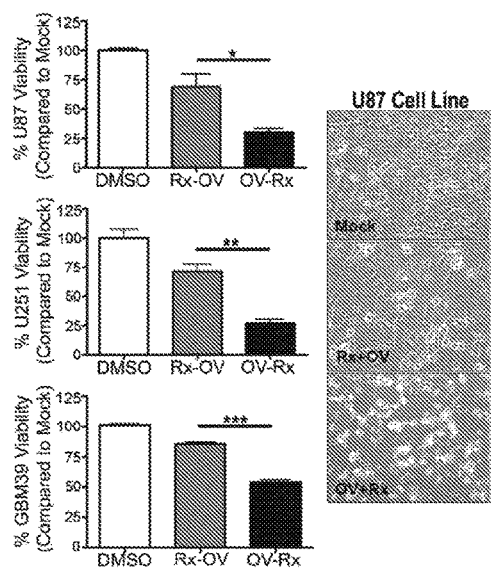
FIGS. 44A and 44B show the optimization of combination therapy in vitro according to one embodiment.
Figure 44B:
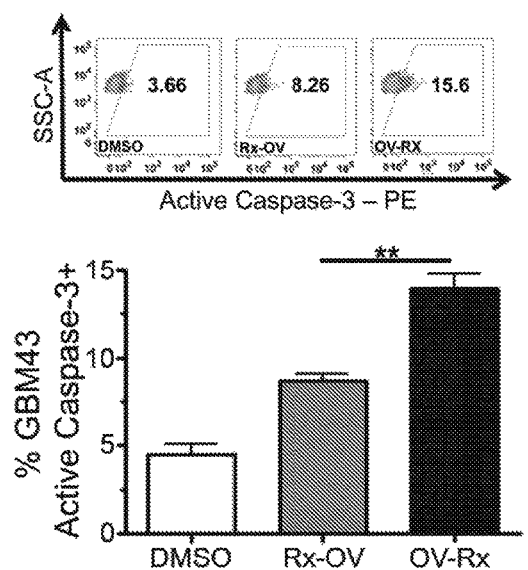

First, both treatment approaches were tested and cell toxicity was measured in both U251 and U87 glioma cell lines. As shown in FIG. 44A, glioma toxicity was dependent on the timing of OV administration. Both U87 and U251 cells showed greater toxicity at 96 hours when treated with oncolytic adenovirus (50 IU) 24 hours prior to treatment with TMZ (respective IC50 for each cell line) and 2 Gy XRT (*, $p<0.05$; , $p<0.01$, respectively). Likewise, the patient-derived GBM39 cell line demonstrated more robust toxicity when treated with oncolytic adenovirus 24 hours prior to XRT-TMZ (Rx) (*, $p<0.001$). Furthermore, at 48 hours after treatment, GBM43 cells that were treated with CRAd-S-pk7 virus 24 hours before XRT-TMZ resulted in a higher percentage of cells that stained positive for the active form of the caspase-3 protein (XRT-TMZ then OV=8.7±0.4% vs. OV then XRT-TMZ=13.99±0.8%) (**, $p<0.01$) (FIG. 44B). Together, this indicates that upfront treatment with OV induces higher levels of cellular apoptosis and cytotoxicity as compared with the alternative treatment approach.

Figure 45A:
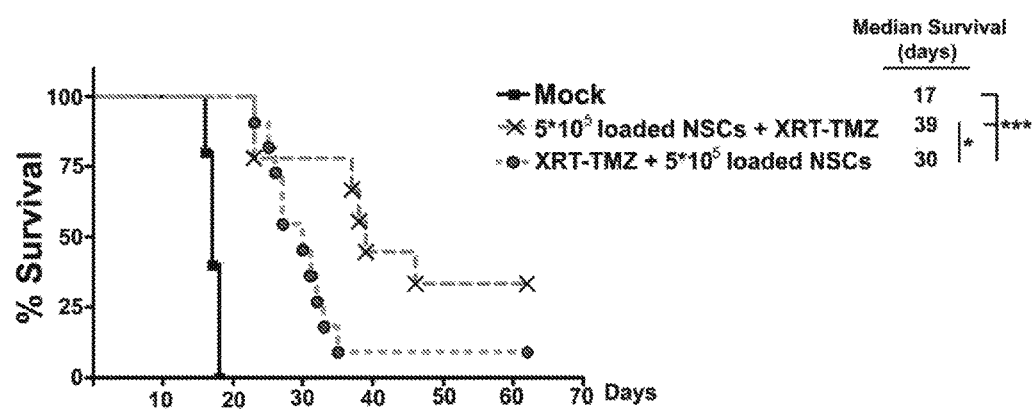
FIGS. 45A and 45B illustrate the scheduling of CRAd-Survivin-pk7 (CRAd-S-pk7)-loaded NSC administration in vivo according to one embodiment.
Figure 45B:
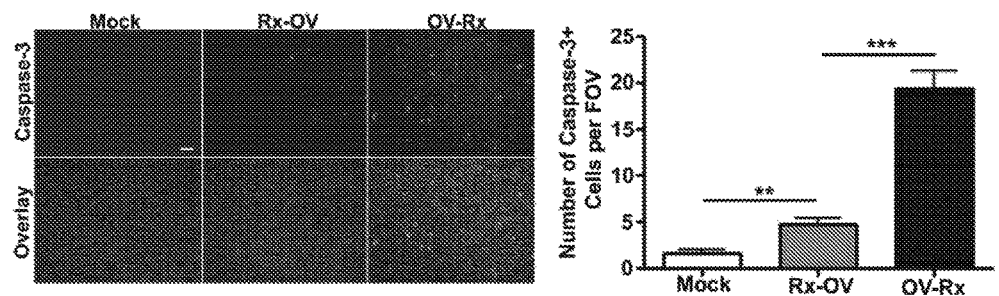

Next, a preclinical scheduling protocol was considered to test whether the relative timing of loaded NSC administration had an effect on animal survival. To test this, we established GBM43 glioma xenografts in nude mice 5 days prior to the beginning of treatment. The mice were split into two treatment groups, and all mice received $5 \times 10^5$ loaded NSCs and 5 days of treatment with 5 mg/kg of TMZ and 2 Gy of XRT. To test timing as a variable for therapeutic outcome, the following treatment schedules were applied: (a) intratumoral (IT) injection of CRAd-loaded NSCs followed by a full cycle of conventional therapy starting 24 hours later or (b) a full cycle of conventional therapy followed by an IT injection of CRAd-loaded NSCs following its completion. What was observed in the animal model was consistent with the in vitro findings. As shown in FIG. 45A, when animals received loaded NSCs before XRT-TMZ, their median survival was 9 days longer compared with the animals that received the reverse treatment schedule (*, $p<0.05$). Furthermore, 33% of mice who received loaded NSCs before TMZ-XRT compared with 9% of mice who received the opposite treatment regimen lived long term (>70 days). In addition, the level of apoptosis in the mouse brain tumors corresponded to the increased survival observed in mice treated with loaded NSCs prior to receiving XRT-TMZ. Immunohistopathological examination of the mouse brains from the two treatment groups revealed a significantly higher number of caspase-3-positive cells in the brain tumors of mice that received treatment with loaded NSCs 24 hours before treatment with standard therapy (Rx). The number of caspase-3-positive cells was counted per ×20 objective field of view (FOV), and brain tumors treated with upfront loaded NSCs showed 19.40±1.860 caspase-3-positive cells per FOV as compared with 4.800±0.5831 caspase-3-positive cells per FOV in the brain tumors treated with the alternative treatment schedule (***, $p<0.001$) (FIG. 45B). Based on these observations, it was concluded that OV-loaded NSCs should be administered prior to conventional therapy.

CRAd-S-pk7 Radiosensitizes Glioma Cells by Inhibiting Radiation-induced DNA Damage Responses. To elucidate the molecular mechanism responsible for the preferential survival observed in animals receiving loaded NSCs prior to conventional glioma therapy, at least two possible explanations were considered: (a) therapy is enhanced through an increase in oncolysis caused by a chemotherapy- and/or radiation-mediated increase in viral replication rates (Kim et al. 2005), or conversely, (b) OV induces a molecular change in tumor cells that leads to an improved response to chemo- or radiotherapy (Stracker et al. 2002; Kuroda et al. 2010). Currently, the interaction between oncolytic adenovirus and conventional therapies for glioma remains unclear (Bieler et al. 2008; Geoerger et al. 2003). Based on previously published data, in addition to evidence from preliminary results that showed no significant increase in viral titers upon exposure to XRT-TMZ (FIG. 41C), it was decided to investigate how CRAd-S-pk7 affects the DNA repair machinery of glioma cells. It has been shown that adenovirus oncoproteins, such as the E1B 55-kDa gene product, can inactivate the Mre11-Rad50-NBS1 (MRN) DNA repair complex in infected cells and suppress the hosts' DNA damage responses during viral DNA replication (Stracker et al. 2002). Based on this, OV infection prior to conventional treatment likely sensitizes the infected glioma cells to radiotherapy.

Figure 46A:
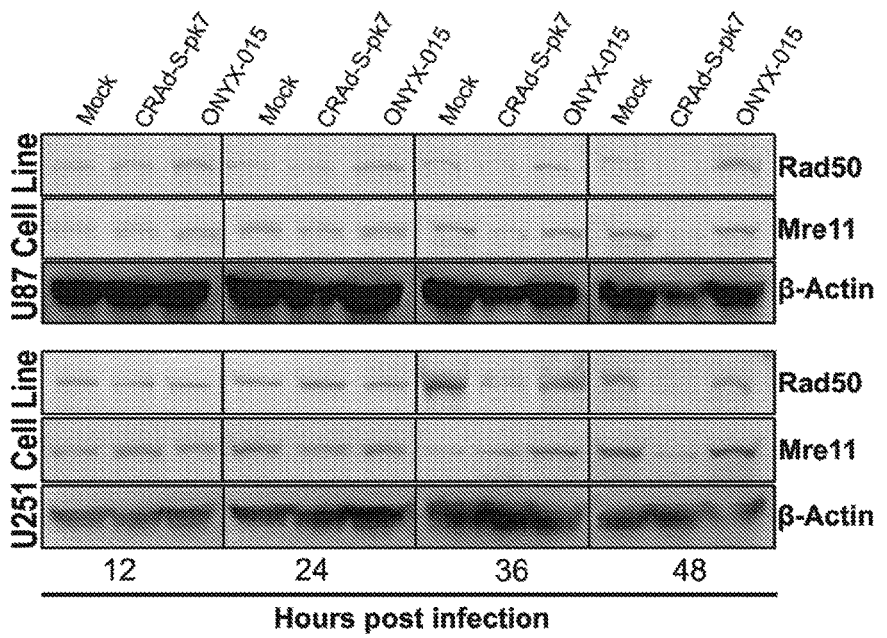
FIGS. 46A, 46B and 46C show the radiosensitizing effect of CRAd-Survivin-pk7 (CRAd-S-pk7) infection on glioma according to one embodiment.

To test this, MRN complex protein levels were measured by Western blot over time after infection with adenoviruses CRAd-S-pk7 and ONYX-015. As shown in FIG. 46A, the levels of Rad50 and Mre11 protein gradually decreased over time after CRAd-Spk7 infection in both U87 and U251 glioma cell lines. At 36 and 48 hours after infection, when the levels of Rad50 and Mre11 protein were at their lowest, the expression of MRN complex proteins remained unchanged in both U87 and U251 glioma cells infected with the E1B attenuated ONYX-015 adenovirus.

Figure 46B:
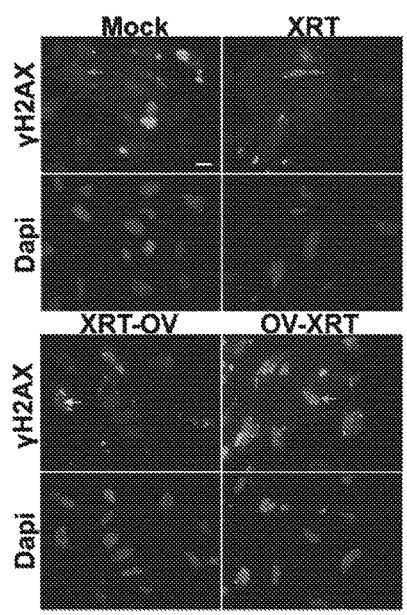
Figure 46C:
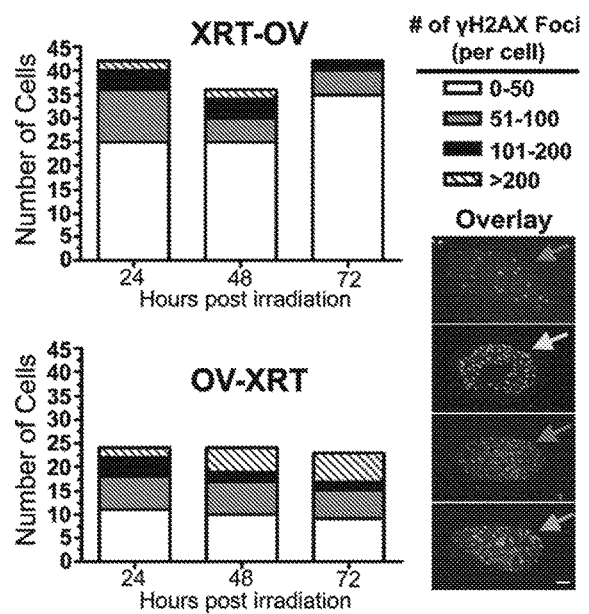

Furthermore, to investigate whether the observed decrease in MRN proteins after CRAd-S-pk7 infection could abrogate the DNA repair process in glioma cells in response to ionizing radiation, the cells' ability to resolve γH2AX foci, a sensitive indicator of DNA double-stranded breaks (DSBs), over time. GBM43 cells were treated with OV either 24 hours prior to or after XRT treatment and collected 24, 48, and 72 hours relative to the time when cells received irradiation. Immunofluorescent staining for γ H2AX foci revealed that at 72 hours, there were a greater number of $^L$ H2AX foci in cells treated with OV before XRT compared with cells treated with XRT before OV or XRT alone (number of γH2AX foci per cell: red arrows, 0-50 foci; yellow arrows, 51-100 foci; blue arrows, 101-200 foci; and orange arrows, 200 foci) (FIG. 46B, 46C). To quantify the rate of γ H2AX foci resolution over time, the number of foci per cell at each consecutive time point was counted, and the effect over time was analyzed by ordinal logistic regression. FIG. 46C reveals, in glioma cells that were irradiated 24 hours prior to receiving OV, a decreasing number of γ H2AX foci over time as the DNA DSBs were repaired (negative time effect; coefficient: −0.024±0.01; p=0.020). Furthermore, glioma cells that were treated with OV 24 hours before irradiation had static γH2AX foci levels over time (no significant time effect; coefficient: 0.009±0.01; p=0.386). These results indicate that infection with CRAd-S-pk7 may increase the sensitivity of glioma cells to XRT treatment by compromising the cells' ability to repair DNA damage induced by ionizing radiation.

Discussion

The investigation and development of superior treatment approaches for highly invasive and therapy-resistant glioblastoma are needed. As described herein, the HB1.F3-CD NSC line has been developed into a cell carrier for specific delivery of the glioma tropic OV CRAd-S-pk7 in the preclinical setting (Thaci et al. 2012).

Translating novel therapies from the laboratory to clinical trials is a complex path with many challenges (Tobias et al. 2013). Every day, promising gene therapy translational research is being conducted, but the outcomes of many phase III clinical trials fail to meet expectations. "Preclinical robustness" is the term coined to refer to how well preclinical studies are designed to accurately predict the efficacy of novel treatments in human patients. It is thought that in order to improve the success rate of novel therapies in clinical trials, preclinical studies need to become more robust. In order to increase the robustness of preclinical data, a novel therapy should be evaluated in a model that is most representative of the human disease and tested in conjunction with the standard of care treatment (Lowenstein et al. 2009). Although a challenging task, the studies and preclinical animal model described above meet several standards of preclinical robustness and therefore stringently support the application of OV-loaded NSCs for treatment of glioblastoma.

First, the function of an NSC carrier was tested in the presence of conventional GBM therapies. A major advantage of a carrier cell-based system to deliver OV is the capacity of stem cells to transport therapeutics to their intended targets located at a distance from the original tumor site. It is important that HB1.F3-CD cells retain their migratory capacity under an environment influenced by XRT-TMZ. Many signaling molecules have been implicated in the regulation of stem cell migration including CXCR4, CD44, VEGFR2, and uPAR (Zhao et al. 2008). Even though the CXCR4 and CD44 transcript levels were decreased in HB1.F3-CD cells upon XRT-TMZ exposure in vitro, no alterations in the tumor-tropic migratory capacity of NSCs were observed (FIG. 40). Although the mechanism is not yet proven, a wealth of convincing data exist showing that vascular endothelial growth factor (VEGF) is copiously expressed in glioma cells and is a strong chemoattractant mediating NSC migration (Ahmed et al. 2011a; Heidenreich et al. 2004; Schmidt et al. 2005; Zhang et al. 2003). As shown in FIG. 40B at 24 hours after XRT-TMZ therapy, NSCs retain their level of VEGFR2 gene expression compared with untreated cells. Taken together, conventional radio- and chemotherapy did not alter the VEGFR2 mRNA expression of NSCs or their migratory capacity, and therefore VEGF-VEGFR2 receptor signaling may be critical for maintaining the tumor pathotropism of HB1.F3-CD cells.

Another benefit of stem cell-based oncolytic virotherapy is the ability of OV-loaded stem cells to serve as in situ factories for viral replication. For this approach to work in conjunction with the standard of care for GBM, NSCs must retain their ability to support therapeutic virus replication. Despite the results that show a slightly diminished viral titer when NSCs are treated with radiation and high-dose chemotherapy on day 4, at lower doses of TMZ the viral titer was unaffected and remained consistent with the titer produced by untreated NSC carriers. Interestingly, although increased viral replication was not seen, an increased cytotoxic effect was observed in both U251 and U87 glioma cell lines when cells were treated with OV in addition to XRT-TMZ (FIG. 42B), which was later attributed to the possible radiosensitizing effect of OV. To test the efficacy of CRAd-loaded NSCs in combination with conventional therapy in vivo, a preclinical model was established. In developing this model factors that would influence the preclinical robustness of the experiments were considered, and shortcomings of previous animal models were addressed. Treating a tumor in its natural environment can significantly influence therapeutic outcome. Many previous studies evaluating the combination of OV and conventional therapy have been limited to subcutaneous tumor models (Ottolino-Perry et al. 2010) or intracranial models established from cell lines passaged in vitro. Therefore, intracranial orthotopic xenografts were established that were derived from an explanted patient GBM and serially passaged in vivo. Furthermore, because GBM patients receive surgery, followed by radiotherapy and temozolomide, it is crucial that novel therapies retain their utility when used with this treatment approach. To incorporate this aspect of the clinical scenario into the preclinical model, the efficacy of concomitant TMZ and fractioned XRT was tested (Stupp et al. 2005) for 5 consecutive days in combination with stem cell-based oncolytic virotherapy (FIG. 43C). This model may capture some of the complexities of treating a human GBM in the clinic and contribute to the preclinical robustness of the results of the studies described above. Additionally, the extent of the disease burden during the time of administration may dictate the treatment effectiveness and therefore should be considered as a variable that may impact outcome. As it is shown in FIG. 48, the disease burden is established prior to treatment on day 5 after implantation. Moreover, in the clinical setting, CRAd-loaded NSCs should be administered after tumor resection and before the patient receives XRT and TMZ. During this time, depending on the extent of resection, approximately 95% of the original tumor volume has been removed (Bloch et al. 2012). In this case, the therapy is intended to treat the minimal volume of residual disease. Thus, because of the careful consideration while developing the xenograft model used in this study, conscious attempts were made to mimic the clinical scenario with respect to disease burden at the proposed time of NSC-based anti-glioma oncolytic virus administration.

Finally, the timing of loaded NSC administration is an additional clinical variable that was explored because the relative timing of treatment could be important both logistically and therapeutically. It was considered that loaded NSCs could be administered to patients before receiving the standard of care or afterward (Lowenstein et al. 2009). It was concluded that loaded NSCs delivered upfront to conventional therapy may be the optimal time for their administration (FIGS. 44 and 45) in order to take advantage of their potential radiosensitizing effects. It is established that ionizing radiation produces a wide variety of lesions in the host DNA, including single- and DSBs, base damage, and cross-linking of DNA-DNA and DNA-protein (Helleday et al. 2008). DSBs play an important role in radiation-induced cell death and are considered to be a critical factor for the therapeutic efficacy of anti-cancer radiotherapy. Upon detection of DNA damage, cells activate the DNA repair pathway by initiating cell cycle arrest and inducing expression of various genes associated with DNA repair mechanisms. MRN is one protein complex that can act as a DSB sensor by rapidly binding to damaged DNA and serving as the link between DNA repair and the cell cycle regulatory pathway (Petrini 1999). It has been reported that adenovirus 5 can effectively inactivate the MRN complex in infected cells that would otherwise inhibit viral DNA replication and packaging (Karen et al. 2009). The viral E1B 55-kDa protein, with cooperation from the E4orf6 viral protein, sequesters the MRN complex in infected cells and induces proteasome-depended degradation (Stracker et al. 2002). Expression of these viral genes in human colorectal carcinoma and GBM cell lines inhibits DNA DSB repair and induces a radiosensitizing effect in infected cells (Hart et al. 2005). Based on this, the advantage of administering OV-loaded NSCs prior to radiotherapy is likely due to a sensitizing effect of CRAd-S-pk7 on glioma cells toward radiotherapy, which one may not observe if OV-loaded NSCs are administered after XRT treatment. As shown in FIG. 46A, the degradation of MRN proteins is most pronounced at 36-48 hours after adenoviral infection in vitro, but it is yet to be determined whether delivery of loaded NSCs 24 hours before the start of conventional therapy is the adequate amount of time to achieve a maximal survival advantage in vivo. Furthermore, although it was shown that loaded NSCs are compatible with TMZ both in vitro and in vivo, a further investigation into possible mechanisms of interaction is warranted.

In summary, it has been demonstrated that stem cell-based oncolytic therapy is well suited to be administered with chemo-radiotherapy. The increased efficacy observed with combination therapy is dependent on the relative timing of administration and that NSCs loaded with CRAd-S-pk7 should be given prior to XRT-TMZ therapy. The potential radiosensitization induced by adenovirus infection may be a powerful tool for targeting therapeutically resistant tumor cells, a hallmark of GBM's malignancy. Furthermore, the use of carrier cells can distribute oncolytic viruses throughout the brain to target disseminated tumor burdens. The future of GBM therapy is dependent on novel therapies, and this investigation has set the foundation for the clinical protocol of stem cell-based oncolytic therapy and brought it one step closer to clinical trials.

Example 10

Toxicology and Biodistribution with NSC-loaded cGMP-grade Clinical Lot Virus

While previous clinical studies have not shown any vector leakage or systemic side effects following intracranial administration of a replication-defective virus (Lang et al. 2003; Germano et al. 2003), similar studies using NSCs loaded with CRAds have not been performed. As a result, the following studies are meant to complement the efficacy studies and evaluate the toxicity, biodistribution, and immune response in terms of intracranial NSC-CRAd-S-pk7 administration. Such studies have formed important components of FDA approved IND applications in support of human clinical gene therapy trials. Therefore, a toxicology study may be performed with NSC-loaded cGMP-grade clinical lot virus according to a plan acceptable to the FDA. Since human Ads replicate only in human cells, toxicology studies with Ad vectors have been hampered by the lack of a permissive nonhuman host. Recent evidence, however, suggests that while the cotton rat is a species that is semipermissive for human Ads (Toth et al. 2005; Wildner & Morris 2002), the Syrian hamster is a rodent species that is fully permissive for human Ads (Thomas et al. 2006).

Materials and Methods

In vivo repeat dose toxicity. As shown in Table 2 below, cotton rats (n=15/sex/group) may be assigned to one of five dose groups, and may be injected by intracerebral (i.c.) injection with vehicle (Groups 1 and 2) or one of two dose levels of CRAd-Spk7-loaded NSCs (Ad/NSC; Groups 3, 4, and 5), as shown in the table below. Animals will receive three doses of the vehicle or NSCs at 2-week intervals (i.e., Days 1, 15, and 29). Because the vector-loaded NSCs may be used in the clinic in conjunction with temozolomide (TMZ), the safety of the vector may be assessed in the presence and the absence of this drug. Animals may be treated by intravenous infusion (90 minutes c.i.v.) with vehicle (Groups 1 and 3) or TMZ (Groups 2, 4, and 5; 75 mg/m²/dose) on Days 1-5, 15-19, and 29-33, to mimic the planned clinical schedule and route.

TABLE 2

| Group | Treatment | Ad/NSC (cells/ animal/ dose) | TMZ (mg/ m²/ dose) | Number of Animals Core Groups | Biodistribution Groups |
|---|---|---|---|---|---|
| 1 | Vehicle | 0 | 0 | 15M/15F | 6M/6F |
| 2 | TMZ | 0 | 75 | 15M/15F | — |
| 3 | CRAd/NSC | High | 0 | 15M/15F | 12M/12F |
| 4 | CRAd/NSC + TMZ | Low | 75 | 15M/15F | — |
| 5 | CRAd/NSC + TMZ | High | 75 | 15M/15F | 12M/12F |

Animals may be observed for clinical signs of toxicity, as well as changes in body weights and food consumption. Clinical pathology (hematology, serum chemistry, and coagulation profile; urinalysis) may be evaluated 5 days after the first and last doses, and at the end of a 28-day recovery period after the last TMZ dose. Five animals/sex/group may be euthanized at each of three time points (Days 6, 34, and 62), and will undergo a full gross necropsy and microscopic evaluation of a full (~50) panel of tissues. A panel of 10-12 organs may be weighed from each animal at necropsy and used to evaluate changes in absolute organ weights, as well as organ-to-body and organ-to-brain weight ratios.

Biodistribution of CRAd/NSC. Biodistribution of the vector-loaded NSCs may be evaluated using animals included in satellite groups within the main toxicity study. The biodistribution assay will include three groups: (1) animals treated with vehicle alone, to provide a baseline, (2) animals treated with the high dose of the Ad/NSCs, to determine whether and to what extent the NSCs reach the systemic circulation and are distributed outside the brain, and (3) animals treated with the high dose of the Ad/NSCs+ TMZ, to determine whether TMZ treatment affects Ad/NSC distribution. Animals in these groups may be euthanized on Days 6, 34, and 62 (2/sex/day from Group 1; 4/sex/day from Groups 3 and 5), and samples of blood and 10-12 tissues (e.g., adrenals, brain, gonads, heart, intestine, kidney, liver, lung, lymph node, and spleen) may be collected and evaluated for the presence of vector DNA using a GLP-validated quantitative real-time PCR (Q-PCR) assay.

Immunological response to CRAd/NSC. The treatment context of glioma gene therapy involves intratumoral gene delivery of adenoviral vectors. Of note, several groups have demonstrated that intratumoral adenoviral vector mediated gene delivery could be effectively achieved, even in the context of pre-existing anti-Ad humoral immunity (Tsai et al. 2004; Li et al. 2005; Atencio et al. 2005). Furthermore, one of the potential benefits deriving from targeting strategies is the mitigation of antivector immunity. This is based on the concept that priming of the immune system against the vector is facilitated by vector uptake by dendritic cells (DC). Thus, the degree to which a vector may be "untargeted" to DCs may be an important parameter predicating its reduced immunogenicity. Whereas these questions can only be answered in a definitive manner in the context of human clinical trials, a preliminary index of the immunological consequences of the Ad modification strategies described herein can be gained by employing an immunocompetent system. Therefore, the magnitude of immune response induction may be determined with respect to the Ad/NSC.

Samples for evaluation of immunogenicity of the Ad/NSC may be collected from the same animals used in the biodistribution assay. On Days 34 and 62, blood samples may be collected, and plasma may be prepared and frozen until used for assay of antibodies against the Ad/NSC using a GLP-validated ELISA assay.

Statistical analysis: The statistical significance of differences in quantitative variables including body weights, food consumption, clinical pathology values, absolute and relative organ weights, copy number of vector in tissues, and, if applicable, levels of antibody may be evaluated using ANOVA followed by Dunnett's test (or t-tests for comparisons between two dose groups). Other statistical tests may also be used as deemed appropriate by the statistician. 15 animals per sex may be used for each group and time point to establish the power to detect significant differences may be larger than 99% (for a Type I error of 0.01). Inter-group comparisons will include Group 2 vs Group 1, Group 3 vs Group 1, Groups 4 and 5 vs Group 1, and Groups 4 and 5 a vs Group 3.

Example 11

Validation of HB1.F3.CD as an Effective Cell Carrier for Targeted Delivery of CRAd-Survivin-pk7 to Glioma Patients Combining the unique tumor tropism of NSCs with an OV's ability to target chemo- and radio-resistant glioma stem cells (GSCs) (Alonso et al. 2012; Kanai et al. 2012) allows the deficiencies intrinsic to each component used alone to be overcome and results in an effective treatment for targeting GBM. The Examples described above demonstrate that: i) NSCs can be used as cellular vehicles for the in vivo delivery of a OV to intracranial gliomas (Tyler et al. 2009), ii) intratumoral delivery of NSCs loaded with the CRAd-S-pk7, a glioma-tropic oncolytic adenovirus regulated by the tumor specific survivin promoter (Tyler et al. 2009; Ulasov et al. 2007a), increased median survival by 50% as compared to animals treated with OV alone in an orthotopic xenograft model of human glioma (Ahmed et al. 2011a), and iii) NSCs demonstrated superior therapeutic efficacy when compared with mesenchymal stem cells (MSCs) as a cell carrier for OV in the context of intracranial gliomas (Ahmed et al 2011b). Since these results support the use of NSCs as targeted cellular delivery vehicles for anti-glioma oncolytic virotherapy, the following important translational studies were performed to validate these results and to justify their application in a phase I clinical trial for patients with GBM: i) identify an optimal NSC-based cell carrier for anti-glioma oncolytic virotherapy, ii) test the selected NSC-based cell carrier in several diverse and clinically relevant glioma xenograft models, iii) develop a non-invasive imaging protocol to monitor in vivo distribution and migratory activity of NSC-based cell carriers in real time, iv) examine the capacity for the NSC-based cell carrier to deliver anti-glioma OV to a distant tumor burden in a glioma xenograft model, and finally v) evaluate the therapeutic efficacy of NSC-based oncolytic virotherapy in a distance-delivery glioma xenograft model.

In the Example below, a detailed evaluation of two immortalized NSC lines as cell carriers for targeted anti-glioma therapy is provided. The results indicate that HB1.F3.CD, an FDA approved NSC line for human clinical trials (NCT01172964) is the most suitable NSC cell carrier for the future application of cell-based OV delivery in the clinical setting. HB1.F3.CD cells were found to effectively hand-off the viral therapeutic payload to distant tumor sites, and significantly prolong median survival in diverse orthotopic models of human glioma. Thus, data presented in this study solidifies the notion that NSCs can be used as cell carriers for the targeted delivery of anti-glioma oncolytic viruses and serves as the foundation of an investigational new drug application (IND) for a human clinical trial involving newly diagnosed and recurrent patients with malignant gliomas.

Materials and Methods

Cell Culture and Establishment of Fluorescent-Labeled Cell Lines.

The U87MG, U118MG, U251 and A172 human glioma cell lines were purchased from the American Type Culture Collection (Manassas, Va., USA) and maintained according to vendor recommendations. U87MG and U118MG cells were cultured in MEM (minimum essential medium) (Hy-Clone, Thermo Fisher Scientific, Waltham, Mass., USA), while U251MG and A172 cells were cultured in DMEM (Dulbecco's modified Eagle's medium) containing 2% penicillin-streptomycin antibiotic (Cellgro; Mediatech, Manassas, Va.) and 10% fetal bovine serum (FBS) (Atlanta Biologicals, Lawrenceville, Ga.). All cells were grown in a humidified atmosphere, with 5% $CO_2$ and 37° C. conditions. All cell lines were sub-cultured for experimentation using 1 ml/$10^6$ cells 0.25% trypsin/2.21 mmol/l EDTA solution (cat. No. 25-053-CI; Mediatech). Trypsin activity was quenched using the appropriate media for each cell type. Cells were then washed at 300 relative centrifugal forces (rcf) and plated at the indicated densities.

Human primary brain tumor specimens (GBM43 and GBM12) were obtained from Dr. David James (UCSF) in accordance with a protocol approved the by IRB at UCSF. Tumor specimens were confirmed as World Health Organization grade IV malignant glioma by an attending neuropathologist. All human tissue specimens were treated with 1% hyaluronidase (Sigma-Aldrich, St. Louis, Mo., USA) and 2% collagenase (Sigma-Aldrich) enzymes and subsequently minced through 70 μm strainers. After several washings in phosphate-buffered saline (PBS) solution, cells were then cultured in flasks containing neural basal media (NBM) (Invitrogen) supplemented with 100 μg mL$^{-1}$ ampicillin/streptomycin and 20 ng mL$^{-1}$ each of EGF (epidermal growth factor) (Millipore, Billerica, Mass., USA) and bFGF (basic fibroblast growth factor) (Millopore). Cells were maintained in a humidified atmosphere containing 5% $CO_2$ at 37° C.

Following previously described protocols (Sarakaria et al. 2006; Barbosa et al. 2006), a human GBM xenograft panel was established and maintained using the cell lines referenced above (GBM43 and GBM12). Shortly, to maintain these cell lines exclusively in animals, patient tumor specimens were implanted into the flank of nude mice and then serially passaged as heterotopic tumors. For primary cell culture and in vitro analyses, flank glioblastoma tissues were minced through 70 μm strainers, mechanically disaggregated and cultured in flasks coated with growth factor reduced Matrigel (Fisher Scientific, Hampton, N.H., USA). After several washings in phosphate-buffered saline (PBS) solution, cells were cultured in DMEM 1% FBS containing 2% penicillin-streptomycin antibiotic (Cellgro; Mediatech, Manassas, Va.).

Human ReNcells (NSCs) were obtained from Millipore (Temecula, Calif.) and maintained according the manufacturer's protocol. Briefly, these NSCs were isolated from the cortical region of 14-week-old fetal tissue and immortalized by retroviral transduction and insertion of the c-myc gene. Cells were characterized according to the expression of nestin, SOX-2, CD133, and CD44 (data not shown) stem cell markers. Subcultures of human NSCs for experimentation were conducted as follows: tissue culture plastic dishes were coated with laminin (Sigma-Aldrich, St Louis, Mo.) at a concentration of 20 μg/ml in serum-free DMEM in 37° C. and 5% $CO_2$ atmospheric conditions 4 hours before NSC plating. NSCs were detached from plastic dishes using 1 ml/10$^6$ cells of Accutase (Millipore), centrifuged at 300 rcf for 5 min, resuspended in ReNcell NSC Maintenance Medium (Millipore), supplemented with 20 ng/ml bFGF (Millipore) and 20 ng/ml EGF (Millipore), and seeded at the indicated cell densities.

HB1.F3-CD, a v-myc immortalized human NSC line that constitutively expresses cytosine deaminase (CD), was extracted from human fetal brain (Aboody et al. 2006). These NSCs were maintained in adherent cultures in DMEM supplemented with 10% FBS (Atlanta Biologicals, Lawrenceville, Ga.), 2 mmol l$^{-1}$ L-glutamine, 100 units ml$^{-1}$ penicillin, 100 μg ml$^{-1}$ streptomycin (Invitrogen, Carlsbad, Calif.).

To detect the distribution of NSCs in vivo, both GFP labeled ReNcell and HB1.F3-CD cell lines were generated. In short, cells were seeded at a density of $5\times10^4$ cells/well (or 50-60% confluence) in six-well plastic culture dishes (Becton Dickinson, Franklin Lakes, N.J.). One day after plating, cells were incubated for 24 h with replication-deficient lentiviral vectors containing GFP expression cassettes. For the establishment of stable clonal populations, 48 hours post-transduction, medium was replaced with fresh DMEM 10% FBS containing 4 μg ml$^{-1}$ puromycin (Sigma-Aldrich). Following selection, FACS was performed to verify GFP expression in HB1.F3-CD NSCs.

To detect tumor location and track tumor volume post-therapy in vivo, stable and fluorescently labeled glioma cell lines were established as follows. Using the same protocol depicted above, U87MG and GBM43 glioma cell lines were incubated for 24 hours with replication-deficient lentiviral vectors containing F-luciferase (Fluc) expression cassettes. After 48 hours, media was replaced with fresh culture media appropriate for each cell type containing 1 μg/ml puromycin (Sigma-Aldrich) for the establishment of stable clonal populations.

To detect NSCs migration in vivo via MRI (Magnetic Resonance Imaging), HB1.F3-CD NSCs were labeled with MPIO contrast reagent. Succinctly, MPIO reagent from Bangs Laboratories (Fisher, Ind., US) (1 mm diameter) was transfected overnight into HB1.F3-CD NSCs, using Fugene transfection reagent (Roche) and Opti-MEM reduced serum medium (Life Technologies) in 37° C. and 5% $CO_2$ at in a ratio of 17 particles per cell. Cells were then returned to their recommended medium and posteriorly used for intracranial injection in U87MG tumor-bearing mice.

Viral Vector. The replication competent adenoviral vector CRAd-S-pk7 contains the wild-type adenovirus replication protein, E1A, under the control of human survivin promoters. This vector has been created by homologous recombination using a shuttle plasmid containing the human survivin promoter upstream to the viral E1A gene. Shuttle plasmids containing these regions were further homologously recombined into adenoviral plasmids modified to contain a polylysine (pk7) incorporation into the C-terminus of the wild-type fiber protein (Ulasov et al. 2007a; Ulasov et al. 2007b).

Analysis of Viral Replication. To detect the level of viral replication by quantitative PCR, NSCs were plated at a density of $2.5\times10^4$ cells/well in 24-well plastic tissue culture dishes. The next day, cells were infected with indicated I.U./cell of CRAd-S-pk7. After a 1-hour incubation period, virus-containing media was removed, cells were washed with 1×PBS, and a fresh portion of complete growth media was added. Infected cells were harvested at indicated time points. Total DNA was extracted from infected cells using a DNeasy Tissue Kit (Qiagen, Hilden, Germany) according to the manufacturer's protocol. Gene expression was quantified by real-time quantitative PCR (qRT-PCR) using SYBR Green PCR Master Mix (Applied Biosystems, Foster City, Calif.) and primers recognizing the viral EIA gene (Ulasov et al. 2007b) In this process, DNA was amplified by using an Opticon 2 system (Bio-Rad, Foster City, Calif.) and was detected by measuring the binding of the fluorescent dye, SYBR green. Each sample was run in triplicates. Results were presented as the average number of EIA copies per ng of DNA (E1A copies per ng DNA).

The Adeno-X Rapid Titer Kit (Clontech, Mountain View, Calif.) was used according to the manufacturer's protocol to titrate the levels of infectious viral progeny. Briefly, infected cells and media from each group were collected and subsequently subjected to three cycles of freezing and thawing. As a consequence, infectious progenies were released from infected cells. Cell lysates were then incubated with adherent HEK293 cells in serial tenfold dilution. Forty-eight hours later, the amount of I.U. was calculated using the Adeno-X Rapid Titer Kit according to vendor recommendations. The titration units (I.U.) used by this protocol are similar to plaque-forming units.

Analysis of the Optimal Ex-vivo Loading. The total number of cells to be injected in vivo was based on the studies described above, where it was reported that infection with 50 I.U. per cell of CRAd-S-pk7 viruses resulted in maximum progeny released over time with minimum toxicity to carrier cells and proved superior survival benefit to glioma-bearing mice. To optimize the ex-vivo loading protocol, infection efficiency of CRAd-S-pk7 virus was examined. For this, cell suspension and monolayer of HB1.F3.CD cells were incubated with DMEM 10% FBS containing 50 I.U. per cell of CRAd-S-pk7 viruses for 1, 2 and 4 hours. Infected cells were washed and cultured for 24 hours. Cells were then harvested and subjected to fluorescence-activated cell sorting analysis with goat anti-hexon FITC-conjugated antibody (Millipore), and the measurement of viral DNA replication was done by the PCR method as described previously.

Evaluation of Relative Gene Expression by qRT-PCR. Total cellular RNA was isolated using an RNeasy kit (Qiagen, Valencia, Calif.) according to the manufacturer's protocol and in each instance 1 μg of purified mRNA was reverse transcribed to complementary DNA using the iScript cDNA conversion kit (Bio-Rad). Quantitative PCR was conducted using the SYBR Green quantitative PCR kit (Invitrogen, Carlsbad, Calif.) for all experiments. Optimization of annealing temperatures for each transcript was first conducted. Each transcript of interest was amplified in triplicates at its proper annealing temperature and products were analyzed using the Opticon 2 software (Bio Rad, Hercules, Calif.). Amplification of the correct product, together with confirmation of product size was verified by running samples on 2% agarose gel electrophoresis. Relative expression was evaluated using the $\Delta CT$ method ($\Delta CT=CT$ gene of interest$-CT$ GAPDH) where a $\Delta CT$ of 3.33 is equivalent to one magnitude change in gene expression. This logarithmic dependence was verified for each gene studied by conducting quantitative PCRs on serial complementary DNA dilutions. Expression data are presented as fold change of the linearized $\Delta CT$ ($2-\Delta CT$) over control expression levels.

Flow Cytometry Analysis of Protein Expression. Cells were labeled and analyzed for both surface and intracellular markers as previously described (Tyler et al. 2009). Briefly, cells were permeabilized, fixed and stained on ice using the Cytofix/Cytoperm buffer (BD Biosciences, San Jose, Calif.) according to manufacturer's instructions. The following antibodies were used: rabbit polyclonal anti-GFAP (Abcam, Cambridge, Mass.). Data was acquired and analyzed using Canto with CellQuest (Becton Dickinson) and FlowJo (TreeStar, Ashland, Oreg.) software.

Evaluation of NSC Migration and Viral Delivery in vitro. To analyze the migratory capacity and oncolytic adenovirus delivery characteristics of HB1.F3-CD and ReNcells in vitro, system that is similar to that described above was used (Ulasov et al. 2007f), with a slight modification. To characterize the specificity of each stem cell carrier migration in response to glioma, a BD Biocoat Tumor Invasion System (BD Biosciences, http://www.bdbiosciences.com) containing BD Falcon Fluoroblock 24-Multiwell inserts (8-μm pore size; PET membrane) was used in accordance with the manufacturer's protocol. To aid in quantification of stem cell migration, fluorescently labeled HB1.F3-CD and ReNcells (described above) were used. The migration was characterized with respect to four different conditioned media and a negative control. Conditioned medium was obtained by culturing $1\times10^5$ cells of each cell type (GBM43, GBM12, U118MG, U87MG, U251MG and A172) in serum-free/growth factor-free medium for 24 h, after which equal amounts of each conditioned medium was aliquoted in the bottom wells of the migration chamber to serve as a chemo attractant. For migration studies without adenovirus, HB1.F3-CD and ReNcells were plated in Serum-free MEM at a density of $5\times10^4$ cells/well. Twenty-four hours after plating HB1.F3-CD and ReNcells into the top insert, the number of migrating cells/field view was determined using an Olympus IX81 inverted microscope and MetaMorph software (Olympus, Tokyo, Japan). Cells were counted in three random field views/well (original objective: 10×). A total of 4 wells were used for each experimental condition (i.e., U118MG=4 wells).

For studies involving HB1.F3-CD and ReNcells-mediated delivery of adenoviruses, the same migration apparatus was used; however, HB1.F3-CD and ReNcells were loaded with different I.U. of CRAd-S-pk7 virus prior to being plated in the top chamber of the migration apparatus ($5\times10^4$ cells/well). Instead of conditioned medium, U87MG cells were plated in the bottom wells of the migration chamber in serum-free MEM supplemented with 20 ng/mL of bFGF and EGF at a density of $5\times10^4$ cells/well two days before NSCs were plated in the top well of the migration chamber. The number of migrating cells was assessed as described above. Non-loaded HB1.F3-CD and ReNcells were plated in chambers immersed in serum-free MEM as a reference control. Nine days after plating loaded NSCs in the top inserts, the number of infectious units in each of the bottom wells (4 wells/experimental condition) was quantified using the Adeno-X Rapid Titer Kit as described above. Cytotoxicity resulting from stem cell release of viral progeny was quantified by counting the number U87MG glioma spheroids/field view (4 original objective) using the same Olympus IX81 inverted microscope. Three random field views per well were captured. There were a total of 4 wells per experimental condition.

Animal Studies. Intracranial glioma xenograft implantation: U87MG glioma cells were implanted via cranial guide screws as described previously. Briefly, mice were anesthetized with a ketamine/xylazine mixture (115/17 mg/kg), and a burr hole was made. Stereotactic injection was carried out by using a 10 μl Hamilton syringe (Hamilton, Reno, Nev.) with a 30-gauge needle, which was inserted through the burr hole to a depth of 3 mm mounted on a mice-exclusive stereotactic apparatus (Harvard Apparatus, Holliston, Mass.). Male athymic/nude mice were obtained from Charles River Laboratory (Wilmington, Mass.). Animals were cared for according to a study-specific animal protocol approved by the University of Chicago Institutional Animal Care and Use Committee.

To detect loaded HB1.F3-CD and ReNcells in vivo, mice were injected with $3\times10^5$ U87MG cells in 2.5 μL of PBS/mouse. Five days later, mice were randomly divided into 6 groups (n=6-9 mice/group) that received the following injections: one group received an injection of 2.5 μL of PBS/mouse (Mock); one group received an injection of $1\times10^5$ HB1.F3-CD NSCs in 2.5 μL of PBS/mouse; one group received an injection of $1\times10^5$ ReNcells in 2.5 μL of PBS/mouse; one group received 2.5 μL injections of $1\times10^5$ HB1.F3-CD NSCs infected with 5 I.U. of CRAd-S-pk7/mouse (NSC+Virus); and one group received 2.5 μL injections of $1\times10^5$ ReNcells infected with 5 I.U. of CRAd-S-pk7/mouse (NSC+Virus). U87MG glioma cells were detected via luciferase expression, and HB1.F3-CD and ReNcells were detected by GFP expression.

Three mice from each group were sacrificed, and their brains were flash frozen in OCT solution at days six, nine, and twelve after the second round of injections (thirteen, sixteen, and nineteen days after U87MG injection). Brains underwent serial coronal sectioning (6 µm/section) for a total of 20-25 slices per tissue, altogether spanning approximately 3 mm of brain tissue. Slices were fixed (4% paraformaldehyde, 10 min) and mounted on glass slides using Prolong Gold Antifade Reagent (Invitrogen). Fluorescent microscope analysis was performed using a Zeiss 200 M Axiovert inverted microscope (Carl Zeiss, Inc., Oberkochen, Germany). U87MG tumors (Luciferase) were detected by using anti-CD44 antibody and HB1.F3-CD and ReNcells (GFP) were detected by using a GFP optical band-pass filter. Fluorescent images were analyzed and rendered for publication using Openlab v5.0 (Improvision, Coventry, England) and Adobe Photoshop CS2 (Adobe Systems, Inc., San Jose, Calif.).

To evaluate the therapeutic efficacy of NSCs loaded with CRAd-S-pk7 oncolytic virus (OV), six groups of seven nude mice were implanted with U87MG cells ($5 \times 10^5$ cells in 2.5 µL of PBS/mouse into the right hemisphere as previously described). Five days post-tumor implantation, mice received an intracranial, intratumoral injection of $5 \times 10^5$ NSCs loaded with OV (50 I.U./cell) or an equal dose of naked virus. Both the stem cells were incubated with the oncolytic adenovirus for 2 h at room temperature, washed 3 times with PBS, resuspended in PBS (5 $10^5$ stem cells in 2.5 µL/mouse) and injected intratumorally in the right hemisphere. Animals losing ≥30% of their body weight or having trouble ambulating, feeding, or grooming were euthanized by $CO_2$ followed by cervical dislocation.

Immunohistochemistry Staining for In Vivo Evaluation of Cell Migration. For immunohistochemistry, brains were sectioned in 10-mm thick sections. After thawing, sections underwent fixation/permeabilization with a solution of 50/50 acetone-methanol, at −20° C. for 5 min. The slides were washed with ice-cold PBS and blocked with 10% bovine serum albumin for 30 min. They were then incubated overnight at 4° C. with primary antibodies, followed by 1 h incubation at room temperature with the secondary antibody. After washing the excess antibody, slides were mounted with Prolong Gold antifade reagent with 4,6-diamidino-2-phenyl indole (Invitrogen). Fluorescent images were documented with an inverted Axiovert200 Zeiss microscope (Carl Zeiss Microscopy, Thornwood, N.Y.). In this process, the following antibodies were used: FITC-conjugated anti-GFP antibody, biotin-conjugated anti-hexon and FITC-conjugated immunoglobulin controls were purchased from Abcam; human CD44 rabbit monoclonal antibody purchased from Epitomics (Burlingame, Calif.); AlexaFluor555-streptavidin and Alexafluor350 donkey anti-rabbit were purchased from Invitrogen.

In Vivo Bioluminescence Imaging. Mice were imaged for Fluc (Luciferase) activity by intraperitoneal injection of D-luciferin (4.5 mg/animal in 150 µL of saline), and photon counts were recorded 10 min after D-luciferin administration by using a cryogenically cooled high efficiency charged-coupled device camera system (Xenogene).

NSC Labeling with Microparticles of Iron Oxide (MPIO). The properties of NSC's that were evaluated included the loading efficiency and retention time, cell viability, the effect on differentiation status, and the loading effect on tumor tropic migration; all in relation to varying doses of MPIO's, introduced into the NSC's using a Lipofectamin (Fugene, Roche) based method.

The relationship between cell number increase and MPIO marked cells (MPIO loading efficiency) was evaluated to see if the cells were receiving the MPIOs and dividing with them still embedded, or if the cell divisions caused a total loss of MPIOs. A total loss of MPIOs would indicate that any divisions of the NSCs before they reached the disseminated tumor burden would cause a loss of signaling, hampering tracking. Loading efficiency was tested using FACS (fluorescence activated cell sorting), with APC-conjugated nanoparticles. The NSCs were transfected 16 hours in advance, and then labeled with violet crystal staining, a dye which becomes more diluted as the cell divides more (as measured by the PacBlue %).

A loading threshold between 17 nanoparticles per cell and 34 nanoparticles per cell was observed (approximately 20 nanoparticles per cell corresponds with a high percentage of nanoparticle uptake). There is a visible increase in cell division over the two-day period, as well as a corresponding decrease in number of APC-conjugated cells over the same timeframe. This would indicate some relationship between the decreases in the percentage of nanoparticle labeled cells with the cell divisions, as measured by PacBlue levels. Additional studies may be performed to optimize APC levels.

Cell viability was evaluated using the Trypan Blue exclusion method. Different dosages were evaluated, using 0 nanoparticles per cell as a control, with 8.5, 17 and 34 nanoparticles per cell as the corresponding dosages. No observable decrease in cell viability over the two-day period post MPIO loading was shown. To the contrary, there were significant increases in cell number for some dosages. Room remains for the cell viability to be evaluated in a longer timeframe.

Loading effect on migration was evaluated using qRT-PCR (quantitative real time polymerase chain reaction. The results for Nestin (stem cell marker), Oct4 (neuro progenitor cell marker), Tuj1 (neuron marker) and VEGFR (marker for migrations) showed no dramatic difference between the control and various dosages of nanoparticles. VEGFR was expressed highly at the RNA level, which indicates no decline in the tumor tropic migrations, meaning that nanoparticles do not inhibit migration. Further validation of protein expression will follow.

In vivo MRI Imaging. MPIO is an important functional imaging tool known to create a potent hypointense contrast effect on MRI imaging (Anthony et al. 2011). In this study, HB1.F3-CD NSCs previously labeled with MPIOs were tracked by magnetic resonance imaging in vivo. Nude mice previously injected or not with U87MG glioma cells on the right brain hemisphere and MPIO-labeled HB1.F3-CD NSCs on the contralateral (left) brain hemisphere were studied two days post-NSC injection on a 33 cm horizontal bore Bruker 9.4 T small animal scanner with a Bruker console (Bruker-Biospin, Billerica, Mass.). The machine was equipped with a 12 cm shielded gradient set with a maximum strength of 600 mT/m and was available through the University of Chicago Core Facility. Prior to MRI study, animals were anesthetized by 2% isoflurane in oxygen and fixed in a prone position during scanning. In order to achieve sufficient resolution to visualize labeled NSCs within the mouse brain, a multi-slice axial and coronal T1/T2-weighted A Fast Low Angle Shot (FLASH) gradient echo sequence was acquired using the following parameters: flip angle 30°; echo time (TE), 4.9 ms; time of repetition (TR), 200 ms; NEX, 4; slice thickness, 0.5 mm; matrix size, 256×256; field of view (FOV), 2.56×2.56 cm. Same level slices were used to track and compare NSCs migration towards U87MG in tumor bearing mice.

Statistical Analysis. All statistical analyses were performed using Graphpad Prism 4 (GraphPad Software Inc., San Diego Calif.). Data represent the results for assays performed in triplicate and repeated at least three different times, and error bars represent 95% confidence intervals. For continuous variables, comparisons between two groups were evaluated by statistical significance of difference of means in independent sample sets and was determined using Students's t test, comparisons between more than two treatment groups were made using one way ANOVA or Kruskal-Wallis with Dunnett's post hoc test. Survival curves were generated by the Kaplan-Meier method, and the log-rank test was used to compare the distributions of survival times. All reported P values were two-sided and were considered to be statistically significant at <0.05. * indicates a p-value<0.001;  indicates a p-value<0.01; * indicates a p-value<0.05.

Results

Phenotypic characterization of the NSC lines and their permissiveness for oncolytic adenovirus. To identify an optimal NSC-based carrier, the phenotypes of the two neural stem cell lines HB1.F3.CD and ReNcell were characterized. The HB1.F3 cells were isolated from fetal human telencephalon cells (at 15 weeks gestation) and subsequently immortalized by retrovirus mediated stable integration of the v-myc gene to create a multipotential neural stem cell line (Kim et al. 2008). This cell line was further modified by retrovirus mediated insertion of the E. coli cytosine deaminase (CD) gene as a suicide gene therapeutic system and is currently being evaluated in a human phase I clinical trial in patients with recurrent high-grade glioma (Aboody et al. 2000). ReNcells were purchased from Millipore and isolated from the ventral mesencephalon region of human fetal brain. This cell line was also immortalized by retroviral transduction with the v-myc oncogene.

Figure 28A:
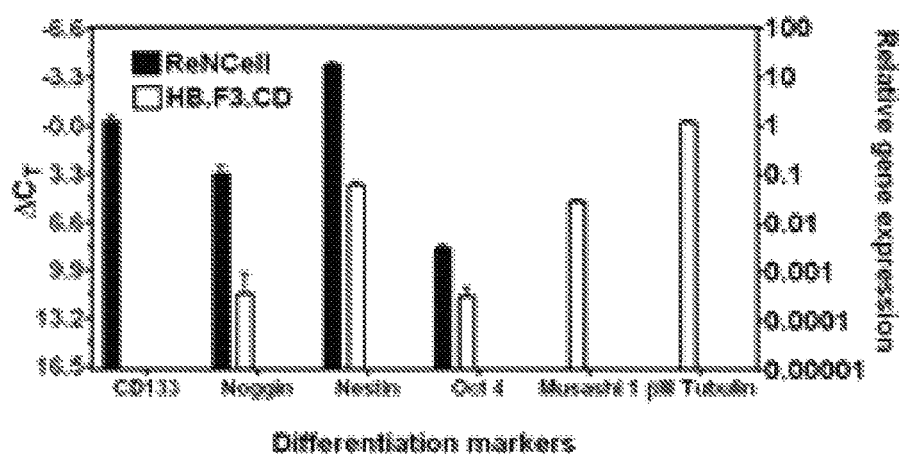
FIGS. 28A, 28B, and 28C show phenotypic characterization of NSCs according to one embodiment.
Figure 28B:
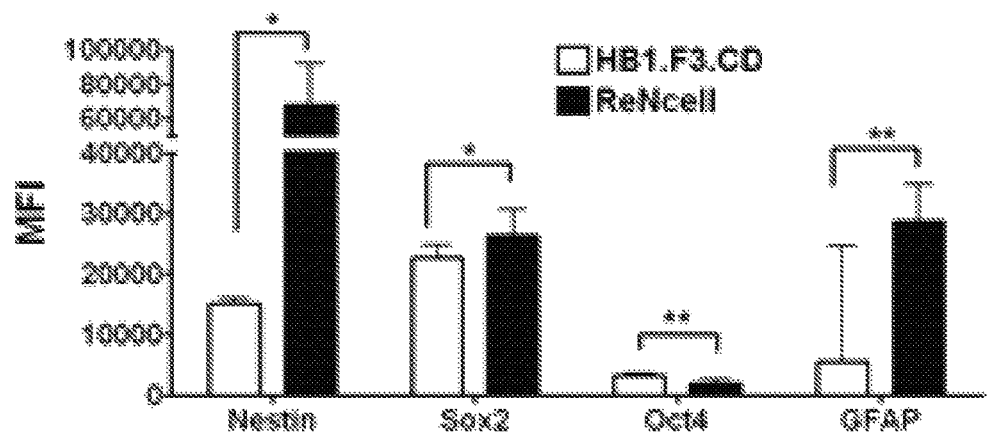
Figure 28C:
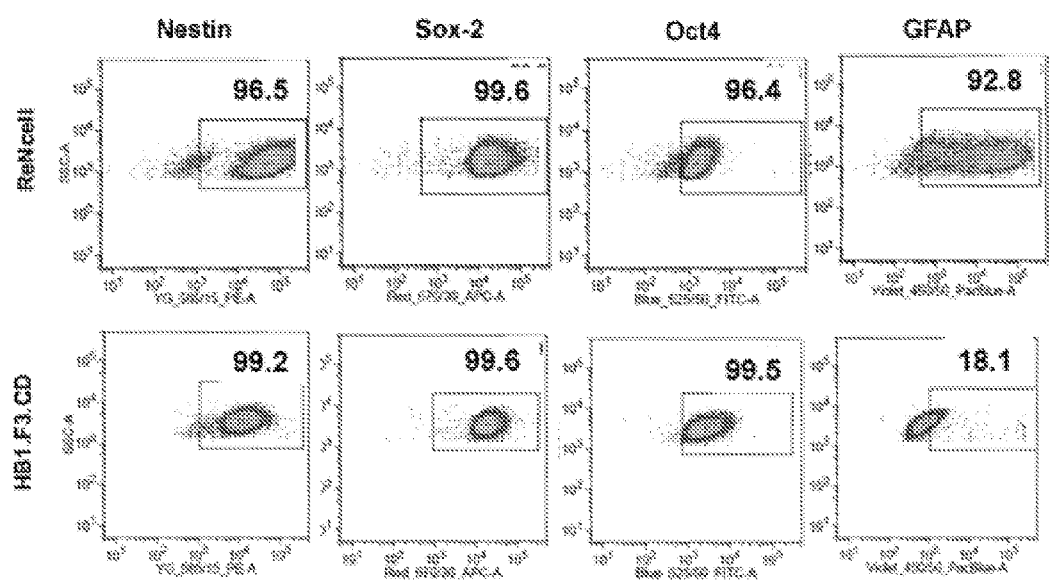

Both cell lines expressed high levels of the pluripotency genes Sox-2, Oct4 and the neural progenitor marker nestin at the mRNA and the protein level (FIGS. 28A, 28B, and 28C). However, the ReNcell line expressed significantly elevated levels of nestin protein per cell bases as indicated by the mean fluorescent intensity (MFI; SF 1B), CD133 mRNA (FIG. 28A) and protein (data not shown) levels. Bars represent the mean values from three independent experiments, error bars refer to 95% confidence intervals Almost 92.8% of ReNcells were positive for GFAP, which is indicative of an astrocytic lineage. On the other hand, HB1.F3.CD cells expressed high levels of Musashi 1 and the neural marker beta-III tubulin transcripts and expressed no CD133 on the transcription (FIG. 28A) or protein level or (data not shown). The immortalized cell lines also retained their functional neural stem cell characteristics such as the ability to form neurosphere like structures and differentiate into neurons, astrocytes or oligodendrocytes in the presence of the appropriate growth factor conditioned media.

Figure 29A:
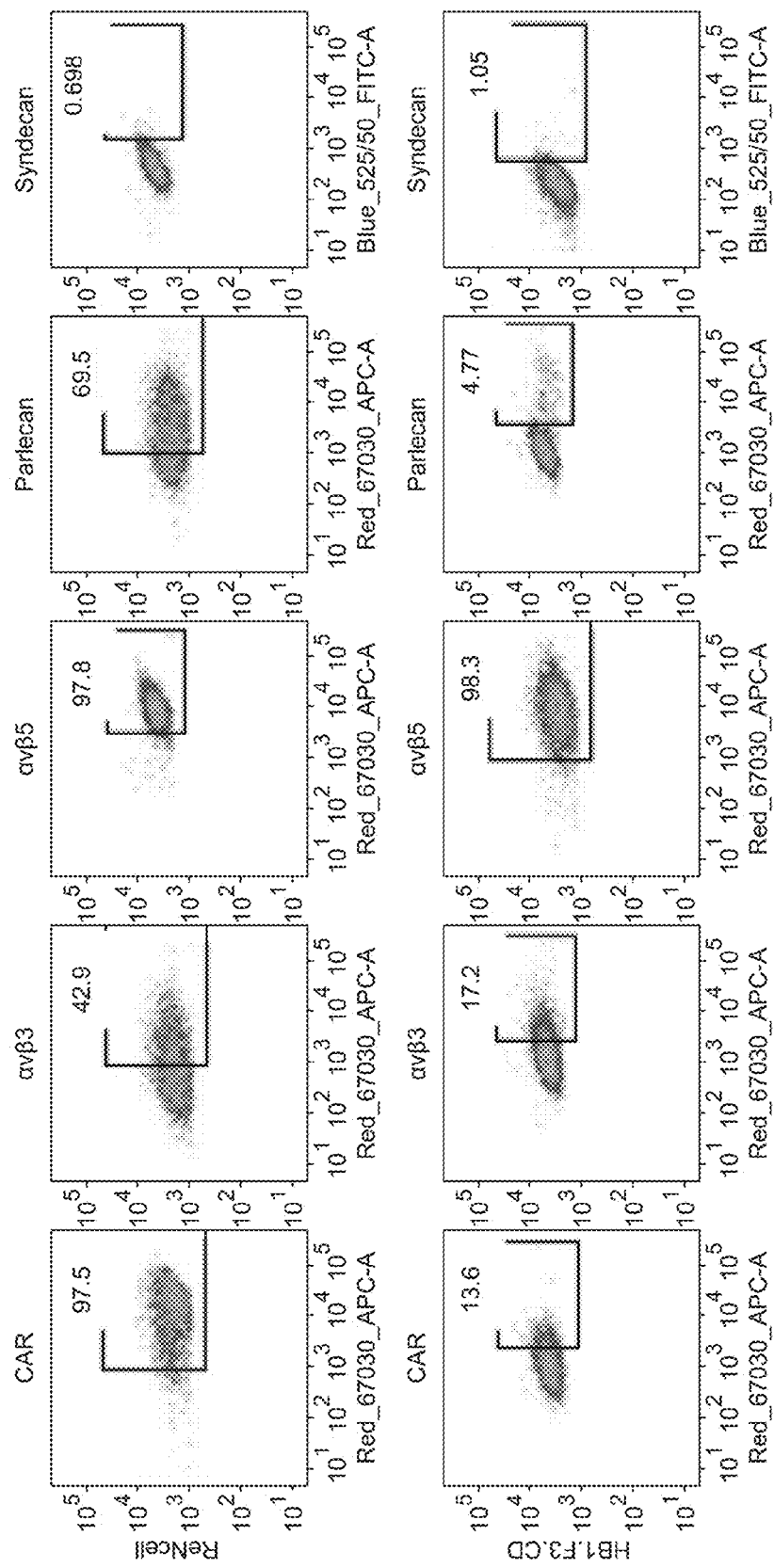
FIGS. 29A, 29B and 29C show adenovirus entry receptor expression in NSCs according to one embodiment.
Figure 29B:
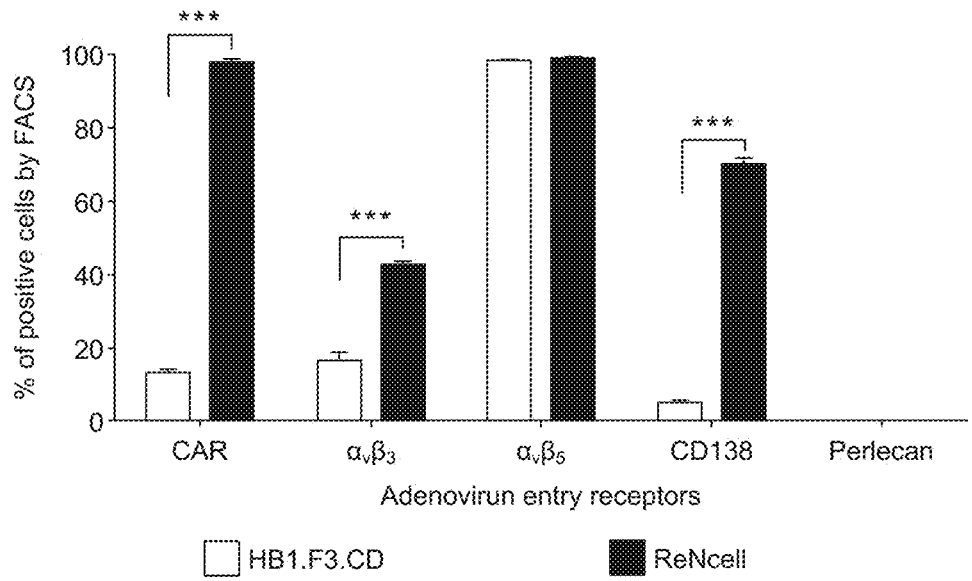
Figure 29C:
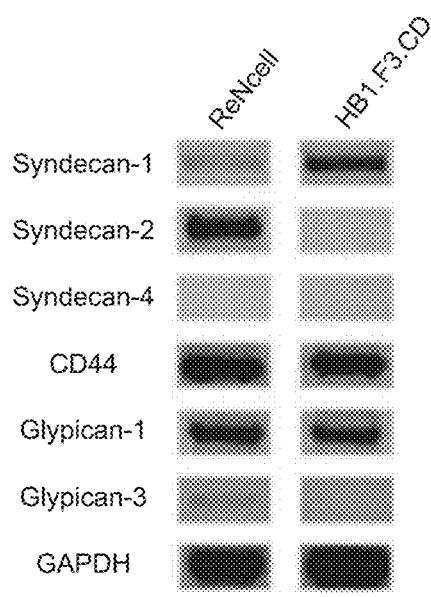

In order to function as an effective cell carrier for anticancer oncolytic virotherapy, a cell system must not only be susceptible to therapeutic viral infection, but also capable of supporting viral replication and amplifying the therapeutic payload at the target site. To identify an optimal NSC-based carrier, the cell lines HB1.F3.CD and ReNcell were compared for their permissiveness to the glioma tropic oncolytic adenovirus CRAd-S-pk7, and assessed their ability to support viral replication in vitro. Fluorescent Activated Cell Sorting (FACS) analysis was conducted to assess the permissiveness to CRAd-S-pk7 infection by examining the expression of adenovirus binding and internalization receptors on the NSCs. The ReNcells expressed significantly higher levels of initial virus attachment Coxsackie Adenovirus Receptor (CAR) (ReN vs. HB1.F3.CD, 97.5% vs. 13.4% difference=84.1%, 95% CI=83.4%-84.8%, P<0.001) and the cell entry receptor integrin $\alpha_v\beta_3$ (ReN vs. HB1.F3.CD, 42.5% vs. 16.6% difference=25.9%, 95% CI=24.2%-27.6%, P<0.001), as well as Syndecan-1 (ReN vs. HB1.F3.CD, 69.8% vs. 5.0% difference=64.8%, 95% CI=63.7%-65.9%, P<0.001) but expressed almost identical levels of integrin $\alpha_v\beta_5$ and Perlecan as compared to HB1.F3.CD cells (FIG. 29A & 29B). Next, heparan sulfate proteoglycan (HSPG) (the pk7 retargeted attachment receptors for CRAd-S-pk7) expression on the NSCs was examined by FACS or reverse transcriptase polymerase chain reaction (RT-PCR) with results shown in FIGS. 29A, 29B, & 29C. This data shows that even though ReNcells expressed a significantly higher level of the primary attachment receptor CAR for adenovirus entry, HSPGs were expressed by both of the tested NSC lines and should allow the entry of CRAd-S-pk7.

Figure 30A:
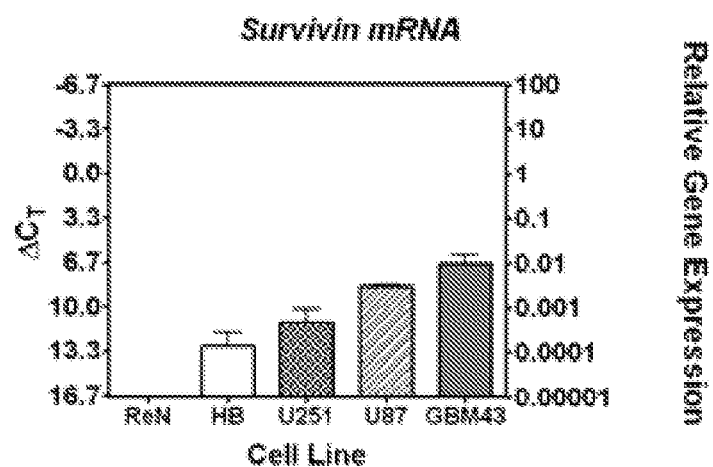
FIGS. 30A, 30B, 30C, 30D and 30E illustrate the permissiveness of NSC lines to adenovirus infection according to one embodiment.
Figure 30B:
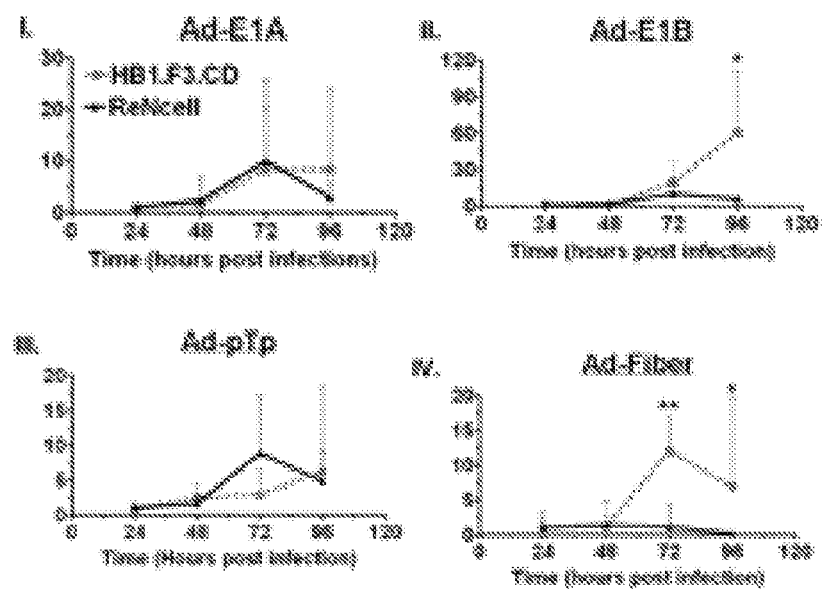

Replication kinetics of CRAd-S-pk7 in NSC carriers. The glioma restricted oncolytic virus CRAd-S-pk7, consists of two genetic modifications: (i) a fiber modification containing polylysine that binds with high affinity to HSPGs and (ii) E1A transcription under the control of the survivin promoter (Ulasov 2007a; Ulasov 2007c). Thus, replication initiation of CRAd-S-pk7 in the host cell population is dependent on the activity of the survivin promoter. As shown in FIG. 30A, survivin mRNA levels is significantly elevated in HB1.F3.CD cells as compared to ReNcells. Moreover, higher survivin transcript levels were observed in the three tested glioma cell lines than the two NSC lines. Next, to evaluate the replication kinetics of CRAd-S-pk7 in NSCs, the mRNA level of replicative essential adenovirus genes were examined by quantitative reverse transcriptase polymerase chain reaction (qRT-PCR). It was observed that HB1.F3.CD cells exhibit a higher mRNA transcript level of E1B (FIG. 30B-II, HB1.F3.CD vs. ReN, 60.43 vs. 6.16 difference=54.27, 95% CI=3.52-10$^5$, P=0.04) as well as the fiber protein (FIG. 30B-IV) (HB1.F3.CD vs. ReN, 6.87 vs. 0.24 difference=6.63, 95% CI=−6.32-19.57, P=0.16) at 4 days post infection (d.p.i.) compared to ReNcells. Additionally, an elevated level of adenovirus EIA copies was observed (data not shown).

Figure 30C:
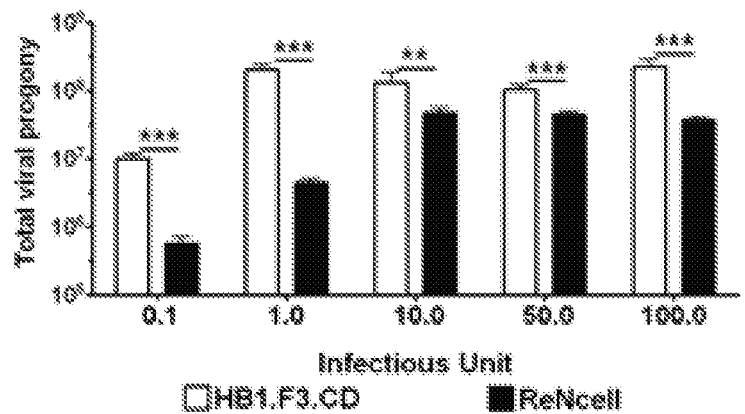

Next, an optimal ex vivo OV loading dose was established by infecting NSCs with differing doses of CRAd-S-pk7 (0.1 I.U./cell-100.0 I.U./cell) and cells were harvested and subjected to total titer evaluation at 3 d.p.i. HB1.F3.CD cells produced a similar total viral progeny from the doses of 1 I.U./cell to 100 I.U./cell whereas ReNcells produced a maximum total viral progeny at the loading dose of 50 I.U./cell, which was over a third of a fold lower than the progeny produced by HB1.F3.CD cells at that loading dose (ReN vs. HB1.F3.CD, 7.7 vs. 8 difference=0.37, 95% CI=0.30-0.43, P<0.001 log scale) (FIG. 30C). Based on this data as well as previous data (Thaci et al. 2012), a dose of 50 I.U./cell was selected as the loading dose for the NSCs in the subsequent studies. Next, to evaluate virus replication and release over time, HB1.F3.CD cells and ReNcells were infected with 50 I.U./cell of CRAd-S-pk7 and harvested the cells and supernatant separately at 2, 3, 4 and 5 d.p.i. At both 4 and 5 d.p.i., HB1.F3.CD cells had a significantly higher cell associated viral titer compared to ReNcells (FIG. 30D-I) (4 d.p.i: HB1.F3.CD vs. ReN, 7.67 vs. 6.92 difference=0.75, 95% CI=0.60-0.88, P<0.001; 5 d.p.i: HB1.F3.CD vs. ReN, 7.66 vs. 6.0 difference=1.66, 95% CI=1.54-1.79, P<0.001; log scale). More importantly as compared to ReNcells, HB1.F3.CD cells released significantly higher levels of CRAd-S-pk7 progeny at 3 (ReN vs. HB1.F3.CD, 5.7 vs. 6.2 difference=0.55, 95% CI=0.41-0.68, P<0.001 log scale), 4 (ReN vs. HB1.F3.CD, 5.8 vs. 6.9 difference=1.04, 95%

Figure 30D:
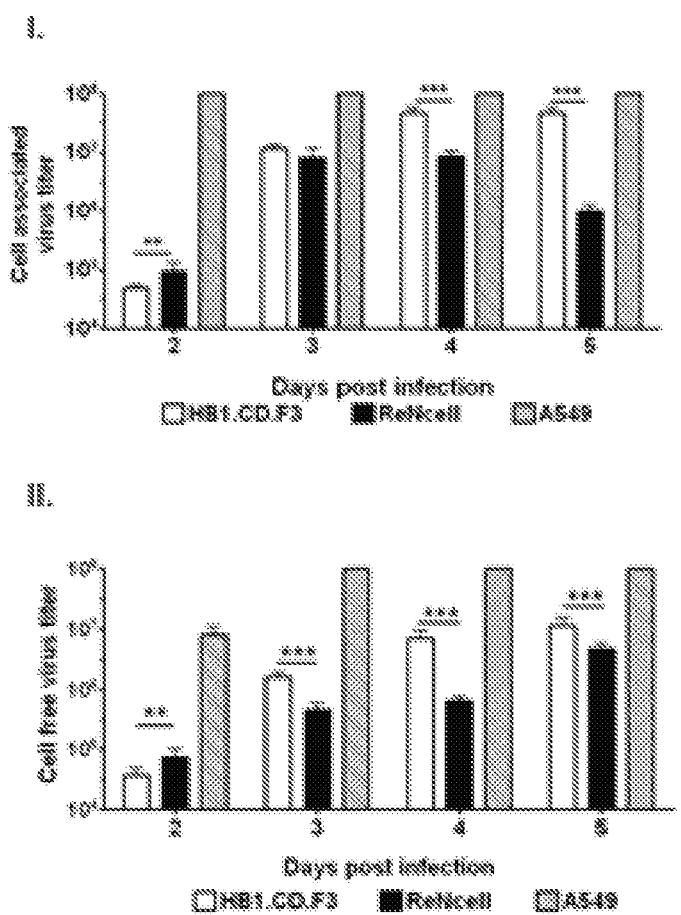

CI=0.92-1.16, P<0.001 log scale) and 5 (ReN vs. HB1.F3.CD, 6.7 vs. 7.0 difference=0.38, 95% CI=0.23-0.54, P<0.001 log scale) d.p.i. (FIG. 30D-II).

Figure 30E:
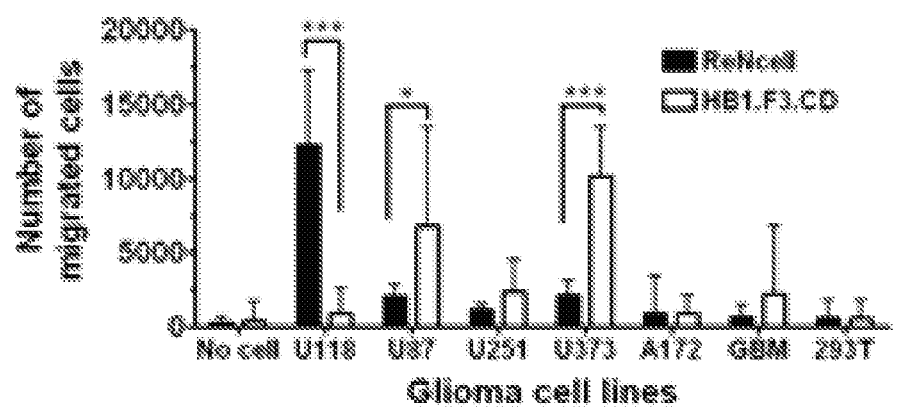

The inherent tumor pathotropism of NSCs is central to their utility as a reliable cell carrier for cancer gene therapy. As such, the glioma tropic migratory capacity of NSC lines was evaluated by using a previously described transwell migration assay (Ahmed et al 2011a). As shown in FIG. 30E, the HB1.F3.CD line showed more robust migration towards several established glioma cell lines as compared to ReNcells, which showed greater migration in response to the U118 glioma line (HB1.F3.CD vs. ReNcell, 888.9 vs. 12220 difference=−11330, 95% CI=−14780 to −7885, P<0.001; 6778 vs. 2000 difference=4778, 95% CI=426.6-9129, P=0.04; 10110 vs. 2111 difference=8000, 95% CI=5754-10250, P<0.001 for U118, U87, U373 respectively).

Loading MPIO into NSCs. To evaluate whether OV-loaded HB1.F3.CD cells migrate to distant tumor foci in animal brains, Magnetic Resonance Imaging (MRI) was employed to non-invasively monitor the migratory behavior of the implanted HB1.F3.CD-loaded with OV in the orthotropic glioma xenograft model. It has been previously reported that MRI-based cell tracking can be achieved by labeling cells with microparticles of iron oxide (MPIO) pre-implantation (Thu et al. 2009). Based on this, an in vitro protocol to label HB1.F3.CD cells with fluorescent-tagged MPIOs (purchased Bang's Laboratory MC03F) was established. The loading of MPIOs into NSCs was achieved by using FuGene6-based transfection reagent according to the manufactures protocol (Roche).

Figure 31:
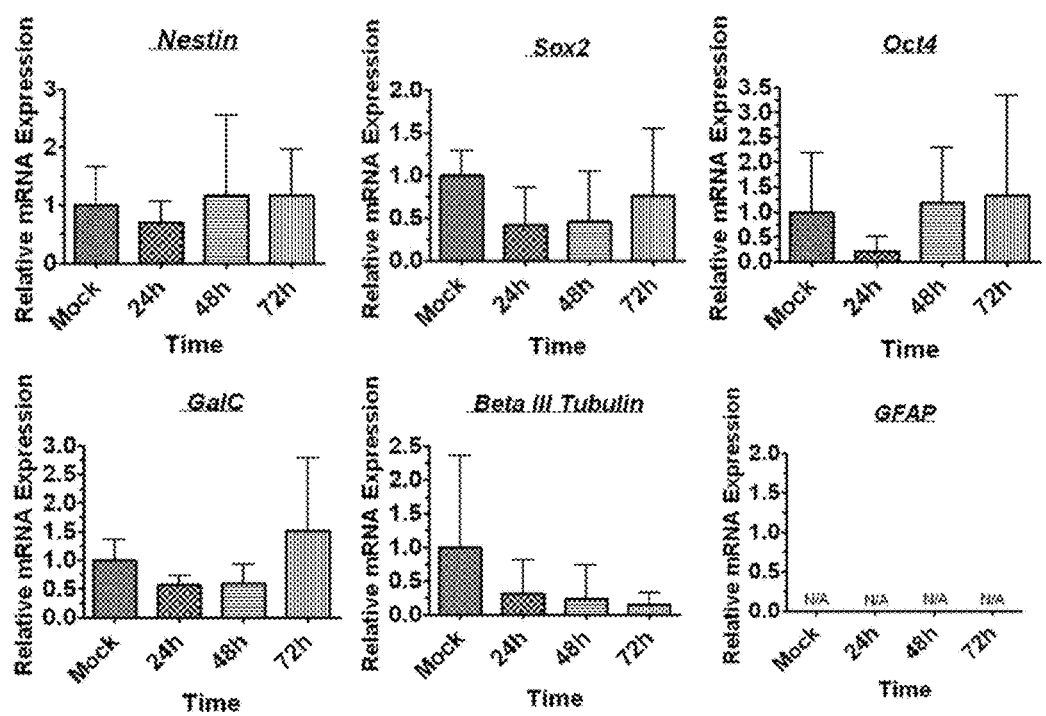
FIG. 31 shows the differentiation status of HB1.F3.CD cell after OV infection according to one embodiment. Expression of genes associated with neural stem cell neural stem cell "stemness" and pluripotency post OV loading. Cells were infected with 50 infectious units (I.U.)/cell. Relative mRNA expression of stem cell markers nestin, Sox2, Oct4 and Galc (oligodendrocyte marker), GFAP (astrocyte), beta-III tubulin (neuronal marker) was measure with quantitative real-time PCR (qRT-PCR). Comparison between groups was performed using student's t test. Bars represent means from three independent experiments, error bars refer to 95% confidence intervals.* P<0.05, P<0.01, *P<0.001. Data shown are Mean±SEM.
Figure 32A:
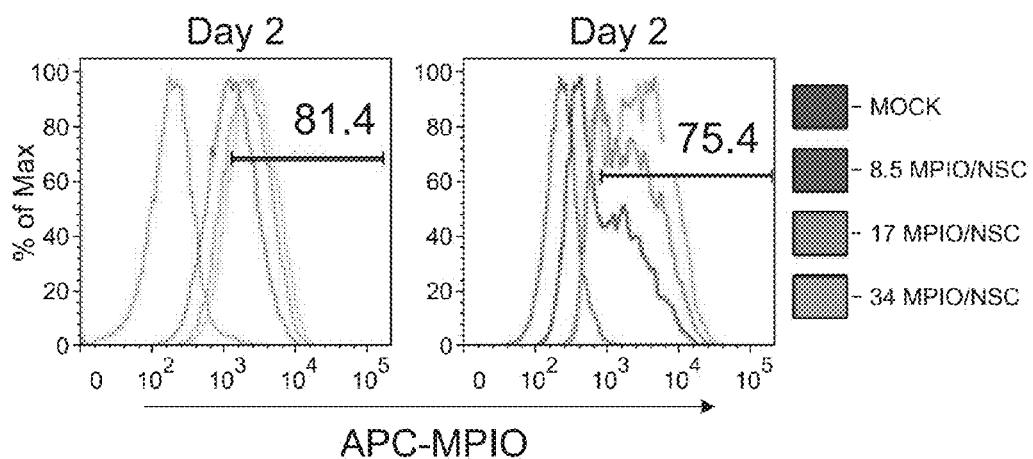
FIGS. 32A, 32B and 32C illustrate fluorescent labeling of HB1.F3.CD cells with MPIOs according to one embodiment.
Figure 32B:
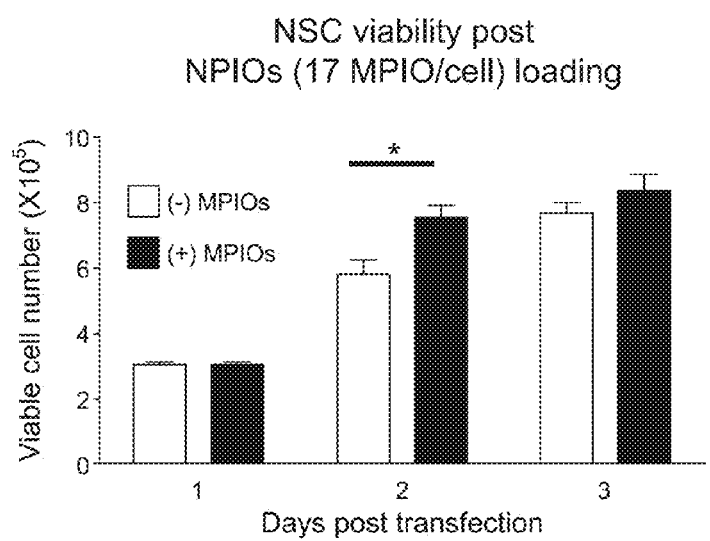
Figure 32C:
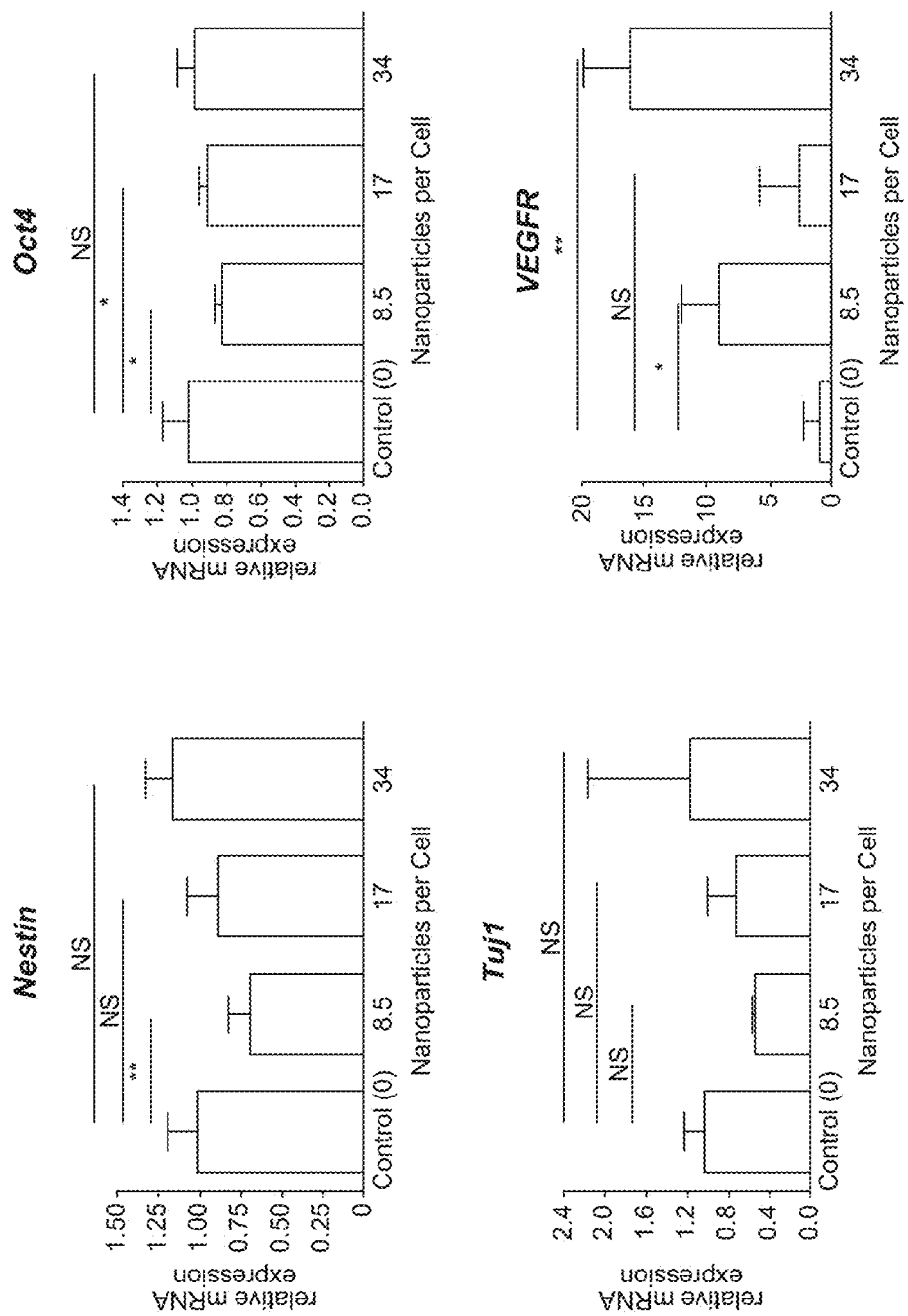

The relationship between cell number increase and MPIO marked cells (MPIO loading efficiency) was evaluated to evaluate whether cells were receiving MPIO's and then dividing with them still embedded within the cell, or if cell division caused a total loss of MPIO's. A total loss of MPIOs would indicate that the division of NSCs before reaching the disseminated tumor burden would cause a loss of signaling, and therefore hamper tracking. Loading efficiency was tested using FACS, with APC-conjugated nanoparticles. The NSCs were transfected 16 hours in advance, and then labeled with violet crystal staining, a dye which becomes more diluted as cellular divisions increase (as measured by the PacBlue %). The loading threshold was found to be between 17 nanoparticles per cell and 34 nanoparticles per cell (FIG. 32A). Approximately 20 nanoparticles per cell corresponds with the highest percentage of nanoparticle uptake, which explains the threshold (Muja & Bulte 2009). At this dose, the viability of HB1.F3.CD cells after loading was unchanged for up to 3 days (FIG. 32B). A significant increase in the proliferation rate of the MPIO-loaded HB1.F3.CD cells was observed at day 2 post loading. However, within 24 h of loading the difference between loaded and non-loaded groups was resolved. When the differentiation status of the MPIO-loaded HB1.F3.CD cells was examined 3 days post loading, only a decreased level in Oct4 mRNA was observed at the loading dose of 17 MPIOs/cell (FIG. 31). Also, the chemoattractant receptor VEGFR transcript level was unchanged at this loading dose (FIG. 32C). Based on this data, a loading dose of 17 MPIOs/cell was selected as an optimal loading dose.

Figure 33A:
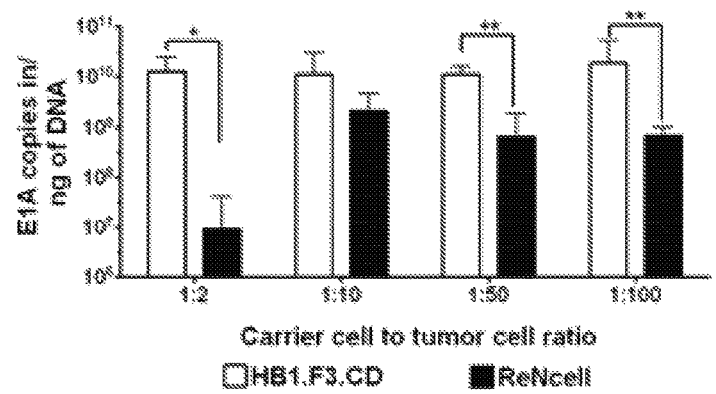
FIGS. 33A, 33B and 33C illustrate the permissiveness of NSC lines for adenovirus replication and efficacy in vitro/vivo according to one embodiment.
Figure 33B:
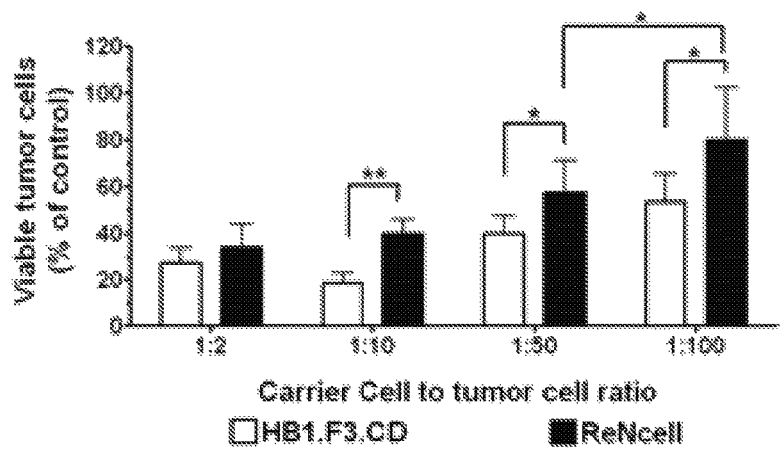

Evaluation of CRAd-S-pk7 progeny and hand-off from NSCs to glioma cells. The initial characterization of both the HB1.F3.CD and ReNcell NSC lines and optimization of OV loading dose for the carrier cells is described in the above and in FIG. 28. Next, the capacity of released viral progeny to lyse targeted tumor cells was examined in both NSC cell lines. Both NSC lines were infected with 50 I.U. of OV/cell, the optimal OV loading dose, and placed in the upper chambers of a transwell plate whereas glioma cells were cultured in the lower chamber at the NSC:glioma cell ratios of 1:2, 1:10, 1:50, and 1:100. Viral E1A copies in the target glioma cells were measured by qPCR from total isolated DNA. At the NSC:glioma cell ratio of 1:50 and 1:100, the recovered E1A copies from glioma cells were about 1.3 (95% CI=0.84-1.81, P=0.002) and 1.4 (95% CI=0.47-2.25, P=0.02) logs less respectively in the co-cultures containing ReNcells as compared to HB1.F3.CD cells (FIG. 33A). Moreover, CRAd-S-pk7 loaded HB1.F3.CD cells demonstrated significantly more killing of the targeted glioma cells as compared to ReNcells at the NSC:glioma cell ratio of 1:10 (ReN vs. HB1.F3.CD, 39.9% vs. 18.7% difference=21.2%, 95% CI=14.4%-28.1%, P<0.001), 1:50 (ReN vs. HB1.F3.CD, 57.5% vs. 39.9% difference=17.6%, 95% CI=3.2%-32.0%, P=0.02) and 1:100 (ReN vs. HB1.F3.CD, 80.1% vs. 53.6% difference=26.4%, 95% CI=5.8%-47.0%, P=0.02) (FIG. 33B).

Next, to evaluate the therapeutic efficacy of different NSC-based anti-glioma virotherapy in vivo, $2.5 \times 10^4$ cells of U87MG were implanted into the right hemisphere of athymic nude (nu/nu) mice. Three days post implantation of the glioma xenograft, a single injection of CRAd-S-pk7 (50 I.U. of pk7/NSC×$5 \times 10^5$ NSCs/mouse=$2.5 \times 10^7$ I.U. of OV total) or $5 \times 10^5$ NSCs loaded with 50 I.U./cell of CRAd-S-pk7 was administered ipsilaterally 2-3 mm away from the original tumor implantation site. The animals were monitored for survival. The median survival for the PBS treated control group was 64 days as compared to 70.5 days for the CRAd-S-pk7 group (p=0.10), 79.5 days for the OV loaded ReNcell group (p=0.055) and 108.5 days for the OV loaded HB1.F3.CD group (p=0.005). Thus, group of animals bearing glioma xenograft treated with CRAd-S-pk7-loaded HB1 survived 29 day longer than the group treated with CRAd-S-pk7-loaded loaded ReNcell. As such, it was determined that that the HB1.F3.CD cell line functions more effectively as a cell carrier for the OV CRAd-S-pk7 both in vitro and in vivo and used it as the OV carrier cell in the remainder of the studies.

Figure 33C:
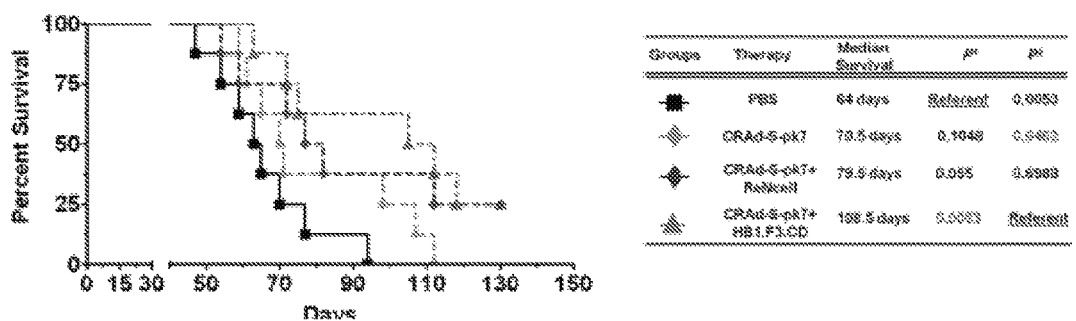
Figure 34C:
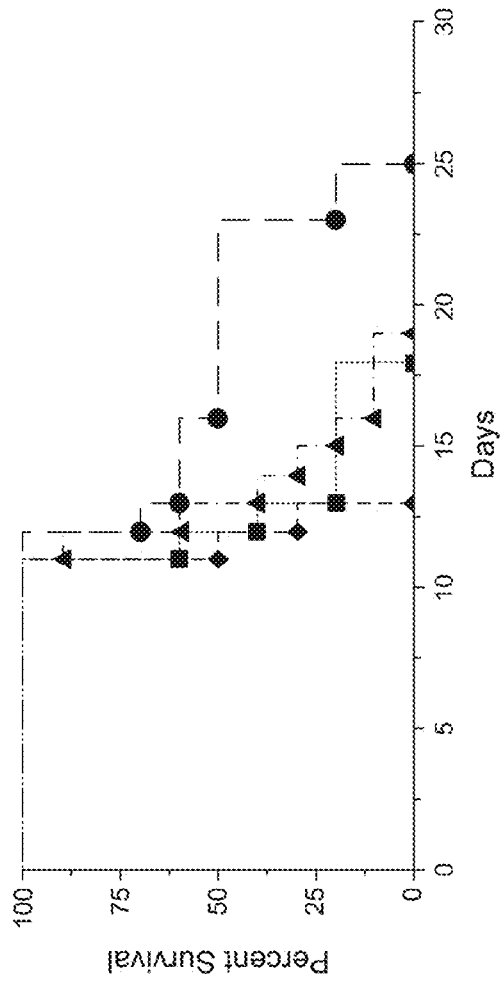
Figure 34D:
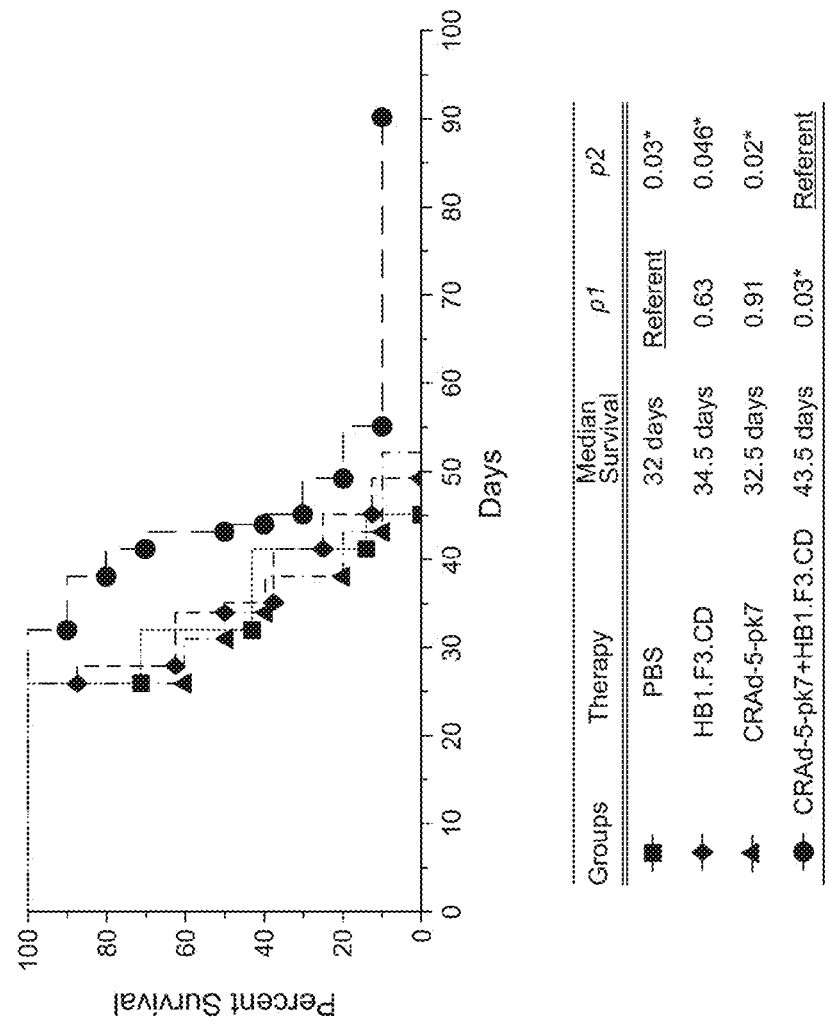

Evaluation of HB1.F3.CD as a cell carrier in multiple clinically relevant GBM patient-derived glioma xenograft models. The OV-NSC system was tested in two patient-derived orthotropic models: GBM43FL and GBM12FL. In order to maintain their intrinsic patient GBM properties, both cell lines were serially propagated in the flank of nude mice (Sarkaria et al. 2006). As shown in FIG. 34A through a FACS assay, after 2 weeks, GBM43FL cells grown in vitro expressed only 0.6% of the CD133$^+$ glioma stem cell population, while 43.31% of GBM43FL propagated in the flanks of nude mice were CD133$^+$. $2.5 \times 10^4$ GBM43FL cells were implanted in the right hemisphere of the brain and kept the HB1.F3.CD loaded with CRAd-S-pk7 injection protocol the same as described in FIG. 33C, with the exception that the therapy was delivered in an ipsilateral intratumoral fashion. Through bioluminescence monitoring, it was shown that 4 out of 10 mice in the group treated with CRAd-S-pk7 loaded in HB1.F3.CD cells had tumors as compared to 8/10 in control PBS and OV alone group (FIG. 34B). The median survival of the group treated with CRAd-S-pk7 loaded HB1.F3.CD cells was 19.5 days, which represented a 6.5 day median survival increase over the OV group (median survival=13 days, p=0.02) and an 8 day median survival increase over the HB1.F3.CD treated group (median survival=11.5 days, p=0.003) (FIG. 34C). In the GBM12FL model, an identical injection protocol was used besides the type of glioma cell line and the median survival for the animals treated with HB1.F3.CD alone was 34.5 days (p=0.046), 32.5 days (p=0.02) for the CRAd-S-pk7 treated group compared to 43.5 days for the HB1.F3.CD loaded CRAd-S-pk7 group (FIG. 34D). The hazard ratio of survival was 2.53 (95% CI=1.21 to 10.38, P=0.02).

Figure 35A:
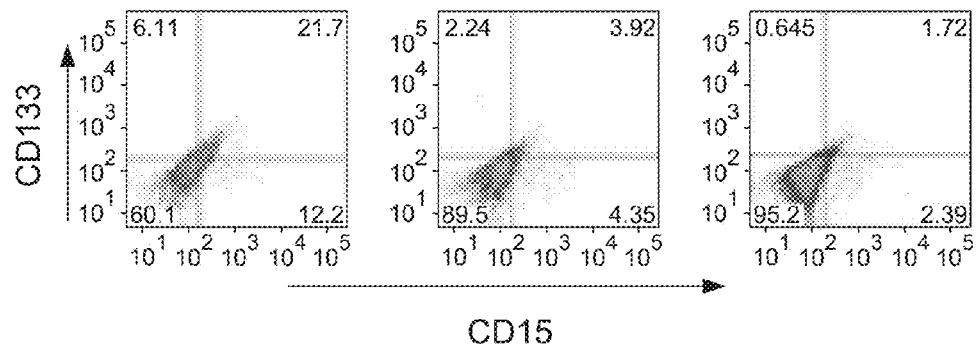
FIGS. 35A, 35B and 35C show the efficacy of HB1.F3.CD NSCs as a cell carrier for CRAd-S-pk7 virus in a glioma stem cell-derived xenograft model according to one embodiment.
Figure 35B:
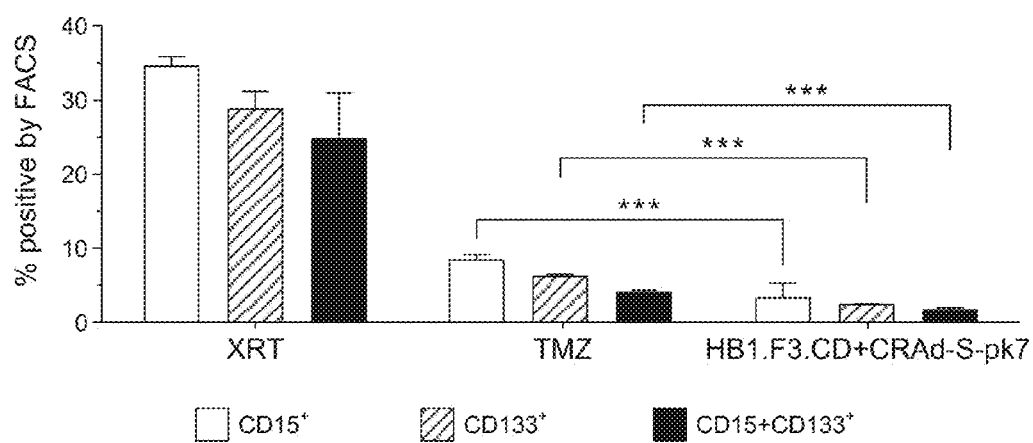
Figure 35C:
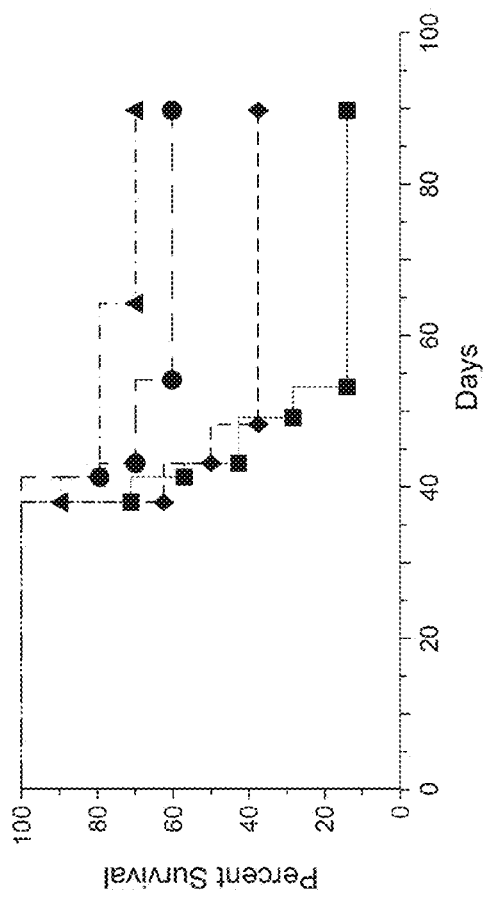

Evaluation of NSC-based anti-glioma oncolytic virotherapy in a glioma stem cell (GSC)-derived xenograft model. To test whether this system is effective at targeting GSCs, an in vitro co-culture experiment was performed with CRAd-S-pk7 loaded HB1.F3.CD cells fluorescently labeled with green fluorescent protein (GFP) and GBM43FL cells. After 72 hours of co-culture, cells were harvested and analyzed for the presence of GSCs (GFP$^-$CD15$^+$, GFP$^-$CD133$^+$ or GFP$^-$CD15$^+$CD133$^+$) by FACS. As shown in FIGS. 35A and 35B, the CRAd-S-pk7 loaded HB1.F3.CD cells significantly decreased the CD15$^+$ population ~10 and 2.5 folds (P<0.001), the CD133$^+$ population ~12 and 2.6 folds (P<0.001), and the CD15$^+$CD133$^+$ population ~15 and 2.4 folds compared with XRT (2 Gy) and TMZ (50 μM) respectively (P<0.001). To evaluate the therapeutic efficacy of OV-loaded HB1.F3.CD cells against GSCs in vivo, the CD133$^+$GSC population of cells was isolated from GBM43FL by FACS sorting (FIG. 34A) and 5×10$^3$ CD133$^+$ cells were implanted intracranially in the right hemisphere of nude mice. Three days post GSC tumor implantation animals were divided into four groups and treated with intratumoral injections of either PBS, HB1.F3.CD alone, CRAd-S-pk7 alone, or CRAd-S-pk7 loaded HB1.F3.CD cells (as described in FIG. 33C). As shown in FIG. 35C, ~60% of animals treated with OV-loaded HB1.F3.CD cells and ~65% of animals treated with OV alone survived for more than 90 days, indicating that NSC-based oncolytic virotherapy can be effective in suppressing GSC-driven tumor growth in an orthotopic human glioma xenograft model.

Figure 36A:
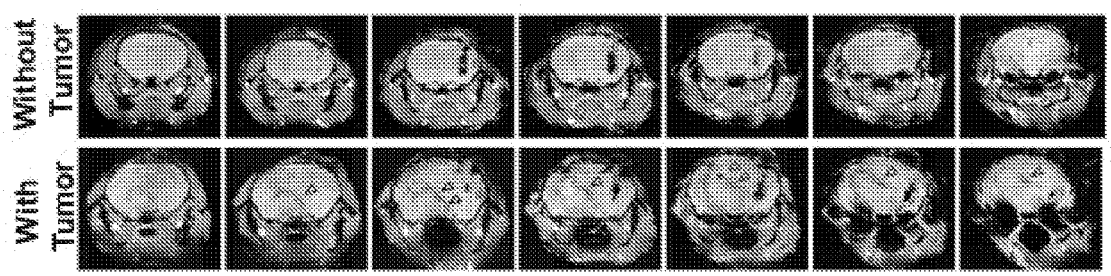
FIGS. 36A, 36B and 36C show MRI imaging of tumortropic migration of OV-HB1.F3.CD NSCs in vivo according to one embodiment. MPIO labeled HB1.F3.CD cells loaded with CRAd-S-pk7 (50 I.U./cell) were implanted in the left hemisphere of control mice (no tumor) or mice bearing U87 xenografts in the contralateral hemisphere.
Figure 36B:
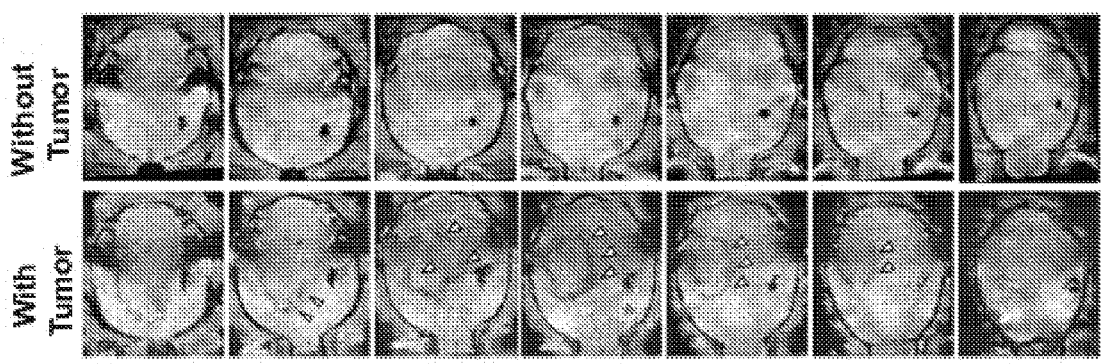
Figure 36C:
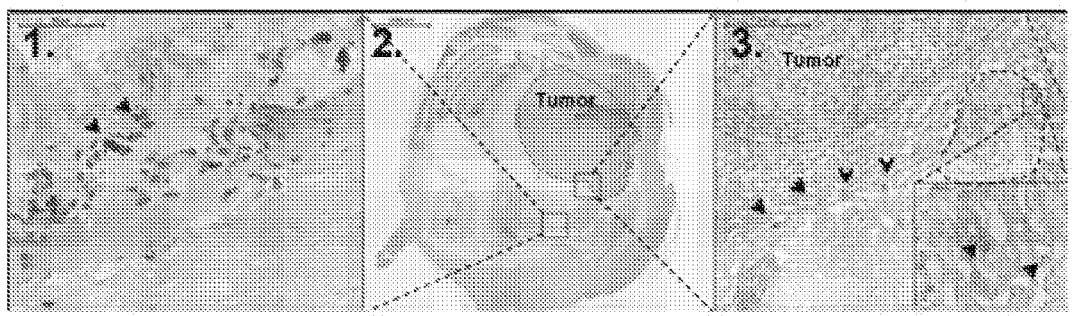

Magnetic Resonance Imaging (MRI) monitoring of NSC migration in vivo. To evaluate whether OV-loaded HB1.F3.CD cells migrate to distant tumor foci in animal brains, microparticles of iron oxide (MPIO)-labeled HB1.F3.CD cells [please refer to materials and methods and FIG. 30 for labeling protocol and (Thu et al. 2009)] with or without OV (50 I.U./cell) were stereotactically implanted in the left hemisphere of the corpus callosum (CC) 10 days after U87 glioma cell or PBS injection in the right hemisphere. The MPIO-labeled HB1.F3.CD grafts resulted in a hypointense area surrounding the injection sites (FIG. 36A). FIGS. 36A & 36B show serial continuous slices of coronal and axial T1 weighted images respectively from representative animals (n=4) at 3 days post implantation of the MPIO-labeled HB1.F3.CD cells loaded with CRAd-S-pk7 in the contralateral hemisphere of the animal brain without (FIGS. 36A & 36B, 1$^{st}$ row) or with a (FIGS. 36A & 36B, 2$^{nd}$ row) U87 xenograft tumor. A hypointense stream directed toward the side of the implanted U87 tumor extended gradually from the HB1.F3.CD cell graft over time, (arrowhead FIG. 36A) suggesting the migration of OV loaded HB1.F3.CD cells towards the tumor site (FIGS. 36A and 36B, image rows with tumor). In contrast, no significant signal changes were observed along the corpus callosum in the animal brain without tumor (FIGS. 36A and 36B, image rows without tumor). Immunohistological verification with Prussian Blue staining of the same animal brain with tumor as shown in FIGS. 36A and 36B is shown in FIG. 36C and revealed the presence of iron from MPIO-labeled HB1.F3.CD (arrowheads) at the implanted site (FIG. 36C-1), at the edges of the tumor mass (dotted line) (FIG. 36C-2), and inside the tumor (FIG. 36C-3). These results confirm that OV-loaded HB1.F3.CD cells retain their tropism for tumor as detected by MRI in vivo and that the real time MRI tracking of NSC migration is a feasible and valuable strategy moving forward from preclinical studies.

Figure 37A:
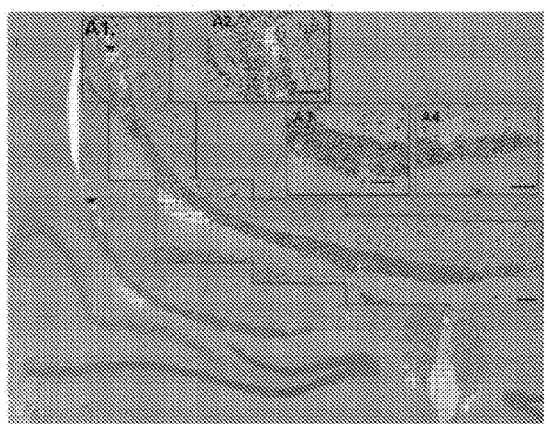
FIGS. 37A, 37B and 37C show in vivo differentiation of CRAd-S-pk7 loaded HB1.F3.CD cells according to one embodiment. To follow the differentiation status of OV-loaded HB1.F3.CD cells implanted into the brain of mice, HB1.F3.CD-GFP$^+$ loaded with CRAd-S-pk7 (50 I.U./cell) were implanted into the contralateral hemisphere of mice bearing U87 glioma xenografts. Mice were sacrificed 24 and 72 hours post NSC implantation and brains were prepared for IHC analysis.
Figure 37B:
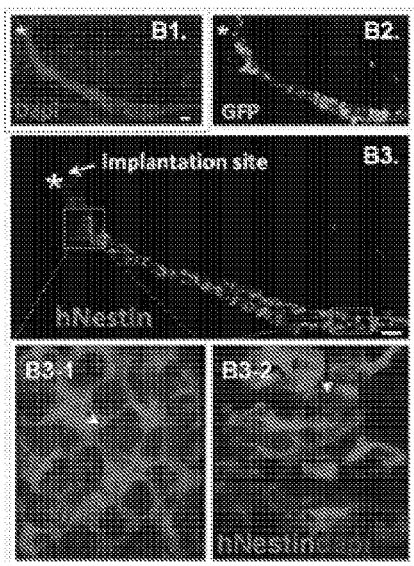
Figure 37C:
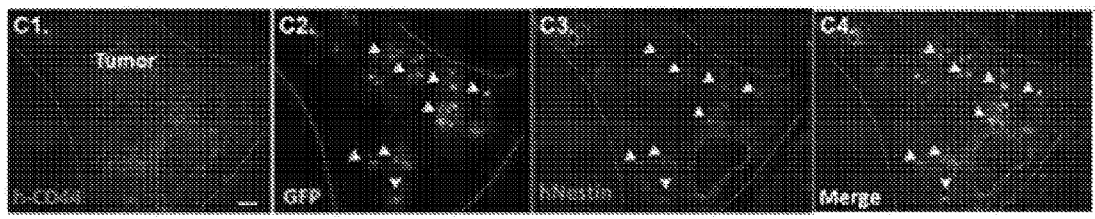

In vivo differentiation status of implanted OV-loaded HB1.F3.CD cells. The in vivo differentiation status of CRAd-S-pk7 loaded HB1.F3.CD cells post implantation is an important issue to consider for both safety (non-oncogenic) as well as tumor homing properties of loaded NSCs (Ahmed et al. 2010b). To examine the differentiation status of transplanted HB1.F3.CD cells loaded with OV in vivo, HB1.F3.CD-GFP$^+$ cells infected with OV were implanted in the contralateral hemisphere of nude mice brains containing U87 glioma xenografts established 10 days earlier. At 24 and 72 hours post NSC implantation animals were sacrificed and their brains were subjected to immunohistochemical analysis. Within 24 hours of implantation, the GFP tagged HB1.F3.CD cells began to cross the midline of the brain and migrate towards the implanted tumor in the contralateral hemisphere. FIG. 37A shows the Hematoxylin and Eosin (H&E) staining of the migratory path of implanted HB1.F3.CD OV-loaded cells, which is validated by the immunofluorescence staining by both dapi (FIG. 37, B1) and GFP (FIG. 37, B2) antibodies on the same animal brain. Next, to evaluate the stemness of implanted HB1.F3.CD cells loaded with CRAd-S-pk7, the slides were counterstained with an anti-human specific nestin antibody and observed that the majority of the GFP$^+$ HB1.F3.CD cells were also nestin$^+$ (FIGS. 37 B3, B3-1 and B3-2). When the implanted xenograft tumor was examined in the contralateral hemisphere 72 hours post NSC implantation, the presence of GFP$^+$ cells (FIG. 37, C2) was observed inside human CD44$^+$ tumor foci (FIG. 37, C1). Additionally, the HB1.F3.CD cells that migrated and reached the tumor site (white doted area) also stained positive for human nestin (FIGS. 37 C3 & C4). Furthermore, as shown in FIG. 29, even though 24 hours after OV infection of HB1.F3.CD cells in vitro the neural stem cell markers Sox2 and Oct4 as well as the differentiation markers Galc (oligodendrocyte marker), GFAP (astrocyte), and beta-III tubulin (neuronal) mRNA levels decreased, by 72 hours gene expression normalized and was insignificantly different from the uninfected control HB1.F3.CD cells (FIG. 30). Further, OV loaded HB1.F3.CD cells implanted intracranially into nude mice did not show any signs that implanted NSCs became tumorigenic as demonstrated by complete animal survival and immunohistochemistry (data not shown). Taken together, these data indicate that implanted HB1.F3.CD cells loaded with CRAd-S-pk7 retained their NSC differentiation fate and displayed substantial pathotropism in an animal model of glioma.

Figure 38A:
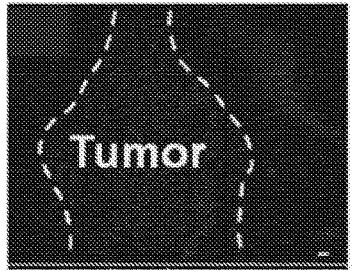
FIGS. 38A, 38B, 38C, 38D, 38E, 38F, 38G, 38H, 38I, 38J, 38K and 38L show that NSCs can hand off and expand OV therapeutic payload at distant tumor foci in vivo according to one embodiment. OV-loaded HB1.F3.CD cells were implanted in the contralateral hemisphere of mice bearing U87 xenograft tumors. Animals were sacrificed 72 hours post NSC implantation and brains were preserved and prepared for IHC analysis.
Figure 38E:
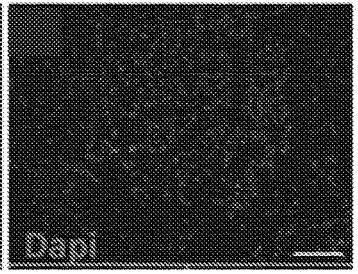
Figure 38I:
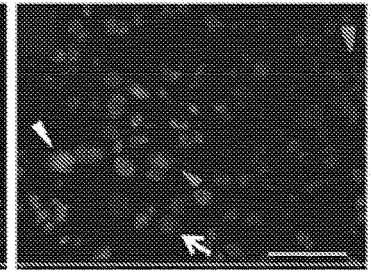
Figure 38B:
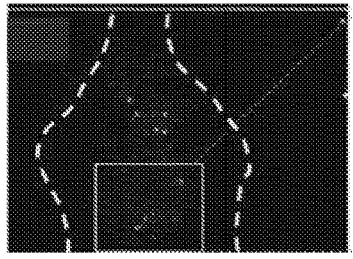
Figure 38F:
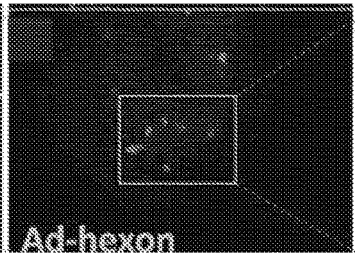
Figure 38J:
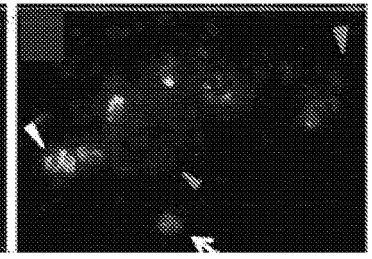
Figure 38C:
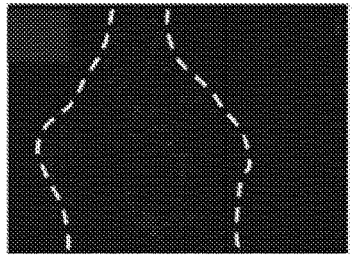
Figure 38G:
Figure 38K:
Figure 38D:
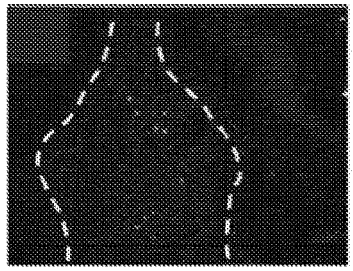
Figure 38H:
Figure 38L:
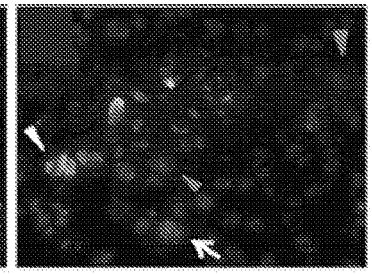

In vivo handoff and expansion of CRAd-S-pk7 at distant tumor sites by HB1.F3.CD cell carrier. To investigate the hand-off and amplification of CRAd-S-pk7 at the targeted tumor site, OV-loaded HB1.F3.CD cells were implanted in the contralateral hemisphere of nude mice bearing U87 xenograft tumors (10 days post tumor implantation). Seventy-two hours post NSC implantation, animal brains were harvested and subjected to immunohistochemical analysis for the expression of the adenoviral early gene E1A (FIGS. 38B, 38F & 38J) and the late gene hexon (FIGS. 38C, 38G & 38K). FIG. 38 illustrates viral hand-off by the presence of newly infected tumor cells as designated by positive staining for E1A. Tumor cells transitioning from an early to late phase of infection are represented by E1A$^+$ hexon$^+$ markers (white arrow in FIGS. 38J, 38K & 38L). Cells that are hexon$^+$ denote a late phase of infection (gray arrowhead in FIGS. 38J, 38K & 38L). Based on these data, OV-loaded HB1.F3.CD cells implanted in the contralateral hemisphere of glioma bearing mice are able to home to, amplify and hand-off their therapeutic payload at distant tumor sites.

Figure 39A:
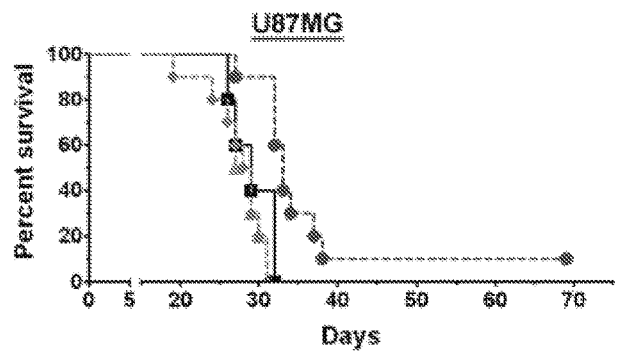
FIGS. 39A and 39B illustrate that contralateral delivery of OV-loaded HB1.F3.CD cells shows therapeutic efficacy in an animal model of glioma according to one embodiment. To examine distance delivery either 5×10$^3$ U87 or GBM43FL cells were implanted into the right hemisphere of nude mice (n=7/group). After 3 days, mice were treated with an injection of either PBS, 5×10$^5$ HB1.F3.CD cells, 5×10$^5$ HB1.F3.CD cells loaded with 50 I.U./cell of CRAd-S-pk7, or 2.5×10$^7$ I.U. of CRAd-S-pk7 into the contralateral left hemisphere of the brain.
Figure 39B:
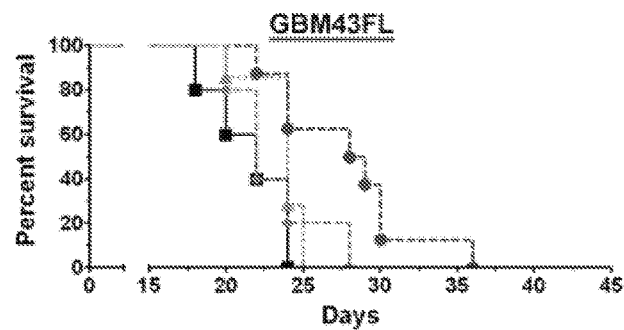

In vivo evaluation of the therapeutic efficacy of distantly delivered NSC-based oncolytic virotherapy. The therapeutic potential of the OV loaded HB1.F3.CD cell carrier when delivered at a site distant from the primary tumor mass was evaluated. $5 \times 10^5$ OV-loaded (50 I.U./cell) HB1.F3.CD cells were stereotactically implanted in the left hemisphere of the cerebral cortex (CC) in nude mice bearing U87 or GBM43FL human glioma xenografts in the contralateral hemisphere ($5 \times 10^3$ glioma cells were implanted 3 days prior to OV-loaded HB1.F3.CD cell implantation). In the U87 model, median survival of the group treated with CRAd-S-pk7 loaded HB1.F3.CD cells was 33 days, which represented an 18% increase in median survival over the OV group (median survival=28 days, $p<0.001$) and 16% increase over the HB1.F3.CD treated group (median survival=28.5 days, $p<0.001$) (FIG. 39A). In the GBM43FL model, an identical injection protocol was used besides the type of glioma cell line and the median survival for the animals treated with HB1.F3.CD alone was 22 days ($p=0.03$), 24 days ($p=0.03$) for the CRAd-S-pk7 treated group and 28.5 days for the HB1.F3.CD loaded CRAd-S-pk7 group (FIG. 39B). These data indicate that NSC carrier-based OV therapy can be effective even when implanted in the contralateral hemisphere of the targeted glioma xenograft.

Discussion

Neural stem cell carrier-based oncolytic virotherapy holds great promise as an alternative and complimentary treatment modality for glioblastoma. In this study, the relative efficacy of two immortalized NSC lines were evaluated as cell carriers for anti-glioma oncolytic virotherapy. The study resulted in the following observations: i) the HB1.F3.CD cells were more efficient in supporting CRAd-S-pk7 OV replication as well as killing glioma cells both in vitro and in vivo as compared to ReNcells; ii) the anti-glioma activity of OV-loaded HB1.F3.CD cells was effective against clinically relevant human-derived glioma models as well as a glioma stem cell-enriched xenograft model; iii) OV-loaded HB1.F3.CD cells can effectively migrate to the contralateral hemisphere and hand-off its therapeutic payload of oncolytic viruses to targeted glioma cells; iv) in vivo distribution and migratory kinetics of the OV loaded HB1.F3.CD cells can be monitored in real-time by MRI imaging and is reported in detail, and finally; v) distance delivery of OV-loaded HB1.F3.CD cells can prolong median survival in orthotopic mouse models with human glioma xenografts. These results further suggest that NSC-based cell carriers may be used for the targeted delivery of oncolytic virus against human glioma. The methods and protocols as well as pre-clinical data generated during this study bridges the gap between pre-clinical animal studies and human clinical trials and will lead to the development of human clinical trial protocol in the future.

The models used in the studies above were selected to represent the inter-patient and intra-tumor heterogeneity widely observed among GBMs. On a molecular level, the GBM43 xenograft model expresses p53 mutant (mt) and PTEN wild type (wt), is negative for epidermal growth factor receptor (EGFR), and expresses elevated levels of the chemo-resistance gene $O^6$-methyltransferase (MGMT) (Sarkaria et al. 2006; Kitange et al. 2009). The GBM12 model expresses p53 null status and wt PTEN (Sarkaria et al. 2006; Kitange et al. 2009), but expresses EGFR. On the other hand U87 contains wild type p53 (wt), PTEN mutant (mt), expresses low levels of wt EGFR, and is MGMT negative (Chahal et al. 2010). With respect to their pathological features, the U87 cell line forms very localized non-infiltrative tumors, while GBM43 tumors are mildly invasive and GBM12 tumors are extremely infiltrative in the rodent brain. It has been well documented that the genetic phenotype of tumor cells is an important determining factor of anti-tumor activity of a oncolytic virus (Yamamoto & Curiel 2010). For example, wt p53 status in tumor cells can facilitate an efficient killing of these tumor cells by OVs (Ulasov et al. 2007a; Sarkaria et al. 2006; van Beusechem et al. 2005). This is consistent with the observation above that the most pronounced efficacy was demonstrated in the p53 wt U87 glioma model.

Furthermore, the data presented in this report convincingly demonstrate that within 24 h post implantation, OV loaded HB1.F3.CD cells are capable of migrating 4-6 mms to the contralateral hemisphere and handing-off therapeutic virus to targeted tumor cells in a rodent model of glioma. Further, the migratory capacity of HB1.F3.CD cells in a larger sized human brain with glioma may be evaluated using an MRI imaging method, such as the protocol described herein, where NSCs can be labeled with MPIOs and subsequently tracked by MRI imaging therefore this technique may help serve as a tool for the dynamic optimization of NSC delivery protocols in the clinical setting.

The fate of the NSC-based cell carrier is an important factor for maintaining tumor pathotropisma (Carney & Shah 2011). A number of recent studies reported that pluripotency and the differentiated status of the NSC is altered upon viral infection (Das & Basu 2011). The data discussed above indicate that upon loading with the oncolytic adenovirus CRAd-S-pk7, the neural stem cell specific markers (nestin, Sox2 and Oct4) or different differentiation markers (Gal C, beta III tubulin or GFAP) at the mRNA level remain unchanged. Moreover, the fate of the transplanted NSC in the mammalian brain has been shown to be influence by the extrinsic factors which can drive their differentiation into either neurons or glia (Gage 2000). The diseased brain seems to create an environment that can stimulate endogenous or exogenous stem cells to differentiate into specific cells types. However, the data discussed above corroborates previous studies, indicating that therapeutic stem cells implanted into the brains of tumor-bearing mice remain in an undifferentiated state (FIG. 37) (Aboody et al. 2000; Miletic et al. 2007; Shah et al 2005). These results strongly suggest that the tumor microenvironment may be deficient in factors necessary for stem cell differentiation.

To prevent allorejection, autologous NSCs may be used in the methods described herein. With recent developments in the field of induced pluripotent stem cells (iPS), one might imagine a future in which medical centers can offer highly customized, patient-focused approaches to NSC-based anti-glioma therapy by using personalized iPS cells or induced NSCs (Ring et al. 2012) catered towards each patient with unique genetic backgrounds (Ring et al. 2012; Izpisua et al. 2009; Yamanaka 2012).

In conclusion, the study described herein shows that NSC-based cell carriers can effectively deliver anti-glioma oncolytic adenovirus to distant tumor sites, release the therapeutic payload at the target sites and increase median survival in a diverse range of orthotropic human glioma xenograft models that stand to recapitulate the heterogeneity of the human disease. In this study, it was demonstrated that the NSC-OV platform has the ability to extend survival in a multitude of invasive models of human glioma and target the therapeutic resistant and disease reinitiating glioma stem cell population, thereby fulfilling two important considerations for successful clinical translation and may serve as a future therapy that can complement the existing standard of care for glioblastoma.

REFERENCES

The references, patents and published patent applications listed below, and all references cited in the specification above are hereby incorporated by reference in their entirety, as if fully set forth herein.

Aboody K S, Brown A, Rainov N G, Bower K A, Liu S, Yang W, Small J E, Herrlinger U, Ourednik V, Black P M, Breakefield X O, Snyder E Y. Neural stem cells display extensive tropism for pathology in adult brain: evidence from intracranial gliomas. Proc Natl Acad Sci USA 2000; 97(23):12846-12851.

Aboody K S, Bush R A, Garcia E, et al. Development of a tumor-selective approach to treat metastatic cancer. PLoS One. 2006; 1:e23.

Aboody K S, Najbauer J, Danks M K. Stem and progenitor cell-mediated tumor selective gene therapy. Gene Ther 2008; 15(10): 739-52.

Ahmed A U, Alexiades N G, Lesniak M S. The use of neural stem cells in cancer gene therapy: predicting the path to the clinic. Curr Opin Mol Ther 2010b; 12(5): 546-52.

Ahmed A U, Lesniak M S. Glioblastoma multiforme: can neural stem cells deliver the therapeutic payload and fulfill the clinical promise? Expert Rev Neurother. June 2011b; 11(6):775-777.

Ahmed A U, Rolle C E, Tyler M A, Han Y, Sengupta S, Wainwright D A et al. Bone marrow mesenchymal stem cells loaded with an oncolytic adenovirus suppress the anti-adenoviral immune response in the cotton rat model. Mol Ther 2010a; 18(10): 1846-56.

Ahmed A U, Thaci B, Alexiades N G, Han Y, Qian S, Liu F et al. Neural Stem Cell-based Cell Carriers Enhance Therapeutic Efficacy of an Oncolytic Adenovirus in an Orthotopic Mouse Model of Human Glioblastoma. Mol Ther 2011a; 19(9): 1714-26.

Ahmed A U, Tyler M A, Thaci B, Alexiades N G, Han Y, Ulasov I V et al. A comparative study of neural and mesenchymal stem cell-based carriers for oncolytic adenovirus in a model of malignant glioma. Mol Pharm 2011 b; 8(5): 1559-72. Alonso M M, Jiang H, Gomez-Manzano C, Fueyo J. Targeting brain tumor stem cells with oncolytic adenoviruses. Methods Mol Biol. 2012; 797:111-125.

Ahmed A U, Ulasov I V, Mercer R W, Lesniak M S. Maintaining and loading neural stem cells for delivery of oncolytic adenovirus to brain tumors. Methods Mol Biol. 2012; 797:97-109.

Anderson S A, Glod J, Arbab A S, Noel M, Ashari P, Fine H A, Frank J A. Noninvasive MR imaging of magnetically labeled stem cells to directly identify neovasculature in a glioma model. Blood 2005; 105(1):420-425. Anthony D C, Sibson N R, McAteer M A, Davis B, Choudhury R P. Detection of brain pathology by magnetic resonance imaging of iron oxide micro-particles. Methods Mol Biol. 2011; 686:213-227.

Arbab A S, Yocum G T, Kalish H, Jordan E K, Anderson S A, Khakoo A Y, Read E J, Frank J A. Efficient magnetic cell labeling with protamine sulfate complexed to ferumoxides for cellular MRI. Blood 2004; 104(4):1217-1223.

Atencio I A, Grace M, Bordens R, Fritz M, Horowitz J A, Hutchins B, Indelicato S, Jacobs S, Kolz K, Maneval D, Musco M L, Shinoda J, Venook A, Wen S, Warren R. Biological activities of a recombinant adenovirus p53 (SCH 58500) administered by hepatic arterial infusion in a Phase 1 colorectal cancer trial. Cancer Gene Ther 2005.

Bantubungi K, Blum D, Cuvelier L, Wislet-Gendebien S, Rogister B, Brouillet E, Schiffmann S N. Stem cell factor and mesenchymal and neural stem cell transplantation in a rat model of Huntington's disease. Mol Cell Neurosci 2008; 37(3):454-470.

Bao S, Wu Q, McLendon R E et al. Glioma stem cells promote radioresistance by preferential activation of the DNA damage response. Nature 2006; 444:756-760.

Bao S, Wu Q, Sathornsumetee S, Hao Y, Li Z, Hjelmeland A B et al. Stem cell-like glioma cells promote tumor angiogenesis through vascular endothelial growth factor. Cancer Res 2006; 66(16): 7843-8. Barbosa M S, Bao S N, Andreotti P F, et al. Glyceraldehyde-3-phosphate dehydrogenase of *Paracoccidioides brasiliensis* is a cell surface protein involved in fungal adhesion to extracellular matrix proteins and interaction with cells. Infect Immun. January 2006; 74(1):382-389.

Barker F G, 2nd, Chang S M, Gutin P H, Malec M K, McDermott M W, Prados M D, Wilson C B. Survival and functional status after resection of recurrent glioblastoma multiforme. Neurosurgery 1998; 42(4):709-720; discussion 720-703.

Beier D, Rohrl S, Pillai D R et al. Temozolomide preferentially depletes cancer stem cells in glioblastoma. Cancer Res 2008; 68: 5706-5715.

Beier D, Schulz J B, Beier C P. Chemoresistance of glioblastoma cancer stem cells: Much more complex than expected. Mol Cancer 2011; 10:128.

Bello L, Lucini V, Giussani C, Carrabba G, Pluderi M, Scaglione F, Tomei G, Villani R, Black P M, Bikfalvi A, Carroll R S. IS201, a specific alphavbeta3 integrin inhibitor, reduces glioma growth in vivo. Neurosurgery 2003; 52(1):177-185; discussion 185-176.

Benedetti S, Pirola B, Polio B, et al. Gene therapy of experimental brain tumors using neural progenitor cells. Nat Med. April 2000; 6(4):447-450.

Bessis N, GarciaCozar F J, Boissier M C. Immune responses to gene therapy vectors: influence on vector function and effector mechanisms. Gene Ther 2004; 11 Suppl 1: S10-7.

Bewig, B., and Schmidt, W. E. (2000) Accelerated titering of adenoviruses, BioTechniques 28, 870-873.

Bieler A, Mantwill K, Holzmuller R et al. Impact of radiation therapy on the oncolytic adenovirus dl520: Implications on the treatment of glioblastoma. Radiother Oncol 2008; 86:419-427.

Bloch O, Han S J, Cha S et al. Impact of extent of resection for recurrent glioblastoma on overall survival: Clinical article. J Neurosurg 2012; 117:1032-1038.

Brada M, Judson I, Beale P et al. Phase I doseescalation and pharmacokinetic study of temozolomide (SCH 52365) for refractory or relapsing malignancies. Br J Cancer 1999; 81:1022-1030.

Brustle, O., Spiro, A. C., Karram, K., Choudhary, K., Okabe, S., and McKay, R. D. (1997) In vitro-generated neural precursors participate in mammalian brain development, Proceedings of the National Academy of Sciences of the United States of America 94, 14809-14814.

Candolfi M, Curtin J F, Nichols W S, Muhammad A G, King G D, Pluhar G E et al. Intracranial glioblastoma models in preclinical neuro-oncology: neuropathological characterization and tumor progression. J Neurooncol 2007; 85(2): 133-48.

Carney B J, Shah K. Migration and fate of therapeutic stem cells in different brain disease models. Neuroscience. Dec. 1, 2011; 197:37-47.

Cattaneo R, Miest T, Shashkova E V, Barry M A. Reprogrammed viruses as cancer therapeutics: targeted, armed and shielded. Nat Rev Microbiol 2008; 6(7): 529-40.

Chahal M, Xu Y, Lesniak D, et al. MGMT modulates glioblastoma angiogenesis and response to the tyrosine kinase inhibitor sunitinib. Neuro Oncol. August 2010; 12(8):822-833.

Chakravarti A, Noll E, Black P M, Finkelstein D F, Finkelstein D M, Dyson N J, Loeffler J S. Quantitatively determined survivin expression levels are of prognostic value in human gliomas. J Clin Oncol 2002; 20(4):1063-1068.

Chakravarti A, Zhai G G, Zhang M, Malhotra R, Latham D E, Delaney M A, Robe P, Nestler U, Song Q, Loeffler J. Survivin enhances radiation resistance in primary human glioblastoma cells via caspaseindependent mechanisms. Oncogene 2004; 23(45):7494-7506.

Chatrchyan S, Khachatryan V, Sirunyan A M et al. Search for supersymmetry in pp collisions at √7 TeV in events with two photons and missing transverse energy. Phys Rev Lett 2011; 106:211802

Chiocca E A, Abbed K M, Tatter S, Louis D N, Hochberg F H, Barker F, Kracher J, Grossman S A, Fisher J D, Carson K, Rosenblum M, Mikkelsen T, Olson J, Markert J, Rosenfeld S, Nabors L B, Brem S, Phuphanich S, Freeman S, Kaplan R, Zwiebel J. A phase I open-label, dose-escalation, multiinstitutional trial of injection with an E1B-Attenuated adenovirus, ONYX-015, into the peritumoral region of recurrent malignant gliomas, in the adjuvant setting. Mol Ther 2004; 10(5):958-966.

Chiocca E A, Aguilar L K, Bell S D, Kaur B, Hardcastle J, Cavaliere R et al. Phase IB Study of Gene-Mediated Cytotoxic Immunotherapy Adjuvant to Up-Front Surgery and Intensive Timing Radiation for Malignant Glioma. J Clin Oncol 2011; 29(27): 3611-9.

Chivukula M, Dincer H, Biller J A, Krouwer H G, Simon G, Shidham V. FNAB cytology of extra-cranial metastasis of glioblastoma multiforme may resemble a lung primary: A diagnostic pitfall. Cytojournal 2005; 2(1):9.

Conti L, Cattaneo E. Neural stem cell systems: physiological players or in vitro entities? Nat Rev Neurosci. March 2010; 11(3):176-187.

Cooney R, Hynes S O, Duffy A M, Sharif F, O'Brien T. Adenoviral-mediated gene transfer of nitric oxide synthase isoforms and vascular cell proliferation. J Vasc Res 2006; 43(5):462-472.

Corot C, Robert P, Idee J M, Port M. Recent advances in iron oxide nanocrystal technology for medical imaging. Adv Drug Deliv Rev 2006; 58(14):1471-1504.

Coukos, G., Makrigiannakis, A., Kang, E. H., Caparelli, D., Benjamin, I., Kaiser, L. R., Rubin, S. C., Albelda, S. M., and Molnar-Kimber, K. L. (1999) Use of carrier cells to deliver a replication-selective herpes simplex virus-1 mutant for the intraperitoneal therapy of epithelial ovarian cancer, Clin Cancer Res 5, 1523-1537.

Das S, Basu A. Viral infection and neural stem/progenitor cell's fate: implications in brain development and neurological disorders. Neurochemistry international. September 2011; 59(3):357-366.

Davison E, Diaz R M, Hart I R, Santis G, Marshall J F. Integrin alpha5beta1-mediated adenovirus infection is enhanced by the integrin-activating antibody TS2/16. J Virol 1997; 71(8):6204-6207.

Dembinski J L, Spaeth E L, Fueyo J, Gomez-Manzano C, Studeny M, Andreeff M et al. Reduction of nontarget infection and systemic toxicity by targeted delivery of conditionally replicating viruses transported in mesenchymal stem cells. Cancer Gene Ther 2010; 17(4): 289-97.

Deorah S, Lynch C F, Sibenaller Z A, Ryken T C. Trends in brain cancer incidence and survival in the United States: Surveillance, Epidemiology, and End Results Program, 1973 to 2001. Neurosurg Focus 2006; 20(4): E1.

Dey M, Ulasov I V, Tyler M A, Sonabend A M, Lesniak M S. Cancer Stem Cells: The Final Frontier for Glioma Virotherapy. Stem Cell Rev 2011; 7(1): 119-29.

Ehtesham M, Kabos P, Gutierrez M A, Chung N H, Griffith T S, Black K L, Yu J S. Induction of glioblastoma apoptosis using neural stem cell-mediated delivery of tumor necrosis factor-related apoptosis-inducing ligand. Cancer Res 2002; 62(24):7170-7174.

Einstein O, Ben-Hur T. The changing face of neural stem cell therapy in neurologic diseases. Arch Neurol 2008; 65(4): 452-6.

Fisher, K. (2006) Striking out at disseminated metastases: the systemic delivery of oncolytic viruses, Current opinion in molecular therapeutics 8, 301-313.

Flax J D, Aurora S, Yang C, Simonin C, Wills A M, Billinghurst L L, Jendoubi M, Sidman R L, Wolfe J H, Kim S U, Snyder E Y. Engraftable human neural stem cells respond to developmental cues, replace neurons, and express foreign genes. Nat Biotechnol 1998; 16(11):1033-1039.

Fueyo J, Gomez-Manzano C, Alemany R, Lee P S, McDonnell T J, Mitlianga P, Shi Y X, Levin V A, Yung W K, Kyritsis A P. A mutant oncolytic adenovirus targeting the Rb pathway produces anti-glioma effect in vivo. Oncogene 2000; 19(1):2-12.

Gage F H. Mammalian neural stem cells. Science. Feb. 25 2000; 287(5457):1433-1438.

Gaspar L E, Fisher B J, Macdonald D R, LeBer D V, Halperin E C, Schold S C, Jr., Cairncross J G. Supratentorial malignant glioma: patterns of recurrence and implications for external beam local treatment. Int J Radiat Oncol Biol Phys 1992; 24(1):55-57.

Geoerger B, Grill J, Opolon P et al. Potentiation of radiation therapy by the oncolytic adenovirus dl1520 (ONYX-015) in human malignant glioma xenografts. Br J Cancer 2003; 89:577-584.

Germano I M, Fable J, Gultekin S H, Silvers A. Adenovirus/herpes simplex-thymidine kinase/ganciclovir complex: preliminary results of a phase I trial in patients with recurrent malignant gliomas. J Neurooncol 2003; 65(3): 279-289.

Giannini C, Sarkaria J N, Saito A et al. Patient tumor EGFR and PDGFRA gene amplifications retained in an invasive intracranial xenograft model of glioblastoma multiforme. Neuro Oncol 2005; 7:164-176.

Grossman S A, Ye X, Piantadosi S et al. Survival of patients with newly diagnosed glioblastoma treated with radiation and temozolomide in research studies in the United States. Clin Cancer Res 2010; 16:2443-2449.

Gul H et al. Valproic Acid Increases CXCR4 Expression in Hematopoietic Stem/Progenitor Cells by Chromatin Remodeling. Stem Cells and Development (2009) 18(6): 831-838.

Guo, Z. S., Thorne, S. H., and Bartlett, D. L. (2008) Oncolytic virotherapy: molecular targets in tumor-selective replication and carrier cell-mediated delivery of oncolytic viruses, Biochimica et biophysica acta 1785, 217-231.

Hanahan, D., and Weinberg, R. A. (2000) The hallmarks of cancer, Cell 100, 57-70.

Hart L S, Yannone S M, Naczki C et al. The adenovirus E4orf6 protein inhibits DNA double strand break repair and radiosensitizes human tumor cells in an E1B-55K-independent manner. J Biol Chem 2005; 280:1474-1481.

Haviv Y S, Blackwell J L, Kanerva A, Nagi P, Krasnykh V, Dmitriev I, Wang M, Naito S, Lei X, Hemminki A, Carey D, Curiel D T. Adenoviral gene therapy for renal cancer requires retargeting to alternative cellular receptors. Cancer Res 2002; 62(15):4273-4281.

Heidenreich R, Machein M, Nicolaus A et al. Inhibition of solid tumor growth by gene transfer of VEGF receptor-1 mutants. Int J Cancer 2004; 111:348-357.

Helleday T, Petermann E, Lundin C et al. DNA repair pathways as targets for cancer therapy. Nat Rev Cancer 2008; 8:193-204.

Hingtgen S, Ren X, Terwilliger E, Classon M, Weissleder R, Shah K. Targeting multiple pathways in gliomas with stem cell and viral delivered S-TRAIL and Temozolomide. Mol Cancer Ther 2008; 7(11):3575-3585.

Hsu W, Lesniak M S, Tyler B M, Brem H. Local delivery of interleukin-2 and adriamycin is synergistic in the treatment of experimental malignant glioma. J Neurooncol 2005: In Press.

Immonen A, Vapalahti M, Tyynela K, Hurskainen H, Sandmair A, Vanninen R, Langford G, Murray N, Yla-Hertuala S. AdvHSV-tk gene therapy with intravenous ganciclovir improves survival in human malignant glioma: a randomised, controlled study. Mol Ther 2004; 10(5):967-972.

Ito H, Kanzawa T, Miyoshi T, Hirohata S, Kyo S, Iwamaru A, Aoki H, Kondo Y, Kondo S. Therapeutic efficacy of PUMA for malignant glioma cells regardless of p53 status. Hum Gene Ther 2005; 16(6):685-698.

Izpisua Belmonte J C, Ellis J, Hochedlinger K, Yamanaka S. Induced pluripotent stem cells and reprogramming: seeing the science through the hype. Nat Rev Genet. December 2009; 10(12):878-883.

Jiang F, Zhang Z, Kalkanis S, Katakowksi M, Robin A M, Zhang X, Gotlib A, Chelst I, Mikkelsen T, Chopp M. A quantitative model of tumor-induced angiogenesis in the nude mouse. Neurosurgery 2005b; 57(2):320-324.

Jiang H, Gomez-Manzano C, Alemany R, Medrano D, Alonso M, Bekele B N, Lin E, Conrad C C, Yung W K, Fueyo J. Comparative effect of oncolytic adenoviruses with E1A-55 kDa or E1B-55 kDa deletions in malignant gliomas. Neoplasia 2005a; 7(1):48-56.

Jiang H, Gomez-Manzano C, Aoki H, Alonso M M, Kondo S, McCormick F et al. Examination of the therapeutic potential of Delta-24-RGD in brain tumor stem cells: role of autophagic cell death. J Natl Cancer Inst 2007; 99(18): 1410-4.

Jiang H, McCormick F, Lang F F, Gomez-Manzano C, Fueyo J. Oncolytic adenoviruses as antiglioma agents. Expert Rev Anticancer Ther 2006; 6(5):697-708.

Kaetzel D M, Reid J Dt, Pedigo N, Zimmer S G, Boghaert E R. A dominant-negative mutant of the platelet-derived growth factor A-chain increases survival of hamsters implanted intracerebrally with the highly invasive CxT24-neo3 glioblastoma cell. J Neurooncol 1998; 39(1): 33-46.

Kajiwara Y, Yamasaki F, Hama S, Yahara K, Yoshioka H, Sugiyama K, Arita K, Kurisu K. Expression of survivin in astrocytic tumors: correlation with malignant grade and prognosis. Cancer 2003; 97(4):1077-1083.

Kanai R, Rabkin S D, Yip S, et al. Oncolytic virus-mediated manipulation of DNA damage responses: synergy with chemotherapy in killing glioblastoma stem cells. J Natl Cancer Inst. Jan. 4 2012; 104(1):42-55.

Karapanagiotou E M, Roulstone V, Twigger K et al. Phase I/II trial of carboplatin and paclitaxel chemotherapy in combination with intravenous oncolytic reovirus in patients with advanced malignancies. Clin Cancer Res 2012; 18:2080-2089.

Karen K A, Hoey P J, Young C S et al. Temporal regulation of the Mre11-Rad50-Nbs1 complex during adenovirus infection. J Virol 2009; 83:4565-4573.

Kawakami Y, Li H, Lam J T, Krasnykh V, Curiel D T, Blackwell J L. Substitution of the adenovirus serotype 5 knob with a serotype 3 knob enhances multiple steps in virus replication. Cancer Res 2003; 63(6):1262-1269.

Kelly E, Russell S J. History of oncolytic viruses: genesis to genetic engineering. Mol Ther 2007; 15(4): 651-9.

Kendall S E, Najbauer J, Johnston H F, Metz M Z, Li S, Bowers M, Garcia E, Kim S U, Barish M E, Aboody K S, Glackin C A. Neural stem cell targeting of glioma is dependent on phosphoinositide 3-kinase signaling. Stem Cells 2008; 26(6):1575-1586.

Kim D E, Tsuji K, Kim Y R, Mueller F J, Eom H S, Snyder E Y, Lo E H, Weissleder R, Schellingerhout D. Neural stem cell transplant survival in brains of mice: assessing the effect of immunity and ischemia by using real-time bioluminescent imaging. Radiology 2006b; 241(3):822-830.

Kim S H, Wong R J, Kooby D A et al. Combination of mutated herpes simplex virus type 1 (G207 virus) with radiation for the treatment of squamous cell carcinoma of the head and neck. Eur J Cancer 2005; 41:313-322.

Kim S K, Kim S U, Park I H, Bang J H, Aboody K S, Wang K C, Cho B K, Kim M, Menon L G, Black P M, Carroll R S. Human neural stem cells target experimental intracranial medulloblastoma and deliver a therapeutic gene leading to tumor regression. Clin Cancer Res 2006a; 12(18):5550-5556.

Kim S U, de Vellis J. Stem cell-based cell therapy in neurological diseases: A review. J Neurosci Res 2009; 87:2183-2200.

Kim S U, Nagai A, Nakagawa E, et al. Production and characterization of immortal human neural stem cell line with multipotent differentiation property. Methods Mol Biol. 2008; 438:103-121.

Kim S U, Nakagawa E, Hatori K, Nagai A, Lee M A, Bang J H. Production of immortalized human neural crest stem cells. Methods Mol Biol 2002; 198:55-65.

Kitange G J, Carlson B L, Schroeder M A, et al. Induction of MGMT expression is associated with temozolomide resistance in glioblastoma xenografts. Neuro Oncol. June 2009; 11(3):281-291.

Klopp A H, Spaeth E L, Dembinski J L, Woodward W A, Munshi A, Meyn R E, Cox J D, Andreeff M, Marini F C. Tumor irradiation increases the recruitment of circulating mesenchymal stem cells into the tumor microenvironment. Cancer Res 2007; 67(24):11687-11695.

Komarova et al. Targeting of mesenchymal stem cells to ovarian tumors via an artificial receptor. Journal of Ovarian Research (2010) 3:12.

Kuroda S, Fujiwara T, Shirakawa Y et al. Telomerase-dependent oncolytic adenovirus sensitizes human cancer cells to ionizing radiation via inhibition of DNA repair machinery. Cancer Res 2010; 70:9339-9348.

Lakka S S, Rajan M, Gondi C, Yanamandra N, Chandrasekar N, Jasti S L, Adachi Y, Siddique K, Gujrati M, Olivero W, Dinh D H, Kouraklis G, Kyritsis A P, Rao J S. Adenovirus-mediated expression of antisense MMP-9 in glioma cells inhibits tumor growth and invasion. Oncogene 2002; 21(52):8011-8019.

Lamfers M, Idema S, van Milligen F, Schouten T, van der Valk P, Vandertop P, Dirven C, Noske D. Homing properties of adipose-derived stem cells to intracerebral glioma and the effects of adenovirus infection. Cancer Lett 2009; 274(1):78-87.

Lang F F, Bruner J M, Fuller G N, Aldape K, Prados M D, Chang S, Berger M S, McDermott M W, Kunwar S M, Junck L R, Chandler W, Zwiebel J A, Kaplan R S, Yung W K. Phase I trial of adenovirus-mediated p53 gene therapy for recurrent glioma: biological and clinical results. J Clin Oncol 2003; 21(13):2508-2518.

Lesniak M S, Brem H. Targeted therapy for brain tumours. Nat Rev Drug Discov 2004; 3(6):499-508.

Lesniak M S, Gabikian P, Tyler B M, Pardoll D M, Brem H. Dexamethasone mediated inhibition of local IL-2 immunotherapy is dose dependent in experimental brain tumors. J Neurooncol 2004; 70(1):23-28.

Lesniak M S, Sampath P, Dimeco F, Viglione M P, Pardoll D M, Brem H. Comparative analysis of paracrine immunotherapy in experimental brain tumors. Neurosurgical Focus 2000; 9(6).

Lesniak M S, Tyler B M, Pardoll D M, Brem H. Gene therapy for experimental brain tumors using a xenogenic cell line engineered to secrete hIL-2. J Neurooncol 2003; 64(1-2):155-160.

Lesniak, M. S. (2005) Brain tumors: controversies and challenges in management, Expert review of neurotherapeutics 5, 1-2.

Lesniak, M. S. (2006) Gene therapy for malignant glioma, Expert review of neurotherapeutics 6, 479-488.

Lesniak, M. S. (2007) Advances in neurooncology: novel therapies and clinical trials, Expert review of anticancer therapy 7, 51.

Li E, Brown S L, Stupack D G, Puente X S, Cheresh D A, Nemerow G R. Integrin alpha(v)beta1 is an adenovirus coreceptor. J Virol 2001; 75(11):5405-5409.

Li J Z, Holman D, Li H, Liu A H, Beres B, Hankins G R, Helm G A. Long-term tracing of adenoviral expression in rat and rabbit using luciferase imaging. J Gene Med 2005; 7(6):792-802.

Lin D, Najbauer J, Salvaterra P M, Mamelak A N, Barish M E, Garcia E, Metz M Z, Kendall S E, Bowers M, Kateb B, Kim S U, Johnson M, Aboody K S. Novel method for visualizing and modeling the spatial distribution of neural stem cells within intracranial glioma. Neuroimage 2007; 37 Suppl 1:S18-26.

Liu C, Zong H. Developmental origins of brain tumors. Curr Opin Neurobiol 2012; 22:844-849.

Lowenstein P R, Castro M G. Uncertainty in the translation of preclinical experiments to clinical trials: Why do most phase III clinical trials fail? Curr Gene Ther 2009; 9:368-374.

Lowenstein P R. Immunology of viral-vector-mediated gene transfer into the brain: an evolutionary and developmental perspective. Trends Immunol 2002; 23(1): 23-30.

Markert J M, Medlock M D, Rabkin S D, Gillespie G Y, Todo T, Hunter W D, Palmer C A, Feigenbaum F, Tornatore C, Tufaro F, Martuza R L. Conditionally replicating herpes simplex virus mutant, G207 for the treatment of malignant glioma: results of a phase I trial. Gene Ther 2000; 7(10):867-874.

Marshall G P, 2nd, Scott E W, Zheng T, Laywell E D, Steindler D A. Ionizing radiation enhances the engraftment of transplanted in vitro-derived multipotent astrocytic stem cells. Stem Cells 2005; 23(9):1276-1285.

Meier O, Boucke K, Hammer S V, Keller S, Stidwill R P, Hemmi S, Greber U F. Adenovirus triggers macropinocytosis and endosomal leakage together with its clathrin-mediated uptake. J Cell Biol 2002; 158(6):1119-1131.

Miletic H, Fischer Y, Litwak S, et al. Bystander killing of malignant glioma by bone marrow-derived tumor-infiltrating progenitor cells expressing a suicide gene. Mol Ther. July 2007; 15(7):1373-1381.

Modo M, Cash D, Mellodew K, Williams S C, Fraser S E, Meade T J, Price J, Hodges H. Tracking transplanted stem cell migration using bifunctional, contrast agent-enhanced, magnetic resonance imaging. Neuroimage 2002; 17(2):803-811.

Modo M, Mellodew K, Cash D, Fraser S E, Meade T J, Price J, Williams S C. Mapping transplanted stem cell migration after a stroke: a serial, in vivo magnetic resonance imaging study. Neuroimage 2004; 21(1):311-317.

Modo M. Understanding stem cell-mediated brain repair through neuroimaging. Curr Stem Cell Res Ther 2006; 1(1):55-63.

Mohan D S, Suh J H, Phan J L, Kupelian P A, Cohen B H, Barnett G H. Outcome in elderly patients undergoing definitive surgery and radiation therapy for supratentorial glioblastoma multiforme at a tertiary care institution. Int J Radiat Oncol Biol Phys 1998; 42(5):981-987.

Mourad P D, Farrell L, Stamps L D, Chicoine M R, Silbergeld D L. Why are systemic glioblastoma metastases rare? Systemic and cerebral growth of mouse glioblastoma. Surg Neurol 2005; 63(6):511-519; discussion 519.

Muja N, Bulte J W. Magnetic resonance imaging of cells in experimental disease models. Prog Nucl Magn Reson Spectrosc. July 2009; 55(1):61-77.

Nandi S, Ulasov I V, Tyler M, Zhu Z B, Lesniak M S. Low dose radiation enhances survivin mediated adenoviral virotherapy against malignant glioma stem cells. Cancer Res 2008a; Revision submitted.

Nandi S, Ulasov I V, Tyler M A, Sugihara A Q, Molinero L, Han Y, Zhu Z B, Lesniak M S. Low-dose radiation enhances survivin-mediated virotherapy against malignant glioma stem cells. Cancer Res 2008b; 68(14):5778-5784.

Nicholas M K, Lukas R V, Chmura S, Yamini B, Lesniak M, Pytel P. Molecular heterogeneity in glioblastoma: therapeutic opportunities and challenges. Semin Oncol. April 2011; 38(2):243-253.

Niewiesk S, Prince G. Diversifying animal models: the use of hispid cotton rats (*Sigmodon hispidus*) in infectious diseases. Lab Anim 2002; 36(4): 357-72.

Niewiesk S. Cotton rats (*Sigmodon hispidus*): an animal model to study the pathogenesis of measles virus infection. Immunol Lett 1999; 65(1-2): 47-50.

Ogungbo B I, Perry R H, Bozzino J, Mahadeva D. Report of GBM Metastasis to the Parotid Gland. J Neurooncol 2005.

Ostermann S, Csajka C, Buclin T et al. Plasma and cerebrospinal fluid population pharmacokinetics of temozolomide in malignant glioma patients. Clin Cancer Res 2004; 10:3728-3736.

Ottolino-Perry K, Diallo J S, Lichty B D et al. Intelligent design: Combination therapy with oncolytic viruses. Mol Ther 2010; 18:251-263.

Parker, J. N., Bauer, D. F., Cody, J. J., and Markert, J. M. (2009) Oncolytic viral therapy of malignant glioma, Neurotherapeutics 6, 558-569.

Petrini J H. The mammalian Mre11-Rad50-nbs1 protein complex: Integration of functions in the cellular DNA-damage response. Am J Hum Genet 1999; 64:1264 1269.

Pluchino S, Quattrini A, Brambilla E, Gritti A, Salani G, Dina G et al. Injection of adult neurospheres induces recovery in a chronic model of multiple sclerosis. Nature 2003; 422(6933): 688-94.

Pluderi M, Lucini V, Caronzolo D, Pannacci M, Costa F, Carrabba G, Giussani C, Grosso S, Colleoni F, Scaglione F, Villani R, Bikfalvi A, Bello L. Long-term inhibition of glioma growth by systemic administration of human PEX. J Neurosurg Sci 2003; 47(2):69-78.

Power A T, Bell J C. Taming the Trojan horse: optimizing dynamic carrier cell/oncolytic virus systems for cancer biotherapy. Gene Ther 2008; 15(10): 772-9.

Pulkkanen K J, Yla-Herttuala S. Gene therapy for malignant glioma: current clinical status. Mol Ther 2005; 12(4): 585-98.

Rahman R, Smith S, Rahman C et al. Antiangiogenic therapy and mechanisms of tumor resistance in malignant glioma. J Oncol 2010; 2010:251231.

Rajagopalan V, Kamar F G, Thayaparan R, Grossbard M L. Bone marrow metastases from glioblastoma multiforme—A case report and review of the literature. J Neurooncol 2005; 72(2):157-161.

Ring K L, Tong L M, Balestra M E, et al. Direct reprogramming of mouse and human fibroblasts into multipotent neural stem cells with a single factor. Cell Stem Cell. Jul. 6 2012; 11(1):100-109.

Rosso L, Brock C S, Gallo J M et al. A new model for prediction of drug distribution in tumor and normal tissues: Pharmacokinetics of temozolomide in glioma patients. Cancer Res 2009; 69:120-127.

Sampson J H, Heimberger A B, Archer G E, Aldape K D, Friedman A H, Friedman H S et al. Immunologic escape after prolonged progression-free survival with epidermal growth factor receptor variant III peptide vaccination in patients with newly diagnosed glioblastoma. J Clin Oncol 2010; 28(31): 4722-9.

Sarkaria J N, Carlson B L, Schroeder M A, et al. Use of an orthotopic xenograft model for assessing the effect of epidermal growth factor receptor amplification on glioblastoma radiation response. Clin Cancer Res. Apr. 1, 2006; 12(7 Pt 1):2264-2271.

Schmidt N O, Przylecki W, Yang W et al. Brain tumor tropism of transplanted human neural stem cells is induced by vascular endothelial growth factor. Neoplasia 2005; 7:623-629.

Schoenfeld D A. Sample-size formula for the proportional-hazards regression model. Biometrics 1983; 39(2):499-503.

Sebestyen Z, de Vrij J, Magnusson M, Debets R, Willemsen R. An oncolytic adenovirus redirected with a tumor-specific T-cell receptor. Cancer Res 2007; 67(23):11309-11316.

Selznick L A, Shamji M F, Fecci P, Gromeier M, Friedman A H, Sampson J. Molecular strategies for the treatment of malignant glioma—genes, viruses, and vaccines. Neurosurg Rev 2008; 31(2): 141-55; discussion 155.

Shah K, Bureau E, Kim D E, Yang K, Tang Y, Weissleder R, Breakefield X O. Glioma therapy and realtime imaging of neural precursor cell migration and tumor regression. Ann Neurol 2005; 57(1):34-41.

Sheehan J P, Shaffrey M E, Gupta B, Lamer J, Rich J N, Park D M. Improving the radiosensitivity of radioresistant and hypoxic glioblastoma. Future Oncol 2010; 6(10): 1591-601.

Singh S K, Hawkins C, Clarke I D, Squire J A, Bayani J, Hide T, Henkelman R M, Cusimano M D, Dirks P B. Identification of human brain tumour initiating cells. Nature 2004; 432(7015):396-401.

Smitt P S, Driesse M, Wolbers J, Kros M, Avezaat C. Treatment of relapsed malignant glioma with an adenoviral vector containing the herpes simplex thymidine kinase gene followed by ganciclovir. Mol Ther 2003; 7(6):851-858.

Sonabend A M, Ulasov I V, Han Y, Lesniak M S. Oncolytic adenoviral therapy for glioblastoma multiforme. Neurosurg Focus 2006; 20(4):E19.

Sonabend A M, Ulasov I V, Han Y, Rolle C E, Nandi S, Cao D, Tyler M A, Lesniak M S. Biodistribution of an oncolytic adenovirus after intracranial injection in permissive animals: a comparative study of Syrian hamsters and cotton rats. Cancer Gene Ther 2009; 16(4):362-372.

Sonabend A M, Ulasov I V, Tyler M A, Rivera A A, Mathis J M, Lesniak M S. Mesenchymal stem cells effectively deliver an oncolytic adenovirus to intracranial glioma. Stem Cells 2008; 26(3): 831-41.

Sonabend A M, Ulasov I V, Tyler M A, Rivera A A, Mathis J M, Lesniak M S. Mesenchymal stem cells effectively deliver an oncolytic adenovirus to intracranial glioma. Stem Cells 2008; 26(3):831-841.

Stoica G, Lungu G, *Martini*-Stoica H, Waghela S, Levine J, Smith R, 3rd. Identification of cancer stem cells in dog glioblastoma. Vet Pathol 2009; 46(3): 391-406.

Stracker T H, Carson C T, Weitzman M D. Adenovirus oncoproteins inactivate the Mre11-Rad50-NBS1 DNA repair complex. Nature 2002; 418:348-352.

Studebaker A W, Hutzen B, Pierson C R, Russell S J, Galanis E, Raffel C. Oncolytic measles virus prolongs survival in a murine model of cerebral spinal fluid-disseminated medulloblastoma. Neuro Oncol 2012; doi: 10.1093/neuonc/nor231.

Stupp R, Hegi M E, Mason W P, van den Bent M J, Taphoorn M J, Janzer R C et al. Effects of radiotherapy with concomitant and adjuvant temozolomide versus radiotherapy alone on survival in glioblastoma in a randomised phase III study: 5-year analysis of the EORTC-NCIC trial. Lancet Oncol 2009; 10(5): 459-66.

Stupp R, Mason W P, van den Bent M J, Weller M, Fisher B, Taphoorn M J, Belanger K, Brandes A A, Marosi C, Bogdahn U, Curschmann J, Janzer R C, Ludwin S K, Gorlia T, Allgeier A, Lacombe D, Cairncross J G, Eisenhauer E, Mirimanoff R O. Radiotherapy plus concomitant and adjuvant temozolomide for glioblastoma. N Engl J Med 2005b; 352(10):987-996.

Stupp R, Weber D C. The role of radio- and chemotherapy in glioblastoma. Onkologie 2005a; 28(6-7):315-317.

Thaci B, Ahmed A U, Ulasov I V, et al. Pharmacokinetic study of neural stem cell-based cell carrier for oncolytic virotherapy: targeted delivery of the therapeutic payload in an orthotopic brain tumor model. Cancer Gene Ther. June 2012; 19(6):431-442.

Thomas M A, Spencer J F, La Regina M C, Dhar D, Tollefson A E, Toth K, Wold W S. Syrian hamster as a permissive immunocompetent animal model for the study of oncolytic adenovirus vectors. Cancer Res 2006; 66(3): 1270-1276.

Thomas M A, Spencer J F, Wold W S. Use of the Syrian hamster as an animal model for oncolytic adenovirus vectors. Methods Mol Med 2007; 130: 169-83.

Thu M S, Najbauer J, Kendall S E, Harutyunyan I, Sangalang N, Gutova M et al. Iron labeling and pre-clinical MRI visualization of therapeutic human neural stem cells in a murine glioma model. PLoS One 2009; 4(9): e7218.

Thumma S R, Elaimy A L, Daines N et al. Longterm survival after gamma knife radiosurgery in a case of recurrent glioblastoma multiforme: A case report and review of the literature. Case Report Med2012; 2012:545492.

Tobias A, Ahmed A, Moon K S et al. The art of gene therapy for glioma: A review of the challenging road to the bedside. J Neurol Neurosurg Psychiatry 2013; 84:213-222.

Toth K, Spencer J F, Tollefson A E, Kuppuswamy M, Doronin K, Lichtenstein D L et al. Cotton rat tumor model for the evaluation of oncolytic adenoviruses. Hum Gene Ther 2005; 16(1): 139-46.

Toth K, Spencer J F, Wold W S. Immunocompetent, semipermissive cotton rat tumor model for the evaluation of oncolytic adenoviruses. Methods Mol Med 2007; 130: 157-68.

Tran B, Rosenthal M A. Survival comparison between glioblastoma multiforme and other incurable cancers. J Clin Neurosci 2010; 17:417-421.

Tsai V, Johnson D E, Rahman A, Wen S F, LaFace D, Philopena J, Nery J, Zepeda M, Maneval D C, Demers G W, Ralston R. Impact of human neutralizing antibodies on antitumor efficacy of an oncolytic adenovirus in a murine model. Clin Cancer Res 2004; 10(21):7199-7206.

Tuominen H, Lohi J, Maiche A, Tormanen J, Baumann P. Mediastinal Metastasis of Glioblastoma Multiforme Evolving from Anaplastic Astrocytoma. J Neurooncol 2005.

Tyler M A, Ulasov I V, Borovjagin A, Sonabend A M, Khramtsov A, Han Y, Dent P, Fisher P B, Curiel D T, Lesniak M S. Enhanced transduction of malignant glioma with a double targeted Ad5/3-RGD fibermodified adenovirus. Mol Cancer Ther 2006; 5(9):2408-2416.

Tyler M A, Ulasov I V, Sonabend A M, Nandi S, Han Y, Marler S et al. Neural stem cells target intracranial glioma to deliver an oncolytic adenovirus in vivo. Gene Ther 2009; 16(2): 262-78.

Ubiali F, Nava S, Nessi V, Frigerio S, Parati E, Bernasconi P et al. Allorecognition of human neural stem cells by peripheral blood lymphocytes despite low expression of MHC molecules: role of TGF-beta in modulating proliferation. Int Immunol 2007; 19(9): 1063-74.

Ulasov I V, Rivera A A, Nettelbeck D M, Rivera L B, Mathis J M, Sonabend A M, Tyler M, Wang M, Douglas J T, Lesniak M S. An oncolytic adenoviral vector carrying the tyrosinase promoter for glioma gene therapy. Int J Oncol 2007d; 31(5):1177-1185.

Ulasov I V, Rivera A A, Sonabend A M, Rivera L B, Wang M, Zhu Z B et al. Comparative evaluation of survivin, midkine and CXCR4 promoters for transcriptional targeting of glioma gene therapy. Cancer Biol Ther 2007b; 6(5): 679-85.

Ulasov I V, Rivera A A, Sonabend A M, Rivera L B, Wang M, Zhu Z B, Lesniak M S. Comparative Evaluation of Survivin, Midkine, and CXCR4 Promoters for Transcriptional Targeting of Glioma Gene Therapy. Cancer Biol Ther 2007e; 6(5). Ulasov I V, Rivera A A, Han Y, Curiel D T, Zhu Z B, Lesniak M S. Targeting adenovirus to CD80 and CD86 receptors increases gene transfer efficiency to malignant glioma cells. J Neurosurg. September 2007f; 107(3):617-627.

Ulasov I V, Sonabend A M, Nandi S, Khramstov A, Han Y, Lesniak M S. Synergistic effect of adenoviral virotherapy and temozolomide chemotherapy for malignant glioma. Mol Ther 2008; In review.

Ulasov I V, Sonabend A M, Nandi S, Khramtsov A, Han Y, Lesniak M S. Combination of adenoviral virotherapy and temozolomide chemotherapy eradicates malignant glioma through autophagic and apoptotic cell death in vivo. Br J Cancer 2009; 100(7):1154-1164.

Ulasov I V, Tyler M A, Han Y, Glasgow J N, Lesniak M S. Novel recombinant adenoviral vector that targets the interleukin-13 receptor alpha2 chain permits effective gene transfer to malignant glioma. Hum Gene Ther 2007c; 18(2):118-129.

Ulasov I V, Zhu Z B, Tyler M A, Han Y, Rivera A A, Khramtsov A et al. Survivin-driven and fiber-modified oncolytic adenovirus exhibits potent antitumor activity in established intracranial glioma. Hum Gene Ther 2007a; 18(7): 589-602.

Utsuki S, Tanaka S, Oka H, Iwamoto K, Sagiuchi T, Fujii K. Glioblastoma multiforme metastasis to the axis. Case report. J Neurosurg 2005; 102(3):540-542.

van Beusechem V W, van den Doel P B, Gerritsen W R. Conditionally replicative adenovirus expressing degradation-resistant p53 for enhanced oncolysis of human cancer cells overexpressing murine double minute 2. Mol Cancer Ther. June 2005; 4(6):1013-1018.

Van Houdt W J, Haviv Y S, Lu B, Wang M, Rivera A A, Ulasov I V, Lamfers M L, Rein D, Lesniak M S, Siegal G P, Dirven C M, Curiel D T, Zhu Z B. The human survivin promoter: a novel transcriptional targeting strategy for treatment of glioma. J Neurosurg 2006; 104(4):583-592.

Vichai V, Kirtikara K. Sulforhodamine B colorimetric assay for cytotoxicity screening. Nat Protoc 2006; 1(3):1112-1116.

Wen P Y, Kesari S. Malignant gliomas in adults. N Engl J Med 2008; 359(5):492-507.

Wickham T J, Mathias P, Cheresh D A, Nemerow G R. Integrins alpha v beta 3 and alpha v beta 5 promote adenovirus internalization but not virus attachment. Cell 1993; 73(2):309-319.

Wildner O, Morris J C. Subcutaneous Administration of a Replication-Competent Adenovirus Expressing HSV-tk to Cotton Rats: Dissemination, Persistence, Shedding, and Pathogenicity. Hum Gene Ther 2002; 13(1):101-112.

Wohlfahrt M E, Beard B C, Lieber A, Kiem H P. A capsid-modified, conditionally replicating oncolytic adenovirus vector expressing TRAIL Leads to enhanced cancer cell killing in human glioblastoma models. Cancer Res 2007; 67(18):8783-8790.

Wu H, Seki T, Dmitriev I, Uil T, Kashentseva E, Han T, Curiel D T. Double modification of adenovirus fiber with RGD and polylysine motifs improves coxsackievirus-adenovirus receptor-independent gene transfer efficiency. Hum Gene Ther 2002; 13(13):1647-1653.

Xu D S, Yang C, Proescholdt M et al. Neuronatin in a subset of glioblastoma multiforme tumor progenitor cells is associated with increased cell proliferation and shorter patient survival. PLoS One 2012; 7:e37811.

Yamada Y, Kuroiwa T, Nakagawa T, Kajimoto Y, Dohi T, Azuma H, Tsuji M, Kami K, Miyatake S. Transcriptional expression of survivin and its splice variants in brain tumors in humans. J Neurosurg 2003; 99(4):738-745.

Yamamoto M, Curiel D T. Current issues and future directions of oncolytic adenoviruses. Mol Ther. February 2010; 18(2):243-250.

Yamanaka S. Induced pluripotent stem cells: past, present, and future. Cell Stem Cell. Jun. 14 2012; 10(6):678-684.

Zhang H, Vutskits L, Pepper M S et al. VEGF is a chemoattractant for FGF-2-stimulated neural progenitors. J Cell Biol 2003; 163: 1375-1384.

Zhang Z, Jiang Q, Jiang F, Ding G, Zhang R, Wang L, Zhang L, Robin A M, Katakowski M, Chopp M. In vivo magnetic resonance imaging tracks adult neural progenitor cell targeting of brain tumor. Neuroimage 2004; 23(1): 281-287.

Zhao D, Najbauer J, Garcia E et al. Neural stem cell tropism to glioma: Critical role of tumor hypoxia. Mol Cancer Res 2008; 6:1819-1829.

Zheng S, Ulasov I V, Han Y, Tyler M A, Zhu Z B, Lesniak M S. Fiber-knob modifications enhance adenoviral tropism and gene transfer in malignant glioma. J Gene Med 2007; 9(3):151-160.

Zhu Y, Guignard F, Zhao D, Liu L, Burns D K, Mason R P, Messing A, Parada L F. Early inactivation of p53 tumor suppressor gene cooperating with NF1 loss induces malignant astrocytoma. Cancer Cell 2005; 8(2):119-130.

Zhu Z B, Makhija S K, Lu B, Wang M, Rivera A A, Kim-Park S et al. Incorporating the survivin promoter in an infectivity enhanced CRAdanalysis of oncolysis and anti-tumor effects in vitro and in vivo. Int J Oncol 2005; 27(1): 237-46.

What is claimed is:

1. A method of killing a tumor cell comprising:
contacting the tumor cell with a tropic cell that carries a modified oncolytic virus, wherein the virus comprises a tumor selective promoter element and/or a capsid protein that binds a tumor-specific cell surface molecule, and wherein the tropic cell is a stem cell from a neural stem cell line HB1.F3-CD.

2. The method of claim 1, wherein the modified oncolytic virus is a modified conditionally replicating adenovirus (CRAd).

3. The method of claim 1, wherein the tumor selective promoter element is a survivin promoter, a cyclooxygenase-2(COX-2) promoter, prostate specific antigen (PSA) promoter, a CXCR4 promoter, or a STAT3 promoter.

4. The method of claim 1, wherein the capsid protein is a fiber, a penton or hexon protein.

5. The method of claim 4, wherein the tumor specific cell surface molecule is selected from an integrin, an EGF receptor family member, a proteoglycan, a disialoganglioside, B7-H3, cancer antigen 125 (CA-125), epithelial cell adhesion molecule (EpCAM), vascular endothelial growth factor receptor 1, vascular endothelial growth factor receptor 2, carcinoembryonic antigen (CEA), a tumor associated glycoprotein, cluster of differentiation 19 (CD19), CD20, CD22, CD30, CD33, CD40, CD44, CD52, CD74, CD152, mucin 1 (MUC1), a tumor necrosis factor receptor, an insulin-like growth factor receptor, folate receptor a, transmembrane glycoprotein NMB, a C-C chemokine receptor, prostate specific membrane antigen (PSMA), recepteur d'origine nantais (RON) receptor, and cytotoxic T-lymphocyte antigen 4.

6. The method of claim 1, wherein the tumor cell is part of a brain tumor, breast tumor, bone tumor, bladder tumor, tumor of the urinary tract, carcinoma, cervical tumor, colon tumor, esophageal tumor, gastric tumor, head and neck tumor, hepatocellular tumor, liver tumor, lung tumor, lymphoma and leukemia, melanoma, ovarian tumor, pancreatic tumor, pituitary tumor, prostate tumor, rectal tumor, renal tumor, sarcoma, testicular tumor, thyroid tumor, and uterine tumor.

7. A method of killing a brain tumor cell comprising contacting the brain tumor cell with a neural stem cell that carries a modified conditionally replicating adenovirus (CRAd) which comprises a tumor selective promoter element and/or a fiber protein that binds heparan sulfate proteoglycans, wherein the neural stem cell is from a neural stem cell line HB1.F3-CD.

8. The method of claim 7, wherein the brain tumor cell is a glioma cell.

9. The method of claim 7, wherein the tumor selective promoter is a survivin promoter.

10. A method of treating cancer comprising administering, to a subject, a therapeutically effective amount of a pharmaceutical composition which comprises a tropic cell that carries a modified oncolytic virus, wherein the virus comprises a tumor selective promoter element and/or a capsid protein that binds a tumor-specific cell surface molecule, and wherein the tropic cell is a stem cell from a neural stem cell line HB1.F3-CD.

11. The method of claim 10, further comprising administering one or more therapeutic agent in combination with the pharmaceutical composition.

12. The method of claim 11, wherein the one or more therapeutic agent is temozolomide (TMZ), radiotherapy or both.

13. The method of claim 10, wherein the modified oncolytic virus is a modified conditionally replicating adenovirus (CRAd).

14. The method of claim 10, wherein the tumor selective promoter element is a survivin promoter.

15. The method of claim 10, wherein the capsid protein is a fiber, a penton or hexon protein.

16. The method of claim 14, wherein the tumor specific cell surface molecule is a heparan sulfate proteoglycan.

17. The method of claim 10, wherein the cancer treated is a glioma.

* * * * *

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: forward primer

<400> SEQUENCE: 1
cctttgattt cgccaat                                                 17

<210> SEQ ID NO 2
<211> LENGTH: 21
<212> TYPE: DNA
<213> ORGANISM: Artificial Sequence
<220> FEATURE:
<223> OTHER INFORMATION: reverse primer

<400> SEQUENCE: 2
gcgagcttct ccgacaccac c                                            21

<210> SEQ ID NO 3
<211> LENGTH: 24
<212> TYPE: DNA
<213> ORGANISM: Artificial Sequence
<220> FEATURE:
<223> OTHER INFORMATION: forward primer

<400> SEQUENCE: 3
tcacagccag atatccagca gctt                                         24

<210> SEQ ID NO 4
<211> LENGTH: 20
<212> TYPE: DNA
<213> ORGANISM: Artificial Sequence
<220> FEATURE:
<223> OTHER INFORMATION: reverse primer

<400> SEQUENCE: 4
acttctcctc ctcctcctcg                                              20

<210> SEQ ID NO 5
<211> LENGTH: 15
<212> TYPE: DNA
<213> ORGANISM: Artificial Sequence
<220> FEATURE:
<223> OTHER INFORMATION: forward primer

<400> SEQUENCE: 5
```

```
cattgacaac tacat                                                    15

<210> SEQ ID NO 6
<211> LENGTH: 19
<212> TYPE: DNA
<213> ORGANISM: Artificial Sequence
<220> FEATURE:
<223> OTHER INFORMATION: reverse primer

<400> SEQUENCE: 6
tctccatggt ggtgaagac                                                19
```